(12) United States Patent
Aubart et al.

(10) Patent No.: US 8,901,119 B2
(45) Date of Patent: Dec. 2, 2014

(54) PEPTIDE DEFORMYLASE INHIBITORS

(75) Inventors: Kelly M. Aubart, Collegeville, PA (US); Andrew B. Benowitz, Collegeville, PA (US); Yuhong Fang, Eagleville, PA (US); James Hoffman, Ardmore, PA (US); Joseph M. Karpinski, Stowe, PA (US); Andrew Nicholson Knox, Philadelphia, PA (US); Xiangmin Liao, Collegeville, PA (US); Donghui Qin, Collegeville, PA (US); Dongchuan Shi, Collegeville, PA (US); Jared T. Spletstoser, Collegeville, PA (US)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 14/004,105

(22) PCT Filed: Mar. 9, 2012

(86) PCT No.: PCT/US2012/028424
§ 371 (c)(1),
(2), (4) Date: Sep. 9, 2013

(87) PCT Pub. No.: WO2012/122450
PCT Pub. Date: Sep. 13, 2012

(65) Prior Publication Data
US 2013/0345120 A1 Dec. 26, 2013

Related U.S. Application Data

(60) Provisional application No. 61/450,784, filed on Mar. 9, 2011.

(51) Int. Cl.
| | | |
|---|---|---|
| A61K 31/5377 | (2006.01) |
| A61K 31/497 | (2006.01) |
| A61K 31/501 | (2006.01) |
| A61K 31/506 | (2006.01) |
| A61K 31/52 | (2006.01) |
| A61K 31/4709 | (2006.01) |
| A61K 31/4725 | (2006.01) |
| A61K 31/4375 | (2006.01) |
| A61K 31/4427 | (2006.01) |
| A61K 31/427 | (2006.01) |
| A61K 31/42 | (2006.01) |
| A61K 31/4155 | (2006.01) |
| A61K 31/415 | (2006.01) |
| A61K 31/4245 | (2006.01) |
| C07D 413/02 | (2006.01) |
| C07D 401/02 | (2006.01) |
| C07D 403/02 | (2006.01) |
| C07D 473/00 | (2006.01) |
| C07D 239/20 | (2006.01) |
| C07D 241/10 | (2006.01) |
| C07D 471/04 | (2006.01) |
| C07D 217/00 | (2006.01) |
| C07D 215/00 | (2006.01) |
| C07D 277/20 | (2006.01) |
| C07D 233/02 | (2006.01) |
| C07D 231/02 | (2006.01) |
| C07D 401/12 | (2006.01) |
| C07K 5/078 | (2006.01) |
| C07D 403/12 | (2006.01) |
| C07D 231/06 | (2006.01) |

(52) U.S. Cl.
CPC ......... *C07K 5/06139* (2013.01); *C07D 401/12* (2013.01); *C12Y 305/01088* (2013.01); *C07D 403/12* (2013.01); *C07D 231/06* (2013.01)
USPC .............. 514/235.5; 514/252.05; 514/255.05; 514/256; 514/263.2; 514/300; 514/307; 514/311; 514/341; 514/364; 514/365; 514/378; 514/394; 514/397; 514/403; 544/122; 544/124; 544/238; 544/264; 544/333; 544/335; 544/336; 546/122; 546/146; 546/175; 546/275.4; 548/143; 548/204; 548/240; 548/306.1; 548/338.1; 548/356.1

(58) Field of Classification Search
USPC ......... 544/122, 124, 238, 264, 333, 335, 336; 546/122, 146, 175, 275.4; 548/143, 548/204, 240, 306.1, 338.1, 356.1; 514/235.5, 252.05, 255.05, 256, 263.2, 514/300, 307, 311, 341, 364, 365, 378, 394, 514/397, 403
See application file for complete search history.

(56) References Cited

U.S. PATENT DOCUMENTS

| | | |
|---|---|---|
| 5,250,700 A | 10/1993 | Bagli et al. |
| 5,574,169 A | 11/1996 | Blanchard et al. |
| 2005/0222412 A1 | 10/2005 | Aubart et al. |
| 2006/0183742 A1 | 8/2006 | Mederski et al. |
| 2009/0069294 A1 | 3/2009 | Chen et al. |
| 2009/0306066 A1 | 12/2009 | Qin et al. |
| 2011/0020386 A1 | 1/2011 | Gierahn et al. |

OTHER PUBLICATIONS

Aubart et al., "Peptide Deformylase Inhibitors", Progress in Medicinal Chemistry, vol. 44, 2006, see. pp. 126, 127, 136.

*Primary Examiner* — Samantha Shterengarts
(74) *Attorney, Agent, or Firm* — Grace C. Hsu; John Lemanowicz

(57) ABSTRACT

The present invention relates to a compound of Formula (I):

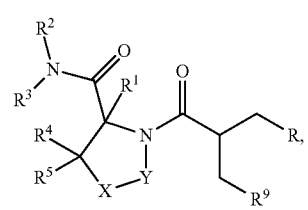

or a pharmaceutically acceptable salt thereof, corresponding pharmaceutical compositions, compound preparation and treatment methods directed to bacterial infections and inhibition of bacterial peptide deformylase (PDF) activity.

19 Claims, No Drawings

(56) References Cited

U.S. PATENT DOCUMENTS

PEPTIDE DEFORMYLASE INHIBITORS

This application is a 371 of International Application No. PCT/US2012/028424, filed 9 Mar. 2012, which is incorporated herein by reference. This application claims priority to and the benefit of U.S. Provisional Application No. 61/450,784, filed 9 Mar. 2011.

FIELD OF THE PRESENT INVENTION

In general, the present invention relates to PDF inhibitor compounds, which are a class of antibacterial agents with a novel mode of action covering a broad spectrum of pathogens. Compounds of the present invention are useful as inhibitors of bacterial peptide deformylase (PDF) activity, and in treatment of associated bacterial infections.

In particular, the present invention relates to novel compounds of Formulas (I) to (IV), respectively, or pharmaceutically acceptable salts thereof, corresponding intermediates, preparation methods and pharmaceutical compositions thereof.

The present invention also relates to methods for treatment of bacterial infections, which comprise administering an effective amount of a compound of Formulas (I) to (IV), respectively, or a pharmaceutically acceptable salt thereof, or a corresponding pharmaceutical composition to a human in need thereof.

BACKGROUND OF THE PRESENT INVENTION

Bacterial protein synthesis starts with N-formyl-methionyl-tRNA and, as a consequence, all newly synthesized polypeptides contain an N-formyl-methionine terminus (Figure I). Peptide deformylase (PDF) is a metalloenzyme that removes the N-formyl group of the polypeptides as they emerge from the ribosome during the elongation process [Adams, J. M. (1968) J. Mol. Biol. 33, 571-589; Livingston, D. M. and Leder, P. (1969) Biochemistry 8, 435-443; Ball, L. A. and Kaesberg, P. (1973) J. Mol. Biol. 79, 531-537]. Depending on the nature of their second amino acid, polypeptides are further processed by methionine amino peptidase (MAP) to yield the mature protein. Deformylation plays an indispensable role in protein maturation as MAP, an essential enzyme for bacterial growth, cannot hydrolyze N-blocked peptides [Solbiati, J., Chapman-Smith, A., Miller, J. L., Miller, C. G. and Cronan Jr., J. E. (1999) J. Mol. Biol. 290, 607-614].

FIG. I. Role of PDF in protein synthesis

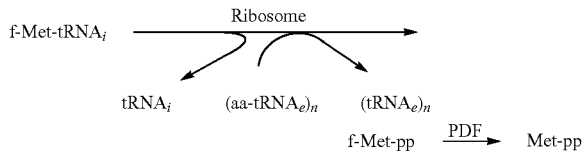

PDF is ubiquitous in bacteria, with at least one pdf gene present in all bacterial genomes sequenced to date [Guilloteau, J. P., Mathieu, M., Giglione, C., Blanc, V., Dupuy, A., Chevrier, M., Gil, P., Famechon, A., Meinnel, T. and Mikol, V. (2002) J. Mol. Biol. 320, 951-962], and it has been shown to be essential for growth in a number of bacterial species [Mazel, D., Pochet, S, and Marliere, P. (1994) EMBO J. 13, 914-923; Meinnel, T. and Blanquet, S. (1994) J. Bacteriol. 176, 7387-7390; Margolis, P. S., Hackbarth, C. J., Young, D. C., Wang, W., Chen, D., Yuan, Z., White, R. and Trias. J. (2000) Antimicrob. Agents Chemother. 44, 1825-1831; Margolis P., Hackbarth, C., Lopez, S., Maniar, M., Wang, W., Yuan, Z., White, R. and Trias. J. (2001) Antimicrob. Agents Chemother. 45, 2432-2435].

PDF does not play a role in eukaryotic cytoplasmic protein synthesis which does not involve N-formylation, but nuclear-encoded PDF proteins, containing a chloroplast/mitochondria localization signal, have been identified in parasites, plants and mammals, including humans [Giglione, C., Serero, A., Pierre, M., Boisson, B. and Meinnel, T. (2000) EMBO J. 19, 5916-5929]. PDF is essential in plant and parasite organelles [Bracchi-Ricard, V., Nguyen, K., Zhou, Y., Rajagopalan, P. T. R., Chakrabarti, D. and Pei, D. (2001) Arch. Biochem. Biophys. 396, 162-170; Serero, A., Giglione, C. and Meinnel, T. (2001) J. Mol. Biol. 314, 695-708] since their genomes encode for a number of proteins which require deformylation for activity [Giglione, C. and Miennel, T. (2001) Emerging Ther. Targets 5, 41-57], but there is evidence to suggest that this is not the case in animals. In fact, characterization of human mitochondrial PDF has shown that it is much less active than its bacterial counterpart. Furthermore, PDF inhibitors which are active against the human PDF enzyme in vitro have no effect on the growth of normal human cell lines [Nguyen, K. T., Hu, X., Colton, C., Chakrabarti, R., Zhu, M. X. and Pei, D. (2003) Biochemistry 42, 9952-9958].

PDF inhibitors represent a promising new class of antibacterial agents with a novel mode of action covering a broad-spectrum of pathogens. The present inventors have discovered novel compounds, which are inhibitors of PDF activity. Such derivatives are useful in the treatment of bacterial infections associated with such PDF activity.

In light of the above, a need exists to develop PDF inhibitor compounds of the present invention, which has a mode of action that covers a broad spectrum of pathogens, corresponding compositions and treatment methods for bacterial infections.

The present invention is directed to overcoming these and other problems encountered in the art.

SUMMARY OF THE PRESENT INVENTION

In general, the present invention relates to PDF inhibitor compounds, which are a class of antibacterial agents with a novel mode of action covering a broad spectrum of pathogens. Compounds of the present invention are useful as inhibitors of bacterial peptide deformylase (PDF) activity, and in treatment of associated bacterial infections.

In particular, the present invention relates to novel compounds of Formulas (I) to (IV), respectively, or pharmaceutically acceptable salts thereof, corresponding intermediates, preparation methods and pharmaceutical compositions thereof.

The present invention also relates to methods for treatment of bacterial infections, which comprise administering an effective amount of a compound of Formulas (I) to (IV), respectively, or a pharmaceutically acceptable salt thereof, or a corresponding pharmaceutical composition to a human in need thereof.

DETAILED DESCRIPTION OF THE PRESENT INVENTION

In general, the present invention relates to PDF inhibitor compounds, which are a class of antibacterial agents with a novel mode of action covering a broad spectrum of pathogens. Compounds of the present invention are useful as inhibitors of bacterial peptide deformylase (PDF) activity, and in treatment of associated bacterial infections.

In particular, the present invention relates to novel compounds of Formulas (I) to (IV), respectively, or pharmaceutically acceptable salts thereof, corresponding intermediates, preparation methods and pharmaceutical compositions thereof.

The present invention also relates to methods for treatment of bacterial infections, which comprise administering an effective amount of a compound of Formulas (I) to (IV), respectively, or a pharmaceutically acceptable salt thereof, or a corresponding pharmaceutical composition to a human in need thereof.

Compounds

In general, the present invention relates to PDF inhibitor compounds, which are a class of antibacterial agents with a novel mode of action covering a broad spectrum of pathogens. Compounds of the present invention are useful as inhibitors of bacterial peptide deformylase (PDF) activity, and in treatment of associated bacterial infections.

In particular, the present invention relates to novel compounds of Formulas (I) to (IV), respectively, or pharmaceutically acceptable salts thereof, corresponding intermediates, preparation methods and pharmaceutical compositions thereof.

In one aspect, the present invention relates to a compound of Formula (I):

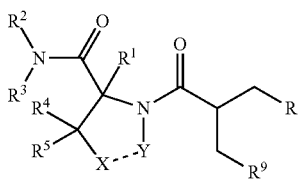

(I)

where:
X—Y is —C(H)$_2$—N(R$^a$)— or —C(H)=N—;
R is —C(O)N(H)OH or —N(OH)C(O)H;
R$^1$ is —H or —C$_1$-C$_6$ alkyl;
R$^2$ is aryl, —(CH$_2$)$_n$aryl, heteroaryl or —(CH$_2$)$_n$heteroaryl.
R$^3$ is —H or —C$_1$-C$_6$ alkyl;
R$^4$ is —H, halo, —OH, C$_1$-C$_3$ alkoxy, —NR$^6$R$^7$ or C$_1$-C$_6$ alkyl;
R$^5$ is —H, halo, —OH, C$_1$-C$_3$ alkoxy, —NR$^6$R$^7$ or C$_1$-C$_6$ alkyl;
R$^9$ is —C$_3$-C$_6$ cycloalkyl or —C$_1$-C$_6$ alkyl;
where:
n is 0 or an integer from 1 to 5;
R$^a$ is —H or —C$_1$-C$_3$ alkyl;
each aryl or heteroaryl as defined in R$^2$ optionally is substituted with one, two, or three R$^8$ groups;
R$^6$ is —H or —C$_1$-C$_6$ alkyl;
R$^7$ is —H or —C$_1$-C$_6$ alkyl;
R$^8$ each independently is selected from —C$_1$-C$_6$ alkyl, —C$_1$-C$_6$ haloalkyl, heterocyclyl, aryl, heteroaryl, —C(O)OR$^{10}$, —OR$^{10}$, —NR$^{10}$R$^{11}$, —O(CH$_2$)$_2$NR$^{10}$R$^{11}$, —(CH$_2$)NR$^{10}$R$^{11}$ or —N(H)(CH$_2$)$_3$—NR$^{10}$R$^{11}$;

where:
R$^{10}$ or R$^{11}$ each independently is —H or —C$_1$-C$_6$ alkyl;
heterocyclyl, aryl or heteroaryl optionally is substituted with at least one R$^{12}$ group;
where:
R$^{12}$ is —C$_1$-C$_6$ alkyl, —NR$^{13}$R$^{14}$, —OR$^{15}$ or halo;
wherein:
R$^{13}$, R$^{14}$ or R$^{15}$ each independently is —H or —C$_1$-C$_6$ alkyl; or
a pharmaceutically acceptable salt thereof.

In a second aspect, the present invention relates to a compound of Formula (II):

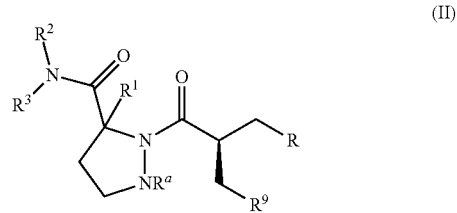

(II)

where:
R$^a$ is —H or —C$_1$-C$_3$ alkyl;
R is —C(O)N(H)OH or —N(OH)C(O)H;
R$^1$ is —H or —C$_1$-C$_6$ alkyl;
R$^2$ is aryl, —(CH$_2$)$_n$aryl, heteroaryl or —(CH$_2$)$_n$heteroaryl.
R$^3$ is —H or —C$_1$-C$_6$ alkyl;
R$^9$ is —C$_3$-C$_6$ cycloalkyl or —C$_1$-C$_6$ alkyl;
where:
each aryl or heteroaryl as defined in R$^2$ optionally is substituted with one, two, or three R$^8$ groups;
R$^8$ each independently is selected from —C$_1$-C$_6$ alkyl, —C$_1$-C$_6$ haloalkyl, heterocyclyl, aryl, heteroaryl, —C(O)OR$^{10}$, —OR$^{10}$, —NR$^{10}$R$^{11}$, —O(CH$_2$)$_2$NR$^{10}$R$^{11}$, —O(CH$_2$)$_2$NR$^{10}$R$^{11}$, —(CH$_2$)NR$^{10}$R$^{11}$ or —N(H)(CH$_2$)$_3$—NR$^{10}$R$^{11}$;
where:
n is 0 or an integer from 1 to 5;
R$^{10}$ or R$^{11}$ each independently is —H or —C$_1$-C$_6$ alkyl;
heterocyclyl, aryl or heteroaryl optionally is substituted with at least one R$^{12}$ group;
where:
R$^{12}$ is —C$_1$-C$_6$ alkyl, —NR$^{13}$R$^{14}$, —OR$^{15}$ or halo;
where:
R$^{13}$, R$^{14}$ or R$^{15}$ each independently is —H or —C$_1$-C$_6$ alkyl; or
a pharmaceutically acceptable salt thereof.

In a third aspect, the present invention relates to a compound of Formula (III):

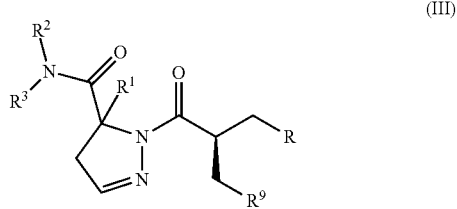

(III)

where:
R is —C(O)N(H)OH or —N(OH)C(O)H
R$^1$ is —H or —C$_1$-C$_6$ alkyl;

$R^2$ is aryl, —$(CH_2)_n$aryl, heteroaryl or —$(CH_2)_n$heteroaryl;
$R^3$ is —H or —$C_1$-$C_6$ alkyl;
  where:
    each aryl or heteroaryl as defined in $R^2$ optionally is substituted with one, two, or three $R^8$ groups;
    $R^8$ each independently is selected from —$C_1$-$C_6$ alkyl, —$C_1$-$C_6$ haloalkyl, heterocyclyl, aryl, heteroaryl, —C(O)OR$^{10}$, —OR$^{10}$, —NR$^{10}$R$^{11}$, —O(CH$_2$)$_2$NR$^{10}$R$^{11}$, —(CH$_2$)NR$^{10}$R$^{11}$ or —N(H)(CH$_2$)$_3$—NR$^{10}$R$^{11}$;
      where:
        $R^{10}$ or $R^{11}$ each independently is —H or —$C_1$-$C_6$ alkyl;
        heterocyclyl, aryl or heteroaryl optionally is substituted with at least one $R^{12}$ group;
          where:
            n is 0 or an integer from 1 to 5;
            $R^{12}$ is —$C_1$-$C_6$ alkyl, —NR$^{13}$R$^{14}$, —OR$^{15}$ or halo;
              where:
                $R^{13}$, $R^{14}$ or $R^{15}$ each independently is —H or —$C_1$-$C_6$ alkyl; or
a pharmaceutically acceptable salt thereof.

In a fourth aspect, the present invention relates to a compound of Formula (IV)

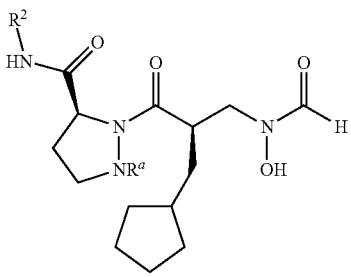

(IV)

where:
$R^a$ is —H or —$C_1$-$C_3$ alkyl;
$R^2$ is aryl, —$(CH_2)_n$aryl, heteroaryl or —$(CH_2)_n$heteroaryl;
  where:
    each aryl or heteroaryl as defined in $R^2$ optionally is substituted with one, two, or three $R^8$ groups;
    $R^8$ each independently is selected from —$C_1$-$C_6$ alkyl, —$C_1$-$C_6$ haloalkyl, heterocyclyl, aryl, heteroaryl, —C(O)OR$^{10}$, —OR$^{10}$, —NR$^{10}$R$^{11}$, —O(CH$_2$)$_2$NR$^{10}$R$^{11}$, —(CH$_2$)NR$^{10}$R$^{11}$ or —N(H)(CH$_2$)$_3$—NR$^{10}$R$^{11}$;
      where:
        n is 0 or an integer from 1 to 5;
        $R^{10}$ or $R^{11}$ each independently is —H or —$C_1$-$C_6$ alkyl;
        heterocyclyl, aryl or heteroaryl optionally is substituted with at least one $R^{12}$ group;
          where:
            $R^{12}$ is —$C_1$-$C_6$ alkyl, —NR$^{13}$R$^{14}$, —OR$^{15}$ or halo;
              wherein:
                $R^{13}$, $R^{14}$ or $R^{15}$ each independently is —H or —$C_1$-$C_6$ alkyl; or
a pharmaceutically acceptable salt thereof.

It is to be understood that reference to compounds of Formulas (I), (II), (III), or (IV), respectively, above and following herein, refers to compounds within the scope of the aforementioned compound formulas as defined above or following with respect to X—Y, R, R$^a$, R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$ or R$^{15}$, as defined herein, i.e., unless specifically limited otherwise.

In one aspect, X—Y is —C(H)$_2$—N(R$^a$)—, wherein R$^a$ is —H or —$C_1$-$C_3$ alkyl; or —C(H)=N—. In another aspect, X—Y is —C(H)$_2$—N(R$^a$)— and R$^a$ is —H. In another aspect, X—Y is —C(H)$_2$—N(R$^a$)— and R$^a$ is —$C_1$-$C_3$ alkyl. In another aspect, X—Y is —C(H)$_2$—N(R$^a$)— and R$^a$ is —CH$_3$. In another aspect, X—Y is —C(H)=N—.

In one aspect, R is —C(O)N(H)OH or —N(OH)C(O)H. In another aspect, R is —C(O)N(H)OH. In another aspect, R is —N(OH)C(O)H.

In one aspect, $R^1$ is —H or —$C_1$-$C_6$ alkyl. In another aspect, $R^1$ is —H. In another aspect, $R^1$ is —$C_1$-$C_6$ alkyl.

In one aspect, $R^2$ is aryl, —$(CH_2)_n$aryl, heteroaryl or —$(CH_2)_n$heteroaryl;

In one aspect, $R^2$ is aryl or —$(CH_2)_n$aryl, each of which optionally is substituted with one, two, or three $R^8$ groups or heteroaryl or —$(CH_2)_n$heteroaryl, each of which optionally is substituted with one, two, or three $R^8$ groups.

In one aspect, $R^2$ is aryl or —$(CH_2)_n$aryl, each of which is optionally substituted with one, two, or three $R^8$ groups.

In one aspect, $R^2$ is aryl or —$(CH_2)_n$aryl, each of which optionally is substituted with one $R^8$ groups. In another aspect, $R^2$ is aryl or —$(CH_2)_n$aryl, each of which optionally is substituted with two $R^8$ groups. In a further aspect, $R^2$ is aryl or —$(CH_2)_n$aryl, each of which optionally is substituted with three $R^8$ groups.

In one aspect, $R^2$ is heteroaryl or —$(CH_2)_n$heteroaryl, each of which optionally is substituted with one, two, or three $R^8$ groups.

In one aspect $R^2$ is heteroaryl or —$(CH_2)_n$heteroaryl, each of which optionally is substituted with one $R^8$ groups. In another aspect, $R^2$ is heteroaryl or —$(CH_2)_n$heteroaryl, each of which optionally is substituted with two $R^8$ groups. In a further aspect, $R^2$ is heteroaryl or —$(CH_2)_n$heteroaryl, each of which optionally substituted with three $R^8$ groups. $R^8$.

In one aspect, $R^2$ defined as heteroaryl or —$(CH_2)_n$heteroaryl, respectively, is selected from pyridinyl, oxidopyridinyl, —$(CH_2)_n$oxidopyridinyl, pyrimidinyl, —$(CH_2)_n$pyrimidinyl, oxidopyrimidinyl, —$(CH_2)_n$oxidopyrimidinyl, quinolinyl, —$(CH_2)_n$quinolinyl, napthyridinyl, —$(CH_2)_n$napthyridinyl, purinyl, —$(CH_2)_n$purinyl, isoquinolinyl, —$(CH_2)_n$ isoquinolinyl, thiazolyl, —$(CH_2)_n$thiazolyl, isoxazolyl, —$(CH_2)_n$isoxazolyl pyridazinyl, —$(CH_2)_n$pyridazinyl, oxadiazolyl, —$(CH_2)_n$oxadiazolyl, pyrazinyl, —$(CH_2)_n$pyrazinyl, imidazolyl, —$(CH_2)_n$imidazolyl, benzimidazolyl, or —$(CH_2)_n$benzimidazolyl, each of which optionally is substituted with one, two, or three $R^8$ groups.

In another aspect, $R^2$ defined as heteroaryl or —$(CH_2)_n$heteroaryl, respectively, is selected from pyridinyl, —$(CH_2)_n$ pyridinyl, oxidopyridinyl, —$(CH_2)_n$ oxidopyridinyl, pyrimidinyl, —$(CH_2)_n$ pyrimidinyl, oxidopyrimidinyl, —$(CH_2)_n$ oxidopyrimidinyl, quinolinyl, —$(CH_2)_n$quinolinyl, isoquinolinyl, —$(CH_2)_n$isoquinolinyl, pyridazinyl, —$(CH_2)_n$pyridazinyl, pyrazinyl, or —$(CH_2)_n$pyrazinyl, all optionally substituted with one, two, or three $R^8$ groups.

In one aspect, $R^2$ defined as heteroaryl or —$(CH_2)_n$heteroaryl, respectively, is selected from pyridinyl, —$(CH_2)_n$ pyridinyl, pyrimidinyl, or —$(CH_2)_n$ pyrimidinyl, all optionally substituted with one, two, or three $R^8$ groups. In one aspect, $R^2$ is pyridinyl or —$(CH_2)_n$pyridinyl, optionally substituted with one, two, or three $R^8$ groups. In another aspect, $R^2$ is pyrimidinyl or —$(CH_2)_n$pyrimidinyl, optionally substituted with one, two, or three $R^8$ groups.

In one aspect, $R^2$ is aryl selected from phenyl, 1,2,3,4-tetrahydroquinolinyl, or 1,2,3-benzotriazolyl, all optionally substituted with one, two, or three $R^8$ groups. In another aspect, $R^2$ is phenyl, optionally substituted with one, two, or three $R^8$ groups.

In one aspect, $R^3$ is —H or —$C_1$-$C_6$ alkyl. In another embodiment, $R^3$ is —H. In another aspect, $R^3$ is —$C_1$-$C_6$ alkyl.

In one aspect, $R^4$ is —H, halo, —OH, $C_1$-$C_3$ alkoxy, —$NR^6R^7$ or $C_1$-$C_6$ alkyl. In another aspect, $R^4$ is —H.

In one aspect, $R^5$ is —H, halo, —OH, $C_1$-$C_3$ alkoxy, —$NR^6R^7$ or $C_1$-$C_6$ alkyl. In another aspect, $R^5$ is —H.

In one aspect, $R^6$ is —H or —$C_1$-$C_6$ alkyl. In another embodiment, $R^6$ is —H. In another aspect, $R^6$ is —$C_1$-$C_6$ alkyl.

In one aspect, $R^7$ is —H or —$C_1$-$C_6$ alkyl. In another embodiment, $R^7$ is —H. In another aspect, $R^7$ is —$C_1$-$C_6$ alkyl.

In one aspect, each $R^8$ is independently halo, —$C_1$-$C_6$ alkyl, —$C(O)OR^{10}$, —$OR^7$, —$NR^6R^7$, —$O(CH_2)_2NR^6R^7$, —$(CH_2)NR^6R^7$, —$N(H)(CH_2)_3$—$NR^6R^7$, —$CF_3$, heterocyclyl optionally substituted with at least one $R^{11}$ group, aryl optionally substituted with at least one $R^{11}$ group, or heteroaryl optionally substituted with at least one $R^{11}$ group.

In one aspect, each $R^8$ is independently —Cl, —F, —$CH_3$, —$CH_2CH_3$, —$C(O)OCH_2CH_3$, —$C(O)OCH_3$, —$C(O)OH$, —$OCH_3$, —OH, —$N(CH_3)CH_3$, —$OCH_2CH_2N(CH_3)CH_3$, —$CH_2N(CH_3)CH_3$, —$CH_2N(CH_3)CH_3$, —$N(H)CH_2CH_2N(CH_3)CH_3$, —$CF_3$, imidazolyl optionally substituted with at least one $R^{11}$ group, pyridinyl optionally substituted with at least one $R^{11}$ group, phenyl optionally substituted with at least one $R^{11}$ group, morpholinyl optionally substituted with at least one $R^{11}$ group, piperazinyl optionally substituted with at least one $R^{11}$ group, pyrrolidinyl optionally substituted with at least one $R^{11}$ group.

In one aspect, $R^9$ is —$C_3$-$C_6$ cycloalkyl or —$C_1$-$C_6$ alkyl. In one aspect, $R^9$ is —$C_3$-$C_6$ cycloalkyl. In one aspect, $R^9$ is cyclopropyl, cyclobutyl, cyclopentyl, cyclohexyl. In one embodiment, $R^9$ is cyclopentyl.

In one aspect, $R^9$ is —$C_1$-$C_6$ alkyl. In one aspect, $R^9$ is methyl, ethyl, n-propyl, or isopropyl, n-butyl, or n-pentyl. In one aspect, $R^9$ is n-butyl.

In one aspect, $R^{10}$ is —H or —$C_1$-$C_6$ alkyl. In another aspect, $R^{10}$ is —H. In another aspect, $R^{10}$ is —$C_1$-$C_6$ alkyl. In another aspect, $R^{10}$ is methyl or ethyl.

In one aspect, $R^{11}$ is —$OR^7$, —$C_1$-$C_6$ alkyl, —$NR^6R^7$, or halo. In another aspect, $R^{11}$ is —$OR^7$, wherein $R^7$ is —H or —$C_1$-$C_6$ alkyl. In another aspect, $R^{11}$ is —$OR^7$, wherein $R^7$ is -methyl. In another aspect, $R^{11}$ is —$C_1$-$C_6$ alkyl. In another aspect, $R^{11}$ is methyl. In one aspect, $R^{11}$ is —$NR^6R^7$. In one aspect, $R^{11}$ is —$N(CH_3)CH_3$. In one aspect, $R^{11}$ is halo. In one aspect, $R^{11}$ is —F.

In one aspect, $R^{12}$ is —$C_1$-$C_6$ alkyl, —$NR^{13}R^{14}$, —$OR^{15}$ or halo; where $R^{13}$, $R^{14}$ or $R^{15}$ each independently is —H or —$C_1$-$C_6$ alkyl.

Also, it is understood in another aspect that the figure "—" between X and Y is either a single or a double bond.

Representative compound of the present invention, include, but are not limited to:

(3S)-2-((2R)-3-Cyclopentyl-2-{[formyl(hydroxy)amino]methyl}propanoyl)-N-(3-methyl-2-pyridinyl)-3-pyrazolidinecarboxamide;

(3S)-2-((2R)-3-Cyclopentyl-2-{[formyl(hydroxy)amino]methyl}propanoyl)-N-(3,4-dimethyl-2-pyridinyl)-3-pyrazolidinecarboxamide;

(3S)-2-((2R)-3-Cyclopentyl-2-{[formyl(hydroxy)amino]methyl}propanoyl)-N-(6-ethyl-3-methyl-2-pyridinyl)-3-pyrazolidinecarboxamide;

(3S)-2-((2R)-3-Cyclopentyl-2-{[formyl(hydroxy)amino]methyl}propanoyl)-N-4-isoquinolinyl-3-pyrazolidinecarboxamide;

(3S)-2-((2R)-3-Cyclopentyl-2-{[formyl(hydroxy)amino]methyl}propanoyl)-N-(6-ethyl-2-pyridinyl)-3-pyrazolidinecarboxamide;

(3S)-2-((2R)-3-Cyclopentyl-2-{[formyl(hydroxy)amino]methyl}propanoyl)-N-(4-ethyl-2-pyridinyl)-3-pyrazolidinecarboxamide;

(3S)-2-((2R)-3-Cyclopentyl-2-{[formyl(hydroxy)amino]methyl}propanoyl)-N-1,3-thiazol-2-yl-3-pyrazolidinecarboxamide;

(3S)—N-(5-Chloro-2-pyridinyl)-2-((2R)-3-cyclopentyl-2-{[formyl(hydroxy)amino]methyl}propanoyl)-3-pyrazolidinecarboxamide;

(3S)-2-((2R)-3-Cyclopentyl-2-{[formyl(hydroxy)amino]methyl}propanoyl)-N-3-isoxazolyl-3-pyrazolidinecarboxamide;

(3S)-2-((2R)-3-Cyclopentyl-2-{[formyl(hydroxy)amino]methyl}propanoyl)-N-(5-phenyl-2-pyridinyl)-3-pyrazolidinecarboxamide;

(3S)-2-((2R)-3-Cyclopentyl-2-{[formyl(hydroxy)amino]methyl}propanoyl)-N-[3-(methyloxy)phenyl]-3-pyrazolidinecarboxamide;

(3S)-2-((2R)-3-Cyclopentyl-2-{[formyl(hydroxy)amino]methyl}propanoyl)-N-(4-fluorophenyl)-3-pyrazolidinecarboxamide;

(3S)-2-((2R)-3-Cyclopentyl-2-{[formyl(hydroxy)amino]methyl}propanoyl)-N-(3-fluorophenyl)-3-pyrazolidinecarboxamide;

(3S)-2-((2R)-3-Cyclopentyl-2-{[formyl(hydroxy)amino]methyl}propanoyl)-N-(4,5-dimethyl-1,3-thiazol-2-yl)-3-pyrazolidinecarboxamide;

(3S)-2-((2R)-3-Cyclopentyl-2-{[formyl(hydroxy)amino]methyl}propanoyl)-N-phenyl-3-pyrazolidinecarboxamide;

(3S)-2-((2R)-3-Cyclopentyl-2-{[formyl(hydroxy)amino]methyl}propanoyl)-N-(5-fluoro-2-pyridinyl)-3-pyrazolidinecarboxamide;

(3S)-2-((2R)-3-Cyclopentyl-2-{[formyl(hydroxy)amino]methyl}propanoyl)-N-2-pyridinyl-3-pyrazolidinecarboxamide;

(3S)-2-((2R)-3-Cyclopentyl-2-{[formyl(hydroxy)amino]methyl}propanoyl)-N-3-pyridinyl-3-pyrazolidinecarboxamide;

(3S)-2-((2R)-3-Cyclopentyl-2-{[formyl(hydroxy)amino]methyl}propanoyl)-N-3-pyridazinyl-3-pyrazolidinecarboxamide;

(3S)-2-((2R)-3-Cyclopentyl-2-{[formyl(hydroxy)amino]methyl}propanoyl)-N-[4-(trifluoromethyl)phenyl]-3-pyrazolidinecarboxamide;

(3S)-2-((2R)-3-Cyclopentyl-2-{[formyl(hydroxy)amino]methyl}propanoyl)-N-(2-fluorophenyl)-3-pyrazolidinecarboxamide;

(3S)-2-((2R)-3-Cyclopentyl-2-{[formyl(hydroxy)amino]methyl}propanoyl)-N-(6-fluoro-2-pyridinyl)-3-pyrazolidinecarboxamide;

(3S)-2-((2R)-3-Cyclopentyl-2-{[formyl(hydroxy)amino]methyl}propanoyl)-N-[4-(trifluoromethyl)-2-pyridinyl]-3-pyrazolidinecarboxamide;

(3S)-2-((2R)-3-Cyclopentyl-2-{[formyl(hydroxy)amino]methyl}propanoyl)-N-(2-pyridinylmethyl)-3-pyrazolidinecarboxamide;

(3S)-2-((2R)-3-Cyclopentyl-2-{[formyl(hydroxy)amino]methyl}propanoyl)-N-(6-methyl-2-pyridinyl)-3-pyrazolidinecarboxamide;

(3S)-2-((2R)-3-Cyclopentyl-2-{[formyl(hydroxy)amino]methyl}propanoyl)-N-[6-(trifluoromethyl)-2-pyridinyl]-3-pyrazolidinecarboxamide;

(3S)-2-((2R)-3-Cyclopentyl-2-{[formyl(hydroxy)amino]
methyl}propanoyl)-N-(4,6-dimethyl-2-pyridinyl)-3-pyra-
zolidinecarboxamide;
Ethyl 5-({[(3S)-2-((2R)-3-cyclopentyl-2-{[formyl(hydroxy)
amino]methyl}propanoyl)-3-pyrazolidinyl]
carbonyl}amino)-1,3,4-oxadiazole-2-carboxylate;
(3S)—N-(6-Chloro-2-pyridinyl)-2-((2R)-3-cyclopentyl-2-
{[formyl(hydroxy)amino]methyl}propanoyl)-3-pyrazo-
lidinecarboxamide;
(3S)-2-((2R)-3-Cyclopentyl-2-{[formyl(hydroxy)amino]
methyl}propanoyl)-N-[6-(4-morpholinyl)-3-pyridinyl]-3-
pyrazolidinecarboxamide;
(3S)-2-((2R)-3-Cyclopentyl-2-{[formyl(hydroxy)amino]
methyl}propanoyl)-N-5-isoquinolinyl-3-pyrazolidinecar-
boxamide;
(3S)-2-((2R)-3-Cyclopentyl-2-{[formyl(hydroxy)amino]
methyl}propanoyl)-N-1-isoquinolinyl-3-pyrazolidinecar-
boxamide;
(3S)-2-((2R)-3-Cyclopentyl-2-{[formyl(hydroxy)amino]
methyl}propanoyl)-N-2-quinolinyl-3-pyrazolidinecar-
boxamide;
(3S)-2-((2R)-3-Cyclopentyl-2-{[formyl(hydroxy)amino]
methyl}propanoyl)-N-3-quinolinyl-3-pyrazolidinecar-
boxamide;
(3S)-2-((2R)-3-Cyclopentyl-2-{[formyl(hydroxy)amino]
methyl}propanoyl)-N-{5-[4-(methyloxy)phenyl]-2-py-
ridinyl}-3-pyrazolidinecarboxamide;
(3S)-2-((2R)-3-Cyclopentyl-2-{[formyl(hydroxy)amino]
methyl}propanoyl)-N-{5-[3-(methyloxy)phenyl]-2-py-
ridinyl}-3-pyrazolidinecarboxamide;
(3S)-2-((2R)-3-Cyclopentyl-2-{[formyl(hydroxy)amino]
methyl}propanoyl)-N-5-quinolinyl-3-pyrazolidinecar-
boxamide;
(3S)-2-((2R)-3-Cyclopentyl-2-{[formyl(hydroxy)amino]
methyl}propanoyl)-N-[6-(4-morpholinyl)-2-pyridinyl]-3-
pyrazolidinecarboxamide;
(3S)-2-((2R)-3-Cyclopentyl-2-{[formyl(hydroxy)amino]
methyl}propanoyl)-N-(1,2,3,4-tetrahydro-5-quinolinyl)-
3-pyrazolidinecarboxamide;
(3S)-2-((2R)-3-Cyclopentyl-2-{[formyl(hydroxy)amino]
methyl}propanoyl)-N-8-quinolinyl-3-pyrazolidinecar-
boxamide;
(3S)-2-((2R)-3-Cyclopentyl-2-{[formyl(hydroxy)amino]
methyl}propanoyl)-N-[5-(4-fluorophenyl)-2-pyridinyl]-
3-pyrazolidinecarboxamide;
(3S)-2-((2R)-3-Cyclopentyl-2-{[formyl(hydroxy)amino]
methyl}propanoyl)-N-[6-(methyloxy)-1,5-naphthyridin-
3-yl]-3-pyrazolidinecarboxamide;
(3S)-2-((2R)-3-Cyclopentyl-2-{[formyl(hydroxy)amino]
methyl}propanoyl)-N-(5-fluoro-1-oxido-2-pyridinyl)-3-
pyrazolidinecarboxamide;
(3S)-2-((2R)-3-Cyclopentyl-2-{[formyl(hydroxy)amino]
methyl}propanoyl)-N-(5-methyl-2-pyridinyl)-3-pyrazo-
lidinecarboxamide;
(3S)-2-((2R)-3-Cyclopentyl-2-{[formyl(hydroxy)amino]
methyl}propanoyl)-N-(1-oxido-2-pyridinyl)-3-pyrazo-
lidinecarboxamide;
Methyl 6-({[(3S)-2-((2R)-3-cyclopentyl-2-{[formyl(hy-
droxy)amino]methyl}propanoyl)-3-pyrazolidinyl]
carbonyl}amino)-2-pyridinecarboxylate;
(3S)-2-((2R)-3-Cyclopentyl-2-{[formyl(hydroxy)amino]
methyl}propanoyl)-N-(5-methyl-3-isoxazolyl)-3-pyrazo-
lidinecarboxamide;
(3S)-2-((2R)-3-Cyclopentyl-2-{[formyl(hydroxy)amino]
methyl}propanoyl)-N-(2-fluoro-3-pyridinyl)-3-pyrazo-
lidinecarboxamide;
(3S)-2-((2R)-3-Cyclopentyl-2-{[formyl(hydroxy)amino]
methyl}propanoyl)-N-(1-oxido-4-pyrimidinyl)-3-pyrazo-
lidinecarboxamide;
(3S)—N-1H-1,2,3-Benzotriazol-5-yl-2-((2R)-3-cyclopen-
tyl-2-{[formyl(hydroxy)amino]methyl}propanoyl)-3-
pyrazolidinecarboxamide;
(3S)-2-((2R)-3-Cyclopentyl-2-{[formyl(hydroxy)amino]
methyl}propanoyl)-1-methyl-N-4-pyrimidinyl-3-pyrazo-
lidinecarboxamide;
(3S)-2-((2R)-3-Cyclopentyl-2-{[formyl(hydroxy)amino]
methyl}propanoyl)-N-(5-fluoro-2-pyridinyl)-1-methyl-3-
pyrazolidinecarboxamide;
(3S)-2-((2R)-3-Cyclopentyl-2-{[formyl(hydroxy)amino]
methyl}propanoyl)-1-methyl-N-2-pyrazinyl-3-pyrazo-
lidinecarboxamide;
(3S)-2-((2R)-3-Cyclopentyl-2-{[formyl(hydroxy)amino]
methyl}propanoyl)-1-methyl-N-[2-(methyloxy)-4-pyrim-
idinyl]-3-pyrazolidinecarboxamide;
(3S)-2-((2R)-3-Cyclopentyl-2-{[formyl(hydroxy)amino]
methyl}propanoyl)-1-methyl-N-[6-(methyloxy)-2-
pyrazinyl]-3-pyrazolidinecarboxamide;
(3S)-2-((2R)-3-Cyclopentyl-2-{[formyl(hydroxy)amino]
methyl}propanoyl)-N-(6-fluoro-2-pyridinyl)-1-methyl-3-
pyrazolidinecarboxamide;
(3S)-2-((2R)-3-Cyclopentyl-2-{[formyl(hydroxy)amino]
methyl}propanoyl)-N-(3-fluoro-4-pyridinyl)-1-methyl-3-
pyrazolidinecarboxamide;
(3S)-2-((2R)-3-Cyclopentyl-2-{[formyl(hydroxy)amino]
methyl}propanoyl)-1-methyl-N-[3-(methyloxy)-2-
pyrazinyl]-3-pyrazolidinecarboxamide;
(3S)-2-((2R)-3-Cyclopentyl-2-{[formyl(hydroxy)amino]
methyl}propanoyl)-N-4-pyrimidinyl-3-pyrazolidinecar-
boxamide;
(3S)-2-((2R)-3-Cyclopentyl-2-{[formyl(hydroxy)amino]
methyl}propanoyl)-N-2-pyrazinyl-3-pyrazolidinecar-
boxamide;
(3S)-2-((2R)-3-Cyclopentyl-2-{[formyl(hydroxy)amino]
methyl}propanoyl)-N-4-pyridinyl-3-pyrazolidinecar-
boxamide;
(3S)-2-((2R)-3-Cyclopentyl-2-{[formyl(hydroxy)amino]
methyl}propanoyl)-N-[6-(1H-imidazol-1-yl)-2-pyridi-
nyl]-3-pyrazolidinecarboxamide;
(3S)-2-((2R)-3-Cyclopentyl-2-{[formyl(hydroxy)amino]
methyl}propanoyl)-N-[5-(1H-imidazol-1-yl)-2-pyridi-
nyl]-3-pyrazolidinecarboxamide;
(3S)-2-((2R)-3-Cyclopentyl-2-{[formyl(hydroxy)amino]
methyl}propanoyl)-N-(3-fluoro-4-pyridinyl)-3-pyrazo-
lidinecarboxamide;
(3S)-2-((2R)-3-Cyclopentyl-2-{[formyl(hydroxy)amino]
methyl}propanoyl)-N-(2-quinolinylmethyl)-3-pyrazolidi-
necarboxamide;
(3S)-2-((2R)-3-Cyclopentyl-2-{[formyl(hydroxy)amino]
methyl}propanoyl)-N-5-pyrimidinyl-3-pyrazolidinecar-
boxamide;
(3S)-2-((2R)-3-Cyclopentyl-2-{[formyl(hydroxy)amino]
methyl}propanoyl)-N-[6-(methyloxy)-4-pyrimidinyl]-3-
pyrazolidinecarboxamide;
(3S)-2-((2R)-3-Cyclopentyl-2-{[formyl(hydroxy)amino]
methyl}propanoyl)-N-(4-methyl-2-pyridinyl)-3-pyrazo-
lidinecarboxamide;
(3S)-2-((2R)-3-Cyclopentyl-2-{[formyl(hydroxy)amino]
methyl}propanoyl)-N-(7-methyl-7H-purin-6-yl)-3-pyra-
zolidinecarboxamide;
(3S)-2-((2R)-3-Cyclopentyl-2-{[formyl(hydroxy)amino]
methyl}propanoyl)-N-[2-(methyloxy)-4-pyrimidinyl]-3-
pyrazolidinecarboxamide;

(3S)-2-((2R)-3-Cyclopentyl-2-{[formyl(hydroxy)amino]methyl}propanoyl)-N-(5-fluoro-4-pyrimidinyl)-3-pyrazolidinecarboxamide;

(3S)-2-((2R)-3-Cyclopentyl-2-{[formyl(hydroxy)amino]methyl}propanoyl)-N-(3-quinolinylmethyl)-3-pyrazolidinecarboxamide;

(3S)-2-((2R)-3-Cyclopentyl-2-{[formyl(hydroxy)amino]methyl}propanoyl)-N-(5-methyl-2-pyrazinyl)-3-pyrazolidinecarboxamide;

(3S)-2-((2R)-3-Cyclopentyl-2-{[formyl(hydroxy)amino]methyl}propanoyl)-N-[6-(methyloxy)-2-pyrazinyl]-3-pyrazolidinecarboxamide;

(3S)-2-((2R)-3-Cyclopentyl-2-{[formyl(hydroxy)amino]methyl}propanoyl)-N-[3-(methyloxy)-2-pyrazinyl]-3-pyrazolidinecarboxamide;

(3S)-2-((2R)-3-Cyclopentyl-2-{[formyl(hydroxy)amino]methyl}propanoyl)-N-(2-fluoro-4-pyrimidinyl)-3-pyrazolidinecarboxamide;

(3S)-2-((2R)-3-Cyclopentyl-2-{[formyl(hydroxy)amino]methyl}propanoyl)-N-[2-(4-methyl-1-piperazinyl)-4-pyrimidinyl]-3-pyrazolidinecarboxamide;

(3S)-2-((2R)-3-Cyclopentyl-2-{[formyl(hydroxy)amino]methyl}propanoyl)-N-[2-(dimethylamino)-4-pyrimidinyl]-3-pyrazolidinecarboxamide;

(3S)-2-((2R)-3-Cyclopentyl-2-{[formyl(hydroxy)amino]methyl}propanoyl)-N-(4-pyrimidinylmethyl)-3-pyrazolidinecarboxamide;

(3S)-2-((2R)-3-Cyclopentyl-2-{[formyl(hydroxy)amino]methyl}propanoyl)-N-{2-[(2R)-2,4-dimethyl-1-piperazinyl]-4-pyrimidinyl}-3-pyrazolidinecarboxamide;

(3S)-2-((2R)-3-Cyclopentyl-2-{[formyl(hydroxy)amino]methyl}propanoyl)-N-(2-{[2-(dimethylamino)ethyl]oxy}-4-pyrimidinyl)-3-pyrazolidinecarboxamide;

(3S)-2-((2R)-3-Cyclopentyl-2-{[formyl(hydroxy)amino]methyl}propanoyl)-N-(2-{[3-(dimethylamino)propyl]amino}-4-pyrimidinyl)-3-pyrazolidinecarboxamide;

(3S)-2-((2R)-3-Cyclopentyl-2-{[formyl(hydroxy)amino]methyl}propanoyl)-N-{2-[(3S)-3-(dimethylamino)-1-pyrrolidinyl]-4-pyrimidinyl}-3-pyrazolidine carboxamide;

(3S)-2-((2R)-3-Cyclopentyl-2-{[formyl(hydroxy)amino]methyl}propanoyl)-N-2-pyrimidinyl-3-pyrazolidinecarboxamide;

(3S)-2-((2R)-3-Cyclopentyl-2-{[formyl(hydroxy)amino]methyl}propanoyl)-N-{6-[(2R)-2,4-dimethyl-1-piperazinyl]-4-pyrimidinyl}-3-pyrazolidinecarboxamide;

(3S)-2-((2R)-3-Cyclopentyl-2-{[formyl(hydroxy)amino]methyl}propanoyl)-N-[2-(4-methyl-4,7-diazaspiro[2.5]oct-7-yl)-4-pyrimidinyl]-3-pyrazolidinecarboxamide;

(3S)-2-((2R)-3-Cyclopentyl-2-{[formyl(hydroxy)amino]methyl}propanoyl)-N-{2-[(2S)-2,4-dimethyl-1-piperazinyl]-4-pyrimidinyl}-3-pyrazolidinecarboxamide;

(3S)-2-((2R)-3-Cyclopentyl-2-{[formyl(hydroxy)amino]methyl}propanoyl)-N-[5-(methyloxy)-2-pyrimidinyl]-3-pyrazolidinecarboxamide;

(3S)-2-((2R)-3-Cyclopentyl-2-{[formyl(hydroxy)amino]methyl}propanoyl)-N-[4-(methyloxy)-2-pyrimidinyl]-3-pyrazolidinecarboxamide;

(3S)-2-((2R)-3-Cyclopentyl-2-{[formyl(hydroxy)amino]methyl}propanoyl)-N-(5-fluoro-2-pyrimidinyl)-3-pyrazolidinecarboxamide;

(3S)-2-((2R)-3-Cyclopentyl-2-{[formyl(hydroxy)amino]methyl}propanoyl)-N-{2-[(dimethylamino)methyl]-4-pyrimidinyl}-3-pyrazolidinecarboxamide;

(5S)-1-((2R)-3-Cyclopentyl-2-{[formyl(hydroxy)amino]methyl}propanoyl)-N-4-pyrimidinyl-4,5-dihydro-1H-pyrazole-5-carboxamide;

(5S)-1-((2R)-3-Cyclopentyl-2-{[formyl(hydroxy)amino]methyl}propanoyl)-N-(5-fluoro-2-pyridinyl)-4,5-dihydro-1H-pyrazole-5-carboxamide;

(5S)-1-((2R)-3-Cyclopentyl-2-{[formyl(hydroxy)amino]methyl}propanoyl)-N-(5-fluoro-4-pyrimidinyl)-4,5-dihydro-1H-pyrazole-5-carboxamide;

(5S)-1-((2R)-3-Cyclopentyl-2-{[formyl(hydroxy)amino]methyl}propanoyl)-N-2-pyrazinyl-4,5-dihydro-1H-pyrazole-5-carboxamide;

(5S)-1-((2R)-3-Cyclopentyl-2-{[formyl(hydroxy)amino]methyl}propanoyl)-N-(2-fluoro-4-pyrimidinyl)-4,5-dihydro-1H-pyrazole-5-carboxamide;

(5S)-1-((2R)-3-Cyclopentyl-2-{[formyl(hydroxy)amino]methyl}propanoyl)-N-(5-methyl-2-pyrazinyl)-4,5-dihydro-1H-pyrazole-5-carboxamide;

(5S)-1-((2R)-3-Cyclopentyl-2-{[formyl(hydroxy)amino]methyl}propanoyl)-N-(6-fluoro-2-pyridinyl)-4,5-dihydro-1H-pyrazole-5-carboxamide;

(5S)-1-((2R)-3-Cyclopentyl-2-{[formyl(hydroxy)amino]methyl}propanoyl)-N-[2-(methyloxy)-4-pyrimidinyl]-4,5-dihydro-1H-pyrazole-5-carboxamide;

(3S)—N-(5-Fluoro-2-pyridinyl)-2-((2R)-2-{[formyl(hydroxy)amino]methyl}heptanoyl)-3-pyrazolidinecarboxamide;

(3S)-2-((2R)-2-{[Formyl(hydroxy)amino]methyl}heptanoyl)-N-4-pyrimidinyl-3-pyrazolidinecarboxamide;

(3S)-2-((2R)-2-{[Formyl(hydroxy)amino]methyl}heptanoyl)-N-2-pyridinyl-3-pyrazolidinecarboxamide;

(3S)-2-((2R)-2-{[Formyl(hydroxy)amino]methyl}heptanoyl)-N-(1-oxido-2-pyridinyl)-3-pyrazolidinecarboxamide;

(3S)—N-(5-Fluoro-1-oxido-2-pyridinyl)-2-((2R)-2-{[formyl(hydroxy)amino]methyl}heptanoyl)-3-pyrazolidinecarboxamide;

(5S)-1-((2R)-3-Cyclopentyl-2-{[formyl(hydroxy)amino]methyl}propanoyl)-N-(1-oxido-2-pyridinyl)-4,5-dihydro-1H-pyrazole-5-carboxamide;

(3S)-2-((2R)-3-Cyclopentyl-2-{[formyl(hydroxy)amino]methyl}propanoyl)-N-1H-imidazol-2-yl-3-pyrazolidinecarboxamide;

(3S)—N-1H-Benzimidazol-2-yl-2-((2R)-3-cyclopentyl-2-{[formyl(hydroxy)amino]methyl}propanoyl)-3-pyrazolidinecarboxamide;

(5S)—N-(5-Fluoro-2-pyridinyl)-1-((2R)-2-{[formyl(hydroxy)amino]methyl}heptanoyl)-4,5-dihydro-1H-pyrazole-5-carboxamide;

(5S)-1-((2R)-2-{[Formyl(hydroxy)amino]methyl}heptanoyl)-N-2-pyridinyl-4,5-dihydro-1H-pyrazole-5-carboxamide;

(5S)-1-((2R)-2-{[Formyl(hydroxy)amino]methyl}heptanoyl)-N-4-pyrimidinyl-4,5-dihydro-1H-pyrazole-5-carboxamide;

(3S)-2-((2R)-2-{[Formyl(hydroxy)amino]methyl}heptanoyl)-N-3-pyridazinyl-3-pyrazolidinecarboxamide;

(3S)-2-((2R)-3-Cyclopentyl-2-{[formyl(hydroxy)amino]methyl}propanoyl)-N-[2-(4-morpholinyl)-5-pyrimidinyl]-3-pyrazolidinecarboxamide;

(3S)-2-((2R)-2-{[Formyl(hydroxy)amino]methyl}hexanoyl)-N-(1-oxido-2-pyridinyl)-3-pyrazolidinecarboxamide;

(3S)—N-(5-Fluoro-1-oxido-2-pyridinyl)-2-((2R)-2-{[formyl(hydroxy)amino]methyl}hexanoyl)-3-pyrazolidinecarboxamide;

(3S)-2-((2R)-2-{[Formyl(hydroxy)amino]
methyl}hexanoyl)-N-4-pyrimidinyl-3-pyrazolidinecarboxamide;
4-({[(3S)-2-((2R)-3-Cyclopentyl-2-{[formyl(hydroxy)
amino]methyl}propanoyl)-3-pyrazolidinyl]
carbonyl}amino)benzoic acid;
(3S)-2-((2R)-3-Cyclopentyl-2-{[formyl(hydroxy)amino]
methyl}propanoyl)-N-(5-hydroxy-2-pyridinyl)-3-pyrazolidinecarboxamide;
6-({[(3S)-2-((2R)-3-Cyclopentyl-2-{[formyl(hydroxy)
amino]methyl}propanoyl)-3-pyrazolidinyl]
carbonyl}amino)-3-pyridinecarboxylic acid;
2-({[(3S)-2-((2R)-3-Cyclopentyl-2-{[formyl(hydroxy)
amino]methyl}propanoyl)-3-pyrazolidinyl]
carbonyl}amino)-4-pyridinecarboxylic acid;
3-({[(3S)-2-((2R)-3-Cyclopentyl-2-{[formyl(hydroxy)
amino]methyl}propanoyl)-3-pyrazolidinyl]
carbonyl}amino)benzoic acid;
(3S)-2-((2R)-3-Cyclopentyl-2-{[formyl(hydroxy)amino]
methyl}propanoyl)-N-(4-hydroxy-2-pyridinyl)-3-pyrazolidinecarboxamide;
(3S)-2-((2R)-3-Cyclopentyl-2-{[formyl(hydroxy)amino]
methyl}propanoyl)-N-(3-hydroxyphenyl)-3-pyrazolidinecarboxamide;
(3S)-2-((2R)-3-Cyclopentyl-2-{[formyl(hydroxy)amino]
methyl}propanoyl)-N-(4-hydroxyphenyl)-3-pyrazolidinecarboxamide;
(3S)-2-((2R)-3-Cyclopentyl-2-{[formyl(hydroxy)amino]
methyl}propanoyl)-N-[2-(2-pyridinyl)-5-pyrimidinyl]-3-pyrazolidinecarboxamide;
(3S)—N-(5-Fluoro-2-pyridinyl)-2-((2R)-2-{[formyl(hydroxy)amino]methyl}hexanoyl)-3-pyrazolidinecarboxamide;
(3S)-2-((2R)-2-{[Formyl(hydroxy)amino]
methyl}hexanoyl)-N-3-pyridazinyl-3-pyrazolidinecarboxamide;
(3S)-2-((2R)-2-{[Formyl(hydroxy)amino]
methyl}hexanoyl)-N-2-pyridinyl-3-pyrazolidinecarboxamide;
(3S)-2-((2R)-3-Cyclopentyl-2-{[formyl(hydroxy)amino]
methyl}propanoyl)-N-[4-(2-pyridinyl)-2-pyrimidinyl]-3-pyrazolidinecarboxamide;
(5S)-1-[(2R)-2-(Cyclopentylmethyl)-4-(hydroxyamino)-4-oxobutanoyl]-N-2-pyrimidinyl-4,5-dihydro-1H-pyrazole-5-carboxamide;
(5S)-1-[(2R)-2-(Cyclopentylmethyl)-4-(hydroxyamino)-4-oxobutanoyl]-N-(6-ethyl-2-pyridinyl)-4,5-dihydro-1H-pyrazole-5-carboxamide;
(5S)-1-[(2R)-2-(cyclopentylmethyl)-4-(hydroxyamino)-4-oxobutanoyl]-N-(5-fluoro-1-oxido-2-pyridinyl)-4,5-dihydro-1H-pyrazole-5-carboxamide;
(5S)-1-[(2R)-2-(Cyclopentylmethyl)-4-(hydroxyamino)-4-oxobutanoyl]-N,N-dimethyl-4,5-dihydro-1H-pyrazole-5-carboxamide;
(3R)-3-(Cyclopentylmethyl)-N-hydroxy-4-[(5S)-5-(4-morpholinylcarbonyl)-4,5-dihydro-1H-pyrazol-1-yl]-4-oxobutanamide;
(5S)-1-[(2R)-2-(Cyclopentylmethyl)-4-(hydroxyamino)-4-oxobutanoyl]-N-phenyl-4,5-dihydro-1H-pyrazole-5-carboxamide;
(5S)-1-[(2R)-2-(Cyclopentylmethyl)-4-(hydroxyamino)-4-oxobutanoyl]-N-(6-ethyl-1-oxido-2-pyridinyl)-4,5-dihydro-1H-pyrazole-5-carboxamide;
(5S)-1-[(2R)-2-(Cyclopentylmethyl)-4-(hydroxyamino)-4-oxobutanoyl]-N-2-pyridinyl-4,5-dihydro-1H-pyrazole-5-carboxamide; or
a pharmaceutically acceptable salt thereof.

In one aspect, a compound of the present invention includes, but is not limited to:
(3S)-2-((2R)-3-Cyclopentyl-2-{[formyl(hydroxy)amino]
methyl}propanoyl)-N-4-pyrimidinyl-3-pyrazolidinecarboxamide:

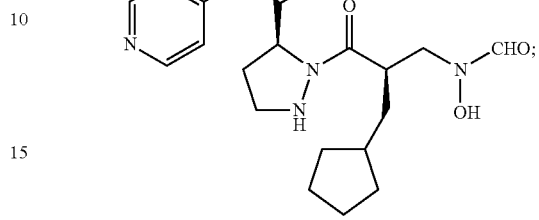

or
a pharmaceutically acceptable salt thereof.

In another aspect, the present invention relates to a compound which is (3S)-2-((2R)-3-Cyclopentyl-2-{[formyl(hydroxy)amino]methyl}propanoyl)-N-4-pyrimidinyl-3-pyrazolidinecarboxamide:

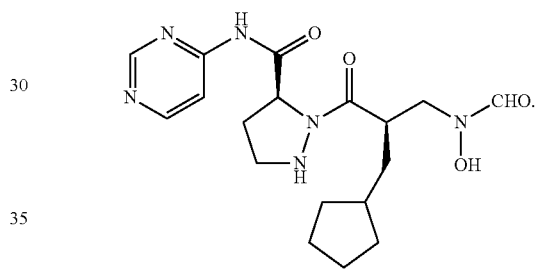

Substituent Definitions

As used herein the term "alkyl" refers to a straight- or branched-chain monovalent hydrocarbon radical having from one to twelve carbon atoms. Such alkyl groups may have a specified number of carbon atoms. For example, the term "$C_1$-$C_6$ alkyl" refers to an alkyl group, as defined above, containing at least 1, and at most 6 carbon atoms and the term "$C_1$-$C_3$ alkyl" refers to an alkyl group, as defined above, containing at least 1, and at most 3 carbon atoms. Examples of "alkyl" as used herein may include, but are not limited to, methyl, ethyl, n-propyl, isopropyl, n-butyl, isobutyl, t-butyl, n-pentyl, isopentyl, and the like.

As used herein, the term "alkylene" refers to a straight or branched chain divalent hydrocarbon radical having from one to ten carbon atoms. Such alkylene groups may have a specified number of carbon atoms. For example, the term "$C_1$-$C_3$ alkylene" refers to an alkylene group, as defined above, which contains at least 1, and at most 3, carbon atoms. Examples of "$C_1$-$C_3$ alkylene" groups useful in the present invention may include, but are not limited to, methylene, ethylene, n-propylene, isopropylene, and the like.

As used herein, the term "halogen" refers to fluorine (F), chlorine (Cl), bromine (Br), or iodine (I) and the term "halo" refers to the halogen radicals: fluoro (—F), chloro (—Cl), bromo (—Br), and iodo (—I).

As used herein, the term "cycloalkyl" refers to a non-aromatic cyclic hydrocarbon ring containing from 3 to 10 carbon atoms and which optionally includes a $C_1$-$C_3$ alkylene linker through which it may be attached. In a like manner the term "$C_3$-$C_6$cycloalkyl" refers to a non-aromatic cyclic hydrocarbon ring having from three to six carbon atoms which optionally includes a $C_1$-$C_3$ alkylene linker through which it may be attached. The $C_1$-$C_3$ alkylene group is as defined above. Exemplary "$C_3$-$C_6$ cycloalkyl" groups useful in the present invention may include, but are not limited to, cyclopropyl, cyclobutyl, cyclopentyl, and cyclohexyl and the like which may optionally be attached through a $C_1$-$C_3$alkylene linker such as methylene.

As used herein, the term "heterocyclyl" refers to a monovalent three to twelve-membered non-aromatic heterocyclic ring, being saturated or having one or more degrees of unsaturation, containing one or more heteroatom substitutions selected from S, S(O), S(O)$_2$, O, or N, Such a ring may be optionally fused to one or more other "heterocyclyl" ring(s) or cycloalkyl ring(s). Examples of "heterocyclyl" moieties may include, but are not limited to, pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,4-dioxanyl, 1,3-oxathiolanyl, 1,3-oxathianyl, 1,3-dithianyl, azetidinyl, isoxazolidine, azabicylo[3.2.1]octyl, azabicylo[3.3.1]nonyl, azabicylo[4.3.0]nonyl, 2,5-diazabicyclo[2.2.1]heptane, octahydropyrrolo[1,2-a]pyrazine, octahydropyrazino[2,1-c][1,4]oxazine, oxabicylo[2.2.1]heptyl and the like.

As used herein, the term "aryl" refers to a monovalent benzene ring or to a monovalent benzene ring system fused to one or more optionally substituted benzene rings or fused to one or more cycloalkyl ring(s) to form, for example, anthracenyl, phenanthrenyl, napthyl, indanyl ring systems. Examples of "aryl" groups may include, but are not limited to, indanyl, phenyl, 2-naphthyl, 1-naphthyl, biphenyl and the like.

As used herein, the term "heteroaryl" refers to a monovalent monocyclic five to seven membered aromatic ring, or to a fused bicyclic or tricyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions. Examples of "heteroaryl" groups used herein, may include, but is not limited to pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazolyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, napthyridinyl, pyrazolopyridyl, pyrazolopyrimidinyl, substituted versions thereof and the like.

As used herein, the term "aralkyl" refers to an aryl or heteroaryl group, as defined herein, attached through a $C_1$-$C_3$ alkylene linker, wherein the $C_1$-$C_3$ alkylene is as defined herein. Examples of "aralkyl" may include, but are not limited to, benzyl, phenylpropyl, 2-pyridylmethyl, 3-isoxazolylmethyl, 5-methyl-3-isoxazolylmethyl, quinolinylmethyl, 2-imidazolyl ethyl and the like.

As used herein, the term "alkoxy" refers to the group $R_aO—$, where $R_a$ is alkyl as defined above and the terms "$C_1$-$C_3$ alkoxy" and "$C_1$-$C_6$ alkoxy" refer to an alkoxy group as defined herein wherein the alkyl moiety contains at least 1, and at most 3 or 6, carbon atoms. Exemplary "$C_1$-$C_3$ alkoxy" and "$C_1$-$C_6$ alkoxy" groups useful in the present invention may include, but are not limited to, methoxy, ethoxy, n-propoxy, isopropoxy, n-butoxy, t-butoxy and the like.

As used herein, the term "substituted" refers to substitution with the named substituent or substituents, multiple degrees of substitution being allowed unless otherwise stated.

As used herein, the term "optionally substituted" means that a group, such as, which may include, but is not limited to alkyl, aryl, heteroaryl and the like, etc., each aforementioned term may be unsubstituted, or the group may be substituted with one or more substituent(s) as defined herein. In the case where groups may be selected from a number of alternative groups the selected groups may be the same or different.

The term "independently" means that where more than one substituent is selected from a number of possible substituents, where those substituents may be the same or different.

The alternative definitions for the various groups and substitutent groups of Formulas (I) to (IV), respectively, or pharmaceutically acceptable salts thereof, provided throughout the specification are intended to particularly describe each compound species disclosed herein, individually, as well as groups of one or more compound species. The scope of this invention includes any combination of these group and substituent group definitions.

It is recognized that the compounds of Formulas (I) to (IV), respectively, or pharmaceutically acceptable salts thereof of the present invention as defined above may exist in forms as stereoisomers, regioisomers, or diastereiomers. These compounds may contain one or more asymmetric carbon atoms and may exist in racemic and optically active forms. For example, compounds of the present invention may exist as a racemic mixture of R(+) and S(−) enantiomers, or in separate respectively optical forms, i.e., existing separately as either the R(+) enantiomer form or in the S(+) enantiomer form. Certain of the compounds of the present invention described herein may contain one or more chiral atoms, or may otherwise be capable of existing as individual enantiomers. The compounds of this invention include mixtures of enantiomers as well as purified enantiomers or enantiomerically enriched mixtures. All of these individual compounds, isomers, and mixtures thereof are included within the scope of the present invention.

Also included within the scope of the present invention are the individual isomers of the compounds represented by Formulas (I) to (IV), respectively, or pharmaceutically acceptable salts thereof, above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of Formulas (I) to (IV), or pharmaceutically acceptable salts thereof, respectively, are included within the scope of said compounds.

As used herein, the term "enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

As used herein, the term "enantiomerically enriched" refers to products whose enantiomeric excess is greater than zero. For example, enantiomerically enriched refers to products whose enantiomeric excess is greater than 50% ee, greater than 75% ee, or greater than 90% ee.

As used herein, the term "Enantiomerically pure" refers to products whose enantiomeric excess is 99% ee or greater.

Salts

Because of their potential use in medicine, the salts of the compounds of Formulas (I) to (IV), respectively, are suitably pharmaceutically acceptable salts. Suitable pharmaceutically acceptable salts include those described by Berge, Bighley and Monkhouse J. Pharm. Sci (1977) 66, pp 1-19.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the present invention.

Compound Preparations

The compounds according to Formulas (I) to (IV), respectively, or pharmaceutically acceptable salts thereof, are prepared using conventional organic syntheses.

Suitable synthetic routes are depicted below in the following general reaction schemes. The skilled artisan will appreciate that if a substituent described herein is not compatible with the synthetic methods described herein, the substituent may be protected with a suitable protecting group that is stable to the reaction conditions. The protecting group may be removed at an necessary or suitable point in the reaction sequence to provide a desired intermediate or target compound.

Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

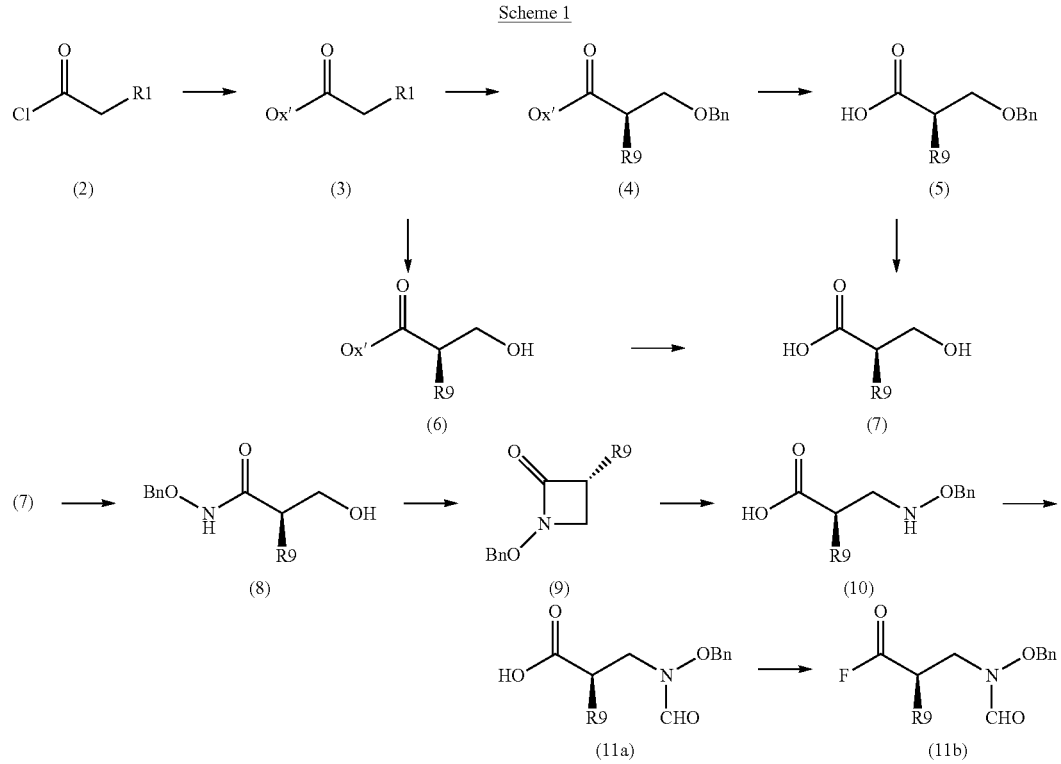

As shown in Scheme 1, (11) can be prepared by reacting an appropriate acid chloride (2) with a chiral agent, such as (S)-(−)-4-benzyl-2-oxazolidinone (Evans' chiral oxazolidinone), in the presence of a base, such as n-butyl lithium, to afford the chiral intermediate (3). Treatment of the compound (3) with a base, such as diisopropylethylamine, in the presence of a chelating agent, such as titanium tetrachloride, in a solvent, such as tetrahydrofuran, followed by addition of an electrophile, such as benzyloxymethylchloride, provides compound (4). Conversion of compound (4) to the corresponding hydroxyacid (7) can be achieved by a sequence comprising oxidative cleavage of the chiral oxazolidinone, using, for example $H_2O_2$ and lithium hydroxide, to the respective intermediate (5), followed by hydrogenolysis, to afford intermediate (7). Compound (3) can also be converted to intermediate (7) in an alternative two-step procedure. For this transformation, (3) can be treated with a base, such as diisopropylethylamine, in the presence of a chelating agent, such as titanium tetrachloride, in a solvent, such as tetrahydrofuran, followed by addition of trioxane or a suitable alternative formaldehyde equivalent to provide compound (6), which is then submitted to oxidative cleavage of the chiral oxazolidinone, using, for example $H_2O_2$ and lithium hydroxide, to the respective acid (7). Coupling of acid (7) with benzyloxyamine in the presence of coupling agents, such as EDC and DMAP, yields the amide (8). This can be cyclized to azetidin-2-one (9) using Mitsunobu conditions. Hydrolysis of the azetidin-2-one (9), using for example lithium hydroxide in an appropriate solvent, gives the corresponding acid (10). Conversion of compound (10) to product (11a) can be achieved using an appropriate formylating agent, such as formic acid/acetic anhydride or methyl formate, in neat reagents or in an appropriate solvent, such as dichloromethane. The chemistry describing specific examples of this type can also be found in WO 2009/061879. Treatment of compound (11a) with cyanuric fluoride in the presence of a base such as DIEA or pyridine in an appropriate solvent such as DCM can yield compound (11b).

Scheme 2

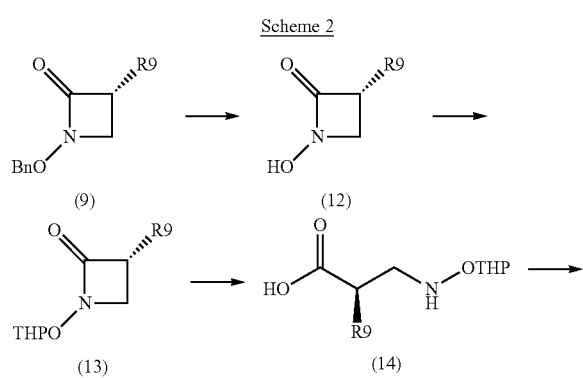

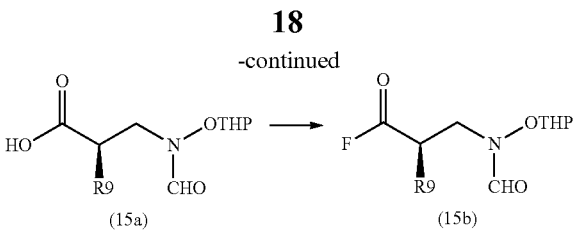

As shown in Scheme 2, THP-protected intermediate (15) can be prepared by hydrogenation of azetidin-2-one (9) using a catalyst, such as 10% Pd/C, in an appropriate solvent, such as ethanol to provide (12). Treatment of (12) with dihydropyran under acid catalysis, such as pyridinium p-toluenesulfonate, in an appropriate solvent, such as methylene chloride, provides THP-protected azetidin-2-one (13). Hydrolysis of azetidin-2-one (13), using for example lithium hydroxide in an appropriate solvent, gives the corresponding acid (14). Conversion of compound (14) to the product (15a) can be achieved using an appropriate formylating agent, such as formic acid/acetic anhydride or methyl formate, in neat reagents or in an appropriate solvent, such as dichloromethane. Conversion of compound (14) to product (15a) can also be accomplished using 5-methyl-2-thioxo-[1,3,4]thiadiazole-3-carbaldehyde (Yazawa, Hisatoyo; Goto, Shunsuke; Tetrahedron Lett. 26; 31; 1985; 3703-3706) as a formylating agent in an appropriate solvent, such as acetone. Intermediate (15a) can also be prepared according to literature procedures [Bracken, Bushell, Dean, Francavilla, Jain, Lee, Seepersaud, Shu, Sundram, Yuan; PCT Int. Appl. (2006), WO 2006127576 A2]. The chemistry describing specific examples of this type can also be found in WO 2009/061879. Treatment of compound (15a) with cyanuric fluoride (2,4,6-trifluoro-1,3,5-triazine) in the presence of a base such as DIEA or pyridine in an appropriate solvent such as DCM can yield compound (15b).

Scheme 3

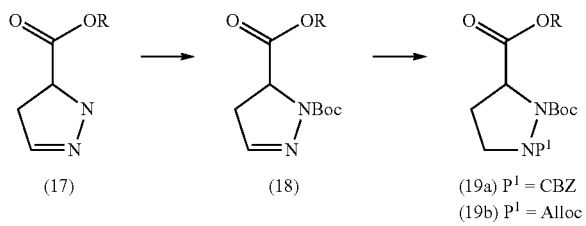

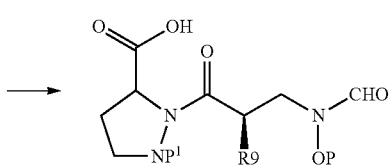

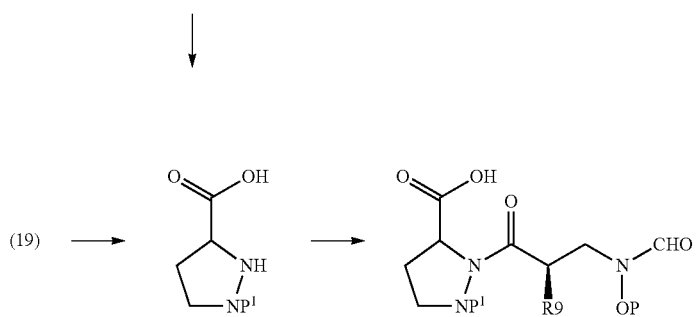

As shown in Scheme 3, treating (16) with TMS-diazomethane in an appropriate solvent such as toluene, THF, or hexane can provide (17). Intermediate (18) can be obtained by the treatment of (17) with Boc anhydride and a base such as TEA in an appropriate solvent such as DCM or THF. Intermediate (19a and/or 19b) can be obtained by the treatment of (18) with an appropriate reducing agent such as NaCNBH$_3$ in an acidic solvent such as AcOH, followed by nitrogen protection using a suitable protecting reagent such as benzyl chloroformate or allyl chloroformate in an appropriate base such as K$_2$CO$_3$, in an appropriate solvent such as MeCN, THF, or DCM. Intermediate (20a and/or 20b) can be obtained by the treatment of (19a and/or 19b) with TFA and water in an appropriate solvent such as DCM. Alternatively, (20a and/or 20b) can be obtained directly from (17) by treatment with NaCNBH$_3$ in an acidic solvent followed by nitrogen protection described above. Finally, intermediate (21a) can be obtained by treating (11b) with (20a) and an appropriate base such as DIPEA in an appropriate solvent such as DMF or DCM. Likewise, (21b) can be obtained by treating (15b) with (20b) and an appropriate base such as DIPEA in an appropriate solvent such as DMF or DCM. Similarly, (21c) can be obtained by treating (20a) with (15b) and an appropriate base such as DIPEA in an appropriate solvent such as DMF or DCM.

Scheme 4

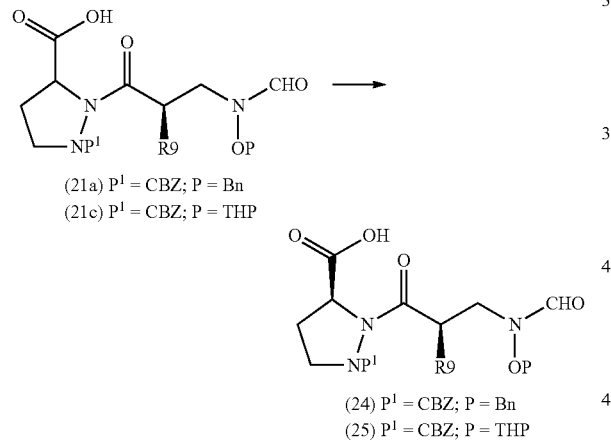

As outlined in Scheme 4, (24) and/or (25) can be obtained by separation of the appropriate diastereomers (21a) and/or (21c) by silica gel column chromatography using appropriate solvents such as ethyl acetate and hexanes and/or re-crystallization from an appropriate solvent such as MeCN or by reverse-phase HPLC using appropriate solvents such as MeCN and water.

Scheme 5

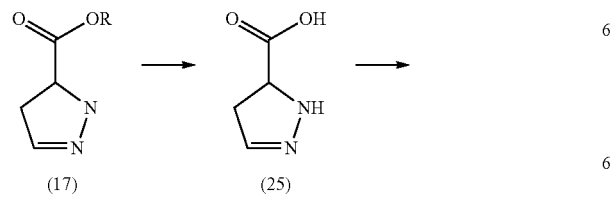

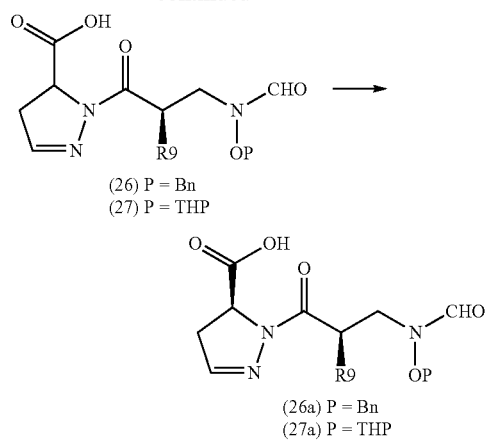

As shown in Scheme 5, intermediates (26) and/or (27) can be obtained by treating either (11b) or (15b) with (25) and an appropriate base such as DIPEA in an appropriate solvent such as DMF or DCM. Additionally, (26a) and/or (27a) can be obtained by separation of the appropriate diastereomers (26) and/or (27) by silica gel column chromatography using appropriate solvents such as ethyl acetate and hexanes and/or re-crystallization from an appropriate solvent such as MeCN or by reverse-phase HPLC using appropriate solvents such as MeCN and water.

Scheme 6

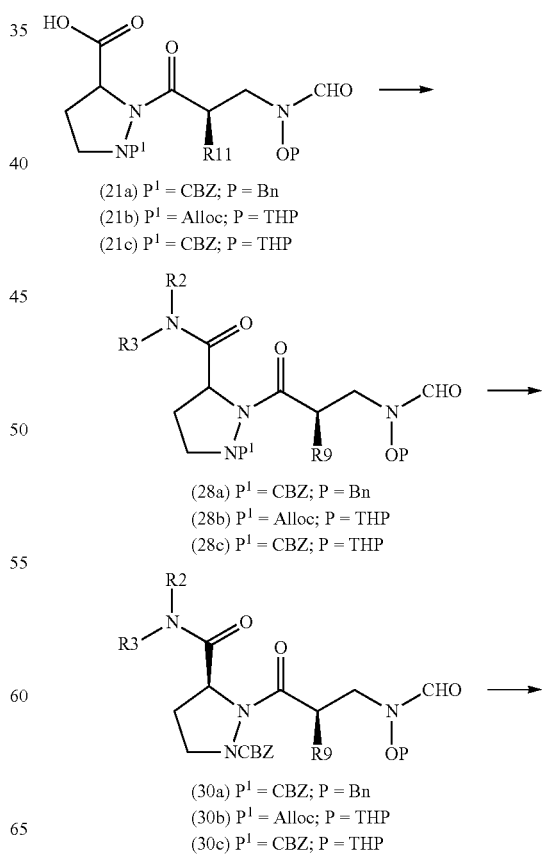

-continued

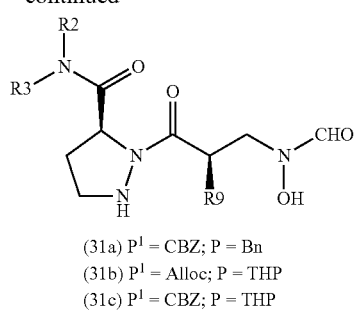

(31a) P¹ = CBZ; P = Bn
(31b) P¹ = Alloc; P = THP
(31c) P¹ = CBZ; P = THP

As shown in Scheme 6, intermediates (21a-c) can be treated with an appropriately substituted amine with a coupling agent such as EDC or PyBOP with an amine such as DIPEA in a solvent such as DMF to obtain (28a-c). Alternatively, compounds (28a-c) can be obtained by treating intermediates (21a-c) with a coupling agent such as DMTMM with an appropriately substituted amine in the presence of a base in a suitable solvent, or by the treatment of intermediates (21a-c) with mesyl chloride and a suitable base such as 1-methyl imidazole and a suitable amine in a solvent such as DCM or DMF. Additionally, intermediates (28a-c) can be obtained by the treatment of intermediates (21a-c) with 2,4,6-trichlorobenzoyl chloride and an appropriate base in a suitable solvent such as THF or toluene followed by the addition of an appropriately substituted amine. The appropriate diasteromer (30a-c)) can be obtained either by reverse phase HPLC or by chiral super critical fluid chromatography. Compound (31a and 31c) can be obtained either by treatment with a catalyst, such as 10% Pd/C, in an appropriate solvent, such as ethanol, in the case that P is Bn or by treatment with 80% acetic acid-water at room temperature or 40° C. in the case that P is THP. Compound (31b) can be obtained by treatment with a catalyst such as (PPh₃)₄Pd in the presence of a base such as morpholine in a solvent such as DCM followed by THP deprotection using a mixture of acetic acid and water.

Scheme 7

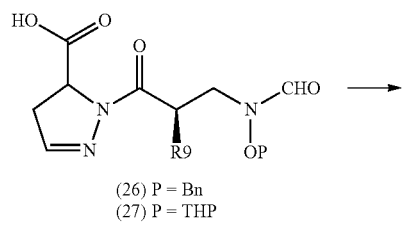

(26) P = Bn
(27) P = THP

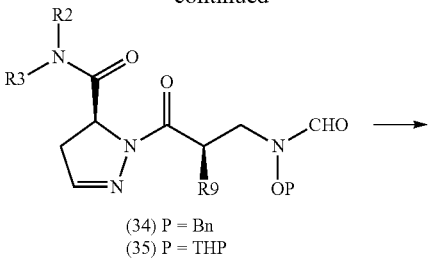

(34) P = Bn
(35) P = THP

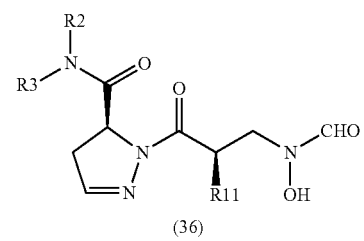

(36)

As shown in Scheme 7, intermediates (26) and/or (27) can be treated with an appropriately substituted amine with a coupling agent such as EDC or PyBOP with an amine such as DIPEA in a solvent such as DMF to obtain (32) and/or (33). Alternatively, compounds (32) and/or (33) can be obtained by treating intermediates (26) and/or (27) with a coupling agent such as DMTMM with an appropriately substituted amine in the presence of a base in a suitable solvent, or by the treatment of intermediates (26) and/or (27) with mesyl chloride and a suitable base such as 1-methyl imidazole and a suitable amine in a solvent such as DCM or DMF. Additionally, intermediates (32) and/or (33) can be obtained by the treatment of intermediates (26) and/or (27) with 2,4,6-trichlorobenzoyl chloride and an appropriate base in a suitable solvent such as THF or toluene followed by the addition of an appropriately substituted amine. The appropriate diastereomer (34) and/or (3S) can be obtained either by reverse phase HPLC or by chiral super critical fluid chromatography. Compound (36) can be obtained either by treatment with a catalyst, such as 10% Pd/C, in an appropriate solvent, such as ethanol, in the case that P is Bn or by treatment with 80% acetic acid-water at room temperature or 40° C. in the case that P is THP.

Scheme 8

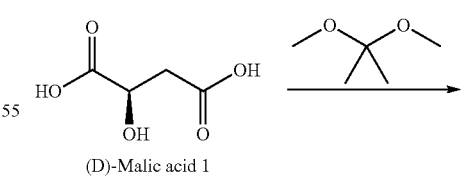

(D)-Malic acid 1

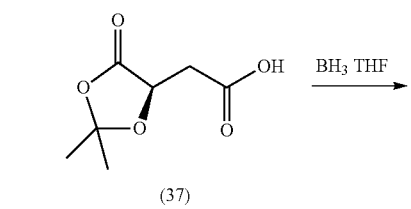

(37)

(32) P = Bn
(33) P = THP

Scheme 9

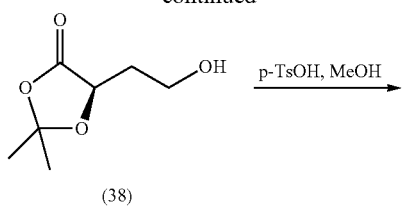

(38)

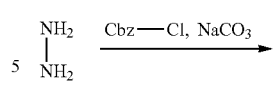

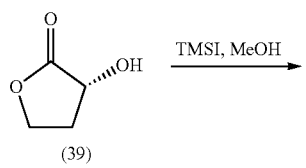

(39)

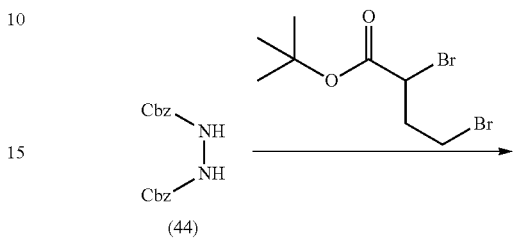

(44)

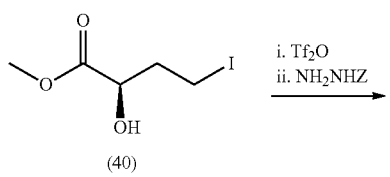

(40)

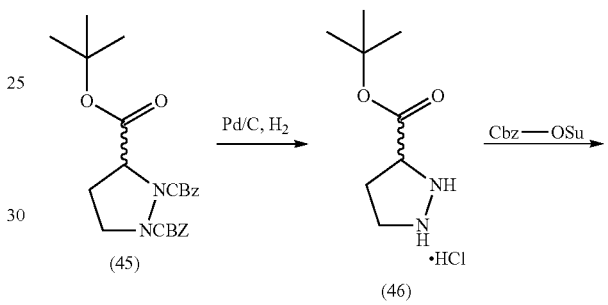

(45) → (46) ·HCl

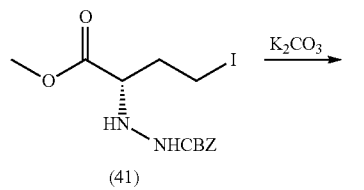

(41)

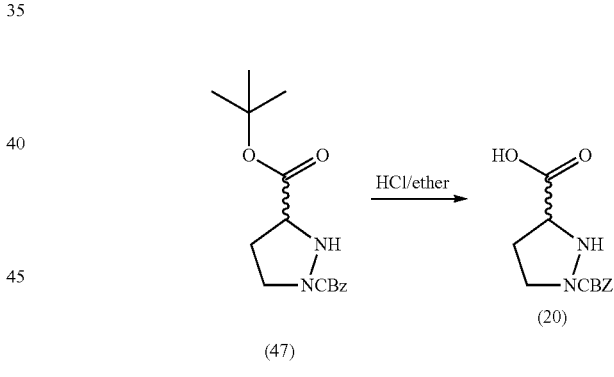

(47) → (20)

(42) → (43) (LiOH, THF)

(3S)-1-{[(Phenylmethyl)oxy]carbonyl}-3-pyrazolidinecarboxylic acid (43) can be prepared as described in Scheme 8. The enantiomerically pure lactone (39) can be prepared from (D)-Malic acid (1) in a three-step process according to literature (Denmark, S. E. and Yang, S.-M. *J. Am. Chem. Soc.* 2004, 126, 12432-12440). Opening of the lactone (39) with iodotrimethylsilane (TMSI) in the presence of methanol can afford alcohol (40). The alcohol (40) can be converted into a triflate and then reacted with Cbz-NHNH$_2$ to afford compound (41), which can readily cyclize in the presence of K$_2$CO$_3$ to afford the methyl ester (42). Finally, hydrolysis of the ester (42) with lithium hydroxide can afford the acid (43).

According to Scheme 9, 1-{[(phenylmethyl)oxy]carbonyl}-3-pyrazolidinecarboxylic acid (20) can be prepared by the treatment of hydrazine with a protecting group such as CBZ-Cl under basic conditions to afford intermediate (44) which then can be cyclized to (45) by the treatment of (44) with an alkylating agent such as 1,1-dimethylethyl-2,4-dibromobutanoate under basic conditions at elevated temperature in a solvent such as acetonitrile. (45) can then be converted to (46) under hydrogenolysis conditions followed by salt formation. (46) can then be converted to (47) by the addition of acylating agent such as CBZ-succinimide using a base such as TEA in a solvent such as DCM. Finally, (20) can be obtained by the treatment of (47) with an acid such as HCl in a solvent such as DCM or ether.

Scheme 10

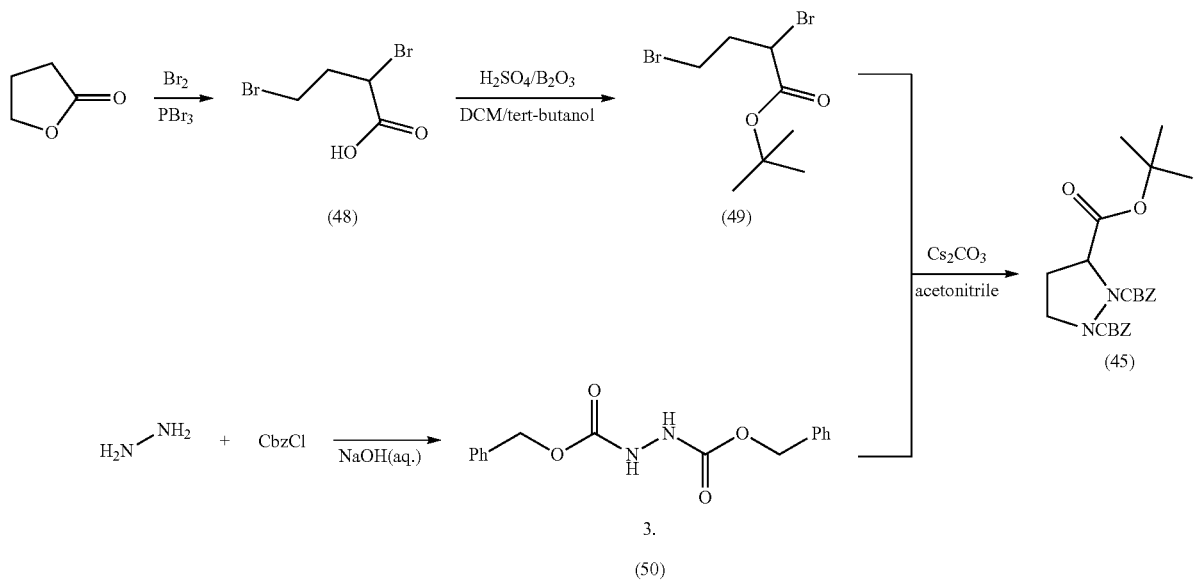

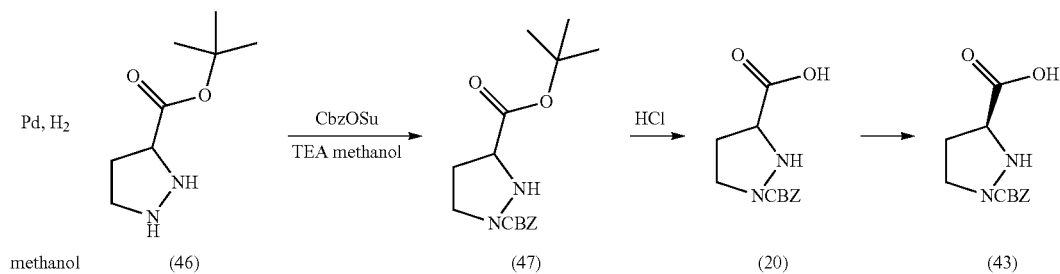

According to Scheme 10, dihydro-2(3H)-furanone can be converted to (48) by the addition of bromine and tribromophosphine at elevated temperature followed by the esterification to (49) under acidic conditions in a solvent such as DCM. (50) can be prepared using standard conditions (Protecting Groups in Organic Synthesis; Greene and Nuts; 3$^{rd}$ ed) using an acylating agent such as CBZ-Cl under basic conditions. (45) can be obtained by the treatment of (50) with (49) under basic conditions at elevated temperature in a solvent such as acetonitrile. Additionally, (46) can be obtained from (45) using standard hydrogenolysis conditions using a catalyst such as Pd/C in a solvent such as methanol. Intermediate (47) can be obtained from (46) using standard conditions with an acylating agent such as CBZ-succinimide using a base such as TEA in a solvent such as methanol. Intermediate (20) can be obtained by the treatment of (47) with an acid such as HCl. Finally, intermediate (43) can be obtained by the resolution of (20) with an optically active amino alcohol (Tsuda, M. et al; Jpn. Kokai Tokkyo Koho; (2002)) in a solvent such as acetonitrile.

Scheme 11

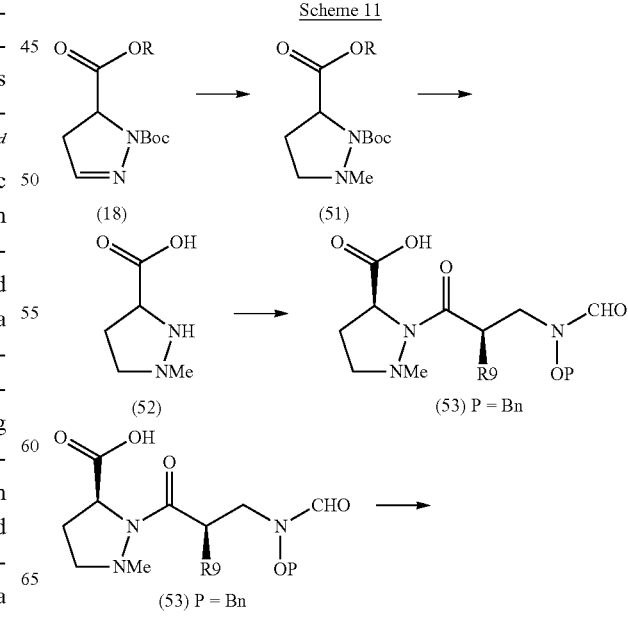

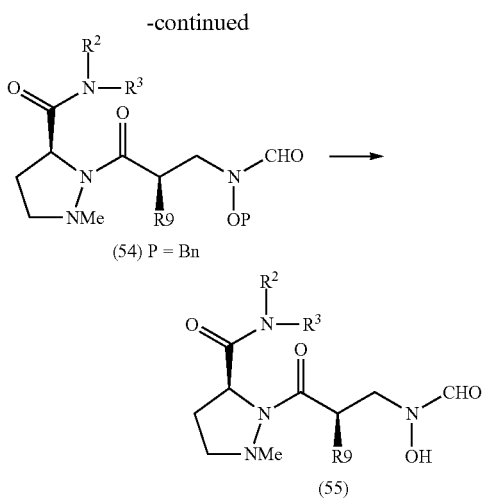

As shown in Scheme 11, intermediate (51) can be obtained by the treatment of (18) with an appropriate reducing agent such as NaCNBH₃ in an acidic solvent such as AcOH, followed by reductive alkylation with an aldehyde such as formaldehyde and an appropriate hydride source such as sodium triacetoxyborohydride in a solvent such as DCE or DCM. Intermediate (52) can be obtained by the treatment of (51) with TFA and water in an appropriate solvent such as DCM. Finally, intermediate (53) can be obtained by treating (52) with (11b) and an appropriate base such as DIPEA in an appropriate solvent such as DMF or DCM followed by diastereomeric separation as outlined in Scheme 4. Intermediate (54) can be obtained by (53) with an appropriately substituted amine using conditions found in Scheme 6. Finally (55) can be obtained from (54) according to conditions found in Scheme 6.

Certain embodiments of the present invention will now be illustrated by way of example only. The physical data obtained for the compounds exemplified is consistent with the assigned structure of those compounds.

Pharmaceutical Compositions

The present invention relates to novel compounds of Formulas (I) to (IV), respectively, or pharmaceutically acceptable salts thereof and corresponding pharmaceutical compositions.

The compounds of Formulas (I) to (IV), respectively, or pharmaceutically acceptable salts thereof, of the present invention will normally, but not necessarily, be formulated into pharmaceutical compositions prior to administration to a patient.

Accordingly, in another aspect, the present invention is directed to pharmaceutical compositions comprising a compound of Formulas (I) to (IV), respectively, or pharmaceutically acceptable salts thereof, of the present invention and one or more pharmaceutically-acceptable excipients.

In particular, the present invention also may relate to a pharmaceutical composition or formulation, which comprises a compound as defined by Formulas (I) to (IV), respectively, or a pharmaceutically acceptable salt thereof, and pharmaceutically acceptable adjuvants, carriers or excipients, and optionally one or more other therapeutic ingredients.

Pharmaceutical compositions of the present invention may be prepared and packaged in bulk form wherein a safe and effective amount of a compound of the present invention can be extracted and then given to the patient such as with powders or syrups. Alternatively, the pharmaceutical compositions of the present invention may be prepared and packaged in unit dosage form wherein each physically discrete unit contains a safe and effective amount of a compound of the present invention. When prepared in unit dosage form, the pharmaceutical compositions of the present invention typically contain from 25 mg to 1.5 g of compound of the present invention.

The pharmaceutical compositions of the present invention typically contain at least one compound of Formulas (I) to (IV), respectively or a pharmaceutically acceptable salt thereof. However, in certain embodiments, the pharmaceutical compositions of the present invention may contain more than one compounds or a pharmaceutically acceptable salt thereof of the present invention. For example, in certain aspects, the pharmaceutical compositions of the present invention may contain at least two compounds Formulas (I) to (IV), respectively, or pharmaceutically acceptable salt(s) thereof of the present invention. In addition, the pharmaceutical compositions of the present invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the present invention when administered to a patient and interactions which would result in pharmaceutical compositions that are not pharmaceutically acceptable are avoided. In addition, each excipient must of course be of sufficiently high purity to render it pharmaceutically-acceptable.

At least one compound of Formulas (I) to (IV), respectively, or a pharmaceutically acceptable salt thereof, of the present invention and the pharmaceutically-acceptable excipient or excipients will typically be formulated into a dosage form adapted for administration to the patient by the desired route of administration.

For example, dosage forms include those adapted for: (1) oral administration such as, but not limited to, tablets, capsules, caplets, pills, troches, powders, syrups, elixers, suspensions, solutions, emulsions, sachets, cachets and the like; (2) parenteral administration such as, but not limited to, sterile solutions, suspensions, powders for reconstitution and the like; (3) transdermal administration such as, but not limited to, transdermal patches and the like; (4) rectal administration such as, but not limited to: suppositories and the like; (5) inhalation such as dry powders, aerosols, suspensions, solutions and the like; and (6) topical administration such as, but not limited to: creams, ointments, lotions, solutions, pastes, sprays, foams, gels and the like.

As used herein, "pharmaceutically-acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the present invention when administered to a patient and interactions which would result in pharmaceutical compositions that are not pharmaceutically-acceptable are avoided. In addition, each excipient must of course be of sufficiently high purity to render it pharmaceutically-acceptable.

Suitable pharmaceutically-acceptable excipients will vary depending upon the particular dosage form chosen. In addition, suitable pharmaceutically-acceptable excipients may be chosen for a particular function that they may serve in the composition.

For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the present invention once administered to the patient from one organ, or portion of the body, to another organ, or another portion of the body. Certain pharmaceutically-acceptable excipients may be chosen for their ability to enhance patient compliance.

Moreover, pharmaceutical compositions, formulations, dosage forms, and the like, etc., may conveniently be presented in unit dosage form and may be prepared by any of the methods well known in the art of pharmacy. All methods include the step of bringing the active ingredient into association with the carrier which constitutes one or more accessory ingredients. In general, pharmaceutical compositions, formulations, dosage forms, and the like, etc. are prepared by uniformly and intimately bringing into association the active ingredient with liquid carriers or finely divided solid carriers or both and then, if necessary, shaping the product into the desired formulation.

Suitable pharmaceutically-acceptable excipients include, but are not limited to, the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, buffering agents and the like.

The skilled artisan will appreciate that certain pharmaceutically-acceptable excipients may serve more than one function and may serve alternative functions depending on how much of the excipient is present in the formulation and what other ingredients are present in the pharmaceutical compositions, formulations, dosage forms, and the like, etc.

Skilled artisans possess the knowledge and skill in the art to enable them to select suitable pharmaceutically-acceptable excipients in appropriate amounts for use in the present invention.

In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the present invention are prepared using techniques and methods known to those skilled in the art. Some of the methods commonly used in the art are described in *Remington's Pharmaceutical Sciences* (Mack Publishing Company).

The compounds of the present invention and the pharmaceutically-acceptable excipient or excipients will typically be formulated into a dosage form adapted for administration to the patient by the desired route of administration.

In one aspect, the present invention is directed to a solid oral dosage form such as, but not limited to, tablet or capsule which comprises a safe and effective amount of a compound of the present invention and a diluent or filler and the like.

Suitable diluents and fillers, include, but are not limited to, lactose, sucrose, dextrose, mannitol, sorbitol, starch (e.g. corn starch, potato starch, pre-gelatinized starch and the like.), cellulose and its derivatives (e.g. microcrystalline cellulose and the like.), calcium sulfate, dibasic calcium phosphate and the like. The oral solid dosage form may further comprise a binder.

Suitable binders include starch (e.g. corn starch, potato starch, pre-gelatinized starch and the like), gelatin, acacia, sodium alginate, alginic acid, tragacanth, guar gum, povidone, cellulose and its derivatives (e.g. microcrystalline cellulose) and like.

Oral solid dosage forms may further comprise a disintegrant. Suitable disintegrants, include, but are not limited to: crospovidone, sodium starch glycolate, croscarmelose, alginic acid, sodium carboxymethyl cellulose and the like.

The oral solid dosage form may further comprise a lubricant. Suitable lubricants include, but are not limited to: stearic acid, magnesium stearate, calcium stearate, talc and like.

In one aspect, the present invention relates to a pharmaceutical composition comprising a compound of Formula (I) or a pharmaceutically acceptable salt thereof and at least one pharmaceutically acceptable excipient(s).

In one aspect, the present invention relates to a pharmaceutical composition comprising a compound of Formula (II) or a pharmaceutically acceptable salt thereof and at least one pharmaceutically acceptable excipient(s).

In one aspect, the present invention relates to a pharmaceutical composition comprising a compound of Formula (III) or a pharmaceutically acceptable salt thereof and at least one pharmaceutically acceptable excipient(s).

In one aspect, the present invention relates to a pharmaceutical composition comprising a compound of Formula (IV) or a pharmaceutically acceptable salt thereof and at least one pharmaceutically acceptable excipient(s).

In one aspect, the present invention relates to a pharmaceutical composition comprising a compound according to claim 5 or a pharmaceutically acceptable salt thereof and a pharmaceutically acceptable excipient(s).

In another aspect, the present invention relates to a pharmaceutical composition, which comprises a compound which is (3S)-2-((2R)-3-Cyclopentyl-2-{[formyl(hydroxy)amino]methyl}propanoyl)-N-4-pyrimidinyl-3-pyrazolidinecarboxamide:

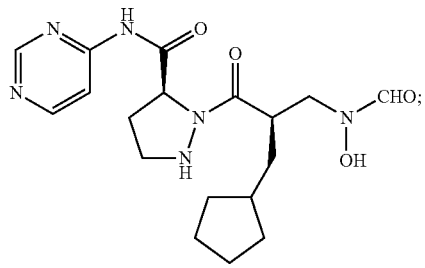 [SMILES: O=CN(O)C[C@@H](CC1CCCC1)C(=O)N1NCC[C@H]1C(=O)Nc1ccncn1]

or a pharmaceutically acceptable salt thereof.

In another aspect, the present invention relates to a pharmaceutical composition, which comprises a compound which is (3S)-2-((2R)-3-Cyclopentyl-2-{[formyl(hydroxy)amino]methyl}propanoyl)-N-4-pyrimidinyl-3-pyrazolidinecarboxamide

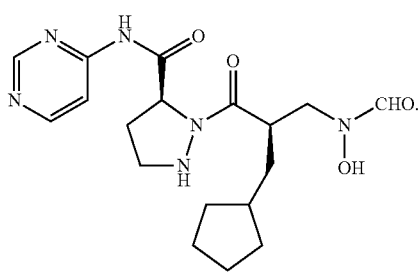 [SMILES: O=CN(O)C[C@@H](CC1CCCC1)C(=O)N1NCC[C@H]1C(=O)Nc1ccncn1]

Administration—Routes of Administration

It will also be recognized by one of skill in the art that the optimal quantity and spacing of individual dosages of a compound of Formulas (I) to (IV), respectively, or a pharmaceutically acceptable salt thereof will be determined by the nature and extent of the condition being treated, the form, route and site of administration, and the particular patient being treated, and that such optimums can be determined by conventional techniques.

It will also be appreciated by one of skill in the art that the optimal course of treatment, i.e., the number of doses of a compound of Formulas (I) to (IV), respectively, or a pharmaceutically acceptable salt thereof given per day for a defined number of days, can be ascertained by those skilled in the art using conventional course of treatment determination tests.

The amount of a compound of Formulas (I) to (IV), respectively, or a pharmaceutically acceptable salt thereof which is required to achieve a therapeutic effect will, of course, vary with the particular compound, the route of administration, the subject under treatment, and the particular disorder or disease being treated.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

While it is possible that, for use in therapy, therapeutically effective amounts of a compound of Formulas (I) to (IV), respectively, or a pharmaceutically acceptable salts thereof, may be administered as the raw chemical, it is possible to present the active ingredient as a pharmaceutical composition. Accordingly, the present invention further provides pharmaceutical compositions, which include therapeutically effective amounts of compounds of the Formulas (I) to (IV), respectively, or pharmaceutically acceptable salt thereof, and one or more pharmaceutically acceptable carriers, diluents, or excipients. Compounds of the Formulas (I) to (IV), respectively, or pharmaceutically acceptable salt thereof are as described herein.

The carrier(s), diluent(s) or excipient(s) must be acceptable in the sense of being compatible with the other ingredients of the formulation and not deleterious to the recipient thereof. In accordance with another aspect of the present invention there is also provided a process for the preparation of a pharmaceutical formulation including admixing a compound of the Formulas (I) to (IV), respectively, or salts thereof, with one or more pharmaceutically acceptable carriers, diluents or excipients.

Pharmaceutical formulations, compositions, formulations, dosage forms, and the like, may be presented in unit dose forms containing a predetermined amount of active ingredient per unit dose. Such a unit of a compound of Formulas (I) to (IV), respectively, or pharmaceutically acceptable salt thereof, typically depends on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations, compositions, formulations, dosage forms, and the like, etc. may be prepared by any of the methods well known in the pharmacy art.

Pharmaceutical formulations, compositions, formulations, dosage forms, and the like, etc., may be adapted for administration by any appropriate route, for example by the oral (including, but are not limited to: buccal, sublingual and the like), rectal, nasal, topical (including, but are not limited to: buccal, sublingual, transdermal and the like), vaginal or parenteral (including, but are not limited to: subcutaneous, intramuscular, intravenous, intradermal and the like) route. Such pharmaceutical compositions, formulations, dosage forms, and the like, may be prepared by any method known in the art of pharmacy, for example by bringing into association the active ingredient with the carrier(s) or excipient(s).

Pharmaceutical formulations, compositions, formulations, dosage forms, and the like, adapted for oral administration may be presented as discrete units such as, but are not limited to: capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as, but are not limited to: ethanol, glycerol, water and the like. Powders are prepared by comminuting the compound to a suitable fine size and mixing with a similarly comminuted pharmaceutical carrier such as, but are not limited: an edible carbohydrate, such as, but is not limited to, for example, starch or mannitol and the like. Flavoring, preservative, dispersing, coloring agent and the like, can also be present in the present invention.

Capsules are made by preparing a powder mixture, as described above, and filling formed gelatin sheaths. Glidants and lubricants such as, but are not limited to: colloidal silica, talc, magnesium stearate, calcium stearate or solid polyethylene glycol and the like, can be added to the powder mixture before the filling operation. A disintegrating or solubilizing agent such as, but are not limited to: agar-agar, calcium carbonate, sodium carbonate and the like, can also be added to improve the availability of the medicament when the capsule is ingested.

Moreover, when desired or necessary, suitable binders, lubricants, disintegrating agents and coloring agents can also be incorporated into the mixture. Suitable binders may include, but are not limited to, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms may include, but are not limited to: sodium oleate, sodium stearate, magnesium stearate, sodium benzoate, sodium acetate, sodium chloride and the like. Disintegrators may include, but are not limited to, without limitation, starch, methyl cellulose, agar, bentonite, xanthan gum and the like. Tablets are formulated, for example, by preparing a powder mixture, granulating or slugging, adding a lubricant and disintegrant and pressing into tablets, etc. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as, but are not limited to: bentonite, kaolin, dicalcium phosphate and the like. The powder mixture can be granulated by wetting with a binder such as, but are not limited to: syrup, starch paste, acadia mucilage or solutions of cellulosic or polymeric materials and the like, forcing through a screen. As an alternative to granulating, the powder mixture can be run through the tablet machine and the result is imperfectly formed slugs broken into granules. The granules can be lubricated to prevent sticking to the tablet forming dies by means of the addition of, but are not limited to: stearic acid, a stearate salt, talc, mineral oil and the like. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as, but are not limited to: ethoxylated isostearyl alcohols, polyoxy ethylene sorbitol ethers, preservatives, flavor additive such as, but are not limited to: peppermint oil, natural sweeteners, saccharin, other artificial sweeteners, and the like can also be added.

Where appropriate, dosage unit pharmaceutical formulations, compositions, formulations, dosage forms, and the like, for oral administration can be microencapsulated. The formulation can also be prepared to prolong or sustain the release as for example by coating or embedding particulate material in polymers, wax or the like.

The compounds of Formulas (I) to (IV), respectively, or a pharmaceutically acceptable salt thereof, of the present invention can also be administered in the form of liposome delivery systems, such as, but are not limited to: small unilamellar vesicles, large unilamellar vesicles, multilamellar vesicles and the like. Liposomes can be formed from a variety of phospholipids, such as, but are not limited to: cholesterol, stearylamine, phosphatidylcholines and the like.

The compounds of Formulas (I) to (IV), respectively, or a pharmaceutically acceptable salt thereof, may also be delivered by the use of monoclonal antibodies as individual carriers to which the compound molecules are coupled.

The compounds of Formulas (I) to (IV), respectively, or a pharmaceutically acceptable salt thereof, may also be coupled with soluble polymers as targetable drug carriers. Such polymers can include, but are not limited to: polyvinylpyrrolidone, pyran copolymer, polyhydroxypropyl-methacrylamide-phenol, polyhydroxyethylaspartamidephenol, polyethyleneoxidepolylysine substituted with palmitoyl residues and the like. Furthermore, the compounds of Formulas (I) to (IV), respectively, or a pharmaceutically acceptable salt thereof, may be coupled to a class of biodegradable polymers useful in achieving controlled release of a drug, for example, such as, but are not limited to: polylactic acid, polepsilon caprolactone, polyhydroxy butyric acid, polyorthoesters, polyacetals, polydihydropyrans, polycyanoacrylates and cross-linked or amphipathic block copolymers of hydrogels and the like.

Pharmaceutical formulations, compositions, formulations, dosage forms, and the like, adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations, compositions, formulations, dosage forms, and the like, adapted for topical administration may be formulated such as, but are not limited to, ointments, creams, suspensions, lotions, powders, solutions, pastes, gels, sprays, aerosols, oils and the like.

For treatments of the eye or other external tissues, for example mouth and skin, the pharmaceutical formulations, compositions, formulations, dosage forms, and the like of the present invention are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations, compositions, formulations, dosage forms, and the like, adapted for topical administrations to the eye include eye drops wherein the active ingredient is dissolved or suspended in a suitable carrier, especially an aqueous solvent.

Pharmaceutical formulations, compositions, formulations, dosage forms, and the like, adapted for topical administration in the mouth include, but are not limited to: lozenges, pastilles, mouth washes and the like.

Pharmaceutical formulations, compositions, formulations, dosage forms, and the like, adapted for rectal administration may be presented as, but are not limited to: suppositories or as enemas and the like.

Pharmaceutical formulations, compositions, formulations, dosage forms, and the like, adapted for nasal administration wherein the carrier is a solid, which may include, but are not limited to: a coarse powder having a particle size for example in the range 20 to 500 microns which is administered in the manner in which snuff is taken, i.e. by rapid inhalation through the nasal passage from a container of the powder held close up to the nose. Suitable pharmaceutical formulations, compositions, formulations, dosage forms, and the like, wherein the carrier is a liquid, for administration as a nasal spray or as nasal drops, include, but are not limited to aqueous or oil solutions of the active ingredient.

Pharmaceutical formulations, compositions, formulations, dosage forms, and the like, adapted for administration by inhalation include, but are not limited to fine particle dusts or mists, which may be generated by means of various types of metered, dose pressurised aerosols, nebulizers or insufflators and the like.

Pharmaceutical formulations, compositions, formulations, dosage forms, and the like, adapted for vaginal administration may be presented as, but are not limited to pessaries, tampons, creams, gels, pastes, foams, spray formulations and the like.

Pharmaceutical formulations, compositions, formulations, dosage forms, and the like, adapted for parenteral administration, include, but are not limited to aqueous and non-aqueous sterile injection solutions, which may include, but are not limited to contain anti-oxidants, buffers, bacteriostats, solutes and the like, which render the formulation isotonic with the blood of the intended recipient; and aqueous and non-aqueous sterile suspensions which may include, but are not limited to suspending agents, thickening agents and the like.

Pharmaceutical formulations, compositions, formulations, dosage forms, and the like, may be presented, but are not limited to in unit-dose or multi-dose containers, for example sealed ampoules, vials and the like, and may be stored in a freeze-dried (lyophilized) condition requiring only the addition of the sterile liquid carrier, for example water for injections, immediately prior to use. Extemporaneous injection solutions and suspensions may be prepared from, but are not limited to sterile powders, granules, tablets and the like.

It should be understood that in addition to the ingredients particularly mentioned above, the pharmaceutical formulations, compositions, formulations, dosage forms, may but are not limited to other agents conventional in the art having regard to the type of pharmaceutical formulations, compositions, formulations, dosage forms, and the like, in question, for example those suitable for oral administration may include, but are not limited to flavouring agents.

A therapeutically effective amount of a compound of Formulas (I) to (IV), respectively, or a pharmaceutically acceptable salt thereof, of the present invention will depend upon a number of factors including, for example, the age and weight of the human or other animal, the precise condition requiring treatment and its severity, the nature of the formulation, and the route of administration, and will ultimately be at the discretion of the attendant physician or veterinarian.

However, an effective amount of a compound of Formulas (I) to (IV), respectively, or a pharmaceutically acceptable salt thereof, for the treatment of a bacterial infection will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same.

An effective amount of a salt thereof, may be determined as a proportion of the effective amount of the compound of Formulas (I) to (IV), respectively, or a pharmaceutically acceptable salt thereof, per se. It is envisaged that similar dosages would be appropriate for treatment of the other conditions referred to above.

Methods of Use

The present invention also relates to methods for treatment of bacterial infections, which comprise administering an effective amount of a compound of Formulas (I) to (IV), respectively, or a pharmaceutically acceptable salt thereof, or a corresponding pharmaceutical composition to a human in need thereof.

The compounds of the present invention are inhibitors of microbial peptide deformylase and are, therefore, capable of or used in preventing bacterial growth. Compounds of the present invention are useful in the treatment and/or prevention of infectious diseases wherein the underlying pathology is (at least in part) attributable to a variety of prokaryotic organisms.

Examples include, but are not limited to, Gram positive and Gram negative aerobic and anaerobic bacteria from the genera *Streptococcus, Staphylococcus, Moraxella, Haemophilus, Neisseria, Mycoplasma, Legionella, Chlamydia, Bacteroides, Fusobacterium* and *Peptostreptococcus*. More particularly, examples include, but are not limited to, Gram positive and Gram negative aerobic and anaerobic bacteria from the genera *Streptococcus*, e.g. *S. pneumoniae* and *S. pyogenes, Staphylococcus*, e.g. *S. aureus, S. epidermidis*, and *S. saprophyticus, Moraxella*, e.g. *M. catarrhalis, Haemophilus*, e.g. *H. influenzae, Neisseria, Mycoplasma*, e.g. *M. pneumoniae, Legionella*, e.g. *L. pneumophila, Chlamydia*, e.g. *C. pneumoniae, Bacteroides, Clostridium, Fusobacterium, Propionibacterium*, and *Peptostreptococcus*.

Suitably, the compounds of Formulas (I) to (IV), respectively, or pharmaceutically acceptable salts thereof, the present invention relates to use or treatment of bacterial infections caused by *Streptococcus*, more suitably *S. pneumoniae* or *S. pyogenes*.

Suitably, the compounds of Formulas (I) to (IV), respectively, or pharmaceutically acceptable salts thereof, of the present invention relates to use or treatment of bacterial infections caused by *Staphylococcus*, more suitably *S. aureus, S. epidermidis*, or *S. saprophyticus*.

Suitably, the compounds of Formulas (I) to (IV), respectively, or pharmaceutically acceptable salts thereof, of the present invention relates to use or treatment of bacterial infections caused by *Moraxella*, more suitably *M. catarrhalis*.

Suitably, the compounds of Formulas (I) to (IV), respectively, or pharmaceutically acceptable salts thereof, of the present invention relates to use or treatment of bacterial infections caused by *Haemophilus*, more suitably *H. influenzae*.

Suitably, the compounds of Formulas (I) to (IV), respectively, or pharmaceutically acceptable salts thereof, of the present invention relates to use or treatment of bacterial infections caused by *Neisseria*.

Suitably, the compounds of Formulas (I) to (IV), respectively, or pharmaceutically acceptable salts thereof, of the present invention relates to use or treatment of bacterial infections caused by *Mycoplasma*, more suitably *M. pneumoniae*.

Suitably, the compounds of Formulas (I) to (IV), respectively, or pharmaceutically acceptable salts thereof, of the present invention relates to use or treatment of bacterial infections caused by *Legionella*, more suitably *L. pneumophila*.

Suitably, the compounds of Formulas (I) to (IV), respectively, or pharmaceutically acceptable salts thereof, of the present invention relates to use or treatment of bacterial infections caused by *Chlamydia*, more suitably *C. pneumoniae*.

Suitably, the compounds of Formulas (I) to (IV), respectively, or pharmaceutically acceptable salts thereof, of the present invention relates to use or treatment of bacterial infections caused by *Bacteroides*.

Suitably, the compounds of Formulas (I) to (IV), respectively, or pharmaceutically acceptable salts thereof, of the present invention relates to use or treatment of bacterial infections caused by *Clostridium*.

Suitably, the compounds of Formulas (I) to (IV), respectively, or pharmaceutically acceptable salts thereof, of the present invention relates to use or treatment of bacterial infections caused by *Fusobacterium*.

Suitably, the compounds of Formulas (I) to (IV), respectively, or pharmaceutically acceptable salts thereof, of the present invention relates to use or treatment of bacterial infections caused by *Propionibacterium*.

Suitably, the compounds of Formulas (I) to (IV), respectively, or pharmaceutically acceptable salts thereof, of the present invention relates to use or treatment of bacterial infections caused by *Peptostreptococcus*.

The compounds of Formulas (I) to (IV), respectively, or pharmaceutically acceptable salts thereof, of the present invention also relates to use or treatment of bacterial infections caused by bacteria that are resistant to β-lactam, quinolone, macrolides, ketolides, glycopeptide, and oxazolidinone classes of antibiotics. Such drug resistant bacterial infections include, but are not limited to, penicillin, macrolide or levofloxacin resistant *S. pneumoniae*; methicillin or macrolide resistant, and vancomycin intermediate *S. aureus*; methicillin resistant *S. epidermidis*; and oxazolidinone resistant *S. aureus*.

The compounds of Formulas (I) to (IV), respectively, or pharmaceutically acceptable salts thereof, of the present invention relates to use to treat, prevent and/or reduce the severity of a bacterial infection. Such infections include, but are not limited to, ear infections, sinusitis, upper and lower respiratory tract infections, genital infections, skin and soft tissue infections, bacterial endocarditis and antibacterial prophylaxis.

The compounds of Formulas (I) to (IV), respectively, or pharmaceutically acceptable salts thereof, of the present invention may also relates to use to prevent a bacterial infection in mammals, specifically humans, such as a bacterial infection that may result from medical or dental procedures.

Suitably, the compounds of Formulas (I) to (IV), respectively, or pharmaceutically acceptable salts thereof, of the present invention relates to use to treat ear infections.

Suitably, the compounds of Formulas (I) to (IV), respectively, or pharmaceutically acceptable salts thereof, of the present invention relates to use to treat sinusitis.

Suitably, the compounds of Formulas (I) to (IV), respectively, or pharmaceutically acceptable salts thereof, of the present invention relates to use to treat upper and lower respiratory tract infections.

Suitably, the compounds of Formulas (I) to (IV), respectively, or pharmaceutically acceptable salts thereof, of the present invention relates to use to treat genital infections.

Suitably, the compounds of Formulas (I) to (IV), respectively, or pharmaceutically acceptable salts thereof, of the present invention relates to use to treat skin and soft tissue infections.

Suitably, the compounds of Formulas (I) to (IV), respectively, or pharmaceutically acceptable salts thereof, of the present invention relates to use to treat bacterial endocarditis.

The methods of treatment of the present invention, specifically methods for the treatment infectious diseases including bacterial infections, comprise administering an effective amount of a compound of Formulas (I) to (IV), respectively, or pharmaceutically acceptable salts thereof, to a human or patient in need thereof.

The methods of treatment of the present invention comprise administering a safe and effective amount of a compound of Formulas (I) to (IV), respectively, or pharmaceutically acceptable salts thereof, to a human or patient in need thereof.

In one embodiment, the present invention relates to a method for treatment of a bacterial infection comprising administering an effective amount of a compound of Formulas (I) to (IV), respectively, or pharmaceutically acceptable salts thereof, to a human or patient in need thereof.

In another embodiment, the present invention relates to a method for treatment of a bacterial infection comprising administering an effective amount of a compound of Formulas (I) to (IV), respectively, or pharmaceutically acceptable salts thereof, to a human or patient in need thereof.

In another embodiment, the present invention relates to a method for treatment of a bacterial infection comprising administering an effective amount of a compound of Formulas (I) to (IV), respectively, or pharmaceutically acceptable salts thereof, to a human or patient in need thereof.

In another embodiment, the present invention relates to a method for treatment of a bacterial infection comprising administering an effective amount of a compound of Formulas (I) to (IV), respectively, or pharmaceutically acceptable salts thereof, to a human or patient in need thereof.

In another embodiment, the present invention relates to a method for treatment of a bacterial infection comprising administering an effective amount of a compound of Formulas (I) to (IV), respectively, or pharmaceutically acceptable salts thereof, to a human or patient in need thereof.

In another embodiment, the present invention relates to a method for treatment of a bacterial infection comprising administering an effective amount of a compound which is (3S)-2-((2R)-3-cyclopentyl-2-{[formyl(hydroxy)amino]methyl}propanoyl)-N-4-pyrimidinyl-3-pyrazolidinecarboxamide

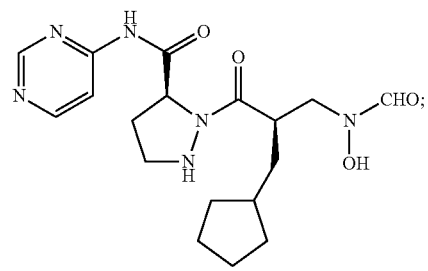 [SMILES: O=CN(O)C[C@@H](CC1CCCC1)C(=O)N1NCC[C@H]1C(=O)Nc1ccncn1]

or
a pharmaceutically acceptable salt thereof.

In another embodiment, the present invention relates to a method for treatment of a bacterial infection comprising administering an effective amount of a compound which is (3S)-2-((2R)-3-cyclopentyl-2-{[formyl(hydroxy)amino]methyl}propanoyl)-N-4-pyrimidinyl-3-pyrazolidinecarboxamide

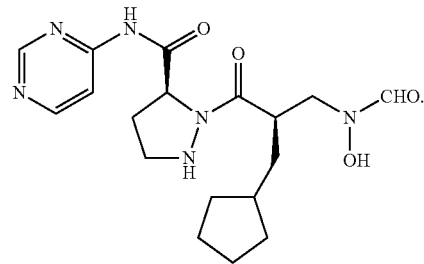 [SMILES: O=CN(O)C[C@@H](CC1CCCC1)C(=O)N1NCC[C@H]1C(=O)Nc1ccncn1]

For each of the method embodiments described herein for the present invention, the bacterial infection is caused by, but may not be limited to *Streptococcus, Staphylococcus, Moraxella, Haemophilus, Neisseria, Mycoplasma, Legionella, Chlamydia, Bacteroides, Clostridium, Fusobacterium, Propionibacterium,* or *Peptostreptococcus*. More particularly, examples include, but are not limited to, Gram positive and Gram negative aerobic and anaerobic bacteria from the genera *Streptococcus*, e.g. *S. pneumoniae* and *S. pyo-*

*genes, Staphylococcus*, e.g. *S. aureus, S. epidermidis*, and *S. saprophyticus, Moraxella*, e.g. *M. catarrhalis, Haemophilus*, e.g. *H. influenzae, Neisseria, Mycoplasma*, e.g. *M. pneumoniae, Legionella*, e.g. *L. pneumophila, Chlamydia*, e.g. *C. pneumoniae, Bacteroides, Clostridium, Fusobacterium, Propionibacterium*, and *Peptostreptococcus*.

As used herein, "infectious disease" refers to any disease characterized by the presence of a microbial infection, such as a bacterial infection.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the present invention or other pharmaceutically-active agent means an amount of the compound sufficient to treat the patient's condition, but low enough to avoid serious side effects (at a reasonable benefit/risk ratio) within the scope of sound medical judgment. A safe and effective amount of a compound will vary with the particular compound chosen (e.g., consider the potency, efficacy, and half-life of the compound); the route of administration chosen; the condition being treated; the severity of the condition being treated; the age, size, weight, and physical condition of the patient being treated; the medical history of the patient being treated; the duration of the treatment; the nature of concurrent therapy; the desired therapeutic effect; and like factors, but can nevertheless be routinely determined by the skilled artisan.

As used herein, "effective amount" in reference to a compound of Formulas (I) to (IV), respectively, or pharmaceutically acceptable salts thereof, to a human or patient in need thereof, of the present invention means an amount of the compound sufficient to treat the patient's condition, but low enough to avoid serious side effects (at a reasonable benefit/risk ratio) within the scope of sound medical judgment. An effective amount of a compound will vary with the particular compound chosen (e.g., consider the potency, efficacy, and half-life of the compound); the route of administration chosen; the condition being treated; the severity of the condition being treated; the age, size, weight, and physical condition of the patient being treated; the medical history of the patient being treated; the duration of the treatment; the nature of concurrent therapy; the desired therapeutic effect; and like factors, and can be routinely determined by the skilled artisan.

As used herein, "patient" refers to a human or other animal.

The compounds of the present invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, intravaginal, and intranasal administration.

The compounds of the present invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the present invention depend on the pharmacokinetic properties of that compound, such as absorption, distribution, and half-life, which can be determined by the skilled artisan.

In addition, suitable dosing regimens, including the duration such regimens are administered, for a compound of the present invention depend on the condition being treated, the severity of the condition being treated, the age and physical condition of the patient being treated, the medical history of the patient being treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 50 mg to 3 g.

Additionally, the compounds of the present invention may be administered as prodrugs. As used herein, a "prodrug" of a compound of the present invention is a functional derivative of the compound which, upon administration to a patient, eventually liberates the compound of the present invention in vivo. Administration of a compound of the present invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The present invention also provides a compound of Formulas (I) to (IV), respectively, or pharmaceutically acceptable salts thereof, to a human or patient in need thereof, of the present invention for use in medical therapy, and particularly in bacterial infections. Thus, in a further aspect, the present invention is directed to the use of a compound of Formulas (I) to (IV), respectively, or pharmaceutically acceptable salts thereof, to a human or patient in need thereof, in the preparation of a medicament for the treatment of bacterial infections.

As stated above, the compounds of the present invention according to Formulas (I) to (IV), respectively, or a pharmaceutically acceptable salt thereof are PDF inhibitors, which are useful in treatment of bacterial infections.

The biological activity of the a compound of Formulas (I) to (IV), respectively, or pharmaceutically acceptable salts thereof, to a human or patient in need thereof, can be determined using suitable assays such as those measuring inhibition of the enzymatic activity of PDF and those evaluating the ability of the compounds to inhibit bacterial growth in vitro or in animal models of infection.

PDF IC50 Assays

Assay 1:

Enzymatic activity of PDF was measured using a formate dehydrogenase (FDH)-coupled assay [Lazennec and Meinnel (1997) Anal. Biochem. 244, 180-182]. Once formate is released from methionine by PDF, it is oxidized by FDH thereby reducing one molecule of NAD to NADH and resulting in an increase in absorbance at 340 nm. Reactions were initiated by adding PDF to microtiter plates containing all other reaction components and were continuously monitored for 20 min at 25° C. The final reaction composition for the *Staphylococcus aureus* PDF (SaPDF) assay was 50 mM potassium phosphate, pH 7.6, 5 units/mL FDH, 7 mM NAD, 1% DMSO, 0.01% CHAPS, 1 nM SaPDF, and 3 mM formyl-Met-Ala-Ser in 40 µL total volume. Serial dilutions of inhibitors were performed in DMSO. Reagents and assay format were identical for *Haemophilus influenzae* PDF except that formyl-Met-Ala-Ser was 6 mM final. In the *Streptococcus pneumoniae* PDF assay, reaction conditions were similar but contained 30 µM enzyme, 4 mM NAD and 4 mM formyl-Met-Ala-Ser. The varying formyl-Met-Ala-Ser concentrations reflect $K_M$ values for substrate using the different PDF isozymes. $IC_{50}$s were determined by fitting to the equation: % Inhibition=$100/1+(IC_{50}/[I])^s$, where s is a slope factor, l is the inhibitor concentration and the $IC_{50}$ is the concentration of compound that causes 50% inhibition.

Assay 2:

Enzymatic activity of PDF was measured using a formate dehydrogenase (FDH)/NAD+/Diaphorase-coupled Fluorescence detection assay. Once formate is released from methionine by PDF, it is oxidized by FDH, thereby reducing one molecule of NAD to NADH. Diaphorase then catalyzes the conversion of Resazurin to Resarufin using the NADH produced by the FDH reaction. The fluorescence intensity of Resarufin is monitored by excitation at 525 nm and emission at 598 nm. The reaction is assembled by first adding the NAD, f-MAS and Resazurin to each well of a 384 well plate containing 50 nl of test compounds. Reactions were initiated by adding PDF in reaction buffer containing FDH and Diaphorase. The final reaction composition for the *Staphylococcus aureus* PDF (SaPDF) assay was 50 mM potassium phosphate, 0.025% CHAPS pH 7.6, 0.25 units/mL FDH, 0.156 µm! Diaphorase; 0.025 mg/ml BSA; 1 mM NAD, 0.5% DMSO, 1 mM formyl-Met-Ala-Ser; 5 uM Resazurin, and 1 nM SaPDF, in 10 µL total volume. Serial dilutions of inhibitors were performed in DMSO. Reagents and assay format were identical for the *Haemophilus influenzae* PDF; in the *Streptococcus pneumoniae* PDF assays, assay composition was the same, except that 150 µM enzyme was used. The endpoint of each reaction was chosen to ensure that all data were collected within the linear range of catalysis. $IC_{50}$s were determined by fitting to the equation: % Inhibition=$100/1+(IC_{50}/[I])^s$, where s is a slope factor, l is the inhibitor concentration and the $IC_{50}$ is the concentration of compound that causes 50% inhibition.

Results

Representative examples 1-2, 5-8, 10-12, 14-21, 23-26, 30-32, 34-44, 46-48, 59, 61-64, 66-68, 74-79, 92-93, 96-97, 100, and 127-128 were tested under Assay 1 conditions and inhibit *S. aureus*, *H. influenzae* and *S. pneumoniae* PDF activities with IC50s≤1 uM.

Representative examples 50-57, 81, 84, 87-91, 101, 103-121, and 123 were tested under Assay 2 conditions and inhibit *S. aureus*, *H. influenzae* and *S. pneumoniae* PDF activities with IC50s≤1 uM.

Antimicrobial Activity Assay

Whole-cell antimicrobial activity was determined by broth microdilution using the Clinical and Laboratory Standards Institute (CLSI, formerly NCCLS) recommended methodology (NCCLS Document M7-A7, "Methods for Dilution Antimicrobial Susceptibility Tests for Bacteria that Grow Aerobically; Approved Standard—Seventh Edition", 2006). Compounds were tested in serial two-fold dilutions ranging from 64 to 0.06 µg/mL against a panel of at least 11 strains. This panel consisted of the following laboratory strains: *Staphylococcus aureus* Oxford, *Staphylococcus aureus* WCUH29, *Enterococcus faecalis* I, *Enterococcus faecalis* 7 or *Enterococcus faecalis* X7501, *Haemophilus influenzae* Q1, *Haemophilus influenzae* NEMC1 or *Haemophilus influenzae* H128, *Moraxella catarrhalis* 1502, *Streptococcus pneumoniae* 1629, *Streptococcus pneumoniae* N1387, *Streptococcus pneumoniae* Ery2 and *Escherichia coli* 7623 or *Escherichia coli* 3. All compounds were also tested against *Haemophilus influenzae* H128 or *Escherichia coli* 7623 efflux minus mutants (strains in which the AcrA efflux pump had been deleted) to ascertain the extent in which the molecules were effluxed out of the bacteria. In addition, the antibacterial activity of some compounds against *Streptococcus pyogenes* 1307006P and *Streptococcus pyogenes* 1308007P was also analyzed. The minimum inhibitory concentration (MIC) was determined as the lowest concentration of compound that inhibited visible growth. A mirror reader was used to assist in determining the MIC endpoint.

Results

Each of the Examples 1-128 have a minimal inhibitory concentration (MIC) ≤4 µg/mL against at least one of the organisms listed above. For at least one strain of every organism listed above, at least one example had an MIC ≤4 µg/mL.

Antimicrobial Activity Data (MIC's in µg/mL) for Specific Examples is Given in Table 2.

TABLE 2

| Organism | Example 45 µg/mL | Example 59 µg/mL | Example 84 µg/mL | Example 91 µg/mL | Example 92 µg/mL |
|---|---|---|---|---|---|
| *S. aureus* Oxford | 1 | 0.5 | 0.5 | 4 | 0.25 |
| *S. aureus* WCUH29 | 0.25 | ≤0.06 | 0.125 | 1 | 0.125 |
| *E. faecalis* I | 2 | 2 | 8 | 16 | 1 |
| *E. faecalis* X7501 | 8 | 1 | 16 | 16 | 1 |
| *H. influenzae* Q1 | 0.5 | 0.25 | 0.125 | 0.5 | 0.5 |
| *H. influenzae* H128 | 1 | 0.5 | 0.5 | 0.5 | 0.5 |
| *M. catarrhalis* 1502 | ≤0.06 | ≤0.06 | ≤0.06 | ≤0.06 | ≤0.06 |
| *S. pneumoniae* 1629 | 0.5 | 1 | 1 | 2 | 0.5 |
| *S. pneumoniae* N1387 | 0.25 | 0.5 | 1 | 0.5 | 0.125 |
| *S. pneumoniae* ERY2 | 0.25 | 0.25 | 1 | 1 | 0.25 |
| *E. coli* 3 | 32 | 16 | 16 | 4 | 16 |
| *S. pyogenes* 1308007P | 4 | 0.25 | 0.5 | 1 | 0.5 |

Animal Models of Infection

All procedures were performed in accordance with protocols approved by the GSK Institutional Animal Care and Use Committee, and meet or exceed the standards of the American Association for the Accreditation of Laboratory Animal Care (AAALAC), the United States Department of Health and Human Services and all local and federal animal welfare laws.

Rat Respiratory Tract Infection (RTI) Model with *H. Influenzae* or *S. Pneumoniae*.

In this model, anesthetized rats (male Sprague Dawley [Cr1:CD (SD)] 100 g) (Charles River) are infected by intrabronchial instillation of $2\text{-}3\times10^6$ bacterial CFU/rat in 100 μL of agar directly into the lungs [G. Smith (1991) Lab Animals vol 25, 46-49]. Animals (n=6 per group) are dosed with different amounts of compound (2-fold dilution ranging from 37.5 to 300 mg/kg) by oral gavage twice daily for 4 days starting 1 h after infection. Control animals are dosed with diluent on the same schedule. The rats are euthanized 96 h post infection and the lungs removed aseptically and homogenized in 1 mL of sterile saline with a stomacher machine. Ten fold serial dilutions are done in sterile saline to enumerate viable bacteria numbers. This rat lung infection model has been shown to be able to predict human efficacy in community-acquired pneumonia (CAP) caused by *S. pneumoniae* [Hoover J. L., C. Mininger, R. Page, R. Straub, S. Rittenhouse, and D. Payne. (2007). Abstract A-17. Proceedings of the 47th ICAAC, Chicago, Ill.].

Murine Groin *S. Aureus* Abscess Model of Skin and Soft Tissue Infection (SSTI).

In this model, anesthetized mice (male CD1, 20 g) (Charles River) are infected with *S. aureus* in semi-solid agar ($1\times10^6$ CFU/mouse) subcutaneously in the groin area (Jarvest, R. L., Berge, J. M., Berry, V., Boyd, H. F., Brown, M. J., Elder, J. S., Forrest, A. K., Fosberry, A. P., Gentry, D. R., Hibbs, M. J., Jaworski, D. D., O'Hanlon, P. J., Pope, A. J., Rittenhouse, S. Sheppard, R. J., Slater-Radosti, C. and Worby, A. (2002) J. Med. Chem., 45, 1959-1962). The animals (n=6 per group) are dosed with different amounts of compound (2-fold dilution ranging from 37.5 to 300 mg/kg) by oral gavage twice daily starting 1 h after infection. Control animals are dosed with diluent on the same schedule. Mice are euthanized 96 h post infection and the abscesses are aseptically removed and homogenized. Ten fold serial dilutions are done in sterile saline to enumerate viable bacteria numbers.

Results

Some of the examples described herein have demonstrated oral efficacy in one or more of the above animal models of infection, reducing the amount of bacteria recovered from lungs or abscesses, with respect to the untreated control animals, by $\geq 3 \log_{10}$ CFU/mL.

EXAMPLES

The following examples illustrate the present invention. These examples are not intended to limit the scope of the present invention, but rather to provide guidance to the skilled artisan to prepare and use the compounds, compositions, and methods of the present invention.

While particular embodiments of the present invention are described, the skilled artisan will appreciate that various changes and modifications can be made without departing from the spirit and scope of the present invention. Some of chemical compounds or pharmaceutically acceptable salts thereof of the present invention may be made by different chemical reaction methods or preparative procedures.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

1. g (grams); mg (milligrams);
2. L (liters); mL (milliliters);
3. μL (microliters); psi (pounds per square inch);
4. M (molar); mM (millimolar);
5. i.v. (intravenous); Hz (Hertz);
6. MHz (megahertz); mol (moles);
7. mmol (millimoles); rt (room temperature);
8. min (minutes); h (hours);
9. mp (melting point); TLC (thin layer chromatography);
10. $T_r$ (retention time); RP (reverse phase);
11. MeOH (methanol); i-PrOH (isopropanol);
12. TEA (triethylamine); TFA (trifluoroacetic acid);
13. TFAA (trifluoroacetic anhydride); THF (tetrahydrofuran);
14. DMSO (dimethylsulfoxide); EtOAc (ethyl acetate);
15. DME (1,2-dimethoxyethane); DCM (dichloromethane);
16. DCE (dichloroethane); DMF (N,N-dimethylformamide);
17. DMPU (N,N'-dimethylpropyleneurea); (CDI (1,1-carbonyldiimidazole);
    IBCF (isobutyl chloroformate); HOAc (acetic acid);
18. HOSu (N-hydroxysuccinimide); HOBT (1-hydroxybenzotriazole);
19. mCPBA (meta-chloroperbenzoic acid; EDC (ethylcarbodiimide hydrochloride);
20. BOC or Boc (tert-butyloxycarbonyl);
21. FMOC (9-fluorenylmethoxycarbonyl);
22. DCC (dicyclohexylcarbodiimide); CBZ (benzyloxycarbonyl);
23. Ac (acetyl); atm (atmosphere);
24. TMSE (2-(trimethylsilyl)ethyl); TMS (trimethylsilyl);
25. TIPS (triisopropylsilyl); TBS (t-butyldimethylsilyl);
26. DMAP (4-dimethylaminopyridine); BSA (bovine serum albumin)
27. ATP (adenosine triphosphate); HRP (horseradish peroxidase);
28. DMEM (Dulbecco's modified Eagle medium);
29. HPLC (high pressure liquid chromatography);
30. BOP (bis(2-oxo-3-oxazolidinyl)phosphinic chloride);
31. TBAF (tetra-n-butylammonium fluoride);
32. HBTU (O-Benzotriazole-1-yl-N,N,N',N'-tetramethyluronium hexafluorophosphate);
33. Red Al (sodium bis(2-methoxyethoxy)aluminum hydride;

-continued

34. HEPES (4-(2-hydroxyethyl)-1-piperazine ethane sulfonic acid);
35. DPPA (diphenylphosphoryl azide);   PCC (pyridinium chlorochromate);
36. fHNO$_3$ (fumed HNO$_3$);   EDTA (ethylenediaminetetraacetic acid);
37. Dess-Martin periodinane or Dess-Martin reagent (1,1,1-tris(acetoxy)-1,1-dihydro-1,2-benziodoxol-3-(1H)-one); and
38. Seyferth-Gilbert reagent or Gilbert-Seyferth reagent (dimethyl 1-diazo-2-oxopropylphosphonate).
39. All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.
40. $^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).
41. Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), atmospheric pressure chemical ionization (APCI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Column chromatography was performed on silica gel (230-400 mesh, Merck) or on an ISCO Sg100c chromatography instrument.
42. Reported HPLC retention times (rt) were obtained on a Waters 2795 instrument attached to a Waters 996 diode array detector reading 210-500 nm. The column used was a Synergi Max-RP (50 × 2 mm) model #00B-4337-B0. Solvent gradient was 15% methanol: water to 100% methanol (0.1% formic acid) over 4 or 6 min. Flow rate was 0.8 mL/min. Injection volume was 3 microliters.

Intermediates

Intermediate Example 1

(3S)-1-{[(Phenylmethyl)oxy]carbonyl}-3-pyrazolidinecarboxylic acid

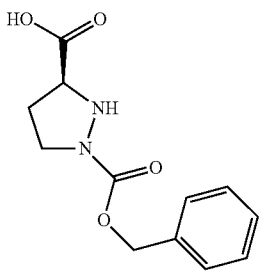 [SMILES: O=C(O)[C@@H]1CCN(C(=O)OCc2ccccc2)N1]

Method A

As outlined in Scheme 8

Part A

Methyl (2R)-2-hydroxy-4-iodobutanoate

To a solution of (3R)-3-hydroxydihydro-2(3H)-furanone (1.6 g, 16 mmol) and methanol (0.65 g, 16 mmol) in dichloromethane (50 mL) under N$_2$ at −10° C. was added TMSI (3.4 g, 17 mmol) over 0.5 hour. The mixture was stirred at the same temperature for 1 hour and was then allowed to warm up to room temperature and stirred for another 3 hours. TLC (PE:EA=1:1) showed that the reaction was completed. The mixture was washed with saturated aqueous NaHCO$_3$ (20 mL), 2% aq. Na$_2$S$_2$O$_3$ (20 mL) and brine (20 mL), dried (Na$_2$SO$_4$), and concentrated in vacuo to provide methyl (2R)-2-hydroxy-4-iodobutanoate as a yellowish oil (3.35 g, 85%). 1H NMR (300 MHz, CDCl$_3$) δ 4.26-4.23 (m, 1H), 3.79 (s, 3H), 3.29-3.26 (t, 2H), 2.83 (s, 1H), 2.38-2.25 (m, 1H), 2.19-2.01 (m, 1H).

Part B

Phenylmethyl 2-{(1S)-3-iodo-1-[(methyloxy)carbonyl]propyl}hydrazinecarboxylate

To a solution of methyl (2R)-2-hydroxy-4-iodobutanoate (3.35 g, 13.7 mmol) in DCM (100 mL) under N$_2$ at −70° C. was added 2,6-lutidine (5.67 g, 55 mmol), followed by triflate anhydride (4.07 g, 144.4 mmol) dropwise. Stirring continued at the same temperature for 1 hour. Phenylmethyl hydrazinecarboxylate (2.74 g, 16.5 mmol) was added in one portion, and the reaction mixture was allowed to warm up to room temperature and stirred for 24 hours. The reaction mixture was concentrated, and the crude oil was purified by column chromatography (PE:EA=20:1 to 1:1) to provide phenylmethyl 2-{(1S)-3-iodo-1-[(methyloxy)carbonyl]propyl}hydrazinecarboxylate as yellow oil (3.7 g, 83%). 1H NMR (300 MHz, CDCl$_3$) δ 7.35-7.34 (m, 5H), 6.51 (s, 1H), 5.13 (s, 2H), 4.27 (s, 1H), 3.76-3.70 (m, 4H), 3.42-3.30 (m, 2H), 2.25-2.06 (m, 2H).

Part C

3-Methyl 1-(phenylmethyl)(3S)-1,3-pyrazolidinedicarboxylate

To a solution of phenylmethyl 2-{(1S)-3-iodo-1-[(methyloxy)carbonyl]propyl}hydrazinecarboxylate (3.38 g, 8.6 mmol) in CH$_3$CN (500 mL) was added K$_2$CO$_3$ (2.38 g, 17.2 mmol), and the mixture was stirred overnight at rt. LC-MS showed that all starting material was consumed. The mixture was filtered, and the filtrate was concentrated to provide the crude 3-methyl 1-(phenylmethyl) (3S)-1,3-pyrazolidinedicarboxylate as an oil (2.77 g, 100%) without further purification.

Part D (3S)-1-{[(Phenylmethyl)oxy]carbonyl}-3-pyrazolidinecarboxylic acid

To a solution of 3-methyl 1-(phenylmethyl) (3S)-1,3-pyrazolidinedicarboxylate (2.77 g, 10.5 mmol) in THF (20 mL) at 0° C. was added a portion of LiOH monohydrate. The mixture was warmed up to rt and stirred for 2 hours. TLC showed that the starting material was consumed completely. THF was distilled off, and the mixture was cooled to 0° C. Citric acid (4.8 g, 25.2 mmol) in water (20 mL) was then added dropwise. The aqueous mixture was extracted with DCM (8×20 mL), the combined organic phases were dried ($Na_2SO_4$), filtered and concentrated to provide (3S)-1-{[(phenylmethyl)oxy]carbonyl}-3-pyrazolidinecarboxylic acid as yellowish solid (1.8 g, 83%). 1H NMR (300 MHz, DMSO-D6) δ 7.43-7.29 (m, 5H), 5.07 (s, 2H), 3.76-3.71 (m, 1H), 3.52-3.37 (m, 2H), 2.25-2.06 (m, 2H).

Method B

As outlined in Scheme 10

(3S)-1-{[(Phenylmethyl)oxy]carbonyl}-3-pyrazolidinecarboxylic acid

Part A 2,4-Dibromobutanoic acid

Dihydrofuran-2(3H)-one (3000 g, 34.88 mol) was charged into a 20 L four necked round bottomed flask with a reflux condenser. Tribromophosphine (70 g, 0.26 mol) was added under N2 (gas). The mixture solution was heated at 110° C. Bromine (5800 g, 36.25 mol) was added dropwise to the above solution while maintaining the temperature at 100° C.~110° C. (The addition completion around 7 h). The mixture solution was reacted for an additional 1 hour. The mixture solution was cooled to room temperature. N2 (gas) was introduced into the reaction solution to remove excess bromine. The crude acid (8000 g, 32.79 mol, 96%) was obtained as brown oil, which was used in the next step without any purification.

Part B 1,1-Dimethylethyl 2,4-dibromobutanoate 2,4-Dibromobutanoic acid (the crude product from above) dissolved in DCM (10 L) in a 50 L-reactor. 2-Methylpropan-2-ol (12000 g, 162.16 mol) and boron anhydride (8000 g, 114.29 mol) were added to the above solution. 1680 g of $H_2SO_4$ was added dropwise to the above solution under N2 (gas) while maintaining the temperature at room temperature (25-30° C.). The mixture was allowed to react for 24 h at room temperature. Then 15 L aqueous $Na_2CO_3$ (sat.) was added to quench the reaction. The organic phase was separated and dried over $Na_2SO_4$. The solvent was removed under vacuum to give the crude product, which was purified by silica gel column chromatography to give tert-butyl 2,4-dibromobutanoate as a brown oil (3800 g, 12.58 mol, 39%).

Part C

Bis(phenylmethyl) 1,2-hydrazinedicarboxylate

A solution of sodium hydroxide (2.50 kg, 62.5 mol) in water (40 L) was charged into an 100 L reactor. Hydrazine hydrate (2.00 kg, 40 mol) and THF (8 L) were added into the above solution. The mixture solution was cooled at 0° C. A pre-prepared solution of Cbz-Cl (13.60 kg CbzCl, 61.99 mol) in 2 L THF was added dropwise to the solution while maintaining the temperature at 0° C. The reaction was allowed to stir for an additional 4 h and a solid precipitated from the solution. The solid was collected by filtration, which was suspended in toluene (5 L). The suspended solution was heated at 80° C., which became clear. The water in the crude product was removed completely under reflux using a Dean-Stark apparatus. The resulting solution was cooled to room temperature and the product precipitated. The product was obtained after filtration to afford bis(phenylmethyl) 1,2-hydrazinedicarboxylate (7.8 Kg, 26 mol, 65%) as a white solid.

Part D 3-(1,1-Dimethylethyl) 1,2-bis(phenylmethyl) 1,2,3-pyrazolidinetricarboxylate A solution of bis(benzyloxycarbonyl)hydrazine (2.65 g, 8.83 mol) in acetonitrile (30 L) was charged into 100 L-reactor. Cesium carbonate (6.00 kg, 18.4 mol) and tert-butyl 2,4-dibromobutyrate (2.65 kg, 8.83 mol) were added into the above solution. The mixture solution was heated at 50° C. for 2.5 h until the two starting materials were completely consumed. The mixture solution was cooled to room temperature. A filtration was performed to remove some undissolved materials. The filtrate was concentrated under vacuum to afford product (4000 g crude product) as a brown oil.

Part E 1,1-Dimethylethyl 3-pyrazolidinecarboxylate

A solution of 3-(1,1-dimethylethyl) 1,2-bis(phenylmethyl) 1,2,3-pyrazolidinetricarboxylate (2.00 kg, 4.54 mol) in 10 L methanol was charged into a 20 L four-necked round-bottomed flask under N2 (gas). Then 200 g Pd/C (10%, 65% water) was added carefully to the mixture solution. H2 (gas) was introduced to exchange N2 (gas) three times. The mixture solution was allowed to react at 25° C. under 1 atm of H2 for 8 h until the starting material was consumed completely. N2 (gas) was introduced to remove excess H2 (gas). A filtration was performed to remove the catalyst. The filtrate can be used in the next step without further purification.

Part F 3-(1,1-Dimethylethyl) 1-(phenylmethyl) 1,3-pyrazolidinedicarboxylate

A solution of 1,1-dimethylethyl 3-pyrazolidinecarboxylate as the filtrate from above, was charged into a 50 L reactor. TEA (1.389 kg, 13.75 mol, 1.1 eq) was added to the above solution under N2 (gas). The mixture solution was cooled to 0° C. Then the pre-prepared solution of Cbz-Osu (3.429 kg, 13.77 mol) in DCM (8 L) was added to the mixture solution while maintaining the temperature at 0° C. The reaction was allowed to react for 1 h. The solvent was removed under vacuum and the crude product was purified by silica gel column chromatography to give the desired crude product (1000 g) as a yellow oil. To this mixture was added 1500 mL of ether. A solid precipitated from the solution. A filtration was performed and the cake was collected to give the product (500 g, 1.63 mol, 18% for 3 steps) as a white solid.

Part G

1-{[(Phenylmethyl)oxy]carbonyl}-3-pyrazolidinecarboxylic acid

To a solution of hydrogen chloride (10 L, 12.2% wt) charged into a 20-L, round-bottomed flask was added 3-(1,1-dimethylethyl) 1-(phenylmethyl) 1,3-pyrazolidinedicarboxylate (1000 g, 3.27 mol at room temperature. The mixture solution was heated at 35° C. for 4 h. The mixture solution was poured into 10 kg of ice and the pH was adjusted to 4 using aqueous NaOH (5M) solution. The product precipitated out and a filtration was performed to give the product (690 g, 1.32 mol, 84%) as a white solid.

Part H (3S)-1-{[(Phenylmethyl)oxy]carbonyl}-3-pyrazolidinecarboxylic acid

1-{[(Phenylmethyl)oxy]carbonyl}-3-pyrazolidinecarboxylic acid (500 g, 1.99 mol) and (1R,2R)-2-amino-1-phenyl-1,3-propanediol (334 g, 1.99 mol) (Tsuda, Makoto; Yamamoto, Keiichiro; Koga, Ichiro. Preparation of optically active pyridyl ketone derivatives and method for preparation thereof by optical resolution using chiral amines. Jpn. Kokai Tokkyo Koho (2002)) were dissolved into a solution of MeCN (3.32 L) and water (0.83 L). The resulting solution was heated under reflux for 1 h. The mixture solution was cooled to 0° C. and stirred slowly for 4 h while maintaining the temperature at 0° C. The undesired salt precipitated out from the mixture solution. A filtration was performed and the filtrate was concentrated to give 750 g of the salt of (3S)-1-{[(phenylmethyl)oxy]carbonyl}-3-pyrazolidinecarboxylic acid as a white solid (Chiral purity: >70%). The 750 g was dissolved into 2 L of ethanol. The solution was heated under reflux for 1 h. The mixture was cooled to 0° C. and allowed to stir slowly at 0° C. for 5 h. The product was filtered and the filtrate cake was washed with cooled alcohol (500 mL) and acetonitrile (1000 ml×2). The cake was collected and dried in the air to give 300 g of the salt of (3S)-1-{[(phenylmethyl)oxy]carbonyl}-3-pyrazolidinecarboxylic acid (ee %≥99%) as a white solid. The resulting 300 g salt was dissolved in 1.5 L water under a nitrogen atmosphere. The pH value was adjusted to 3-4 using HCl (6M) while maintaining the temperature at 0° C. The suspended solution was stirred for 0.5 hour. The product was again filtered and dried under vacuum (40° C.) to give afford 115 g of (3S)-1-{[(phenylmethyl)oxy] carbonyl}-3-pyrazolidinecarboxylic acid (ee %≥99%, y=23%) product as white solid.

Intermediate Example 2

1-{[(Phenylmethyl)oxy]carbonyl}-3-pyrazolidinecarboxylic acid

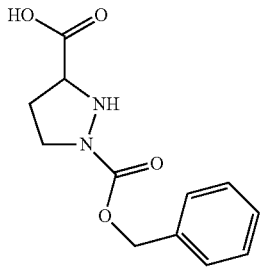 [SMILES: O=C(O)C1CCN(C(=O)OCc2ccccc2)N1]

As outlined in Scheme 9

Method A

Part A

Bis(phenylmethyl) 1,2-hydrazinedicarboxylate

Benzyl chloroformate (19.73 mL, 140 mmol) was added dropwise to a solution of hydrazine (2 mL, 63.7 mmol) in methanol (200 mL). Approximately half way through the addition, dropwise addition of a solution of sodium carbonate (14.86 g, 140 mmol) in water (150 mL) commenced. The resulting slurry was stirred for about 45 min before being filtered under suction, isolating a solid which was washed with ice water. The resulting filtrate was concentrated to remove the methanol, yielding a small quantity of solid material upon filtration. This solid material was again washed with ice water. The combined solids were recrystallized from straight toluene. The resulting white solid was dried in a vacuum oven at 60° C. for 5 hours. This yielded bis(phenylmethyl) 1,2-hydrazinedicarboxylate (13.74 g, 45.8 mmol, 71.8% yield) as a white crystalline solid.

Part B 3-(1,1-Dimethylethyl) 1,2-bis(phenylmethyl) 1,2,3-pyrazolidinetricarboxylate Bis(phenylmethyl) 1,2-hydrazinedicarboxylate (5.91 g, 19.68 mmol) was placed in a 500 ml round bottomed flask and acetonitrile (150 ml) was added followed by cesium carbonate (14.11 g, 43.3 mmol). 1,1-Dimethylethyl 2,4-dibromobutanoate (4.00 ml, 19.68 mmol) was added dropwise and the reaction was heated to 60° C. and stirred overnight. The resulting solution was cooled to room temperature and passed through a pad of celite. The filtrate was concentrated and purified via combiflash silica gel chromatography (0-100% EtOAC in hex) yielding 3-(1,1-dimethylethyl) 1,2-bis(phenylmethyl) 1,2,3-pyrazolidinetricarboxylate (5.3 g, 12.03 mmol, 61.1% yield) as a pale yellow oil.

Part C 1,1-Dimethylethyl 3-pyrazolidinecarboxylate 3-(1,1-Dimethylethyl) 1,2-bis(phenylmethyl) 1,2,3-pyrazolidinetricarboxylate (5.30 g, 12.03 mmol) was dissolved in methanol (100 mL) and 10% Pd/C (degussa type) (1.06 g, 0.996 mmol) was added. The mixture was stirred under a balloon of hydrogen for 60 min. LCMS showed clean deprotection. HCl in ether (6.02 mL, 12.03 mmol) was added, and the mixture was stirred 5 min. The catalyst was filtered off and the filtrate was evaporated, yielding 1,1-dimethylethyl 3-pyrazolidinecarboxylate.HCl (2.45 g, 11.74 mmol, 98% yield) as an orange solid.

Part D 3-(1,1-Dimethylethyl) 1-(phenylmethyl) 1,3-pyrazolidinedicarboxylate

At 0° C., to a 50 mL round bottomed flask charged with 1,1-dimethylethyl 3-pyrazolidinecarboxylate (0.054 g, 0.259 mmol) and stirrer in dichloromethane (DCM) (3 mL), was added triethylamine (0.079 mL, 0.569 mmol). After a couple of minutes, N-(benzyloxycarbonyloxy)succinimide (CBz-OSu) (0.064 g, 0.259 mmol) in dichloromethane (DCM) (1.5 mL) was added dropwise. The reaction mixture stirred at 0°

C. for one hour, then warmed to r.t. After 2 hr at r.t., the solvent was evaporated and the residue was dissolved in EtOAc (30 mL), washed with water (15 mL×2), sat. NaHCO$_3$ (15 ml), brine (15 mL), dried over Na$_2$SO$_4$ and concentrated to afford the crude product as a colorless gum (88 mg).

Part E

1-{[(Phenylmethyl)oxy]carbonyl}-3-pyrazolidinecarboxylic acid

At r.t., to a 50 mL round bottomed flask containing crude 3-(1,1-dimethylethyl) 1-(phenylmethyl) 1,3-pyrazolidinedicarboxylate (88 mg) in dichloromethane (DCM) (0.5 mL), was added HCl in ether (2M) (3.59 mL, 7.18 mmol), then the reaction vessel was equipped with a glass stopper. The reaction mixture was stirred at r.t. for 48 hr. The solid was filtered and washed with ether, providing the product as an off-white solid. (58.4 mg, 71% over two steps).

Method B

1-{[(Phenylmethyl)oxy]carbonyl}-3-pyrazolidinecarboxylic acid

Part A 1,1-Dimethylethyl 4,5-dihydro-1H-pyrazole-5-carboxylate

To a solution of t-butyl acrylate (17 g, 133 mmol) dissolved in toluene (200 mL) and n-hexanes (200 mL) was added TMS-diazomethane (99 mL, 199 mmol) over 10 minutes. After 1 h the reaction mixture was concentrated and the residue diluted with DCM (300 mL) and TFA (20.44 mL, 265 mmol) was added slowly over 15 minutes. After 30 minutes the reaction mixture was concentrated, basified with 1N NaOH and extracted into DCM (400 mL). The organic layer was dried over anhydrous sodium sulfate, filtered, concentrated, and purified by filtration through a pad of silica gel eluting the product with 50% ethyl acetate/hexanes to afford 10 g (54.6 mmol) of 1,1-dimethylethyl 4,5-dihydro-1H-pyrazole-5-carboxylate as a yellow oil. LC-MS (ES) m/e 170.91 (M+H)$^+$.

Part B 3-(1,1-Dimethylethyl) 1-(phenylmethyl) 1,3-pyrazolidinedicarboxylate

To a solution of 1,1-dimethylethyl 4,5-dihydro-1H-pyrazole-5-carboxylate (5 g, 29.4 mmol) dissolved in acetic acid (75 mL) was added sodium cyanoborohydride (3.69 g, 58.8 mmol) over 10 minutes. After 30 min. the reaction mixture was concentrated. The intermediate was diluted with ethyl acetate and basified with sat. Na$_2$CO$_3$. The ethyl acetate was dried over sodium sulfate, filtered, and concentrated. The intermediate was diluted with tetrahydrofuran (THF) (75 mL), and triethylamine was added (8.19 mL, 58.8 mmol), followed by Cbz-Cl (2.1 mL, 14.69 mmol). After 2 h, the organic salts were filtered and the crude product was purified by silica gel column using 20-80% EtOAc/hexanes to afford 2.8 g (9.14 mmol) of 3-(1,1-dimethylethyl) 1-(phenylmethyl) 1,3-pyrazolidinedicarboxylate. LC-MS (ES) m/e 307.0 (M+H)$^+$.

Part C

1-{[(Phenylmethyl)oxy]carbonyl}-3-pyrazolidinecarboxylic acid

To a solution of 3-(1,1-dimethylethyl) 1-(phenylmethyl) 1,3-pyrazolidinedicarboxylate (2.8 g, 9.14 mmol) in dichloromethane (DCM) (50 mL) was added TFA (42.2 mL, 548 mmol) and 10 mL of water. The reaction was stirred at 25° C. for 72 h. The solvent was removed under reduced pressure to give 1-{[(phenylmethyl)oxy]carbonyl}-3-pyrazolidinecarboxylic acid (2.2 g, 8.79 mmol,) which was used directly without further purification. LC-MS (ES) m/e 250.8 (M+H)$^+$.

Method C

1-{[(Phenylmethyl)oxy]carbonyl}-3-pyrazolidinecarboxylic acid

Part A 1,1-Dimethylethyl 4,5-dihydro-1H-pyrazole-5-carboxylate 1,1-Dimethylethyl 2-propenoate (10.25 ml, 70 mmol) was added to a round-bottom flask equipped with a stirring bar and charged with toluene (100 ml) and tetrahydrofuran (THF) (100 ml) under nitrogen, and then TMS-diazomethane (42.0 ml, 84 mmol) was added. After 4 h, the reaction solvents and excess TMS-diazomethane were removed in vacuo. The residue was dissolved in dichloromethane (150 mL). TFA (6.26 ml, 84 mmol) was added at 0° C. and the resulting mixture was stirred at room temperature overnight. After this time, the reaction was quenched with sat. Na$_2$CO$_3$ and extracted with dichloromethane. The organic layer was dried over Na$_2$SO$_4$. The solvent was removed under reduced pressure to give the crude product as yellow oil, which was purified by silica gel chromatography (Combiflash, 120 g column, hexane/ethyl acetate 0-30% 60 min) to yield the desired product 1,1-dimethylethyl 4,5-dihydro-1H-pyrazole-5-carboxylate (9.7 g, 81% yield) as yellow oil.

Part B

Bis(1,1-dimethylethyl) 4,5-dihydro-1H-pyrazole-1,5-dicarboxylate

To a solution of 1,1-dimethylethyl 4,5-dihydro-1H-pyrazole-5-carboxylate (9.7 g, 57.0 mmol) and bis(1,1-dimethylethyl)dicarbonate (14.93 g, 68.4 mmol) in dichloromethane (86 ml) was added triethylamine (15.89 ml, 114 mmol). The reaction mixture was stirred for 4 days at 25° C. The reaction solution was then washed with 1N HCl (1×500 mL), dried over Na$_2$SO$_4$, filtered, and concentrated to give a residue. The residue was purified by silica gel chromatography (CombiFlash, column: 220 g, 0-50% ethyl acetate in hexane, 60 min) to afford the desired product as light yellow oil.

Part C

Di-tert-butyl pyrazolidine-1,5-dicarboxylate

Di-tert-butyl 4,5-dihydropyrazole-1,5-dicarboxylate (12.65 g, 46.8 mmol) was dissolved in acetic acid (69.2 ml), and the solution was cooled in a water bath. Sodium cyanoborohydride (5.88 g, 94 mmol) was added portionwise under N$_2$. The reaction was stirred at 25° C. for 5 hrs. The solvent was then removed under reduced pressure to give a residue. The residue was diluted with EtOAc (150 mL), and Na₂CO₃ (sat.) (100 mL) was cautiously added to the solution. The layers were separated and the aq. solution was extracted with EtOAc (2×30 mL), and the organics were dried over Na₂SO₄. The solvent was removed under reduced pressure to give the crude product di-tert-butyl pyrazolidine-1,5-dicarboxylate (12.74 g) as light yellow oil, which was used directly in the next step.

Part D

1-Benzyl 2,3-di-tert-butyl pyrazolidine-1,2,3-tricarboxylate

Sat. aq. K₂CO₃ (210 mL) was added into a solution of benzyl chloroformate (12.0 ml, 84 mmol) and crude di-tert-butyl pyrazolidine-1,5-dicarboxylate (12.74 g, assumed 46.8 mmol) in acetonitrile (137 ml) at 0° C. The reaction was allowed to warm to room temperature and was stirred for 4.5 hrs. The aqueous phase was extracted with EtOAc (3×100 mL), and the organic layers were dried over Na₂SO₄. The solvents were removed in vacuo, and the crude product was purified by silica gel chromatography (CombiFlash, Column: 220 g; 0-35% ethyl acetate in hexane; 60 min) to provide the desired product 1-benzyl 2,3-di-tert-butyl pyrazolidine-1,2,3-tricarboxylate (14.15 g, 74% yield) as a white solid.

Part E

1-{[(Phenylmethyl)oxy]carbonyl}-3-pyrazolidinecarboxylic acid

1-Benzyl 2,3-di-tert-butyl pyrazolidine-1,2,3-tricarboxylate (14.15 g, 34.8 mmol) was dissolved in dichloromethane (68.6 ml) under N₂ at room temperature. TFA (80 ml, 1045 mmol) and water (9.41 ml, 522 mmol) were then added in one portion. The reaction was stirred at 25° C. for 2 days. The solvent was then removed under reduced pressure to give 1-{[(phenylmethyl)oxy]carbonyl}-3-pyrazolidinecarboxylic acid (8.72 g, 34.8 mmol, 100% yield).

Intermediate Example 3

2-[(2R)-3-Cyclopentyl-2-({formyl[(phenylmethyl)oxy]amino}methyl)propanoyl]-1-{[(phenylmethyl)oxy]carbonyl}-3-pyrazolidinecarboxylic acid

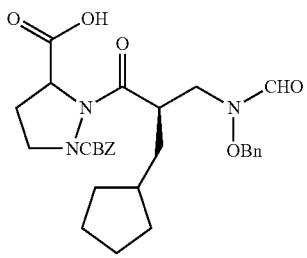

Part A (2R)-3-Cyclopentyl-2-({formyl[(phenylmethyl)oxy]amino}methyl)propanoyl fluoride To a solution of (2R)-3-cyclopentyl-2-({formyl[(phenylmethyl)oxy]amino}methyl)propanoic acid (as prepared in Scheme 1; also described in WO 2009061879) (5.2 g, 17.03 mmol) dissolved in dichloromethane (DCM) (75 mL) was added 2,4,6-trifluoro-1,3,5-triazine (1.5 mL, 17.9 mmol) followed by pyridine (1.51 mL, 18.7 mmol). The reaction mixture was stirred at 25° C. for 2 h, and then the reaction mixture was diluted with DCM (100 mL) and washed (1×50 mL) with 5% citric acid followed by 50 mL of sat. NaHCO₃. The organic layer was dried over magnesium sulfate, filtered, and concentrated to give (2R)-3-cyclopentyl-2-({formyl[(phenylmethyl)oxy]amino}methyl)propanoyl fluoride as a pale yellow oil. LC-MS (ES) m/e 306.8 (M+H)⁺.

Part B

2-[(2R)-3-Cyclopentyl-2-({formyl[(phenylmethyl)oxy]amino}methyl)propanoyl]-1-{[(phenylmethyl)oxy]carbonyl}-3-pyrazolidinecarboxylic acid To a solution of (2R)-3-cyclopentyl-2-({formyl[(phenylmethyl)oxy]amino}methyl)propanoyl fluoride (3.24 g, 10.55 mmol) in DMF (30 mL) was added 1-{[(phenylmethyl)oxy]carbonyl}-3-pyrazolidinecarboxylic acid (2.2 g, 8.79 mmol) followed by DIPEA (3.07 mL, 17.58 mmol). The reaction was stirred at 25° C. for 18 hrs. The reaction was concentrated and purified by reverse-phase HPLC to afford 2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid as a mixture of diastereomers. LC-MS (ES) m/e 538.8 (M+H)⁺.

Additionally, 2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid can be purified by silica gel chromatography, producing a mixture of diastereomers enriched in the desired diastereomer, (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid. 2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid can also be purified by automated chiral prep SFC, providing the pure diastereomer, (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid.

Intermediate Example 4

(3S)-2-[(2R)-3-Cyclopentyl-2-({formyl[(phenylmethyl)oxy]amino}methyl)propanoyl]-1-{[(phenylmethyl)oxy]carbonyl}-3-pyrazolidinecarboxylic acid

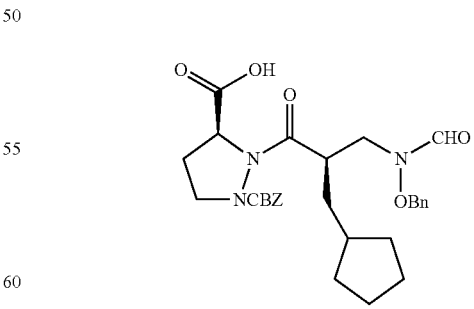

Method A (2R)-3-Cyclopentyl-2-({formyl[(phenylmethyl)oxy]amino}methyl)propanoyl fluoride (see Intermediate 3, Part A) (4 g, 13.0 mmol) was added into a solution of (3S)-1-{[(phenylmethyl)oxy]carbonyl}-3-pyrazolidinecarboxylic acid (3.58 g, 14.3 mmol) in dichloromethane (52.9 ml), followed by Hunig's base (6.80 ml, 39.0 mmol). The reaction mixture was stirred at 25° C. for 2.5 hrs. The reaction was then diluted with dichloromethane (200 ml), and acetic acid (9 ml) was added. The resulting solution was washed with aqueous NH$_4$Cl (200 mL). The aqueous solution was extracted with dichloromethane (2×50 mL). The combined organic layers were dried over Na$_2$SO$_4$, filtered and concentrated to provide a residue. The desired product crashed out after the addition of a few milliliters of ethyl acetate. The desired product was filtered and washed with ethyl acetate, providing 3.49 g as a white solid. The filtrates were purified by silica gel chromatography (CombiFlash; Column: 40 g; 0-100% ethyl acetate in hexane; 30 min). The third peak was collected, and the solvent was removed to provide a solid. The solid was washed with approximately 10 ml of acetonitrile, and the mixture was filtered to give a second batch of the desired product (870 mg) as a white solid. Both batches were combined to yield the final batch of product, (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (4.36 g, 8.1 mmol, 62% yield).

Method B (3S)-2-[(2R)-3-Cyclopentyl-2-({formyl[(phenylmethyl)oxy]amino}methyl)propanoyl]-1-{[(phenylmethyl)oxy]carbonyl}-3-pyrazolidinecarboxylic acid

Part A (2R)-3-Cyclopentyl-2-({formyl[(phenylmethyl)oxy]amino}methyl)propanoyl fluoride 2,4,6-Trifluoro-1,3,5-triazine (10.7 g, 79 mmol) was added into a solution of pyridine (6.4 ml, 79 mmol) and (2R)-3-cyclopentyl-2-({formyl[(phenylmethyl)oxy]amino}methyl)propanoic acid (WO 2009061879) (22 g, 72.0 mmol) in dichloromethane (348 ml) at room temperature. The resulting solution was stirred overnight. Dichloromethane (300 mL) was added to the reaction solution, followed by 1000 mL of 5% citric acid, and the mixture was filtrated. The solids were washed with DCM (300 ml). The organic layer of the filtrate was separated and washed with sat. NaHCO$_3$ (2×300 mL). The organic layer was dried over Na$_2$SO$_4$, filtered and concentrated to yield a yellow oil, which was purified by silica gel chromatography (CombiFlash, Column: 220 g; 0-20% ethyl acetate in hexane; 50 min) to provide (2R)-3-cyclopentyl-2-({formyl[(phenylmethyl)oxy]amino}methyl)propanoyl fluoride (14.32 g, 64.7% yield) as a colorless oil.

Part B (3S)-2-[(2R)-3-Cyclopentyl-2-({formyl[(phenylmethyl)oxy]amino}methyl)propanoyl]-1-{[(phenylmethyl)oxy]carbonyl}-3-pyrazolidinecarboxylic acid (2R)-3-Cyclopentyl-2-({formyl[(phenylmethyl)oxy]amino}methyl)propanoyl fluoride (8.18 g, 26.6 mmol) was added into a solution of 1-{[(phenylmethyl)oxy]carbonyl}-3-pyrazolidinecarboxylic acid (8.65 g, 34.6 mmol) in dichloromethane (85 ml), and followed by Hunig's base (23.2 ml, 133 mmol). The reaction mixture was stirred at 25° C. for 5 hrs. The reaction was then diluted with DCM (50 ml), and acetic acid (6 ml) was added. The resulting solution was washed with aqueous NH$_4$Cl (2×200 mL). The aqueous solution was extracted with DCM (2×100 mL). The combined organic layers were dried over Na$_2$SO$_4$, filtered and concentrated to provide a residue. The residue was purified by silica gel chromatography (CombiFlash, Column: 220 g; 0-100% ethyl acetate in hexane; 40 min). The first ⅔ of the eluting fractions were combined, and the solvent was removed to give a residue. Acetonitrile (~5 ml) was added to the residue. The diastereomer (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid remained as a white solid. The white solid was filtered, washed with MeCN (3×0.5 mL), and air dried to give (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid as a white solid (1.94 g). The solvent was removed from the filtrates, and ethyl acetate was added. Solid precipitated again, and the solvent was removed by filtration to give another portion of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid as a white solid (274 mg). The filtrates were dried to give a oily residue. The oily residue was dissolved into ethyl acetate (5 ml), hexane was added, and the solvent was decanted to give a residue. This procedure was repeated several times to yield another portion of solid (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (250 mg). The three batches of desired product were combined to form the final batch of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (2.46 g, 17% yield).

Intermediate Example 5

(3S)-2-[(2R)-2-({Formyl[(phenylmethyl)oxy]amino}methyl)hexanoyl]-1-{[(phenylmethyl)oxy]carbonyl}-3-pyrazolidinecarboxylic acid

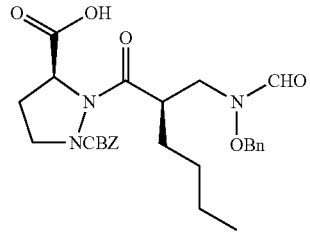

Part A (4S)-3-Hexanoyl-4-(phenylmethyl)-1,3-oxazolidin-2-one

To a 3000 mL RB flask was added (4S)-4-(phenylmethyl)-1,3-oxazolidin-2-one (100 g, 0.564 mol) in THF (1500 mL). The solution was cooled to −78° C. and n-butyl lithium (1.6 M in hexanes, 387 mL, 0.62 mol) was added dropwise. Stirring continued for 30 min. Hexanoyl chloride (74.8 g, 0.62 mol) was then added dropwise and the reaction was monitored by TLC. The reaction was quenched by addition of NH$_4$Cl (400 mL), and extracted with DCM (2×500 mL). The product was purified by flash column eluting with ethyl acetate/petroleum ether (1:50 to 1:20) to afford the title compound (118 g, 76%). LCMS: (M+H)+: 276.1.

Part B (4S)-3-[(2R)-2-(Hydroxymethyl)hexanoyl]-4-(phenylmethyl)-1,3-oxazolidin-2-one To a 3000 mL RB flask was added (4S)-3-hexanoyl-4-(phenylmethyl)-1,3-oxazolidin-2-one (3) (118 g, 0.429 mol) in DCM (1500 mL). The solution was cooled to 0° C. and $TiCl_4$ (50 mL, 0.45 mol) in DCM (40 mL) was added dropwise. After 10 min, DIPEA was added dropwise. The mixture became dark-red and was stirred at 0° C. for 1 h. Trioxane (46.3 g, 0.515 mol) in DCM (400 mL) was then added dropwise, followed by another portion of $TiCl_4$ (50 mL, 0.45 mol) in DCM (40 mL). TLC indicated the reaction was completed after 80 min. The reaction was quenched by sat $NH_4Cl$ (1200 mL) and extracted with DCM (2×500 mL). the combined organic solution was washed with water (700 mL), brine (700 mL), and dried ($MgSO_4$). The organic solvent was removed to afford the title compound as a yellow solid (147 g, 112%).

Part C (2R)-2-(Hydroxymethyl)hexanoic acid

To a 2000 mL roundbottom flask was added (4S)-3-[(2R)-2-(hydroxymethyl)hexanoyl]-4-(phenylmethyl)-1,3-oxazolidin-2-one (4) (82 g, 0.268 mol) in THF/water (4:1, 750 mL). The solution was cooled to 0° C. and $H_2O_2$ (130 mL, 1.07 mol) was added dropwise, followed by lithium hydroxide monohydrate (22.58 g, 0.537 mol) in water (130 mL). The reaction mixture was warmed up to rt and stirred overnight. THF was removed under vacuum, and the aqueous solution was washed with ethyl acetate. The aqueous solution was then acidified to pH ~3.0 and extracted with ethyl acetate. The extracts were dried (Na2SO4), filtered and concentrated to provide the title compound (42 g, 107%). LCMS: (2M+H)+: 313.2.

Part D (2R)-2-(Hydroxymethyl)-N-[(phenylmethyl)oxy]hexanamide

To a 3000 mL roundbottom flask was added (2R)-2-(hydroxymethyl)hexanoic acid (5) (77 g, 0.527 mol) in THF/water (4:1, 1800 mL), followed by benzylhydroxylamine hydrochloride (100 g, 0.632 mol). The mixture was cooled to 0° C. and was adjusted with 1 N HCl to pH ~4.5. EDCI (202 g, 1.05 mol) was added in one portion. The mixture was stirred at 0° C. for 2 h, while the pH of the mixture was maintained at ~4.5 by addition of 1 N HCl. THF was then removed under vacuum, and the white solid was collected by filtration to afford the titled compound as a crude mixture (100 g). Further purification by flash column eluting with ethyl acetate/petroleum ether (1:10) provided the pure product (52 g, 39%). LCMS: (M+H)+: 252.2.

Part E (3R)-3-Butyl-1-[(phenylmethyl)oxy]-2-azetidinone

To a solution of (2R)-2-(hydroxymethyl)-N-[(phenylmethyl)oxy]hexanamide (6) (52 g, 0.21 mol) and $Ph_3P$ (60 g, 0.23 mol) in THF (1500 mL) at 0° C. was added DIAD (41.8 g, 0.21 mol). The mixture was warmed up to rt and stirred overnight. TLC indicated completion of the reaction. THF was removed under vacuum. The residue was titurated with ethyl acetate/petroleum ether (1:10) and filtered. The filtrate was concentrated and the residue was purified by flash column chromatography to provide the title compound (52.8 g, 110%). LCMS: (M+H)+: 234.2.

Part F (2R)-2-({[(Phenylmethyl)oxy]amino}methyl)hexanoic acid

To a solution of (3R)-3-butyl-1-[(phenylmethyl)oxy]-2-azetidinone (7) (52.8 g, 0.23 mol) in THF/MeOH (3:1, 1500 mL) at 0° C. was added Lithium hydroxide monohydrate (11.4 g, 0.27 mol) in water (375 mL). The mixture was warmed up to rt and stirred overnight. TLC indicated completion of the reaction. Organic solvents were removed under vacuum, and the aqueous solution was washed with DCM, acidified with 4 N HCl to pH ~2.0, and extracted with DCM. The extracts were dried, filtered and concentrated to provide the title compound (40 g, 69%). LCMS: (M+H)+: 252.2.

Part G (2R)-2-({Formyl[(phenylmethyl)oxy]amino}methyl)hexanoic acid

To a solution of 1H-1,2,3-benzotriazole-1-carbaldehyde (26 g, 0.18 mol) in THF (200 ml) at 0° C. was added dropwise a solution of (2R)-2-({[(phenylmethyl)oxy]amino}methyl)hexanoic acid (8) (40 g, 0.16 mol) in THF (200 mL). The reaction mixture was warmed up to rt and stirred overnight. LC/MS indicated completion of the reaction. To the reaction mixture at 0° C. was added water (400 mL), $Na_2CO_3$ (36 g), and $Boc_2O$ (43.6 g, 0.36 mol). The mixture was stirred for 3 h. THF was removed under vacuum. The aqueous mixture was washed with ether and then acidified to pH ~2.0 with acetic acid, and extracted with ethyl acetate. The extracts were dried and concentrated to provide the title compound (36.8 g, 80%). LCMS: (M+H)+: 280.2.

Part H (2R)-2-({Formyl[(phenylmethyl)oxy]amino}methyl)hexanoyl fluoride

To a solution of (2R)-2-({formyl[(phenylmethyl)oxy]amino}methyl)hexanoic acid (9) (1.7 g, 6.1 mmol) in DCM (20 mL) was added pyridine (0.53 g, 6.7 mmol), followed by 2,4,6-trifluoro-1,3,5-triazine (0.86 g, 6.4 mmol) dropwise. The reaction mixture was stirred for 4 h and TLC indicated completion of the reaction. The reaction mixture was washed with 10% aqueous citric acid and brine, dried over Na2SO4, and concentrated to provide the title compound (1.7 g, 100%) as red oil. 1H NMR (300 MHz, DMSO) δ ppm 0.86 (t, J=6.7 Hz, 3H), 1.16-1.38 (m, 4H), 1.57 (m, 2H), 3.03 (m, 1H), 3.87 (m, 2H), 4.91 (s, 2H), 7.41 (m, 5H).

Part I (3S)-2-[(2R)-2-({Formyl[(phenylmethyl)oxy]amino}methyl)hexanoyl]-1-{[(phenylmethyl)oxy]carbonyl}-3-pyrazolidinecarboxylic acid To a solution of 1-{[(phenylmethyl)oxy]carbonyl}-3-pyrazolidinecarboxylic acid 91.52 g, 6.1 mmol) and DIPEA (3.15 g, 24.4 mmol) in DMF (8 mL) was added (2R)-2-({formyl[(phenylmethyl)oxy]amino}methyl)hexanoyl fluoride (10) (1.7 g, 6.1 mmol) in DMF. The reaction mixture was stirred at rt overnight and LC/MS indicated completion of the reaction. The mixture was diluted with ethyl acetate (20 mL), and washed with 5% aqueous citric acid, brine, dried over $Na_2SO_4$, and concentrated. The residue was purified by column chromatography eluting with ethyl acetate/petroleum ether (1:1) followed by DCM/MeOH (200:1) to provide the title compound (0.48 g, 32%). LCMS: $(M+H)^+$: 512.0. 1H NMR (300 MHz, $CDCl_3$) δ ppm 0.79 (t, J=6.0 Hz, 3H), 1.10 (m, 4H), 1.40 (m, 1H), 1.57 (m, 1H), 1.77 (m, 1H), 2.17 (m, 1H), 2.97 (m, 2H), 3.25-3.69 (m, 1H), 4.13 (m, 3H), 4.56-4.93 (m, 2H), 5.12 (s, 2H), 7.34 (m, 10H), 7.74 (s, 0.3H), 8.36 (s, 0.6H).

Intermediate Example 6

4,5-Dihydro-1H-pyrazole-5-carboxylic acid

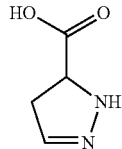

To a solution of 1,1-dimethylethyl 4,5-dihydro-1H-pyrazole-5-carboxylate (5.0 g, 29.4 mmol) (see Intermediate Example 2) in dichloromethane (DCM) (56 mL) was added TFA (56 mL, 734 mmol) at room temperature, and the resulting mixture was stirred overnight. LCMS indicated that the reaction was complete. The solvent and TFA were removed under reduced pressure to afford the product, 4,5-dihydro-1H-pyrazole-5-carboxylic acid. MS: 115 ([M+H].

Intermediate Example 7

1-{(2R)-2-(Cyclopentylmethyl)-4-[(1,1-dimethylethyl)oxy]-4-oxobutanoyl}-4,5-dihydro-1H-pyrazole-5-carboxylic acid

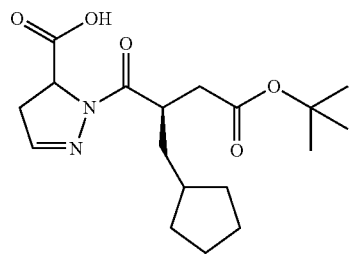 [SMILES: CC(C)(C)OC(=O)C[C@@H](CC1CCCC1)C(=O)N1N=CCC1C(=O)O]

Part A 1,1-Dimethylethyl (3R)-3-(cyclopentylmethyl)-4-fluoro-4-oxobutanoate

To a solution of (2R)-2-(cyclopentylmethyl)-4-[(1,1-dimethylethyl)oxy]-4-oxobutanoic acid (Tetrahedron, 2001, 57(36), 7675-7683) (4.0 g, 15.60 mmol) in DCM was added pyridine (1.38 ml, 17.2 mmol) and a solution of 2,4,6-trifluoro-1,3,5-triazine (2.3 g, 17.2 mmol) in DCM (10 mL). The reaction was stirred at room temperature for 2 h. The solution was then washed with citric acid (20 mL×2) and brine (20 mL), then concentrated to provide the crude product, 1,1-dimethylethyl (3R)-3-(cyclopentylmethyl)-4-fluoro-4-oxobutanoate, as a yellow oil (3.8 g, 57% yield), which was used directly in the next step. MS: 257 $([M-H]^+)$.

Part B

1-{(2R)-2-(Cyclopentyl methyl)-4-[(1,1-dimethylethyl)oxy]-4-oxobutanoyl}-4,5-dihydro-1H-pyrazole-5-carboxylic acid To a solution of 4,5-dihydro-1H-pyrazole-5-carboxylic acid (1.44 g, 8.8 mmol) in dichloromethane (DCM) (62 ml) at 0° C. was added Hunig's base (9.25 ml, 53.0 mmol) followed by 1,1-dimethylethyl (3R)-3-(cyclopentylmethyl)-4-fluoro-4-oxobutanoate (3.8 g, 8.8 mmol) in 10 mL DCM. The resulting mixture was allowed to warm to room temperature and stirred for 4 hours. The mixture was then cooled to 0° C. and acetic acid (2.5 ml, 44.1 mmol) was added, followed by sat. aq ammonium chloride (15 mL). The phases were separated and the aqueous phase was extracted once with DCM (20 mL). The combined organics were washed with brine (15 mL), dried over sodium sulfate, and concentrated to yield a yellow oil. This crude product was purified by Combiflash automated silica gel chromatography (0-100% EtOAc in hex) to afford 1-{(2R)-2-(cyclopentylmethyl)-4-[(1,1-dimethylethyl)oxy]-4-oxobutanoyl}-4,5-dihydro-1H-pyrazole-5-carboxylic acid (1.78 g, 5.05 mmol, 57% yield) as a clear oil. MS: 353 ([M+H]+).

Intermediate Example 8

(5S)-1-{[(1,1-Dimethylethyl)oxy]carbonyl}-4,5-dihydro-1H-pyrazole-5-carboxylic acid

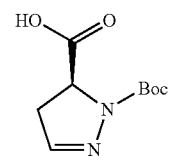

Part A (3S)-2-{[(1,1-Dimethylethyl)oxy]carbonyl}-1-{[(phenylmethyl)oxy]carbonyl}-3-pyrazolidinecarboxylic acid To a 100 ml round bottom flask was added (3S)-1-{[(phenylmethyl)oxy]carbonyl}-3-pyrazolidinecarboxylic acid (1.98 g, 7.9 mmol) in tetrahydrofuran (THF) (40 mL), followed by triethylamine (1.3 mL, 9.5 mmol) and $(Boc)_2O$ (1.9 mL, 8.3 mmol). The mixture was stirred at room temperature overnight. The organic solution was concentrated under vacuum and the residue was dissolved in DCM (30 mL) and extracted with ice-cooled 0.5 M LiOH (2×25 mL). The combined aqueous solution was cooled to 0° C. and acidified to ~pH 2.0 with 6 N HCl, and then extracted with DCM (3×30 mL). The combined organic solution was dried ($Na_2SO_4$), filtered and concentrated to afford (3S)-2-{[(1,1-dimethylethyl)oxy]carbonyl}-1-{[(phenylmethyl)oxy]carbonyl}-3-pyrazolidinecarboxylic acid (1.84 g, 5.25 mmol, 66% yield) as a foamy solid.

Part B (3S)-2-{[(1,1-Dimethylethyl)oxy]carbonyl}-3-pyrazolidinecarboxylic acid

To a 100 ml round bottom flask was added (3S)-2-{[(1,1-dimethylethyl)oxy]carbonyl}-1-{[(phenylmethyl)oxy]carbonyl}-3-pyrazolidinecarboxylic acid (1.84 g, 5.25 mmol) in methanol (30 mL), followed by Pd(OH)$_2$ on carbon (20%, wet) (24.7 mg, 0.035 mmol). The mixture was degassed and stirred under an H$_2$ atmosphere (balloon) at room temperature until LCMS indicated completion of the reaction (1 h). The catalyst was filtered off, and the filtrate was concentrated under vacuum to afford (3S)-2-{[(1,1-dimethylethyl)oxy]carbonyl}-3-pyrazolidinecarboxylic acid (1.03 g, 4.77 mmol, 91% yield) as an off white solid.

Part C (5S)-1-{[(1,1-Dimethylethyl)oxy]carbonyl}-4,5-dihydro-1H-pyrazole-5-carboxylic acid To a 50 ml round bottom flask was added (3S)-2-{[(1,1-dimethylethyl)oxy]carbonyl}-3-pyrazolidinecarboxylic acid (431 mg, 1.99 mmol) in methanol (15 mL), followed by iodobenzene diacetate (770 mg, 2.39 mmol). The mixture was stirred at room temperature for 10 min, and LCMS indicated the reaction was complete. The organic solvent was removed under vacuum, and the residue was taken up in 1 M aq. NaHCO$_3$ (30 mL). The aqueous mixture was washed with DCM (3×20 mL), acidified with 6 N HCl to ~pH 2.0, and then extracted with DCM (3×30 mL). The combined organic extracts were dried (Na$_2$SO$_4$), filtered, and concentrated under vacuum to afford (5S)-1-{[(1,1-dimethylethyl)oxy]carbonyl}-4,5-dihydro-1H-pyrazole-5-carboxylic acid (273 mg, 1.27 mmol, 64% yield) as a clear oil.

COMPOUND EXAMPLES

Example 1

(3S)-2-((2R)-3-Cyclopentyl-2-{[formyl(hydroxy)amino]methyl}propanoyl)-N-(3-methyl-2-pyridinyl)-3-pyrazolidinecarboxamide Part A Phenylmethyl (3S)-2-[(2R)-3-cyclopentyl-2-({formyl[(phenylmethyl)oxy]amino}methyl)propanoyl]-3-{[(3-methyl-2-pyridinyl)amino]carbonyl}-1-pyrazolidine carboxylate To a solution of 2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid (as a mixture of diastereomers enriched in (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid) (250 mg, 0.465 mmol) in tetrahydrofuran (3 ml) was added N,N-diisopropylethylamine (405 µl, 2.325 mmol) and 2,4,6-trichlorobenzoyl chloride (0.087 mL, 0.558 mmol). The mixture was stirred for 2 h and then the solvent was evaporated. The residue was then diluted with toluene (3 mL). The resulting suspension was treated with 2-amino-3-methylpyridine (61 mg, 0.56 mmol) followed by DMAP (11.3 mg, 0.093 mmol). After 2 h, 15 minutes, the solvent mixture was removed. The residue was diluted with MeOH and purified by reverse-phase HPLC to afford 179 mg (61%) of the title compound as a white solid. LC/MS: (M+H)$^+$: 628.5.

Part B (3S)-2-((2R)-3-Cyclopentyl-2-{[formyl(hydroxy)amino]methyl}propanoyl)-N-(3-methyl-2-pyridinyl)-3-pyrazolidinecarboxamide To a solution of phenylmethyl (3S)-2-[(2R)-3-cyclopentyl-2-({formyl[(phenylmethyl)oxy]amino}methyl)propanoyl]-3-{[(3-methyl-2-pyridinyl)amino]carbonyl}-1-pyrazolidinecarboxylate (179 mg, 0.285 mmol) in methanol (6 ml) was added 20% palladium hydroxide on carbon (72 mg, 0.285 mmol). The mixture was hydrogenated under balloon pressure for 1 h 15 min and then filtered. The mixture was purified by reverse-phase HPLC to yield (3S)-2-((2R)-3-cyclopentyl-2-{[formyl(hydroxy)amino]methyl}propanoyl)-N-(3-methyl-2-pyridinyl)-3-pyrazolidinecarboxamide (44 mg, 0.105 mmol, 37% yield). LC/MS: (M+H)$^+$: 404.

The following Examples 2 to 18 were prepared according to a method similar to that disclosed in Example 1 except that the resulting suspension in Part A, Example 1 was treated with the indicated compound instead of 2-amino-3-methylpyridine.

Example 2

(3S)-2-((2R)-3-Cyclopentyl-2-{[formyl(hydroxy)amino]methyl}propanoyl)-N-(3,4-dimethyl-2-pyridinyl)-3-pyrazolidinecarboxamide

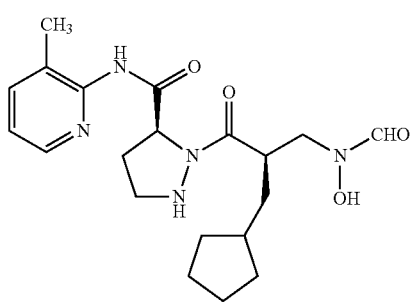 [SMILES: Cc1cccnc1NC(=O)[C@@H]1CCNN1C(=O)[C@H](CC1CCCC1)CN(O)C=O]

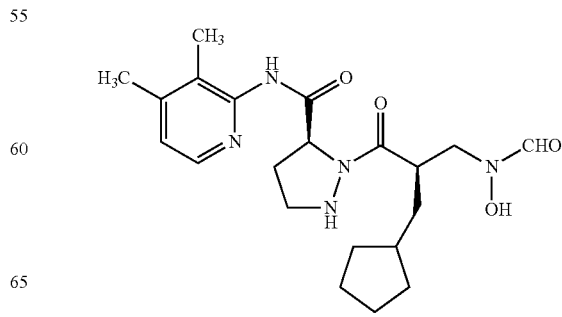

2-amino-5,6-dimethylpyridine (68.2 mg, 0.558 mmol). LC/MS: (M+H)+: 417.9. 1H NMR (400 MHz, METHANOL-d4) ppm 1.04-1.26 (m, 2H) 1.32-1.48 (m, 1H) 1.48-1.69 (m, 4H) 1.69-1.99 (m, 4H) 2.14-2.32 (m, 4H) 2.41 (s, 3H) 2.46-2.62 (m, 1H) 2.80-3.01 (m, 1H) 3.16-3.31 (m, 1H) 3.51 (dd, J=14.15, 4.55 Hz, 1H) 3.62-3.86 (m, 2H) 3.95 (dt, J=9.35, 4.67 Hz, 1H) 4.57-4.79 (m, 1H) 7.49 (d, J=8.34 Hz, 1H) 7.80 (d, J=8.08 Hz, 1H) 7.88 (s, 1H).

Example 3

(3S)-2-((2R)-3-Cyclopentyl-2-{[formyl(hydroxy)amino]methyl}propanoyl)-N-(6-ethyl-3-methyl-2-pyridinyl)-3-pyrazolidinecarboxamide

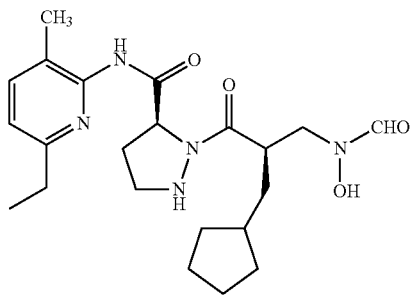 [SMILES: CCc1ccc(C)c(NC(=O)[C@@H]2CCNN2C(=O)[C@H](CC2CCCC2)CN(O)C=O)n1]

2-amino-3-ethyl-6-methylpyridine (78 mg, 0.558 mmol). LC/MS: (M+H)+: 432.2

Example 4

(3S)-2-((2R)-3-Cyclopentyl-2-{[formyl(hydroxy)amino]methyl}propanoyl)-N-4-isoquinolinyl-3-pyrazolidinecarboxamide

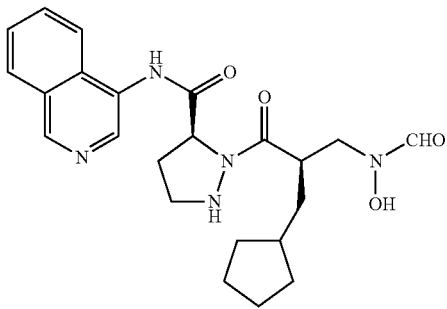 [SMILES: O=CN(O)C[C@@H](CC1CCCC1)C(=O)N1NCC[C@H]1C(=O)Nc1cncc2ccccc12]

4-aminoisoquinoline (97 mg, 0.67 mmol). LC/MS: (M+H)$^+$: 440.9.

Example 5

(3S)-2-((2R)-3-Cyclopentyl-2-{[formyl(hydroxy)amino]methyl}propanoyl)-N-(6-ethyl-2-pyridinyl)-3-pyrazolidinecarboxamide

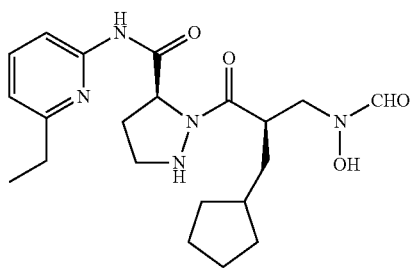 [SMILES: CCc1cccc(NC(=O)[C@@H]2CCNN2C(=O)[C@H](CC2CCCC2)CN(O)C=O)n1]

2-amino-6-ethylpyridine (84 mg, 0.67 mmol). LC/MS: (M+H)$^+$: 417.9. $^1$H NMR (400 MHz, METHANOL-d$_4$) δ ppm 1.03-1.24 (m, 2H) 1.36-1.48 (m, 1H) 1.48-1.70 (m, 4H) 1.70-2.00 (m, 4H) 2.16-2.36 (m, 1H) 2.55 (ddd, J=12.13, 6.32, 2.53 Hz, 1H) 2.83-3.01 (m, 1H) 3.15-3.31 (m, 1H) 3.51 (dd, J=13.89, 4.55 Hz, 1H) 3.59-3.86 (m, 2H) 3.96 (dt, J=9.41, 4.77 Hz, 1H) 4.70 (t, J=7.83 Hz, 1H) 6.99 (d, J=7.33 Hz, 1H) 7.67 (t, J=7.83 Hz, 1H) 7.79-7.97 (m, 2H).

Example 6

(3S)-2-((2R)-3-Cyclopentyl-2-{[formyl(hydroxy)amino]methyl}propanoyl)-N-(4-ethyl-2-pyridinyl)-3-pyrazolidinecarboxamide

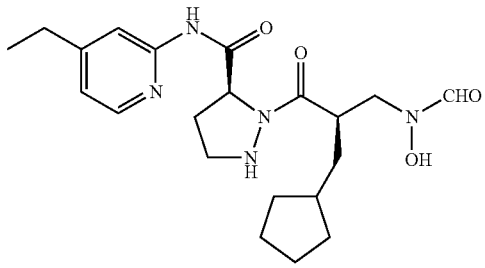 [SMILES: CCc1ccnc(NC(=O)[C@@H]2CCNN2C(=O)[C@H](CC2CCCC2)CN(O)C=O)c1]

2-amino-4-ethylpyridine (84 mg, 0.67 mmol). LC/MS: (M+H)$^+$: 417.9. $^1$H NMR (400 MHz, METHANOL-d$_4$) δ ppm 1.05-1.23 (m, 2H) 1.36-1.48 (m, 1H) 1.48-1.70 (m, 4H) 1.70-2.00 (m, 4H) 2.18-2.36 (m, 1H) 2.44-2.62 (m, 1H) 2.82-3.01 (m, 1H) 3.16-3.31 (m, 1H) 3.51 (dd, J=14.02, 4.42 Hz, 1H) 3.63-3.85 (m, 2H) 3.95 (dd, J=9.09, 4.80 Hz, 1H) 4.59-4.82 (m, 1H) 7.01 (dd, J=5.05, 1.52 Hz, 1H) 7.88 (s, 1H) 7.98 (s, 1H) 8.17 (d, J=5.05 Hz, 1H).

Example 7

(3S)-2-((2R)-3-Cyclopentyl-2-{[formyl(hydroxy)amino]methyl}propanoyl)-N-1,3-thiazol-2-yl-3-pyrazolidinecarboxamide

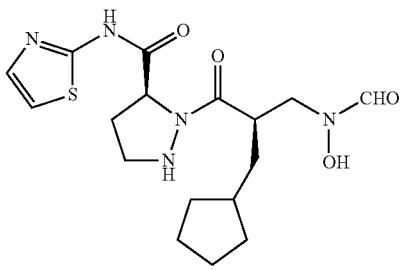 [SMILES: O=CN(O)C[C@@H](CC1CCCC1)C(=O)N1NCC[C@H]1C(=O)Nc1nccs1]

2-aminothiazole (69 mg, 0.67 mmol). LC/MS: (M+H)$^+$: 396.0.

Example 8

(3S)—N-(5-Chloro-2-pyridinyl)-2-((2R)-3-cyclopentyl-2-{[formyl(hydroxy)amino]methyl}propanoyl)-3-pyrazolidinecarboxamide

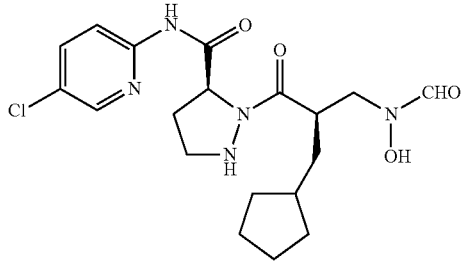 [SMILES: O=CN(O)C[C@@H](CC1CCCC1)C(=O)N1NCC[C@H]1C(=O)Nc1ccc(Cl)cn1]

2-amino-5-chloropyridine (86 mg, 0.67 mmol). LC/MS: (M+H)+: 423.7. ¹H NMR (400 MHz, METHANOL-d₄) δ ppm 1.02-1.27 (m, 2H) 1.29-1.48 (m, 1H) 1.48-1.69 (m, 4H) 1.69-1.99 (m, 4H) 2.16-2.35 (m, 1H) 2.54 (ddd, J=12.06, 6.25, 2.40 Hz, 1H) 2.79-3.05 (m, 1H) 3.15-3.31 (m, 1H) 3.51 (dd, J=14.02, 4.42 Hz, 1H) 3.62-3.85 (m, 2H) 3.95 (dt, J=9.41, 4.77 Hz, 1H) 4.62-4.80 (m, 1H) 7.79 (dd, J=8.97, 2.65 Hz, 1H) 7.87 (s, 1H) 8.14 (d, J=8.84 Hz, 1H) 8.24-8.34 (m, 1H).

Example 9

(3S)-2-((2R)-3-Cyclopentyl-2-{[formyl(hydroxy)amino]methyl}propanoyl)-N-3-isoxazolyl-3-pyrazolidinecarboxamide

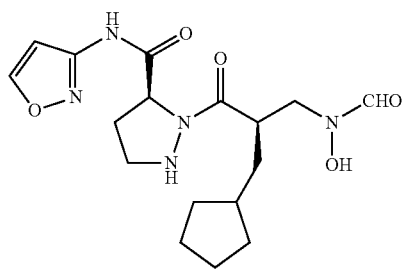 [SMILES: O=CN(O)C[C@@H](CC1CCCC1)C(=O)N1NCC[C@H]1C(=O)Nc1ccon1]

3-aminoisoxazole (59 mg, 0.67 mmol). LC/MS: (M+H)+: 380.4.

Example 10

(3S)-2-((2R)-3-Cyclopentyl-2-{[formyl(hydroxy)amino]methyl}propanoyl)-N-(5-phenyl-2-pyridinyl)-3-pyrazolidinecarboxamide

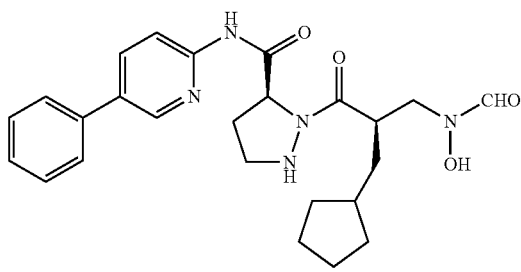 [SMILES: O=CN(O)C[C@@H](CC1CCCC1)C(=O)N1NCC[C@H]1C(=O)Nc1ccc(-c2ccccc2)cn1]

2-amino-5-phenylpyridine (92 mg, 0.539 mmol). LC/MS: (M+H)+: 466.0. ¹H NMR (400 MHz, METHANOL-d₄) δ ppm 1.14 (dd, J=7.20, 3.92 Hz, 2H) 1.42 (dd, J=7.58, 5.56 Hz, 1H) 1.46-1.65 (m, 4H) 1.70-1.94 (m, 4H) 2.14 (qd, J=9.89, 7.45 Hz, 1H) 2.52 (td, J=12.63, 6.32 Hz, 1H) 2.89 (dd, J=10.23, 5.43 Hz, 1H) 3.18-3.33 (m, 2H) 3.66-3.82 (m, 2H) 4.43-4.67 (m, 3H) 7.33 (dd, J=7.07, 5.31 Hz, 1H) 7.49 (d, J=8.08 Hz, 1H) 7.82 (td, J=7.71, 1.77 Hz, 1H) 8.49 (d, J=4.80 Hz, 1H).

Example 11

(3S)-2-((2R)-3-Cyclopentyl-2-{[formyl(hydroxy)amino]methyl}propanoyl)-N-[3-(methyloxy)phenyl]-3-pyrazolidinecarboxamide

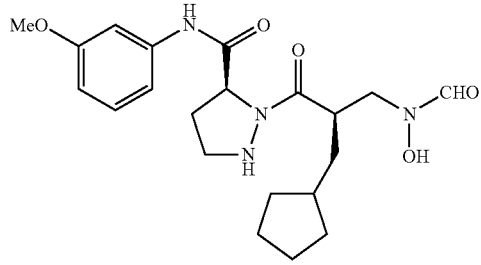 [SMILES: COc1cccc(NC(=O)[C@@H]2CCNN2C(=O)[C@H](CC2CCCC2)CN(O)C=O)c1]

m-anisidine (76 mg, 0.614 mmol). LC/MS: (M+H)+: 419.0. ¹H NMR (400 MHz, METHANOL-d₄) δ ppm 1.17 (br. s., 2H) 1.42 (dd, J=12.88, 5.81 Hz, 1H) 1.48-1.69 (m, 4H) 1.77 (d, J=13.89 Hz, 2H) 1.91 (br. s., 2H) 2.12-2.29 (m, 1H) 2.53 (br. s., 1H) 2.91 (br. s., 1H) 3.28 (br. s., 1H) 3.44-3.58 (m, 1H) 3.74 (br. s., 2H) 3.95 (br. s., 1H) 4.44-4.69 (m, 1H) 6.69 (d, J=8.34 Hz, 1H) 7.08 (d, J=8.08 Hz, 1H) 7.22 (t, J=8.08 Hz, 1H) 7.29 (br. s., 1H) 7.86 (s, 1H).

Example 12

(3S)-2-((2R)-3-Cyclopentyl-2-{[formyl(hydroxy)amino]methyl}propanoyl)-N-(4-fluorophenyl)-3-pyrazolidinecarboxamide

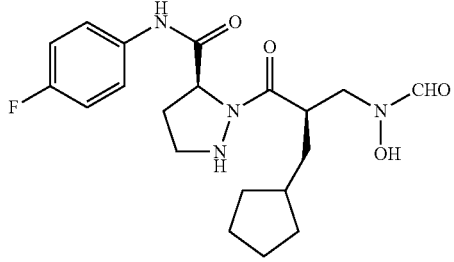 [SMILES: O=CN(O)C[C@@H](CC1CCCC1)C(=O)N1NCC[C@H]1C(=O)Nc1ccc(F)cc1]

4-fluoroaniline (74 mg, 0.670 mmol). LC/MS: (M+H)+: 407.2. ¹H NMR (400 MHz, METHANOL-d₄) δ ppm 1.00-1.27 (m, 2H) 1.31-1.49 (m, 1H) 1.49-1.68 (m, 4H) 1.68-1.85 (m, 2H) 1.85-2.03 (m, 2H) 2.07-2.31 (m, 1H) 2.54 (dd, J=5.68, 2.65 Hz, 1H) 2.92 (d, J=6.32 Hz, 1H) 3.43-3.60 (m, 1H) 3.69-3.83 (m, 1H) 3.88-4.07 (m, 1H) 4.46-4.72 (m, 1H) 6.94-7.15 (m, 2H) 7.42-7.71 (m, 2H) 7.86 (s, 1H).

Example 13

(3S)-2-((2R)-3-Cyclopentyl-2-{[formyl(hydroxy)amino]methyl}propanoyl)-N-(3-fluorophenyl)-3-pyrazolidinecarboxamide

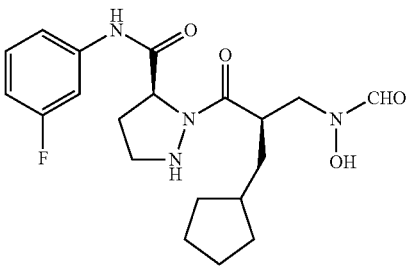 [SMILES: O=CN(O)C[C@@H](CC1CCCC1)C(=O)N1NCC[C@H]1C(=O)Nc1cccc(F)c1]

3-fluoroaniline (99 mg, 0.893 mmol). LC/MS: (M+H)+: 407.1.

Example 14

(3S)-2-((2R)-3-Cyclopentyl-2-{[formyl(hydroxy)amino]methyl}propanoyl)-N-(4,5-dimethyl-1,3-thiazol-2-yl)-3-pyrazolidinecarboxamide

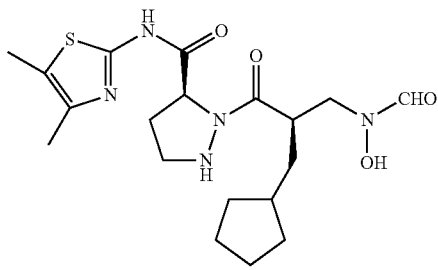 [SMILES: Cc1nc(NC(=O)[C@@H]2CCNN2C(=O)[C@H](CC2CCCC2)CN(O)C=O)sc1C]

2-amino-4,5-dimethyl thiazole hydrochloride (147 mg, 0.893 mmol). LC/MS: (M+H)+: 423.8.

Example 15

(3S)-2-((2R)-3-Cyclopentyl-2-{[formyl(hydroxy)amino]methyl}propanoyl)-N-phenyl-3-pyrazolidinecarboxamide

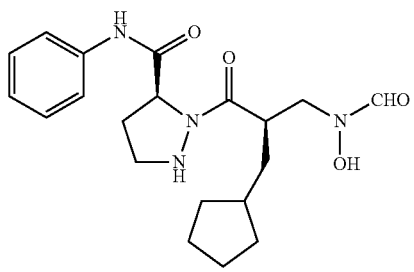 [SMILES: O=CN(O)C[C@@H](CC1CCCC1)C(=O)N1NCC[C@H]1C(=O)Nc1ccccc1]

Two batches of an intermediate prepared with methods similar that of Example 1, Part A were prepared from aniline (21 mg, 0.223 mmol) and aniline (35 mg, 0.379 mmol). The batches were combined (70 mg, 0.114 mmol), and the Title Compound prepared according to methods similar to Example 1, Part B. LC/MS: (M+H)+: 388.9. $^1$H NMR (400 MHz, CHLOROFORM-d) δ ppm 0.97-1.21 (m, 2H) 1.37-1.65 (m, 5H) 1.77 (t, J=7.58 Hz, 3H) 2.28-2.44 (m, 1H) 2.44-2.69 (m, 1H) 2.94 (d, J=6.82 Hz, 1H) 3.25-3.37 (m, 1H) 3.55 (dd, J=13.77, 3.92 Hz, 1H) 3.69-3.98 (m, 1H) 4.64-4.87 (m, 1H) 7.02-7.10 (m, 1H) 7.15 (t, J=7.83 Hz, 1H) 7.21-7.33 (m, 2H) 7.36-7.53 (m, 2H) 7.85 (s, 1H) 9.39 (s, 1H).

Example 16

(3S)-2-((2R)-3-Cyclopentyl-2-{[formyl(hydroxy)amino]methyl}propanoyl)-N-(5-fluoro-2-pyridinyl)-3-pyrazolidinecarboxamide

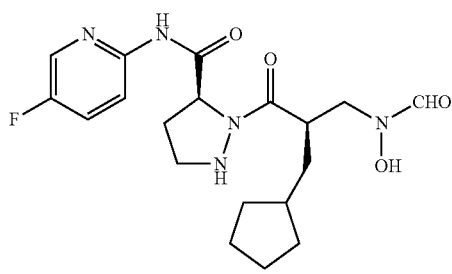 [SMILES: O=CN(O)C[C@@H](CC1CCCC1)C(=O)N1NCC[C@H]1C(=O)Nc1ccc(F)cn1]

5-fluoro-2-pyridinamine (77 mg, 0.690 mmol). LC/MS: (M+H)+: 408.1. $^1$H NMR (400 MHz, DMSO-d$_6$) δ ppm 0.93-1.17 (m, 2H) 1.28 (t, J=12.76 Hz, 1H) 1.35-1.51 (m, 2H) 1.56 (d, J=7.33 Hz, 2H) 1.63 (br. s., 1H) 1.80 (br. s., 2H) 2.03 (d, J=7.83 Hz, 1H) 2.39 (br. s., 1H) 2.75 (d, J=6.57 Hz, 1H) 3.51-3.75 (m, 2H) 4.59 (t, J=7.71 Hz, 1H) 5.44 (d, J=4.04 Hz, 1H) 7.75 (td, J=8.72, 3.03 Hz, 1H) 8.10 (dd, J=9.09, 3.79 Hz, 1H) 8.33 (d, J=3.03 Hz, 1H) 10.48-10.70 (m, 1H).

Example 17

(3S)-2-((2R)-3-Cyclopentyl-2-{[formyl(hydroxy)amino]methyl}propanoyl)-N-2-pyridinyl-3-pyrazolidinecarboxamide

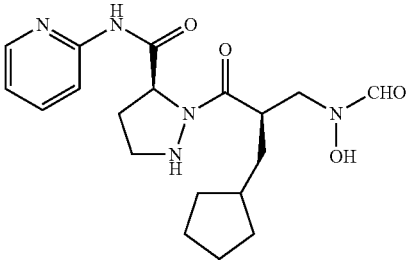 [SMILES: O=CN(O)C[C@@H](CC1CCCC1)C(=O)N1NCC[C@H]1C(=O)Nc1ccccn1]

2-aminopyridine (58.9 mg, 0.626 mmol). LC/MS: (M+H)+: 389.9. $^1$H NMR (400 MHz, METHANOL-d$_4$) δ ppm 1.16 (dd, J=11.49, 6.95 Hz, 2H) 1.43 (dd, J=13.14, 5.81 Hz, 1H) 1.49-1.67 (m, 4H) 1.72-1.97 (m, 4H) 2.27 (td, J=4.80, 2.53 Hz, 1H) 2.53 (dd, J=6.32, 2.53 Hz, 1H) 2.83-3.00 (m, 1H) 3.28 (d, J=9.60 Hz, 1H) 3.65-3.88 (m, 2H) 4.72 (t, J=7.45 Hz, 1H) 7.12 (dd, J=7.33, 5.05 Hz, 1H) 7.73-7.84 (m, 1H) 8.10 (d, J=8.08 Hz, 1H) 8.30 (d, J=4.55 Hz, 1H).

Example 18

(3S)-2-((2R)-3-Cyclopentyl-2-{[formyl(hydroxy)amino]methyl}propanoyl)-N-3-pyridinyl-3-pyrazolidinecarboxamide

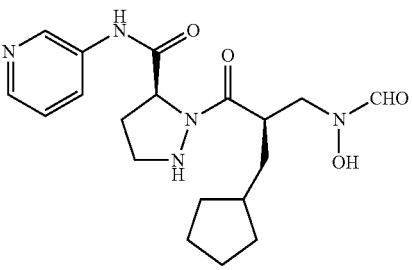 [SMILES: O=CN(O)C[C@@H](CC1CCCC1)C(=O)N1NCC[C@H]1C(=O)Nc1cccnc1]

3-aminopyridine (56 mg, 0.600 mmol). LC/MS: (M+H)+: 389.8. $^1$H NMR (400 MHz, METHANOL-d$_4$) δ ppm 1.04-1.24 (m, 2H) 1.42 (dd, J=13.26, 5.43 Hz, 1H) 1.48-1.68 (m, 4H) 1.68-1.98 (m, 4H) 2.12-2.30 (m, 1H) 2.41-2.68 (m, 1H) 2.94 (dd, J=10.11, 6.57 Hz, 1H) 3.21-3.31 (m, 1H) 3.52 (dd, J=14.15, 4.55 Hz, 1H) 3.68-3.83 (m, 2H) 3.94 (dd, J=9.35, 4.80 Hz, 1H) 4.62 (q, J=7.49 Hz, 1H) 7.32-7.52 (m, 1H) 7.87 (s, 1H) 8.12 (d, J=8.34 Hz, 1H) 8.24-8.34 (m, 1H) 8.69-8.82 (m, 1H).

The following Examples 19 to 28 were prepared according to a method similar to that disclosed in Example 1 except that the resulting suspension in Part A, Example 1 was treated with the indicated compound instead of 2-amino-3-methylpyridine, and (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid) was used as a single diastereomer instead of 2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid as a mixture of diastereomers.

Example 19

(3S)-2-((2R)-3-Cyclopentyl-2-{[formyl(hydroxy)amino]methyl}propanoyl)-N-3-pyridazinyl-3-pyrazolidinecarboxamide

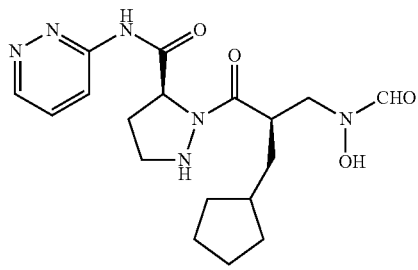

3-aminopyridazine (54 mg, 0.569 mmol). LC/MS: (M+H)+: 390.9.

Example 20

(3S)-2-((2R)-3-Cyclopentyl-2-{[formyl(hydroxy)amino]methyl}propanoyl)-N-[4-(trifluoromethyl)phenyl]-3-pyrazolidinecarboxamide

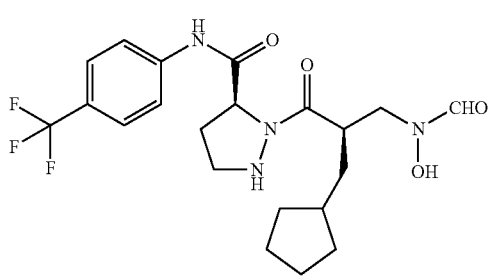 [SMILES: O=CN(O)C[C@@H](CC1CCCC1)C(=O)N1NCC[C@H]1C(=O)Nc1ccc(C(F)(F)F)cc1]

4-(trifluoromethyl)aniline (45 mg, 0.279 mmol) LC/MS: (M+H)+: 456.9.

Example 21

(3S)-2-((2R)-3-Cyclopentyl-2-{[formyl(hydroxy)amino]methyl}propanoyl)-N-(2-fluorophenyl)-3-pyrazolidinecarboxamide

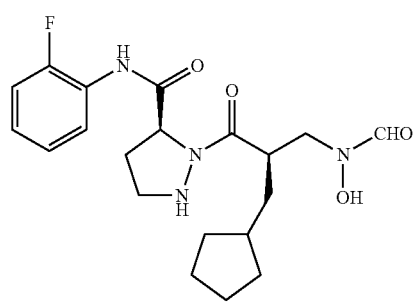 [SMILES: O=CN(O)C[C@@H](CC1CCCC1)C(=O)N1NCC[C@H]1C(=O)Nc1ccccc1F]

2-fluoroaniline (37 mg, 0.335 mmol). LC/MS: (M+H)+: 407.2 $^1$H NMR (400 MHz, METHANOL-d$_4$) δ ppm 1.16 (dd, J=12.51, 7.71 Hz, 2H) 1.32-1.58 (m, 3H) 1.62 (br. s., 2H) 1.67-1.96 (m, 4H) 2.21-2.42 (m, 1H) 2.43-2.64 (m, 1H) 2.91 (br. s., 1H) 3.45-3.62 (m, 1H) 3.67-3.87 (m, 2H) 3.88-4.11 (m, 1H) 4.67-4.81 (m, 1H) 7.01-7.28 (m, 3H) 7.88 (s, 1H) 7.96-8.11 (m, 1H).

Example 22

(3S)-2-((2R)-3-Cyclopentyl-2-{[formyl(hydroxy)amino]methyl}propanoyl)-N-(6-fluoro-2-pyridinyl)-3-pyrazolidinecarboxamide

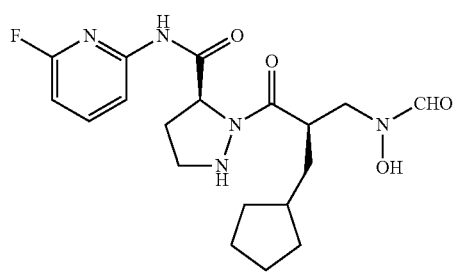

6-fluoro-2-pyridinamine (28 mg, 0.251 mmol). LC/MS: (M+H)+: 408.1. $^1$H NMR (400 MHz, METHANOL-d$_4$) δ ppm 1.16 (dd, J=12.51, 7.20 Hz, 2H) 1.43 (dd, J=7.71, 5.68 Hz, 1H) 1.48-1.67 (m, 4H) 1.71-1.96 (m, 4H) 2.22 (td, J=7.20, 3.28 Hz, 1H) 2.54 (ddd, J=9.54, 6.63, 2.27 Hz, 1H) 2.91 (dd, J=10.36, 6.57 Hz, 1H) 3.26 (dd, J=11.12, 5.05 Hz, 1H) 3.76 (ddd, J=17.18, 7.45, 7.20 Hz, 1H) 4.69 (t, J=7.83 Hz, 1H) 6.74 (dd, J=7.96, 2.40 Hz, 1H) 7.88 (q, J=7.92 Hz, 1H) 7.88 (s, 1H) 7.95-8.07 (m, 1H).

Example 23

(3S)-2-((2R)-3-Cyclopentyl-2-{[formyl(hydroxy)amino]methyl}propanoyl)-N-[4-(trifluoromethyl)-2-pyridinyl]-3-pyrazolidinecarboxamide

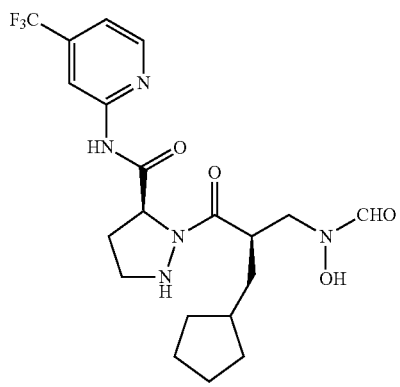 [SMILES: O=CN(O)C[C@@H](CC1CCCC1)C(=O)N1NCC[C@H]1C(=O)Nc1cc(C(F)(F)F)ccn1]

4-(trifluoromethyl)-2-pyridinamine (46 mg, 0.285 mmol). LC/MS: (M+H)+: 458.0.

Example 24

(3S)-2-((2R)-3-Cyclopentyl-2-{[formyl(hydroxy)amino]methyl}propanoyl)-N-(2-pyridinylmethyl)-3-pyrazolidinecarboxamide

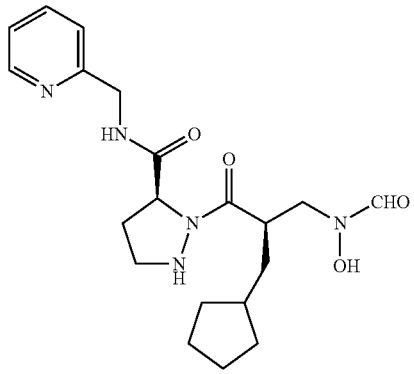 [SMILES: O=CN(O)C[C@@H](CC1CCCC1)C(=O)N1NCC[C@H]1C(=O)NCc1ccccn1]

2-pyridyl ethylamine (29.2 mg, 0.270 mmol). LC/MS: (M+H)+: 404.0. $^1$H NMR (400 MHz, METHANOL-d$_4$) δ ppm 1.14 (dd, J=7.20, 3.92 Hz, 2H) 1.42 (dd, J=7.58, 5.56 Hz, 1H) 1.46-1.65 (m, 4H) 1.70-1.94 (m, 4H) 2.14 (qd, J=9.89, 7.45 Hz, 1H) 2.52 (td, J=12.63, 6.32 Hz, 1H) 2.89 (dd, J=10.23, 5.43 Hz, 1H) 3.18-3.33 (m, 2H) 3.66-3.82 (m, 2H) 4.43-4.67 (m, 3H) 7.33 (dd, J=7.07, 5.31 Hz, 1H) 7.49 (d, J=8.08 Hz, 1H) 7.82 (td, J=7.71, 1.77 Hz, 1H) 8.49 (d, J=4.80 Hz, 1H).

Example 25

(3S)-2-((2R)-3-Cyclopentyl-2-{[formyl(hydroxy)amino]methyl}propanoyl)-N-(6-methyl-2-pyridinyl)-3-pyrazolidinecarboxamide

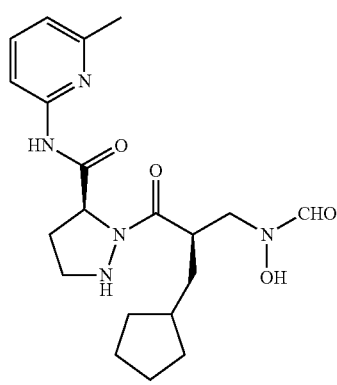 [SMILES: Cc1cccc(NC(=O)[C@@H]2CCNN2C(=O)[C@H](CC2CCCC2)CN(O)C=O)n1]

2-amino-6-methylpyridine (52.6 mg, 0.487 mmol). LC/MS: (M+H)+: 404.3. $^1$H NMR (400 MHz, METHANOL-d$_4$) δ ppm 1.20 (t, J=7.07 Hz, 2H) 1.07-1.30 (m, 1H) 1.44 (dd, J=7.58, 5.56 Hz, 1H) 1.49-1.68 (m, 4H) 1.73-1.97 (m, 4H) 2.18-2.37 (m, J=4.89, 4.89, 4.74, 2.91 Hz, 1H) 2.45 (s, 3H) 2.53 (ddd, J=6.19, 3.03, 2.91 Hz, 1H) 2.91 (t, J=10.61 Hz, 1H) 3.27 (dd, J=7.83, 2.78 Hz, 1H) 3.45-3.58 (m, 1H) 3.64-3.84 (m, 2H) 4.69 (t, J=7.96 Hz, 1H) 6.99 (d, J=7.33 Hz, 1H) 7.65 (t, J=7.83 Hz, 1H) 7.81-7.95 (m, 2H).

Example 26

(3S)-2-((2R)-3-Cyclopentyl-2-{[formyl(hydroxy)amino]methyl}propanoyl)-N-[6-(trifluoromethyl)-2-pyridinyl]-3-pyrazolidinecarboxamide

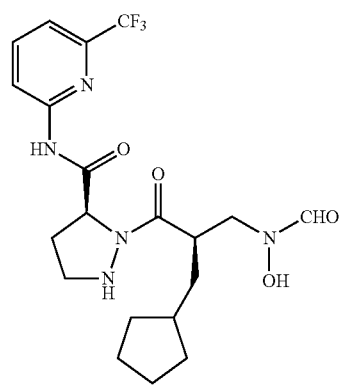 [SMILES: O=CN(O)C[C@@H](CC1CCCC1)C(=O)N1NCC[C@H]1C(=O)Nc1cccc(C(F)(F)F)n1]

2-amino-6-trifluoromethylpyridine (49.5 mg, 0.305 mmol). LC/MS: (M+H)+: 458.2.

Example 27

(3S)-2-((2R)-3-Cyclopentyl-2-{[formyl(hydroxy)amino]methyl}propanoyl)-N-(4,6-dimethyl-2-pyridinyl)-3-pyrazolidinecarboxamide

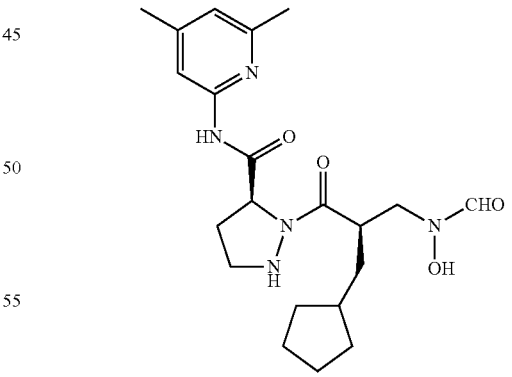

4,6-dimethyl-2-pyridinamine (39.8 mg, 0.326 mmol). LC/MS: (M+H)+: 418.2. $^1$H NMR (400 MHz, METHANOL-d$_4$) δ ppm 1.13 (d, J=4.29 Hz, 2H) 1.39 (dd, J=13.14, 6.06 Hz, 1H) 1.45-1.64 (m, 4H) 1.69-1.94 (m, 4H) 2.22 (d, J=10.11 Hz, 1H) 2.29 (s, 3H) 2.37 (s, 3H) 2.49 (d, J=5.56 Hz, 1H) 2.74-2.98 (m, 1H) 3.14-3.28 (m, 1H) 3.29 (s, 1H) 3.56-3.81 (m, 2H) 4.66 (t, J=7.20 Hz, 1H) 6.81 (s, 1H) 7.71 (s, 1H).

Example 28

Ethyl 5-({[(3S)-2-((2R)-3-cyclopentyl-2-{[formyl(hydroxy)amino]methyl}propanoyl)-3-pyrazolidinyl]carbonyl}amino)-1,3,4-oxadiazole-2-carboxylate

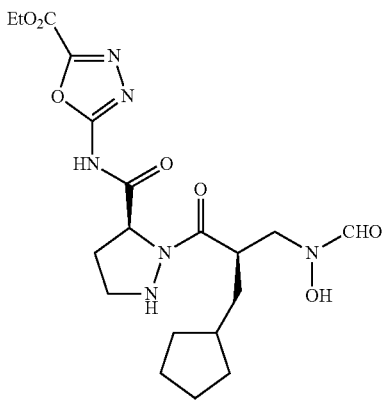 [SMILES: CCOC(=O)c1nnc(NC(=O)[C@@H]2CCNN2C(=O)[C@H](CC2CCCC2)CN(O)C=O)o1]

ethyl 5-amino-1,3,4-oxadiazole-2-carboxylate (59.3 mg, 0.377 mmol). LC/MS: (M+H)+: 453.0.

Example 29

(3S)—N-(6-Chloro-2-pyridinyl)-2-((2R)-3-cyclopentyl-2-{[formyl(hydroxy)amino]methyl}propanoyl)-3-pyrazolidinecarboxamide

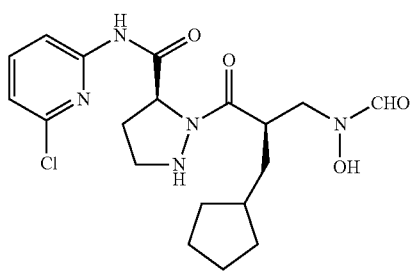 [SMILES: O=CN(O)C[C@@H](CC1CCCC1)C(=O)N1NCC[C@H]1C(=O)Nc1cccc(Cl)n1]

Part A

Phenylmethyl (3S)-3-{[(6-chloro-2-pyridinyl)amino]carbonyl}-2-[(2R)-3-cyclopentyl-2-({formyl[(phenylmethyl)oxy]amino}methyl)propanoyl]-1-pyrazolidinecarboxylate To a solution of 2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid (as a mixture of diastereomers enriched in (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid) (300 mg, 0.558 mmol) in dichloromethane (5 ml) was added 1-methylimidazole (133 µl, 1.674 mmol) and cooled to 0° C. Mesyl chloride (56 µL, 0.725 mmol) was added dropwise at 0° C. and stirred for 1 hr at rt. The mixture was then treated with 2-amino-6-chloropyridine (86 mg, 0.67 mmol). The solvent mixture was removed. The residue was diluted with MeOH and purified by reverse-phase HPLC to afford 268 mg (0.413 mmol, 74%) of the title compound. LC/MS: (M+H)+: 648.3.

Part B (3S)—N-(6-Chloro-2-pyridinyl)-2-((2R)-3-cyclopentyl-2-{[formyl(hydroxy)amino]methyl}propanoyl)-3-pyrazolidinecarboxamide To a solution of phenylmethyl (3S)-3-{[(6-chloro-2-pyridinyl)amino]carbonyl}-2-[(2R)-3-cyclopentyl-2-({formyl[(phenylmethyl)oxy]amino}methyl)propanoyl]-1-pyrazolidinecarboxylate (268 mg, 0.413 mmol) in methanol (8 ml) was added 20% palladium hydroxide on carbon (80 mg, 0.413 mmol). The mixture was hydrogenated under balloon pressure for 1 h 20 min. and then filtered. The filtrate was purified by reverse-phase HPLC to yield (3S)—N-(6-chloro-2-pyridinyl)-2-((2R)-3-cyclopentyl-2-{[formyl(hydroxy)amino]methyl}propanoyl)-3-pyrazolidinecarboxamide (55 mg, 0.129 mmol, 31% yield). LC/MS: (M+H)+: 423.9. $^1$H NMR (400 MHz, METHANOL-$d_4$) δ ppm 1.06-1.31 (m, 2H) 1.31-1.47 (m, 1H) 1.47-1.69 (m, 4H) 1.69-1.98 (m, 4H) 2.11-2.37 (m, 1H) 2.40-2.66 (m, 1H) 2.79-3.01 (m, 1H) 3.17-3.31 (m, 1H) 3.51 (dd, J=14.15, 4.55 Hz, 1H) 3.61-3.85 (m, 2H) 3.95 (td, J=9.54, 4.93 Hz, 1H) 4.60-4.76 (m, 1H) 7.14 (d, J=7.83 Hz, 1H) 7.75 (t, J=7.96 Hz, 1H) 7.88 (s, 1H) 8.08 (d, J=8.08 Hz, 1H).

The following Examples 30 to 42 were prepared according to a method similar to that disclosed in Example 29 except that the mixture in Part A was treated with the indicated compound instead of 2-amino-6-chloropyridine.

Example 30

(3S)-2-((2R)-3-Cyclopentyl-2-{[formyl(hydroxy)amino]methyl}propanoyl)-N-[6-(4-morpholinyl)-3-pyridinyl]-3-pyrazolidinecarboxamide

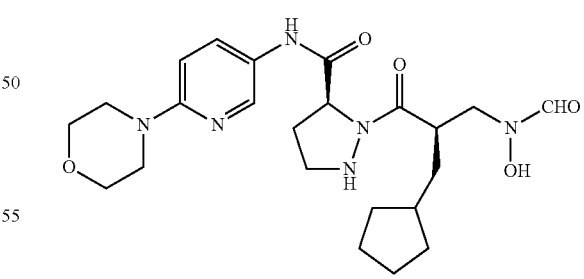

6-morpholinopyridin-3-amine (124 mg, 0.67 mmol). LC/MS: (M+H)+: 474.8. $^1$H NMR (400 MHz, METHANOL-$d_4$) δ ppm 1.01-1.28 (m, 2H) 1.30-1.48 (m, 1H) 1.50-1.69 (m, 4H) 1.71-1.96 (m, 4H) 2.05-2.34 (m, 1H) 2.46-2.62 (m, 1H) 2.78-3.05 (m, 1H) 3.15-3.31 (m, 1H) 3.40-3.63 (m, 5H) 3.63-3.83 (m, 6H) 3.94 (dd, J=9.22, 4.67 Hz, 1H) 4.58 (q, J=7.83 Hz, 1H) 6.83 (d, J=9.09 Hz, 1H) 7.79-7.98 (m, 2H) 8.22-8.43 (m, 1H).

Example 31

(3S)-2-((2R)-3-Cyclopentyl-2-{[formyl(hydroxy)amino]methyl}propanoyl)-N-5-isoquinolinyl-3-pyrazolidinecarboxamide

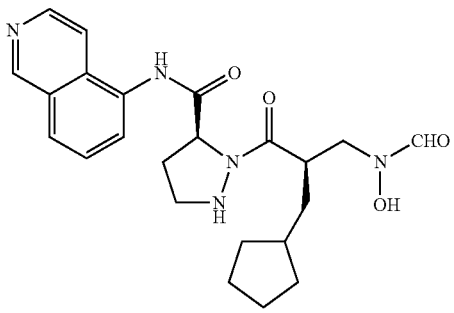

5-aminoisoquinoline (98 mg, 0.670 mmol). LC/MS: (M+H)+: 439.9.

Example 32

(3S)-2-((2R)-3-Cyclopentyl-2-{[formyl(hydroxy)amino]methyl}propanoyl)-N-1-isoquinolinyl-3-pyrazolidinecarboxamide

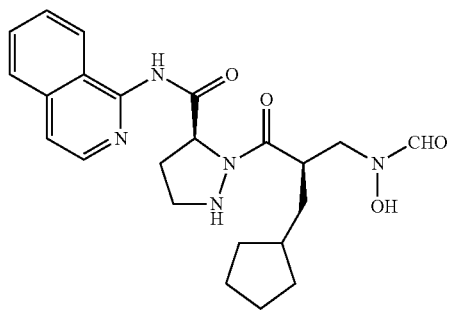 [SMILES: O=CN(O)C[C@@H](CC1CCCC1)C(=O)N1NCC[C@H]1C(=O)Nc1nccc2ccccc12]

1-aminoisoquinoline (98 mg, 0.670 mmol). LC/MS: (M+H)+: 439.8.

Example 33

(3S)-2-((2R)-3-Cyclopentyl-2-{[formyl(hydroxy)amino]methyl}propanoyl)-N-2-quinolinyl-3-pyrazolidinecarboxamide

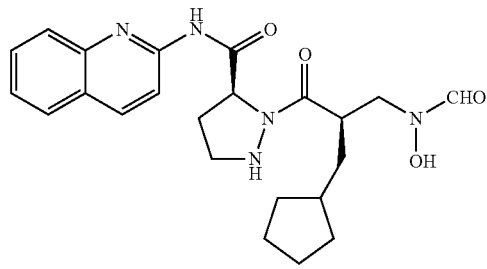 [SMILES: O=CN(O)C[C@@H](CC1CCCC1)C(=O)N1NCC[C@H]1C(=O)Nc1ccc2ccccc2n1]

2-aminoquinoline (97 mg, 0.670 mmol). LC/MS: (M+H)+: 439.8. 1H NMR (400 MHz, METHANOL-d4) δ ppm 1.02-1.28 (m, 2H) 1.39-1.69 (m, 5H) 1.71-2.00 (m, 4H) 2.20-2.46 (m, 1H) 2.47-2.73 (m, 1H) 2.83-3.09 (m, 1H) 3.16-3.31 (m, 1H) 3.53 (dd, J=14.02, 4.42 Hz, 1H) 3.62-3.88 (m, 2H) 3.97 (td, J=9.47, 5.05 Hz, 1H) 4.77 (br. s., 1H) 7.37-7.57 (m, 1H) 7.70 (ddd, J=8.46, 6.95, 1.52 Hz, 1H) 7.79-8.00 (m, 3H) 8.13-8.41 (m, 2H).

Example 34

(3S)-2-((2R)-3-Cyclopentyl-2-{[formyl(hydroxy)amino]methyl}propanoyl)-N-3-quinolinyl-3-pyrazolidinecarboxamide

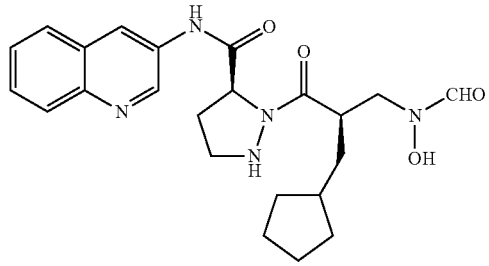 [SMILES: O=CN(O)C[C@@H](CC1CCCC1)C(=O)N1NCC[C@H]1C(=O)Nc1cnc2ccccc2c1]

3-aminoquinoline (192 mg, 1.33 mmol). LC/MS: (M+H)+: 439.9. 1H NMR (400 MHz, METHANOL-d4) δ ppm 1.01-1.30 (m, 2H) 1.31-1.49 (m, 1H) 1.49-1.71 (m, 4H) 1.71-2.01 (m, 4H) 2.17-2.36 (m, 1H) 2.52-2.70 (m, 1H) 2.88-3.11 (m, 1H) 3.53 (dd, J=14.02, 4.42 Hz, 1H) 3.63-3.89 (m, 2H) 3.97 (dd, J=9.09, 4.80 Hz, 1H) 4.62-4.78 (m, 1H) 7.44-7.74 (m, 2H) 7.75-8.02 (m, 2H) 8.53-8.76 (m, 1H) 8.83-9.01 (m, 1H).

Example 35

(3S)-2-((2R)-3-Cyclopentyl-2-{[formyl(hydroxy)amino]methyl}propanoyl)-N-{5-[4-(methyloxy)phenyl]-2-pyridinyl}-3-pyrazolidinecarboxamide

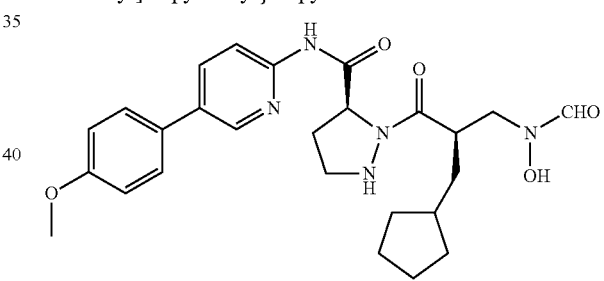

Pre Step A

5-[4-(Methyloxy)phenyl]-2-pyridinamine

An-oven dried Schlenk tube was charged with Pd2(dba)3 (37 mg, 0.04 mmol), S-Phos (66 mg, 0.16 mmol), 4-methoxyphenyl boronic acid (0.912 g, 6.0 mmol), powdered, anhydrous K3PO4 (1.70 g, 8.0 mmol) and 2-amino-5-chloropyridine (0.514 g, 4.0 mmol).

The tube was capped with a rubber septum, evacuated and backfilled with N2.

To this mixture was added n-butanol (8 mL) via syringe. The septum was then replaced with a Teflon screwcap and the Schlenk tube was sealed. The reaction mixture was heated to 120° C. for 24 h. The reaction was cooled to rt and filtered through a silica pad and washed with EtOAc to afford the title compound (670 mg, 3.35 mmol, 84%).

A procedure similar to Example 29 Parts A and B was used, except that 5-[4-(methyloxy)phenyl]-2-pyridinamine (209 mg, 1.042 mmol) was used instead of 2-amino-6-chloropyridine to treat the mixture in Part A, to provide the Title compound. LC/MS: (M+H)+: 496.1.

Example 36

(3S)-2-((2R)-3-Cyclopentyl-2-{[formyl(hydroxy)amino]methyl}propanoyl)-N-{5-[3-(methyloxy)phenyl]-2-pyridinyl}-3-pyrazolidinecarboxamide

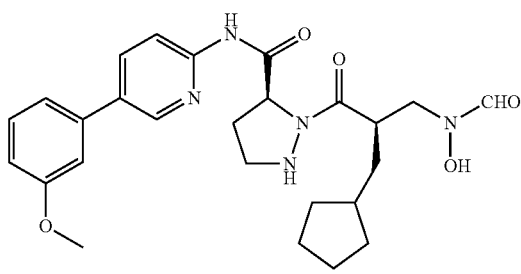 [SMILES: COc1cccc(-c2ccc(NC(=O)[C@@H]3CCNN3C(=O)[C@H](CC3CCCC3)CN(O)C=O)nc2)c1]

Pre Step A

5-[3-(Methyloxy)phenyl]-2-pyridinamine

An-oven dried Schlenk tube was charged with Pd2(dba)3 (37 mg, 0.04 mmol), S-Phos (66 mg, 0.16 mmol), 3-methoxyphenyl boronic acid (0.912 g, 6.0 mmol), powdered, anhydrous K3PO4 (1.70 g, 8.0 mmol) and 2-amino-5-chloropyridine (0.514 g, 4.0 mmol).

The tube was capped with a rubber septum, evacuated and backfilled with N2. To this mixture was added n-butanol (8 mL) via syringe. The septum was then replaced with a Teflon screwcap and the Schlenk tube was sealed. The reaction mixture was heated to 120° C. for 24 h. The reaction was cooled to rt and filtered through a silica pad and washed with EtOAc to afford the title compound (538 mg, 2.69 mmol, 67%).

A procedure similar to Example 29, Parts A and B was used, except that 5-[3-(methyloxy)phenyl]-2-pyridinamine (209 mg, 1.042 mmol) was used instead of 2-amino-6-chloropyridine to treat the mixture in Part A, to provide the Title compound. LC/MS: (M+H)+: 496.1.

Example 37

(3S)-2-((2R)-3-Cyclopentyl-2-{[formyl(hydroxy)amino]methyl}propanoyl)-N-5-quinolinyl-3-pyrazolidinecarboxamide

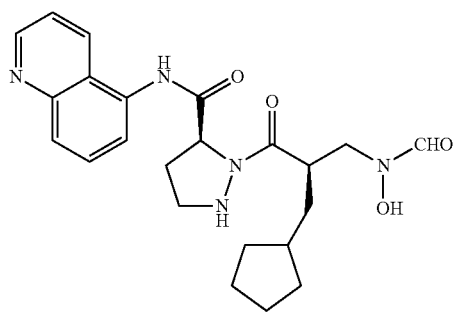 [SMILES: O=CN(O)C[C@@H](CC1CCCC1)C(=O)N1NCC[C@H]1C(=O)Nc1cccc2ncccc12]

5-aminoquinoline (150 mg, 1.042 mmol). LC/MS: (M+H)+: 439.9.

Example 38

(3S)-2-((2R)-3-Cyclopentyl-2-{[formyl(hydroxy)amino]methyl}propanoyl)-N-[6-(4-morpholinyl)-2-pyridinyl]-3-pyrazolidinecarboxamide

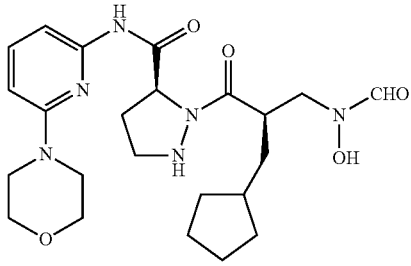 [SMILES: O=CN(O)C[C@@H](CC1CCCC1)C(=O)N1NCC[C@H]1C(=O)Nc1cccc(N2CCOCC2)n1]

Pre Step A

6-(4-Morpholinyl)-2-pyridinamine

6-Chloro-2-pyridinamine (1 g, 7.78 mmol) was dissolved in morpholine (6.80 ml, 78 mmol) and heated to 225° C. in a microwave reactor for 60 minutes (~400 W; 5 mbar). The reaction was cooled to rt and concentrated. The crude product was taken up in DCM (50 mL). After filtration of white solids the crude product was concentrated and purified by silica gel column chromatography eluting with 20-50% EtOAc/hexanes to afford 1 g (5.58 mmol, 72%) of the title compound as a pale yellow solid. LC/MS: (M+H)+: 179.9.

A procedure similar to Example 29, Parts A and B was used, except that 6-(4-morpholinyl)-2-pyridinamine (173 mg, 0.967 mmol) was used instead of 2-amino-6-chloropyridine to treat the mixture in Part A, to provide the Title compound. LC/MS: (M+H)+: 475.2. $^1$H NMR (400 MHz, METHANOL-$d_4$) δ ppm 1.04-1.27 (m, 2H) 1.38-1.46 (m, 1H) 1.47-1.68 (m, 4H) 1.69-1.99 (m, 4H) 2.13-2.35 (m, 1H) 2.41-2.64 (m, 1H) 2.77-3.01 (m, 1H) 3.16-3.31 (m, 1H) 3.58-3.75 (m, 1H) 3.96 (dt, J=9.47, 4.86 Hz, 1H) 4.60-4.81 (m, 1H) 6.52 (d, J=8.34 Hz, 1H) 7.42 (d, J=7.83 Hz, 1H) 7.54 (t, J=8.08 Hz, 1H) 7.87 (s, 1H).

Example 39

(3S)-2-((2R)-3-Cyclopentyl-2-{[formyl(hydroxy)amino]methyl}propanoyl)-N-(1,2,3,4-tetrahydro-5-quinolinyl)-3-pyrazolidinecarboxamide

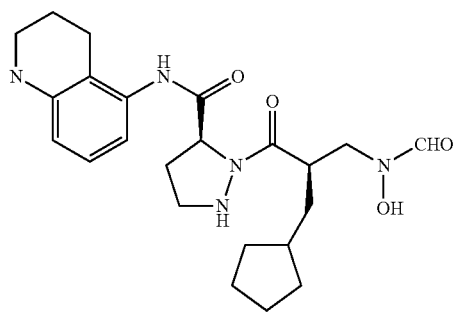 [SMILES: O=CN(O)C[C@@H](CC1CCCC1)C(=O)N1NCC[C@H]1C(=O)Nc1cccc2c1CCCN2]

5-aminoquinoline (150 mg, 1.042 mmol). LC/MS: (M+H)+: 443.9.

Example 40

(3S)-2-((2R)-3-Cyclopentyl-2-{[formyl(hydroxy)amino]methyl}propanoyl)-N-8-quinolinyl-3-pyrazolidinecarboxamide

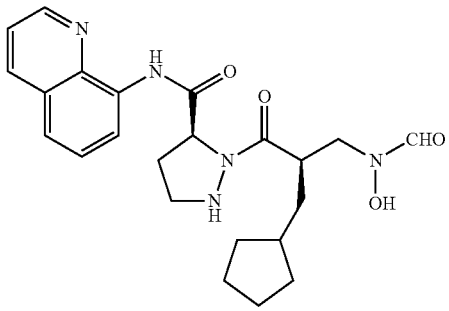 [SMILES: O=CN(O)C[C@@H](CC1CCCC1)C(=O)N1NCC[C@H]1C(=O)Nc1cccc2cccnc12]

8-aminoquinoline (192 mg, 1.33 mmol). LC/MS: (M+H)+: 439.9. $^1$H NMR (400 MHz, METHANOL-d$_4$) δ ppm 1.04-1.30 (m, 2H) 1.36-1.65 (m, 5H) 1.74 (ddd, J=11.87, 7.71, 4.42 Hz, 1H) 1.79-2.09 (m, 3H) 2.22-2.51 (m, 1H) 2.51-2.71 (m, 1H) 2.84-3.01 (m, 1H) 3.56 (dd, J=14.15, 4.55 Hz, 1H) 3.83 (td, J=13.77, 10.11 Hz, 1H) 4.05 (dd, J=8.72, 4.42 Hz, 1H) 7.46-7.75 (m, 3H) 7.91 (s, 1H) 8.20-8.43 (m, 1H) 8.69 (d, J=7.58 Hz, 1H) 8.87 (dd, J=4.17, 1.64 Hz, 1H).

Example 41

(3S)-2-((2R)-3-Cyclopentyl-2-{[formyl(hydroxy)amino]methyl}propanoyl)-N-[5-(4-fluorophenyl)-2-pyridinyl]-3-pyrazolidinecarboxamide

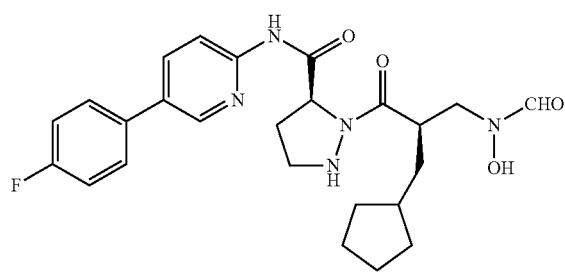 [SMILES: O=CN(O)C[C@@H](CC1CCCC1)C(=O)N1NCC[C@H]1C(=O)Nc1ccc(-c2ccc(F)cc2)cn1]

Pre Step A 5-(4-Fluorophenyl)-2-pyridinamine

An-oven dried Schlenk tube was charged with Pd$_2$(dba)$_3$ (37 mg, 0.04 mmol), S-Phos (66 mg, 0.16 mmol), 4-fluorobenzeneboronic acid (0.840 g, 6.0 mmol), powdered, anhydrous K$_3$PO$_4$ (1.70 g, 8.0 mmol) and 2-amino-5-chloropyridine (0.514 g, 4.0 mmol).

The tube was capped with a rubber septum, evacuated and backfilled with N$_2$.

To this mixture was added n-butanol (8 mL) via syringe. The septum was then replaced with a Teflon screwcap and the Schlenk tube was sealed. The reaction mixture was heated to 120° C. for 24 h. The reaction was cooled to rt and filtered through a silica pad and washed with EtOAc to afford the title compound (594 mg, 3.16 mmol, 79%).

A procedure similar to Example 29, Parts A and B was used, except that in Part A DMF was used instead of dichloromethane and 5-(4-fluorophenyl)-2-pyridinamine (105 mg, 0.558 mmol) was used instead of 2-amino-6-chloropyridine, to provide the Title compound. LC/MS: (M+H)+: 483.9.

Example 42

(3S)-2-((2R)-3-Cyclopentyl-2-{[formyl(hydroxy)amino]methyl}propanoyl)-N-[6-(methyloxy)-1,5-naphthyridin-3-yl]-3-pyrazolidinecarboxamide

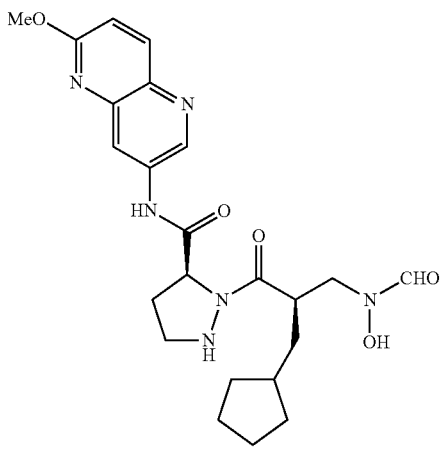 [SMILES: COc1ccc2ncc(NC(=O)[C@@H]3CCNN3C(=O)[C@H](CC3CCCC3)CN(O)C=O)cc2n1]

Pre Step A 6-(Methyloxy)-1,5-naphthyridin-3-amine

Dissolved 4-bromo-6-(methyloxy)-1,5-naphthyridin-3-amine (as prepared in WO2006081179 A1) (372 mg, 1.464 mmol) in methanol. Added sodium bicarbonate (246 mg, 2.93 mmol) followed by 10% palladium on carbon (312 mg, 0.293 mmol). The mixture was flushed with nitrogen and hydrogenated under balloon pressure for 1 h. After 1 h, filtered reaction mixture and concentrated to afford 155 mg (0.885 mmol, 60%) of the title compound as a white solid. 1H NMR (400 MHz, CHLOROFORM-d) d ppm 4.05 (s, 3H) 6.90 (d, J=9.09 Hz, 1H) 7.38 (br. s., 1H) 8.16 (d, J=8.84 Hz, 1H) 8.54 (br. s., 1H).

A procedure similar to Example 29, Parts A and B was used, except that in Part A DMF was used instead of dichloromethane, 6-(methyloxy)-1,5-naphthyridin-3-amine (65.2 mg, 0.372 mmol) was used instead of 2-amino-6-chloropyridine, and (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid) was used as a single diastereomer instead of 2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid as a mixture of diastereomers to provide the Title compound. LC/MS: (M+H)+: 470.8. $^1$H NMR (400 MHz, METHANOL-d$_4$) δ ppm 1.20 (br. s., 2H) 1.30 (br. s., 1H) 1.37-1.53 (m, 1H) 1.53-1.73 (m, 4H) 1.80 (br. s., 1H) 1.86-2.10 (m, 3H) 2.25 (br. s., 1H) 2.60 (br. s., 1H) 3.01 (br. s., 1H) 3.54 (d, J=10.61 Hz, 1H) 3.78-3.95 (m, 1H) 4.71 (br. s., 1H)

7.01 (dd, J=14.27, 8.97 Hz, 1H) 7.86 (br. s., 1H) 8.01 (dd, J=17.68, 8.84 Hz, 1H) 8.50 (d, J=9.60 Hz, 1H) 8.65-8.88 (m, 1H).

Example 43

(3S)-2-((2R)-3-Cyclopentyl-2-{[formyl(hydroxy)amino]methyl}propanoyl)-N-(5-fluoro-1-oxido-2-pyridinyl)-3-pyrazolidinecarboxamide

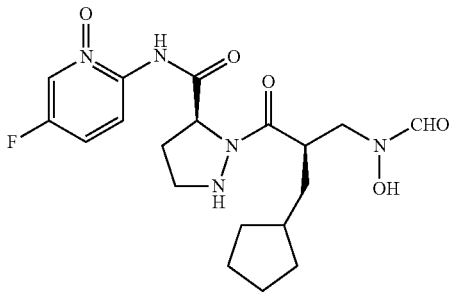 [SMILES: O=CN(O)C[C@@H](CC1CCCC1)C(=O)N1NCC[C@H]1C(=O)Nc1ccc(F)c[n+]1[O-]]

Part A

Phenyl methyl (3S)-2-[(2R)-3-cyclopentyl-2-({formyl[(phenylmethyl)oxy]amino}methyl)propanoyl]-3-{[(5-fluoro-2-pyridinyl)amino]carbonyl}-1-pyrazolidinecarboxylate To a solution of 2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid (600 mg, 1.116 mmol) in dichloromethane (7 ml) was added 1-methylimidazole (374 μl, 4.69 mmol) and cooled to 0° C. Mesyl chloride (112 μL, 1.451 mmol) was added dropwise at 0° C., and the resulting mixture was stirred for 30 min at rt. The mixture was then treated 2-amino-5-fluoropyridine (163 mg, 1.451 mmol). The solvent mixture was removed. The residue was diluted with MeOH and purified by reverse-phase HPLC to afford 101 mg (0.160 mmol, 14%) of the title compound. LC/MS: (M+H)$^+$: 632.2.

Part B

Phenyl methyl 2-[(2R)-3-cyclopentyl-2-({formyl[(phenylmethyl)oxy]amino}methyl)propanoyl]-3-{[(5-fluoro-1-oxido-2-pyridinyl)amino]carbonyl}-1-pyrazolidinecarboxylate To a solution of phenylmethyl (3S)-2-[(2R)-3-cyclopentyl-2-({formyl [(phenylmethyl)oxy]amino}methyl)propanoyl]-3-{[(5-fluoro-2-pyridinyl)amino]carbonyl}-1-pyrazolidinecarboxylate (101 mg, 0.16 mmol) in DCM (4 mL) cooled to 0° C. was added mCPBA (107 mg, 0.48 mmol, 77 wt %) and stirred for 16 hr. The reaction was quenched by the addition of sat. aq. NaHCO$_3$ and extracted into dichloromethane. The organic solvent was removed to give the crude product which was used without further purification to yield 104 mg (0.161 mmol, 100%) of the title compound as a foam. LC/MS: (M+H)$^+$: 648.2.

Part C (3S)-2-((2R)-3-Cyclopentyl-2-{[formyl(hydroxy)amino]methyl}propanoyl)-N-(5-fluoro-1-oxido-2-pyridinyl)-3-pyrazolidinecarboxamide To a solution of phenylmethyl 2-[(2R)-3-cyclopentyl-2-({formyl[(phenylmethyl)oxy]amino}methyl)propanoyl]-3-{[(5-fluoro-1-oxido-2-pyridinyl)amino]carbonyl}-1-pyrazolidinecarboxylate (104 mg, 0.161 mmol) in methanol (4 ml) was added 20% palladium hydroxide on carbon (50 mg, 0.161 mmol). The mixture was hydrogenated under balloon pressure for 1 h and then filtered. The filtrate was purified by reverse-phase HPLC to yield (3S)-2-((2R)-3-cyclopentyl-2-{[formyl(hydroxy)amino]methyl}propanoyl)-N-(5-fluoro-1-oxido-2-pyridinyl)-3-pyrazolidinecarboxamide (13 mg, 0.028 mmol, 18% yield). LC/MS: (M+H)$^+$: 423.8. $^1$H NMR (400 MHz, METHANOL-d$_4$) δ ppm 1.00-1.27 (m, 2H) 1.39-1.69 (m, 5H) 1.70-1.99 (m, 4H) 2.25-2.45 (m, 1H) 2.45-2.64 (m, 1H) 2.84-3.03 (m, 1H) 3.18-3.30 (m, 1H) 3.53 (dd, J=14.02, 4.42 Hz, 1H) 3.74-3.88 (m, 1H) 3.98 (td, J=9.28, 4.93 Hz, 1H) 4.74-4.87 (m, 1H) 7.37-7.54 (m, 1H) 7.89 (s, 1H) 8.37-8.60 (m, 2H).

Example 44

(3S)-2-((2R)-3-Cyclopentyl-2-{[formyl(hydroxy)amino]methyl}propanoyl)-N-(5-methyl-2-pyridinyl)-3-pyrazolidinecarboxamide

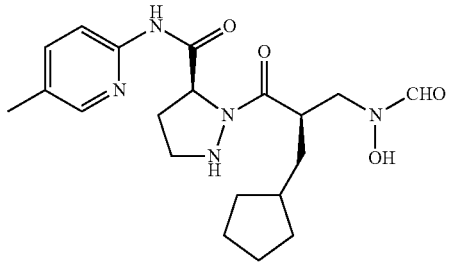 [SMILES: Cc1ccc(NC(=O)[C@@H]2CCNN2C(=O)[C@H](CC2CCCC2)CN(O)C=O)nc1]

Part A

Phenylmethyl (3S)-2-[(2R)-3-cyclopentyl-2-({formyl[(phenylmethyl)oxy]amino}methyl)propanoyl]-3-{[(5-methyl-2-pyridinyl)amino]carbonyl}-1-pyrazolidinecarboxylate Batch 1:
To a solution of 2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (250 mg, 0.465 mmol) in DMF (3.5 ml) was added 1-methylimidazole (156 μl, 1.953 mmol) and cooled to 0° C. Mesyl chloride (40 μL, 0.512 mmol) was added dropwise at 0° C., and the resulting mixture was stirred for 40 min. at rt. The mixture was then treated with 6-amino-3-picoline (60 mg, 0.558 mmol). The solvent mixture was removed. The residue was diluted with MeOH and purified by reverse-phase HPLC to afford 94 mg (0.150 mmol, 32%) of the title compound.
Batch 2:
To a solution of 2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (290 mg, 0.539 mmol) in tetrahydrofuran (3 ml) was added N,N-diisopropylethylamine (470 µl, 2.7 mmol) and 2,4,6-trichlorobenzoyl chloride (0.101 mL, 0.647 mmol). The mixture was stirred for 2 h and then the solvent was evaporated. The residue was then diluted with toluene (3 mL). The resulting suspension was treated with 6-amino-3-picoline (64 mg, 0.593 mmol) followed by DMAP (13.2 mg, 0.108 mmol). After 18 h, the solvent mixture was removed. The residue was diluted with MeOH and purified by reverse-phase HPLC to afford 48 mg (0.076 mmol, 14%) of the title compound as a white solid. LC/MS: $(M+H)^+$: 628.5.

Part B (3S)-2-((2R)-3-Cyclopentyl-2-{[formyl(hydroxy)amino]methyl}propanoyl)-N-(5-methyl-2-pyridinyl)-3-pyrazolidinecarboxamide To a solution of phenylmethyl (3S)-2-[(2R)-3-cyclopentyl-2-({formyl[(phenylmethyl)oxy]amino}methyl)propanoyl]-3-{[(5-methyl-2-pyridinyl)amino]carbonyl}-1-pyrazolidinecarboxylate (combined from Part A, Batches 1 and 2, 142 mg, 0.226 mmol) in methanol (6 ml) was added 20% palladium hydroxide on carbon (70 mg, 0.226 mmol). The mixture was hydrogenated under balloon pressure for 1 h 30 min. and then filtered. The mixture was purified by reverse-phase HPLC to yield (3S)-2-((2R)-3-cyclopentyl-2-{[formyl(hydroxy)amino]methyl}propanoyl)-N-(5-methyl-2-pyridinyl)-3-pyrazolidine carboxamide (68 mg, 0.170 mmol, 75% yield). LC/MS: $(M+H)^+$: 404.0. $^1$H NMR (400 MHz, METHANOL-$d_4$) δ ppm 1.06-1.26 (m, 2H) 1.35-1.48 (m, 1H) 1.48-1.69 (m, 4H) 1.69-1.99 (m, 4H) 2.17-2.31 (m, 3H) 2.45-2.64 (m, 1H) 2.80-3.01 (m, 1H) 3.16-3.31 (m, 1H) 3.51 (dd, J=14.02, 4.42 Hz, 1H) 3.66-3.84 (m, 2H) 3.95 (dt, J=9.35, 4.67 Hz, 1H) 4.70 (td, J=7.96, 4.04 Hz, 1H) 7.61 (dd, J=8.08, 2.02 Hz, 1H) 7.88 (s, 1H) 7.98 (d, J=8.34 Hz, 1H) 8.13 (d, J=2.27 Hz, 1H).

Example 45

(3S)-2-((2R)-3-Cyclopentyl-2-{[formyl(hydroxy)amino]methyl}propanoyl)-N-(1-oxido-2-pyridinyl)-3-pyrazolidinecarboxamide

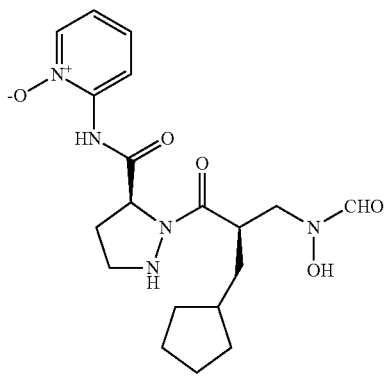

Part A

Phenylmethyl (3S)-2-[(2R)-3-cyclopentyl-2-({formyl[(phenylmethyl)oxy]amino}methyl)propanoyl]-3-{[(1-oxido-2-pyridinyl)amino]carbonyl}-1-pyrazolidinecarboxylate To a solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid (176 mg, 0.327 mmol) in DMF (2 ml) was added 1-methylimidazole (52 µl, 0.655 mmol) and cooled to 0° C. Mesyl chloride (27 µL, 0.344 mmol) was added dropwise at 0° C., and the resulting mixture was stirred for 30 min followed by the addition of 2-amino pyridine N-oxide (36 mg, 0.327 mmol). The reaction was warmed to rt. After 2 h, the reaction mixture was concentrated, diluted with methanol, and purified by reverse phase HPLC to afford 105 mg (0.167 mmol, 51%) of the title compound. LC/MS: $(M+H)^+$: 629.8.

Part B (3S)-2-((2R)-3-Cyclopentyl-2-{[formyl(hydroxy)amino]methyl}propanoyl)-N-(1-oxido-2-pyridinyl)-3-pyrazolidinecarboxamide To a solution of phenylmethyl (3S)-2-[(2R)-3-cyclopentyl-2-({formyl[(phenylmethyl)oxy]amino}methyl)propanoyl]-3-{[(1-oxido-2-pyridinyl)amino]carbonyl}-1-pyrazolidine carboxylate (105 mg, 0.167 mmol) in methanol (10 ml) was added 10% palladium on carbon (17.75 mg, 0.017 mmol). The mixture was hydrogenated under balloon pressure for 72 h and then filtered. The mixture was purified by reverse-phase HPLC to yield (3S)-2-((2R)-3-cyclopentyl-2-{[formyl(hydroxy)amino]methyl}propanoyl)-N-(1-oxido-2-pyridinyl)-3-pyrazolidinecarboxamide (35 mg, 0.086 mmol, 52% yield). LC/MS: $(M+H)^+$: 06.4. $^1$H NMR (400 MHz, METHANOL-$d_4$) δ ppm 1.07-1.28 (m, 3H) 1.39-1.69 (m, 5H) 1.69-1.84 (m, 2H) 1.84-2.02 (m, 2H) 2.29-2.46 (m, 1H) 2.46-2.64 (m, 1H) 2.84-3.00 (m, 1H) 3.19-3.31 (m, 1H) 3.46-3.61 (m, 1H) 3.76-3.90 (m, 1H) 3.93-4.14 (m, 1H) 4.76-4.87 (m, 1H) 7.10-7.34 (m, 1H) 7.58 (t, J=8.08 Hz, 1H) 7.90 (s, 1H) 8.34 (d, J=6.32 Hz, 1H) 8.49 (dd, J=8.59, 1.52 Hz, 1H).

The following Examples 46 to 49 were prepared according to a method similar to that disclosed in Example 45 except that to the mixture in Part A was added the indicated compound instead of 2-amino pyridine N-oxide.

Example 46

Methyl 6-({[(3S)-2-((2R)-3-cyclopentyl-2-{[formyl(hydroxy)amino]methyl}propanoyl)-3-pyrazolidinyl]carbonyl}amino)-2-pyridinecarboxylate

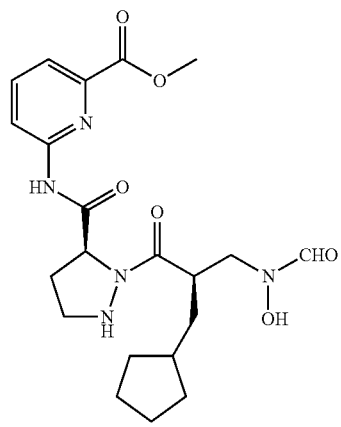 [SMILES: COC(=O)c1cccc(NC(=O)[C@@H]2CCNN2C(=O)[C@H](CC2CCCC2)CN(O)C=O)n1]

methyl 6-amino-2-pyridinecarboxylate (43.9 mg, 0.288 mmol). LC/MS: (M+H)+: 447.9.

Example 47

(3S)-2-((2R)-3-Cyclopentyl-2-{[formyl(hydroxy)amino]methyl}propanoyl)-N-(5-methyl-3-isoxazolyl)-3-pyrazolidinecarboxamide

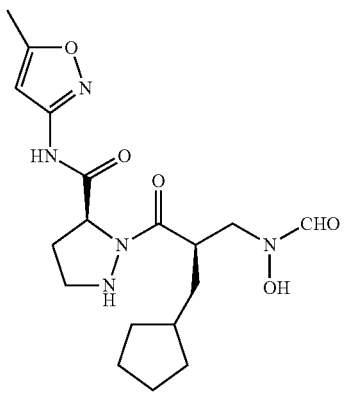 [SMILES: Cc1cc(NC(=O)[C@@H]2CCNN2C(=O)[C@H](CC2CCCC2)CN(O)C=O)no1]

5-methyl-3-isoxazolamine (29.9 mg, 0.305 mmol. LC/MS: (M+H)+: 394.2. ¹H NMR (400 MHz, METHANOL-d₄) δ ppm 1.04-1.27 (m, 2H) 1.41 (dd, J=7.71, 5.43 Hz, 1H) 1.52-1.69 (m, 4H) 1.70-1.95 (m, 4H) 2.10-2.31 (m, J=7.23, 4.78, 4.78, 2.65 Hz, 1H) 2.40 (s, 3H) 2.46-2.61 (m, 1H) 2.91 (dd, J=10.11, 6.57 Hz, 1H) 3.18-3.33 (m, 2H) 3.62-3.84 (m, 2H) 4.61 (t, J=7.33 Hz, 1H) 6.60 (s, 1H).

Example 48

(3S)-2-((2R)-3-Cyclopentyl-2-{[formyl(hydroxy)amino]methyl}propanoyl)-N-(2-fluoro-3-pyridinyl)-3-pyrazolidinecarboxamide

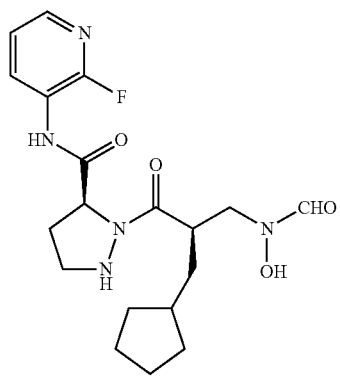 [SMILES: O=CN(O)C[C@@H](CC1CCCC1)C(=O)N1NCC[C@H]1C(=O)Nc1cccnc1F]

Example 48 was prepared according to a method similar to that disclosed in Example 45 except that to the mixture in Part A was added 3-amino-2-fluoropyridine instead of 2-amino pyridine N-oxide, and palladium hydroxide on carbon was used in Part B instead of palladium on carbon. LC/MS: (M+H)+: 408.1. ¹H NMR (400 MHz, METHANOL-d₄) δ ppm 1.16 (dd, J=12.13, 7.07 Hz, 2H) 1.39-1.47 (m, 1H) 1.48-1.67 (m, 4H) 1.71-1.96 (m, 4H) 2.20-2.40 (m, 1H) 2.44- 2.64 (m, 1H) 2.92 (dd, J=10.36, 6.57 Hz, 1H) 3.26 (t, J=8.21 Hz, 1H) 3.65-3.86 (m, 2H) 4.75 (td, J=7.96, 3.54 Hz, 1H) 7.30 (dd, J=7.96, 4.93 Hz, 1H) 7.92 (d, J=4.80 Hz, 1H) 8.60 (dd, J=17.68, 1.52 Hz, 1H).

Example 49

(3S)-2-((2R)-3-Cyclopentyl-2-{[formyl(hydroxy)amino]methyl}propanoyl)-N-(1-oxido-4-pyrimidinyl)-3-pyrazolidinecarboxamide

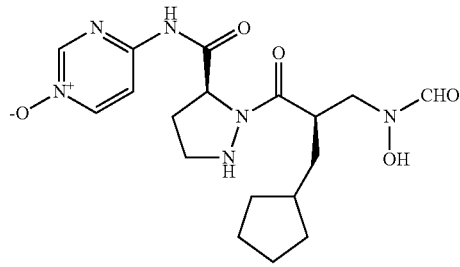

Pre Step A

4-Pyrimidinamine 1-oxide

A rb flask equipped with a stirring bar was charged with 4-aminopyrimidine (462 mg, 4.86 mmol) in dichloromethane (DCM) (25 mL). To this was added m-CPBA (1198 mg, 5.34 mmol). After 2, the mixture was concentrated and purified by washing through a pad of silica eluting with 80:20:1:DCM:MeOH:NH4OH to afford 350 mg (3.15 mmol, 65%) of the title compound. LC/MS: (M+H)+: 111.8.

A procedure similar to Example 45, Parts A and B was used, except that 4-pyrimidinamine 1-oxide (124 mg, 1.116 mmol) was used instead of 2-amino pyridine N-oxide to treat the mixture in Part A, to provide the Title compound. LC/MS: (M+H)+: 407.3.

Example 50

(3S)—N-1H-1,2,3-Benzotriazol-5-yl-2-((2R)-3-cyclopentyl-2-{[formyl(hydroxy)amino]methyl}propanoyl)-3-pyrazolidinecarboxamide

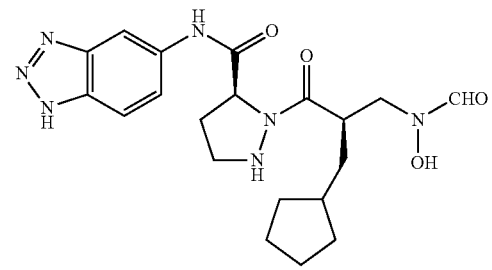 [SMILES: O=CN(O)C[C@@H](CC1CCCC1)C(=O)N1NCC[C@H]1C(=O)Nc1ccc2[nH]nnc2c1]

Part A

Phenylmethyl (3S)-3-[(1H-1,2,3-benzotriazol-5-ylamino)carbonyl]-2-[(2R)-3-cyclopentyl-2-({formyl[(phenylmethyl)oxy]amino}methyl)propanoyl]-1-pyrazolidinecarboxylate To a solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid (103.1 mg, 0.192 mmol), 1H-1,2,3-benzotriazol-5-amine (56.6 mg, 0.422 mmol), and N-methylmorpholine (46.4 μl, 0.422 mmol) in acetonitrile (1.87 ml) was added DMTMM tetrafluoroborate (69.2 mg, 0.211 mmol). The solution was stirred for 3 days, and then concentrated in vacuo. The residue was dissolved in EtOAc (100 mL), and washed with 1 N aq. HCl (50 mL), followed by 5% aq. NaHCO$_3$. The organic phase was dried over anhydrous Na$_2$SO$_4$, filtered, and concentrated in vacuo. The residue was purified by Gilson RPLC (20% to 90% MeCN in water, 8 min gradient), and the desired fractions were combined, and concentrated in vacuo. The residue was azeotroped with MeOH (2×30 mL) to give phenylmethyl (3S)-3-[(1H-1,2,3-benzotriazol-5-ylamino)carbonyl]-2-[(2R)-3-cyclopentyl-2-({formyl[(phenylmethyl)oxy]amino}methyl)propanoyl]-1-pyrazolidinecarboxylate (87.2 mg, 0.133 mmol, 69.6% yield) as a light yellow oil. LC/MS: (M+H)$^+$: 654.5. Reference for DMTMM tetrafluoroborate: Raw, S. A. *Tetrahedron Lett.* 2009, 50, 946.

Part B (3S)—N-1H-1,2,3-Benzotriazol-5-yl-2-((2R)-3-cyclopentyl-2-{[formyl(hydroxy)amino]methyl}propanoyl)-3-pyrazolidinecarboxamide To a solution of phenylmethyl (3S)-3-[(1H-1,2,3-benzotriazol-5-ylamino)carbonyl]-2-[(2R)-3-cyclopentyl-2-({formyl[(phenylmethyl)oxy]amino}methyl)propanoyl]-1-pyrazolidinecarboxylate (87.2 mg, 0.133 mmol) in methanol (2.7 ml) was added 20% palladium hydroxide on carbon, 50% water (18.73 mg, 0.133 mmol). The mixture was hydrogenated under balloon pressure for 3 h, and was then filtered through a 0.2 μm PTFE membrane. The solution was concentrated in vacuo, and the residue was azeotroped with EtOAc (10 mL). The residue was triturated with 30% EtOAc in hexanes, and the solid was collected by vacuum filtration to give (3S)—N-1H-1,2,3-benzotriazol-5-yl-2-((2R)-3-cyclopentyl-2-{[formyl(hydroxy)amino]methyl}propanoyl)-3-pyrazolidinecarboxamide (43.2 mg, 0.101 mmol, 75% yield) as a white solid. LC/MS: (M+H)$^+$: 430.1.

Example 51

(3S)-2-((2R)-3-Cyclopentyl-2-{[formyl(hydroxy)amino]methyl}propanoyl)-1-methyl-N-4-pyrimidinyl-3-pyrazolidinecarboxamide

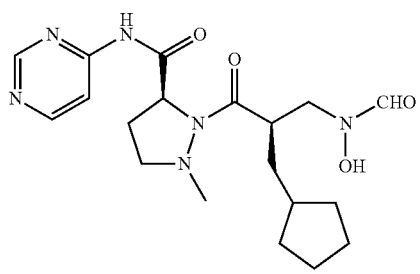 [SMILES: CN1CC[C@@H](C(=O)Nc2ccncn2)N1C(=O)[C@H](CC1CCCC1)CN(O)C=O]

Part A 1,1-Dimethylethyl 4,5-dihydro-1H-pyrazole-5-carboxylate

A 1 L rb flask was charged with t-butylacrylate (11.33 mL, 78 mmol) in toluene (100 mL) and tetrahydrofuran (THF) (100 mL). To this was added via addition funnel TMS-diazomethane (50.5 mL, 101 mmol) dropwise over 25 minutes under N$_2$. The reaction mixture was stirred at 25° C. for 4.5 h. The solvent was evaporated under reduced pressure. The crude product was dissolved in dichloromethane (70 mL) and cooled in an ice bath. To this solution was added TFA (7.21 mL, 94 mmol.) dissolved in 30 mL of dichloromethane via addition funnel. After addition was complete the mixture was stirred at 25° C. for 0.5 h. The solvent was evaporated and the residue was neutralized by the addition of sat. NaHCO$_3$ and extracted into DCM. The organic layer was dried over Na$_2$SO$_4$, filtered, and concentrated to give the crude product which was purified by automated silica gel column chromatography (column: 120 g, 0-38% ethyl acetate in hexane, 34 min). The solvent was removed under reduced pressure to afford 8 g (47 mmol, 60%) of 1,1-dimethylethyl 4,5-dihydro-1H-pyrazole-5-carboxylate as pale yellow oil. LC-MS (ES) m/e 171.1 (M+H)$^+$.

Part B

Bis(1,1-dimethyl)4,5-dihydro-1H-pyrazole-1,5-dicarboxylate

Boc-anhydride (18.27 mL, 78.67 mmol) and 1,1-dimethylethyl 4,5-dihydro-1H-pyrazole-5-carboxylate (8 g, 47.0 mmol) were dissolved in dichloromethane (DCM) (71 mL). To this mixture was added TEA (13.10 mL, 94 mmol). The reaction mixture was stirred at 25° C. for 72 h. The reaction solution was washed with 1N HCl (1×500 mL), extracted with DCM, dried over anhydrous Na$_2$SO$_4$, filtered, and concentrated. The crude product was purified by automated silica gel column chromatography (column 300 g: 0-50% ethyl acetate in hexane) to afford 8.89 g (32.9 mmol, 70%) of bis(1,1-dimethyl)4,5-dihydro-1H-pyrazole-1,5-dicarboxylate as pale yellow oil. LC-MS (ES) m/e 271.2 (M+H)$^+$.

Part C

Di-tert-butylpyrazolidine-1,5-dicarboxylate

Bis(1,1-dimethyl)4,5-dihydro-1H-pyrazole-1,5-dicarboxylate (8.5 g, 31.4 mmol) was dissolved in acetic acid (50 mL) and the solution was cooled in ice-water bath. Sodium cyanoborohydride (3.95 g, 62.9 mmol) was added into the reaction mixture in portions under N$_2$. The reaction was stirred at 25° C. for 2 h. The solvent was evaporated under reduced pressure to give a residue which was diluted with ethyl acetate (208 mL) and saturated Na$_2$CO$_3$ solution (140 mL). The crude product was extracted into the ethyl acetate solution and dried over Na$_2$SO$_4$. The solvent was removed under reduced pressure and the resulting crude product was purified by silica gel column chromatography to afford 7 g (25.7 mmol, 82%) of di-tert-butylpyrazolidine-1,5-dicarboxylate as a colorless oil. LC-MS (ES) m/e 273.3 (M+H)$^+$.

Part D

Bis(1,1-dimethylethyl) 2-methyl-1,5-pyrazolidinedicarboxylate

To a solution of di-tert-butylpyrazolidine-1,5-dicarboxylate (7 g, 25.7 mmol) dissolved in 1,2-dichloroethane (DCE) (80 mL) were added HCHO (2.224 g, 69.4 mmol), sodium triacetoxyborohydride (14.71 g, 69.4 mmol), and acetic acid (8 mL). The reaction was stirred at rt for appropriate time. The solvent was then removed and the residue was diluted with DCM and saturated NaHCO$_3$ (150 mL). The aqueous layer was extracted with DCM. The organic layer was dried over Na$_2$SO$_4$, filtered, and evaporated. The residue was purified by silica gel column chromatography to afford 4 g (13.97 mmol, 54.3% yield) of bis(1,1-dimethylethyl) 2-methyl-1,5-pyrazolidinedicarboxylate as a pale yellow oil. LC-MS (ES) m/e 287.1 (M+H)$^+$.

Part E

1-Methyl-3-pyrazolidinecarboxylic acid

To a solution of bis(1,1-dimethylethyl) 2-methyl-1,5-pyrazolidinedicarboxylate dissolved in dichloromethane (DCM) (25 mL) was added TFA (30.7 mL, 398 mmol) and water (3.59 mL, 199 mmol). The reaction was stirred at rt and monitored by LCMS. When the reaction was deemed complete, the solvent was evaporated under reduced pressure to give a residue which was azeotroped from toluene (50 mL×3) in order to remove the TFA and water. The crude product was obtained as a colorless oil (97% yield based on TFA Salt), which was used directly for the next step. LC-MS (ES) m/e 130.9 (M+H)$^+$.

Part F (3S)-2-[(2R)-3-Cyclopentyl-2-({formyl[(phenylmethyl)oxy]amino}methyl)propanoyl]-1-methyl-3-pyrazolidinecarboxylic acid To a solution of (2R)-3-cyclopentyl-2-({formyl[phenylmethyl)oxy]amino}methyl)propanoyl fluoride (3.14 g, 10.21 mmol) in DMF (10 mL) was added 1-methyl-3-pyrazolidinecarboxylic acid (1.727 g, 13.27 mmol) and DIPEA (14.23 ml, 82 mmol) in DMF (30 mL). The solution was stirred at 25° C. The reaction mixture was diluted with EtOAc and then washed with sat. NH$_4$Cl solution (2×30 mL). The aqueous layer was extracted with EtOAc followed by CHCl$_3$:MeOH: 80:20. The organic layers were dried over anhydrous Na$_2$SO$_4$. The solvent was evaporated under reduced pressure to give a pale yellow residue which was purified via reverse-phase HPLC (30×100 mm, 10 min, 30-95% MeCN in H2O, 45 ml/min) to afford 1.1 g (2.63 mmol, 26%) of (3S)-2-[(2R)-3-cyclopentyl-2-({formyl[(phenylmethyl)oxy]amino}methyl)propanoyl]-1-methyl-3-pyrazolidinecarboxylic acid as a white solid.

Part G (3S)-2-[(2R)-3-Cyclopentyl-2-({formyl [(phenylmethyl)oxy]amino}methyl)propanoyl]-1-methyl-N-4-pyrimidinyl-3-pyrazolidinecarboxamide 1-Methylimidazole (38.2 µl, 0.479 mmol) was added into a solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid (100 mg, 0.240 mmol) in 1.0 ml of DMF. The solution was cooled to 0° C., and then mesyl chloride (24.26 µl, 0.311 mmol) was added dropwise at 0° C. 4-Aminopyrimidine (34.2 mg, 0.359 mmol) dissolved in another 1.0 ml of DMF was then added. The reaction mixture was stirred for 3.5 h at rt. The reaction mixture was concentrated and purified by RP-HPLC to afford (3S)-2-[(2R)-3-cyclopentyl-2-({formyl[(phenylmethyl)oxy] amino}methyl)propanoyl]-1-methyl-N-4-pyrimidinyl-3-pyrazolidinecarboxamide (95 mg, 0.192 mmol, 80%) as a white foam solid. LC-MS (ES) m/e 495.3 (M+H)+.

Part H (3S)-2-((2R)-3-Cyclopentyl-2-{[formyl(hydroxy)amino]methyl}propanoyl)-1-methyl-N-4-pyrimidinyl-3-pyrazolidinecarboxamide (3S)-2-[(2R)-3-Cyclopentyl-2-({formyl[(phenylmethyl)oxy]amino}methyl)propanoyl]-1-methyl-N-4-pyrimidinyl-3-pyrazolidinecarboxamide (120 mg, 0.243 mmol) was dissolved in methanol (14 mL). To this mixture was added palladium hydroxide on carbon (34.1 mg, 0.049 mmol). The reaction mixture was degassed and placed under 1 atm of H2. After 2 h, the reaction mixture was filtered and concentrated. The residue was purified by RP-HPLC to afford (3S)-2-((2R)-3-cyclopentyl-2-{[formyl(hydroxy)amino] methyl}propanoyl)-1-methyl-N-4-pyrimidinyl-3-pyrazolidinecarboxamide (70 mg, 0.173 mmol, 71.3% yield) as white foam solid. LC-MS (ES) m/e 405.3 (M+H)+.

Example 52

(3S)-2-((2R)-3-Cyclopentyl-2-{[formyl(hydroxy)amino]methyl}propanoyl)-N-(5-fluoro-2-pyridinyl)-1-methyl-3-pyrazolidinecarboxamide

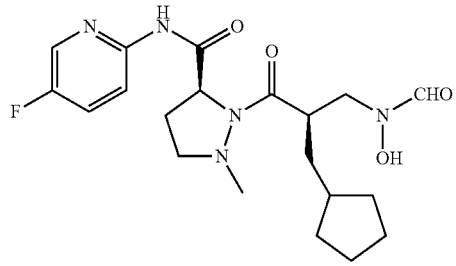 [SMILES: CN1CC[C@@H](C(=O)Nc2ccc(F)cn2)N1C(=O)[C@H](CC1CCCC1)CN(O)C=O]

Part A

1-Methylimidazole (38.2 µl, 0.479 mmol) was added into a solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid (100 mg, 0.240 mmol) in 1.0 ml of DMF. The solution was cooled to 0° C., and then mesyl chloride (24.26 µl, 0.311 mmol) was added dropwise at 0° C. and then 5-fluoro-2-pyridinamine (40.3 mg, 0.359 mmol) dissolved in another 1.0 ml of DMF was added. The reaction mixture was stirred for 3.5 h at rt. The reaction mixture was concentrated and purified by RP-HPLC to afford (3S)-2-[(2R)-3-cyclopentyl-2-({formyl[(phenylmethyl)oxy] amino}methyl)propanoyl]-N-(5-fluoro-2-pyridinyl)-1-methyl-3-pyrazolidinecarboxamide (84 mg, 0.164 mmol, 68.6% yield) as a white solid. LC-MS (ES) m/e 512.3 (M+H)+.

Part B (3S)-2-((2R)-3-Cyclopentyl-2-{[formyl(hydroxy)amino]methyl}propanoyl)-N-(5-fluoro-2-pyridinyl)-1-methyl-3-pyrazolidinecarboxamide (3S)-2-[(2R)-3-Cyclopentyl-2 ({formyl[(phenylmethyl)oxy]amino}methyl)propanoyl]-N-(5-fluoro-2-pyridinyl)-1-methyl-3-pyrazolidinecarboxamide (84 mg, 0.164 mmol) was dissolved in methanol (9.66 ml). To this mixture was added 20% palladium hydroxide on carbon (23.06 mg, 0.033 mmol). The reaction mixture was degassed and placed under 1 atm of H$_2$. After 2 h, the reaction mixture was filtered and concentrated. The residue was purified by RP-HPLC to afford (3S)-2-((2R)-3-cyclopentyl-2-{[formyl(hydroxy)amino]methyl}propanoyl)-N-(5-fluoro-2-pyridinyl)-1-methyl-3-pyrazolidinecarboxamide (40 mg, 0.095 mmol, 57.8% yield) as white foam solid. LC-MS (ES) m/e 422.1 (M+H)+.

The following Examples 53 to 57 were prepared according to a method similar to that disclosed in Example 52 except that to the solution in Part A was added the indicated compound (dissolved in 1.0 ml DMF if necessary) instead of 5-fluoro-2-pyridinamine.

Example 53

(3S)-2-((2R)-3-Cyclopentyl-2-{[formyl(hydroxy)amino]methyl}propanoyl)-1-methyl-N-2-pyrazinyl-3-pyrazolidinecarboxamide

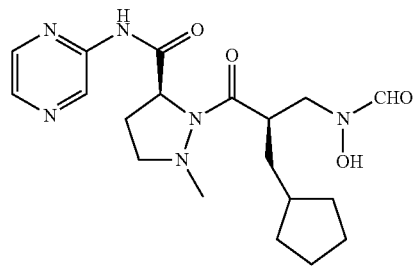 [SMILES: CN1CC[C@@H](C(=O)Nc2cnccn2)N1C(=O)[C@H](CC1CCCC1)CN(O)C=O]

2-aminopyrazine (34.2 mg, 0.359 mmol). LC-MS (ES) m/e 405.3 (M+H)+.

Example 54

(3S)-2-((2R)-3-Cyclopentyl-2-{[formyl(hydroxy)amino]methyl}propanoyl)-1-methyl-N-[2-(methyloxy)-4-pyrimidinyl]-3-pyrazolidinecarboxamide

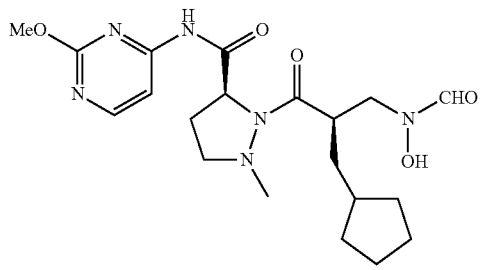 [SMILES: COc1nccc(NC(=O)[C@@H]2CCN(C)N2C(=O)[C@H](CC2CCCC2)CN(O)C=O)n1]

2-(methyloxy)-4-pyrimidinamine (67.4 mg, 0.539 mmol). LC-MS (ES) m/e 435.3 (M+H)+.

Example 55

(3S)-2-((2R)-3-Cyclopentyl-2-{[formyl(hydroxy)amino]methyl}propanoyl)-1-methyl-N-[6-(methyloxy)-2-pyrazinyl]-3-pyrazolidinecarboxamide

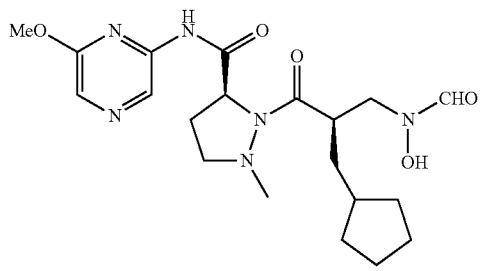 [SMILES: COc1cncc(NC(=O)[C@@H]2CCN(C)N2C(=O)[C@H](CC2CCCC2)CN(O)C=O)n1]

6-(methyloxy)-2-pyrazinamine (67.4 mg, 0.539 mmol). LC-MS (ES) m/e 435.4 (M+H)+.

Example 56

(3S)-2-((2R)-3-Cyclopentyl-2-{[formyl(hydroxy)amino]methyl}propanoyl)-N-(6-fluoro-2-pyridinyl)-1-methyl-3-pyrazolidinecarboxamide

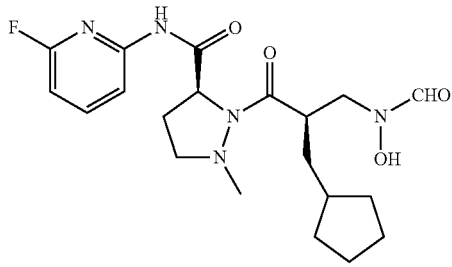 [SMILES: CN1CC[C@@H](C(=O)Nc2cccc(F)n2)N1C(=O)[C@H](CC1CCCC1)CN(O)C=O]

6-fluoro-2-pyridinamine (60.4 mg, 0.539 mmol). LC-MS (ES) m/e 422.1 (M+H)+.

Example 57

(3S)-2-((2R)-3-Cyclopentyl-2-{[formyl(hydroxy)amino]methyl}propanoyl)-N-(3-fluoro-4-pyridinyl)-1-methyl-3-pyrazolidinecarboxamide

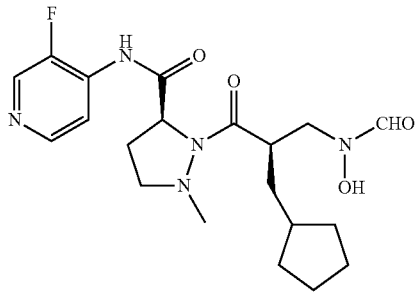 [SMILES: CN1CC[C@@H](C(=O)Nc2ccncc2F)N1C(=O)[C@H](CC1CCCC1)CN(O)C=O]

3-fluoro-4-pyridinamine (60.4 mg, 0.539 mmol). LC-MS (ES) m/e 422.0 (M+H)+.

Example 58

(3S)-2-((2R)-3-Cyclopentyl-2-{[formyl(hydroxy)amino]methyl}propanoyl)-1-methyl-N-[3-(methyloxy)-2-pyrazinyl]-3-pyrazolidinecarboxamide

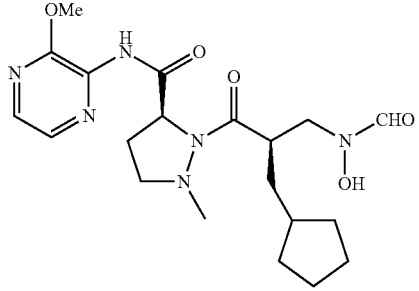 [SMILES: COc1nccnc1NC(=O)[C@@H]1CCN(C)N1C(=O)[C@H](CC1CCCC1)CN(O)C=O]

Part A (3S)-2-[(2R)-3-Cyclopentyl-2-({formyl[(phenylmethyl)oxy]amino}methyl)propanoyl]-1-methyl-N-[3-(methyloxy)-2-pyrazinyl]-3-pyrazolidine carboxamide 4-Methylmorpholine (47.4 μl, 0.431 mmol) was added into a solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (150 mg, 0.359 mmol) and 4-[4,6-bis(methyloxy)-1,3,5-triazin-2-yl]-4-methylmorpholin-4-ium (141 mg, 0.431 mmol) in acetonitrile (5.94 ml). The resulting solution was cooled to 0° C. and stirred at 0° C. for 15 min. To the reaction mixture was added 3-(methyloxy)-2-pyrazinamine (67.4 mg, 0.539 mmol). The reaction mixture was stirred for 2 days at rt. The reaction mixture was concentrated in vacuo and the residue was dissolved in DCM, washed with saturated NaHCO$_3$ solution, followed by brine. The solution was dried over sodium sulfate and filtered. The solvent was removed to give a residue which was redissolved in DMF (3.75 ml) and purified by RP-HPLC to afford (3S)-2-[(2R)-3-cyclopentyl-2-({formyl[(phenylmethyl)oxy]amino}methyl)propanoyl]-1-methyl-N-[3-(methyloxy)-2-pyrazinyl]-3-pyrazolidine carboxamide (96 mg, 0.183 mmol, 51% yield) as a white solid. LC-MS (ES) m/e 525.5 (M+H)+.

Part B (3S)-2-((2R)-3-Cyclopentyl-2-{[formyl(hydroxy) amino]methyl}propanoyl)-1-methyl-N-[3-(methyloxy)-2-pyrazinyl]-3-pyrazolidinecarboxamide (3S)-2-[(2R)-3-Cyclopentyl-2-({formyl[(phenylmethyl)oxy]amino}methyl)propanoyl]-1-methyl-N-[3-(methyloxy)-2-pyrazinyl]-3-pyrazolidinecarboxamide (96 mg, 0.183 mmol) was dissolved in methanol (11 mL). To this mixture was added 20% palladium hydroxide on carbon (26.8 mg, 0.038 mmol). The reaction mixture was degassed and placed under 1 atm of H$_2$. After 1 h, the reaction mixture was filtered and concentrated. The residue was purified by RP-HPLC to afford (3S)-2-((2R)-3-cyclopentyl-2-{[formyl(hydroxy)amino]methyl}propanoyl)-1-methyl-N-[3-(methyloxy)-2-pyrazinyl]-3-pyrazolidinecarboxamide (45 mg, 0.104 mmol, 54.3% yield) as white foam solid. LC-MS (ES) m/e 435.4 (M+H)+.

Example 59

(3S)-2-((2R)-3-Cyclopentyl-2-{[formyl(hydroxy) amino]methyl}propanoyl)-N-4-pyrimidinyl-3-pyrazolidinecarboxamide

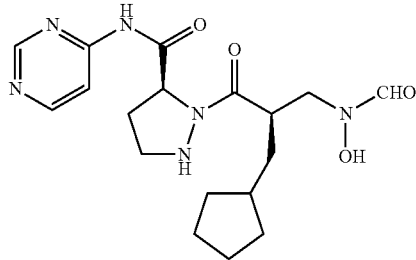 [SMILES: O=CN(O)C[C@@H](CC1CCCC1)C(=O)N1NCC[C@H]1C(=O)Nc1ccncn1]

Method A

Part A 1,1-Dimethylethyl 4,5-dihydro-1H-pyrazole-5-carboxylate 1,1-Dimethylethyl 2-propenoate (10.25 ml, 70 mmol) was added to a round-bottom flask equipped with a stirring bar and charged with toluene (100 ml) and tetrahydrofuran (THF) (100 ml) under nitrogen, and then TMS-Diazomethane (42.0 ml, 84 mmol) was added. After 4 h, the reaction solvents and excess TMS-Diazomethane were removed in vacuo. The residue was dissolved in dichloromethane (150 mL). TFA (6.26 ml, 84 mmol) was added at 0° C. and the resulting mixture was stirred at room temperature overnight. After this time, the reaction was quenched with sat. Na$_2$CO$_3$ and extracted with dichloromethane. The organic layer was dried over Na$_2$SO$_4$. The solvent was removed under reduced pressure to give the crude product as yellow oil, which was purified by silica gel chromatography (Combiflash, 120 g column, hexane/ethyl acetate 0-30% 60 min) to yield the desired product 1,1-dimethylethyl 4,5-dihydro-1H-pyrazole-5-carboxylate (9.7 g, 81% yield) as yellow oil.

Part B

Bis(1,1-dimethylethyl) 4,5-dihydro-1H-pyrazole-1,5-dicarboxylate

To a solution of 1,1-dimethylethyl 4,5-dihydro-1H-pyrazole-5-carboxylate (9.7 g, 57.0 mmol) and bis(1,1-dimethylethyl)dicarbonate (14.93 g, 68.4 mmol) in dichloromethane (86 ml) was added triethylamine (15.89 ml, 114 mmol). The reaction mixture was stirred for 4 days at 25° C. The reaction solution was then washed with 1N HCl (1×500 mL), dried over Na$_2$SO$_4$, filtered, and concentrated to give a residue. The residue was purified by silica gel chromatography (CombiFlash, column: 220 g, 0-50% ethyl acetate in hexane, 60 min) to afford the desired product as light yellow oil.

Part C

Di-tert-butyl pyrazolidine-1,5-dicarboxylate

Di-tert-butyl 4,5-dihydropyrazole-1,5-dicarboxylate (12.65 g, 46.8 mmol) was dissolved in acetic acid (69.2 ml), and the solution was cooled in a water bath. Sodium cyanoborohydride (5.88 g, 94 mmol) was added portionwise under N$_2$. The reaction was stirred at 25° C. for 5 hrs. The solvent was then removed under reduced pressure to give a residue. The residue was diluted with EtOAc (150 mL), and Na$_2$CO$_3$ (sat.) (100 mL) was cautiously added to the solution. The layers were separated and the aq. solution was extracted with EtOAc (2×30 mL), and the organics were dried over Na$_2$SO$_4$. The solvent was removed under reduced pressure to give the crude product di-tert-butyl pyrazolidine-1,5-dicarboxylate (12.74 g) as light yellow oil, which was used directly in the next step.

Part D

1-Benzyl 2,3-di-tert-butyl pyrazolidine-1,2,3-tricarboxylate

Sat. aq. K$_2$CO$_3$ (210 mL) was added into a solution of benzyl chloroformate (12.0 ml, 84 mmol) and crude di-tert-butyl pyrazolidine-1,5-dicarboxylate (12.74 g, assumed 46.8 mmol) in acetonitrile (137 ml) at 0° C. The reaction was allowed to warm to room temperature and was stirred for 4.5 hrs. The aqueous phase was extracted with EtOAc (3×100 mL), and the organic layers were dried over Na$_2$SO$_4$. The solvents were removed in vacuo, and the crude product was purified by silica gel chromatography (CombiFlash, Column: 220 g; 0-35% ethyl acetate in hexane; 60 min) to provide the desired product 1-benzyl 2,3-di-tert-butyl pyrazolidine-1,2,3-tricarboxylate (14.15 g, 74% yield) as a white solid.

Part E

1-{[(Phenylmethyl)oxy]carbonyl}-3-pyrazolidinecarboxylic acid

1-Benzyl 2,3-di-tert-butyl pyrazolidine-1,2,3-tricarboxylate (14.15 g, 34.8 mmol) was dissolved in dichloromethane (68.6 ml) under $N_2$ at room temperature. TFA (80 ml, 1045 mmol) and water (9.41 ml, 522 mmol) were then added in one portion. The reaction was stirred at 25° C. for 2 days. The solvent was then removed under reduced pressure to give 1-{[(phenylmethyl)oxy]carbonyl}-3-pyrazolidinecarboxylic acid (8.72 g, 34.8 mmol, 100% yield).

Part F

(2R)-3-Cyclopentyl-2-({formyl[(phenylmethyl)oxy] amino}methyl)propanoyl fluoride 2,4,6-Trifluoro-1,3,5-triazine (10.7 g, 79 mmol) was added into a solution of pyridine (6.4 ml, 79 mmol) and (2R)-3-cyclopentyl-2-({formyl[(phenylmethyl)oxy]amino}methyl)propanoic acid (WO 2009061879) (22 g, 72.0 mmol) in dichloromethane (348 ml) at room temperature. The resulting solution was stirred overnight. Dichloromethane (300 mL) was added to the reaction solution, followed by 1000 mL of 5% citric acid, and the mixture was filtrated. The solids were washed with DCM (300 ml). The organic layer of the filtrate was separated and washed with sat. $NaHCO_3$ (2×300 mL). The organic layer was dried over $Na_2SO_4$, filtered and concentrated to yield a yellow oil, which was purified by silica gel chromatography (CombiFlash, Column: 220 g; 0-20% ethyl acetate in hexane; 50 min) to provide (2R)-3-cyclopentyl-2-({formyl[(phenylmethyl)oxy]amino}methyl)propanoyl fluoride (14.32 g, 64.7% yield) as a colorless oil.

Part G

(3S)-2-[(2R)-3-Cyclopentyl-2-({formyl[(phenylmethyl)oxy]amino}methyl)propanoyl]-1-{[(phenylmethyl)oxy]carbonyl}-3-pyrazolidinecarboxylic acid (2R)-3-Cyclopentyl-2-({formyl[(phenylmethyl)oxy] amino}methyl)propanoyl fluoride (8.18 g, 26.6 mmol) was added into a solution of 1-{[(phenylmethyl)oxy]carbonyl}-3-pyrazolidinecarboxylic acid (8.65 g, 34.6 mmol) in dichloromethane (85 ml), and followed by Hunig's base (23.2 ml, 133 mmol). The reaction mixture was stirred at 25° C. for 5 hrs. The reaction was then diluted with DCM (50 ml), and acetic acid (6 ml) was added. The resulting solution was washed with aqueous $NH_4Cl$ (2×2 00 mL). The aqueous solution was extracted with DCM (2×100 mL). The combined organic layers were dried over $Na_2SO_4$, filtered and concentrated to provide a residue. The residue was purified by silica gel chromatography (CombiFlash, Column: 220 g; 0-100% ethyl acetate in hexane; 40 min). The first ⅔ of the eluting fractions were combined, and the solvent was removed to give a residue. Acetonitrile (~5 ml) was added to the residue. The diastereomer (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid remained as a white solid. The white solid was filtered, washed with MeCN (3×0.5 mL), and air dried to give (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid as a white solid (1.94 g). The solvent was removed from the filtrates, and ethyl acetate was added. Solid precipitated again, and the solvent was removed by filtration to give another portion of (3S)-2-[(2R)-3-cyclopentyl-2-({formyl[(phenylmethyl)oxy] amino}methyl)propanoyl]-1-{[(phenylmethyl)oxy]carbonyl}-3-pyrazolidinecarboxylic acid as a white solid (274 mg). The filtrates were dried to give a oily residue. The oily residue was dissolved into ethyl acetate (5 ml), hexane was added, and the solvent was decanted to give a residue. This procedure was repeated several times to yield another portion of solid (3S)-2-[(2R)-3-cyclopentyl-2-({formyl[(phenylmethyl)oxy] amino}methyl)propanoyl]-1-{[(phenylmethyl)oxy]carbonyl}-3-pyrazolidinecarboxylic acid (250 mg). The three batches of desired product were combined to form the final batch of (3S)-2-[(2R)-3-cyclopentyl-2-({formyl[(phenylmethyl)oxy]amino}methyl)propanoyl]-1-{[(phenylmethyl) oxy]carbonyl}-3-pyrazolidinecarboxylic acid (2.46 g, 17. % yield).

Part H

Phenylmethyl(3S)-2-[(2R)-3-cyclopentyl-2-({formyl [(phenylmethyl)oxy]amino}methyl)propanoyl]-3-[(4-pyrimidinylamino)carbonyl]-1-pyrazolidinecarboxylate 1-Methylimidazole (0.53 ml, 6.7 mmol) was added into a solution of (3S)-2-[(2R)-3-cyclopentyl-2-({formyl[(phenylmethyl)oxy]amino}methyl)propanoyl]-1-{[(phenylmethyl) oxy]carbonyl}-3-pyrazolidinecarboxylic acid (1.2 g, 2.23 mmol) in N,N-dimethylformamide (DMF) (15.9 ml). The resulting solution was cooled to 0° C., and then mesyl chloride (0.18 ml, 2.34 mmol) was added dropwise at 0° C. Then 4-pyrimidinamine (0.255 g, 2.68 mmol) was added, and the reaction mixture was stirred for 1 h at room temperature. The reaction solution was purified via reverse phase HPLC (Gilson) to yield phenylmethyl (3S)-2-[(2R)-3-cyclopentyl-2-({formyl[(phenylmethyl)oxy]amino}methyl)propanoyl]-3-[(4-pyrimidinylamino)carbonyl]-1-pyrazolidinecarboxylate (1.21 g, 88% yield).

Part I

(3S)-2-((2R)-3-Cyclopentyl-2-{[formyl(hydroxy) amino]methyl}propanoyl)-N-4-pyrimidinyl-3-pyrazolidinecarboxamide A mixture of phenylmethyl (3S)-2-[(2R)-3-cyclopentyl-2-({formyl[(phenylmethyl)oxy]amino}methyl)propanoyl]-3-[(4-pyrimidinylamino)carbonyl]-1-pyrazolidinecarboxylate (1.21 g, 1.96 mmol) and Pearlman's catalyst (0.276 g, 0.39 mmol) in methanol (109 ml) was degassed and placed under 1 atm of $H_2$ at 25° C. After 2 hrs, the reaction mixture was filtered and concentrated. Purification by reverse phase HPLC (Gilson) provided (3S)-2-((2R)-3-cyclopentyl-2-{[formyl(hydroxy)amino]methyl}propanoyl)-N-4-pyrimidinyl-3-pyrazolidinecarboxamide (554 mg, 70% yield).

Method B

(3S)-2-((2R)-3-Cyclopentyl-2-{[formyl(hydroxy) amino]methyl}propanoyl)-N-4-pyrimidinyl-3-pyrazolidinecarboxamide

Part A

Phenylmethyl (3S)-2-[(2R)-3-cyclopentyl-2-({formyl[(phenylmethyl)oxy]amino}methyl)propanoyl]-3-[(4-pyrimidinylamino)carbonyl]-1-pyrazolidinecarboxylate 1-Methylimidazole (1.78 mL, 22.3 mmol) was added into a solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (4 g, 7.4 mmol) in dichloromethane (50.8 mL). The resulting solution was cooled to 0° C., and then methanesulfonyl chloride (0.6 mL, 7.8 mmol) was added dropwise at 0° C. To the reaction mixture was added 4-pyrimidinamine (849 mg, 8.9 mmol) and stirring continued for 1.5 h at ambient temperature. The reaction solution was filtered to remove unreacted 4-pyrimidinamine, and the filtrate was concentrated to provide a residue. The residue was dissolved in a mixed solution of ethyl acetate and acetonitrile, and was purified by silica gel chromatography (CombiFlash; Column: 220 g; 0-85% ethyl acetate in hexane; 60 min). The solvent was removed under reduced pressure to yield the desired product, phenylmethyl (3S)-2-[(2R)-3-cyclopentyl-2-({formyl[(phenylmethyl)oxy]amino}methyl)propanoyl]-3-[(4-pyrimidinylamino)carbonyl]-1-pyrazolidinecarboxylate (4.22 g, 92% yield). (ES+) m/z 615.2 (MH+).

Part B (3S)-2-((2R)-3-Cyclopentyl-2-{[formyl(hydroxy)amino]methyl}propanoyl)-N-4-pyrimidinyl-3-pyrazolidinecarboxamide A mixture of phenylmethyl (3S)-2-[(2R)-3-cyclopentyl-2-({formyl[(phenylmethyl)oxy]amino}methyl)propanoyl]-3-[(4-pyrimidinylamino)carbonyl]-1-pyrazolidinecarboxylate (4.22 g, 6.87 mmol) and Pearlman's catalyst (964 mg, 1.37 mmol) in methanol (381 mL) was degassed and placed under 1 atm of $H_2$ at 25° C. After 2 hrs, the reaction mixture was filtered and concentrated to give a crude residue which was purified by RP-HPLC to provide (3S)-2-((2R)-3-cyclopentyl-2-{[formyl(hydroxy)amino]methyl}propanoyl)-N-4-pyrimidinyl-3-pyrazolidinecarboxamide as a foamy solid (1.8 g, 67% yield). The material was dissolved and evaporated from acetonitrile (2×5 mL) to provide a white solid. MS (ES+) m/z 391.2 (MH+). $^1$H NMR (400 MHz, METHANOL-$d_4$) δ ppm 1.06-1.23 (m, 2H) 1.34-1.47 (m, 1H) 1.47-1.67 (m, 4H) 1.69-1.97 (m, 4H) 2.15-2.29 (m, 1H) 2.45-2.60 (m, 1H) 2.85-2.99 (m, 1H) 3.20-3.28 (m, 1H) 3.49 (dd, J=13.89, 4.55 Hz, 1H) 3.59-3.85 (m, 1H) 3.94 (dt, J=9.41, 4.77 Hz, 1H) 4.64-4.74 (m, 1H) 7.86 (s, 0.7H) 8.17 (dd, J=6.06, 1.26 Hz, 1H) 8.25 (s, 0.3H) 8.60 (d, J=6.06 Hz, 1H) 8.82 (s, 1H).

The following Examples 60 to 82 were prepared according to a method similar to that disclosed in Example 59, Method B, except that to the reaction mixture in Part A was added the indicated compound instead of 4-pyrimidinamine.

Example 60

(3S)-2-((2R)-3-Cyclopentyl-2-{[formyl(hydroxy)amino]methyl}propanoyl)-N-2-pyrazinyl-3-pyrazolidinecarboxamide

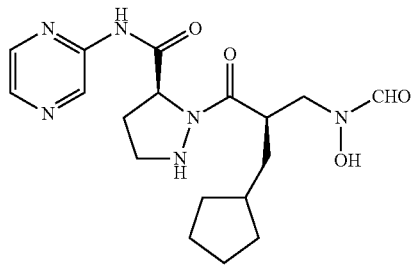 [SMILES: O=CN(O)C[C@@H](CC1CCCC1)C(=O)N1NCC[C@H]1C(=O)Nc1cnccn1]

2-pyrazinamine (58.4 mg, 0.614 mmol). MS (ES+) m/z 391.3 (MH+).

Example 61

(3S)-2-((2R)-3-Cyclopentyl-2-{[formyl(hydroxy)amino]methyl}propanoyl)-N-4-pyridinyl-3-pyrazolidinecarboxamide

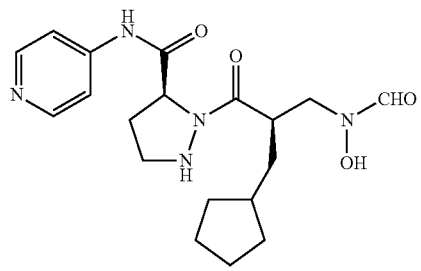 [SMILES: O=CN(O)C[C@@H](CC1CCCC1)C(=O)N1NCC[C@H]1C(=O)Nc1ccncc1]

4-pyridinamine (38.5 mg, 0.409 mmol). MS (ES+) m/z 390.3 (MH+). $^1$H NMR (400 MHz, METHANOL-$d_4$) δ ppm 1.05-1.23 (m, 2H) 1.33-1.45 (m, 1H) 1.45-1.68 (m, 4H) 1.68-1.98 (m, 4H) 2.12-2.27 (m, 1H) 2.45-2.60 (m, 1H) 2.85-3.00 (m, 1H) 3.21-3.29 (m, 1H) 3.49-3.93 (m, 3H) 4.59 (q, J=7.75 Hz, 1H) 7.59-7.69 (m, 2H) 7.85 (s, 0.7H) 8.26 (s, 0.3H) 8.38 (d, J=5.05 Hz, 2H)

Example 62

(3S)-2-((2R)-3-Cyclopentyl-2-{[formyl(hydroxy)amino]methyl}propanoyl)-N-[6-(1H-imidazol-1-yl)-2-pyridinyl]-3-pyrazolidinecarboxamide

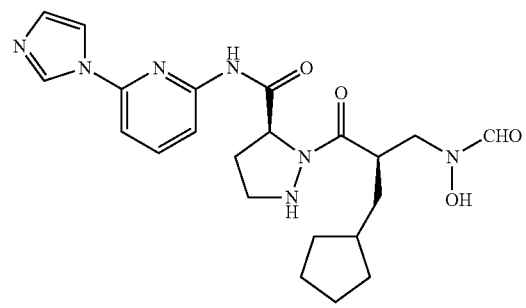 [SMILES: O=CN(O)C[C@@H](CC1CCCC1)C(=O)N1NCC[C@H]1C(=O)Nc1cccc(-n2ccnc2)n1]

6-(1H-imidazol-1-yl)-2-pyridinamine (65.5 mg, 0.409 mmol). MS (ES+) m/z 455.7 (MH+). $^1$H NMR (400 MHz, METHANOL-$d_4$) δ ppm 1.05-1.21 (m, 2H) 1.36-1.66 (m, 5H) 1.68-1.97 (m, 4H) 2.17-2.32 (m, 1H) 2.47-2.62 (m, 1H) 2.86-3.00 (m, 1H) 3.21-3.29 (m, 1H) 3.51 (dd, J=14.15, 4.55 Hz, 1H) 3.63-3.85 (m, 1H) 3.95 (tt, J=9.51, 4.89 Hz, 1H) 4.68-4.78 (m, 1H) 7.13 (s, 1H) 7.30-7.38 (m, 1H) 7.81-7.91 (m, 2.7H) 8.01-8.10 (m, 1H) 8.27 (s, 0.3H) 8.50 (s, 1H)

Example 63

(3S)-2-((2R)-3-Cyclopentyl-2-{[formyl(hydroxy)amino]methyl}propanoyl)-N-[5-(1H-imidazol-1-yl)-2-pyridinyl]-3-pyrazolidinecarboxamide

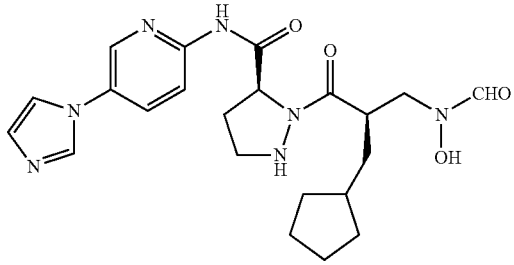 [SMILES: O=CN(O)C[C@@H](CC1CCCC1)C(=O)N1NCC[C@H]1C(=O)Nc1ccc(-n2ccnc2)cn1]

5-(1H-imidazol-1-yl)-2-pyridinamine (65.5 mg, 0.409 mmol). MS (ES+) m/z 455.7 (MH$^+$). $^1$H NMR (400 MHz, METHANOL-d$_4$) δ ppm 1.03-1.23 (m, 2H) 1.36-1.66 (m, 5H) 1.68-1.98 (m, 4H) 2.17-2.32 (m, 1H) 2.47-2.62 (m, 1H) 2.84-2.99 (m, 1H) 3.19-3.29 (m, 1H) 3.50 (dd, J=14.02, 4.42 Hz, 1H) 3.59-3.85 (m, 1H) 3.95 (tt, J=9.51, 4.89 Hz, 1H) 4.66-4.78 (m, 1H) 7.17 (s, 1H) 7.59 (s, 1H) 7.87 (s, 0.7H) 7.98 (dd, J=9.09, 2.78 Hz, 1H) 8.16 (s, 1H) 8.22-8.32 (m, 1.3H) 8.54 (d, J=2.53 Hz, 1H).

Example 64

(3S)-2-((2R)-3-Cyclopentyl-2-{[formyl(hydroxy)amino]methyl}propanoyl)-N-(3-fluoro-4-pyridinyl)-3-pyrazolidinecarboxamide

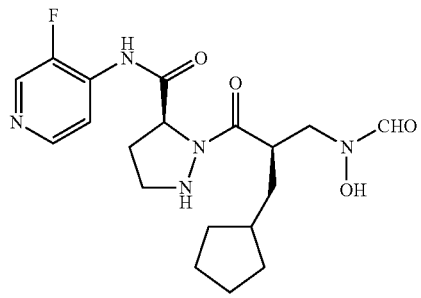

3-fluoro-4-pyridinamine (41.7 mg, 0.372 mmol). MS (ES+) m/z 408.0 (MH$^+$). $^1$H NMR (400 MHz, METHANOL-d$_4$) δ ppm 1.02-1.22 (m, 2H) 1.36-1.66 (m, 5H) 1.67-1.95 (m, 4H) 2.25-2.41 (m, 1H) 2.42-2.54 (m, 1H) 2.83-2.99 (m, 1H) 3.19-3.29 (m, 1H) 3.51 (dd, J=14.15, 4.55 Hz, 1H) 3.59-3.86 (m, 1H) 3.96 (tt, J=9.57, 4.96 Hz, 1H) 4.73-4.83 (m, 1H) 7.87 (s, 0.7H) 8.06-8.29 (m, 1.3H) 8.32-8.38 (m, 1H) 8.41 (d, J=2.78 Hz, 1H)

Example 65

(3S)-2-((2R)-3-Cyclopentyl-2-{[formyl(hydroxy)amino]methyl}propanoyl)-N-(2-quinolinylmethyl)-3-pyrazolidinecarboxamide

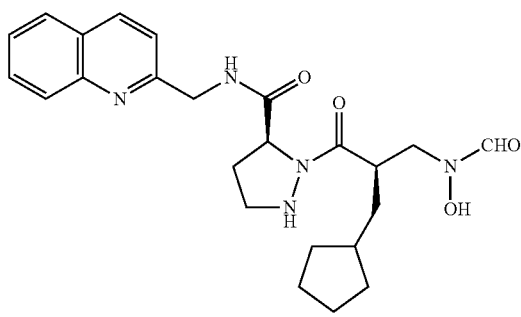 [SMILES: O=CN(O)C[C@@H](CC1CCCC1)C(=O)N1NCC[C@H]1C(=O)NCc1ccc2ccccc2n1]

(2-quinolinylmethyl)amine (80 mg, 0.409 mmol). MS (ES+) m/z 453.8 (MH$^+$).

Example 66

(3S)-2-((2R)-3-Cyclopentyl-2-{[formyl(hydroxy)amino]methyl}propanoyl)-N-5-pyrimidinyl-3-pyrazolidinecarboxamide

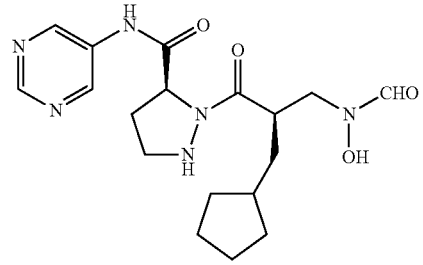

5-pyrimidinamine (38.9 mg, 0.409 mmol). MS (ES+) m/z 391.2 (MH$^+$).

Example 67

(3S)-2-((2R)-3-Cyclopentyl-2-{[formyl(hydroxy)amino]methyl}propanoyl)-N-[6-(methyloxy)-4-pyrimidinyl]-3-pyrazolidinecarboxamide

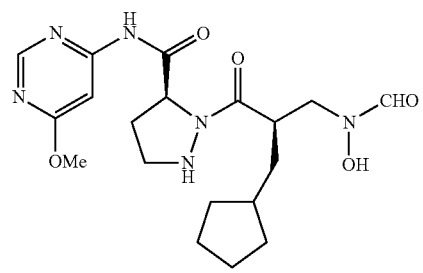 [SMILES: COc1cc(NC(=O)[C@@H]2CCNN2C(=O)[C@H](CC2CCCC2)CN(O)C=O)ncn1]

6-(methyloxy)-4-pyrimidinamine (38.4 mg, 0.307 mmol). MS (ES+) m/z 420.8 (MH$^+$). $^1$H NMR (400 MHz, METHANOL-d$_4$) δ ppm 1.05-1.22 (m, 2H) 1.40 (dd, J=12.63, 6.57 Hz, 1H) 1.46-1.66 (m, 4H) 1.66-1.96 (m, 4H) 2.14-2.30 (m, 1H) 2.42-2.57 (m, 1H) 2.83-2.98 (m, 1H) 3.18-3.29 (m, 1H) 3.49 (dd, J=14.02, 4.42 Hz, 1H) 3.59-3.84 (m, 1H) 3.84-4.00 (m, 4H) 4.62-4.74 (m, 1H) 7.46 (s, 1H) 7.85 (s, 0.7H) 8.25 (s, 0.3H) 8.44 (s, 1H)

Example 68

(3S)-2-((2R)-3-Cyclopentyl-2-{[formyl(hydroxy)amino]methyl}propanoyl)-N-(4-methyl-2-pyridinyl)-3-pyrazolidinecarboxamide

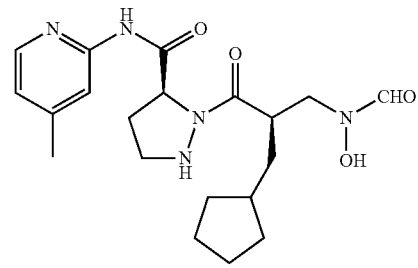

4-methyl-2-pyridinamine (30.2 mg, 0.279 mmol). MS (ES+) m/z 404.0 (MH$^+$). $^1$H NMR (400 MHz, METHANOL-d$_4$) δ ppm 1.14 (dd, J=11.75, 6.95 Hz, 2H) 1.33-1.46 (m, 1H) 1.46-1.67 (m, 4H) 1.68-1.96 (m, 4H) 2.16-2.29 (m, 1H) 2.35 (s, 3H) 2.42-2.59 (m, 1H) 2.78-2.97 (m, 1H) 3.17-3.29 (m, 1H) 3.49 (dd, J=13.89, 4.29 Hz, 1H) 3.58-3.84 (m, 1H) 3.84-4.01 (m, J=9.13, 4.93, 4.59, 4.59 Hz, 1H) 4.69 (t, J=7.20 Hz, 1H) 6.95 (d, J=5.05 Hz, 1H) 7.86 (s, 0.7H) 7.92 (s, 1H) 8.12 (d, J=5.05 Hz, 1H) 8.25 (s, 0.3H)

Example 69

(3S)-2-((2R)-3-Cyclopentyl-2-{[formyl(hydroxy)amino]methyl}propanoyl)-N-(7-methyl-7H-purin-6-yl)-3-pyrazolidinecarboxamide

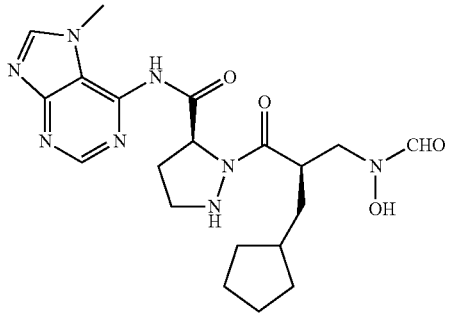 [SMILES: Cn1cnc2ncnc(NC(=O)[C@@H]3CCNN3C(=O)[C@H](CC3CCCC3)CN(O)C=O)c21]

7-methyl-7H-purin-6-amine (45.8 mg, 0.307 mmol). MS (ES+) m/z 444.9 (MH+). ¹H NMR (400 MHz, METHANOL-d₄) δ ppm 1.04-1.23 (m, 2H) 1.37-1.67 (m, 5H) 1.70-2.00 (m, 4H) 2.25-2.39 (m, 1H) 2.48-2.65 (m, 1H) 2.87-3.05 (m, 1H) 3.23-3.30 (m, 1H) 3.51 (dd, J=14.02, 4.42 Hz, 1H) 3.67-3.85 (m, 1H) 3.90-4.01 (m, 1H) 4.03 (s, 3H) 4.76-4.86 (m, 1H) 7.88 (s, 0.7H) 8.27 (s, 0.3H) 8.49 (s, 1H) 8.53-8.63 (m, 1H)

Example 70

(3S)-2-((2R)-3-Cyclopentyl-2-{[formyl(hydroxy)amino]methyl}propanoyl)-N-[2-(methyloxy)-4-pyrimidinyl]-3-pyrazolidinecarboxamide

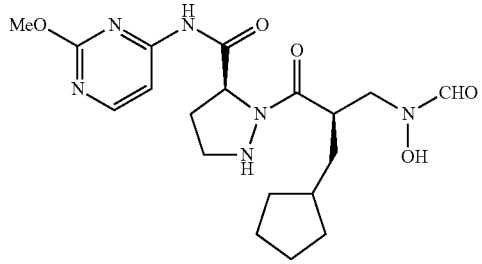 [SMILES: COc1nccc(NC(=O)[C@@H]2CCNN2C(=O)[C@H](CC2CCCC2)CN(O)C=O)n1]

Pre Step A 2-(Methyloxy)-4-pyrimidinamine

A mixture of 2-chloro-4-pyrimidinamine (150 mg, 1.158 mmol) and sodium methoxide (188 mg, 3.47 mmol) in methanol (2.9 ml) was heated to 100° C. via a Biotag microwave for 40 min. The crude product mixture was purified by RP-HPLC to give 2-(methyloxy)-4-pyrimidinamine (73 mg, 0.583 mmol, 50% yield). MS (ES+) m/z 126.0 (MH+).

A procedure similar to Example 59 (Method B), Parts A and B was used, except that 2-(methyloxy)-4-pyrimidinamine (34.9 mg, 0.279 mmol) was used instead of 4-pyrimidinamine to add to the reaction mixture in Part A, to provide the Title compound. MS (ES+) m/z 421.2 (MH+). ¹H NMR (400 MHz, MeOD) δ ppm 1.15 (dd, J=12.51, 7.20 Hz, 2H) 1.32-1.45 (m, 1H) 1.47-1.68 (m, 4H) 1.69-1.97 (m, 4H) 2.16-2.28 (m, 1H) 2.45-2.60 (m, 1H) 2.84-3.00 (m, 1H) 3.17-3.29 (m, 1H) 3.49 (dd, J=13.89, 4.55 Hz, 1H) 3.58-3.84 (m, 2H) 3.96 (s, 3H) 4.69 (q, J=7.49 Hz, 1H) 7.77 (d, J=5.56 Hz, 1H) 7.85 (s, 0.7H) 8.25 (s, 0.3H) 8.37 (d, J=5.81 Hz, 1H).

Example 71

(3S)-2-((2R)-3-Cyclopentyl-2-{[formyl(hydroxy)amino]methyl}propanoyl)-N-(5-fluoro-4-pyrimidinyl)-3-pyrazolidinecarboxamide

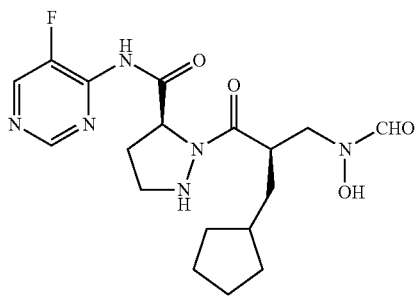

Pre Step A

5-Fluoro-4-pyrimidinamine

A mixture of 4-chloro-5-fluoropyrimidine (200 mg, 1.509 mmol) and ammonia (3.3 ml, 45.3 mmol) in methanol (580 μl) was heated to 110° C. via a microwave reactor for 30 min. The reaction was filtered and the solid was dried to give 5-fluoro-4-pyrimidinamine (100 mg, 0.875 mmol, 58% yield) as a white solid. MS (ES+) m/z 114.1 (MH+).

A procedure similar to Example 59 (Method B), Parts A and B was used, except that 5-fluoro-4-pyrimidinamine (47.3 mg, 0.419 mmol) was used instead of 4-pyrimidinamine to add to the reaction mixture in Part A, to provide the Title compound. MS (ES+) m/z 409.1 (MH+). ¹H NMR (400 MHz, METHANOL-d₄) δ ppm 1.05-1.23 (m, 2H) 1.34-1.44 (m, 1H) 1.45-1.68 (m, 4H) 1.68-1.97 (m, 4H) 2.22-2.36 (m, 1H) 2.49-2.63 (m, 1H) 2.85-3.03 (m, 1H) 3.21-3.29 (m, 1H) 3.50 (dd, J=14.02, 4.42 Hz, 1H) 3.58-3.85 (m, 1H) 3.95 (tt, J=9.47, 4.93 Hz, 1H) 4.78-4.86 (m, 1H) 7.86 (s, 0.7H) 8.25 (s, 0.3H) 8.63 (d, J=3.03 Hz, 1H) 8.71 (d, J=2.02 Hz, 1H)

Example 72

(3S)-2-((2R)-3-Cyclopentyl-2-{[formyl(hydroxy)amino]methyl}propanoyl)-N-(3-quinolinylmethyl)-3-pyrazolidinecarboxamide

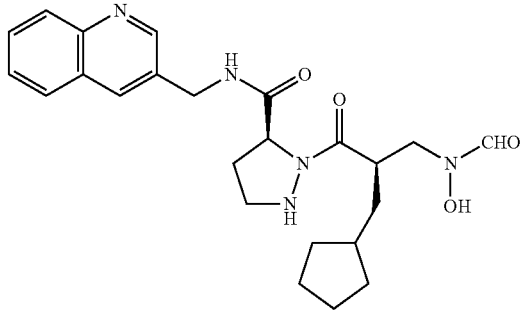 [SMILES: O=CN(O)C[C@@H](CC1CCCC1)C(=O)N1NCC[C@H]1C(=O)NCc1cnc2ccccc2c1]

(3-quinolinylmethyl)amine (58.9 mg, 0.372 mmol). MS (ES+) m/z 453.9 (MH+). ¹H NMR (400 MHz, METHANOL-d₄) δ ppm 1.05 (m, J=15.44, 15.44, 11.94, 7.89, 7.89 Hz, 2H) 1.31-1.57 (m, 5H) 1.59-1.65 (m, 1H) 1.67-1.84 (m, 3H) 2.05-2.18 (m, 1H) 2.49 (m, J=12.32, 8.27, 6.13, 6.13 Hz, 1H) 2.75-2.93 (m, 1H) 3.18-3.29 (m, 1H) 3.43-3.61 (m, 1H) 3.64-3.94 (m, 2H) 4.47-4.62 (m, 2H) 4.62-4.72 (m, 1H) 7.57-7.67 (m, 1H) 7.71-7.80 (m, 1H) 7.82-7.91 (m, 0.7H) 7.94 (d, J=8.08 Hz, 1H) 8.01 (d, J=8.59 Hz, 1H) 8.20-8.24 (m, 0.3H) 8.28-8.37 (m, 1H) 8.82 (br. s., 1H)

Example 73

(3S)-2-((2R)-3-Cyclopentyl-2-{[formyl(hydroxy)amino]methyl}propanoyl)-N-(5-methyl-2-pyrazinyl)-3-pyrazolidinecarboxamide

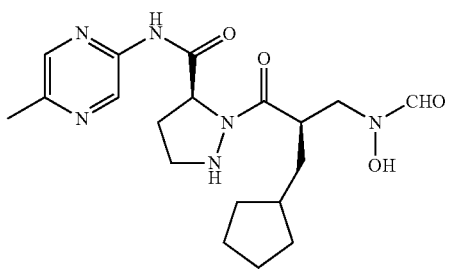 [SMILES: Cc1cnc(NC(=O)[C@@H]2CCNN2C(=O)[C@H](CC2CCCC2)CN(O)C=O)cn1]

5-methyl-2-pyrazinamine (45.7 mg, 0.419 mmol). MS (ES+) m/z 405.1 (MH+). ¹H NMR (400 MHz, METHANOL-$d_4$) δ ppm 1.04-1.24 (m, 2H) 1.34-1.45 (m, 1H) 1.45-1.68 (m, 4H) 1.68-1.97 (m, 4H) 2.16-2.30 (m, 1H) 2.49 (s, 3H) 2.51-2.58 (m, 1H) 2.83-2.98 (m, 1H) 3.20-3.28 (m, 1H) 3.49 (dd, J=14.02, 4.42 Hz, 1H) 3.58-3.84 (m, 1H) 3.93 (tt, J=9.47, 5.05 Hz, 1H) 4.63-4.75 (m, 1H) 7.85 (s, 0.7H) 8.25 (s, 0.3H) 8.26 (s, 1H) 9.21 (s, 1H)

Example 74

(3S)-2-((2R)-3-Cyclopentyl-2-{[formyl(hydroxy)amino]methyl}propanoyl)-N-[6-(methyloxy)-2-pyrazinyl]-3-pyrazolidinecarboxamide

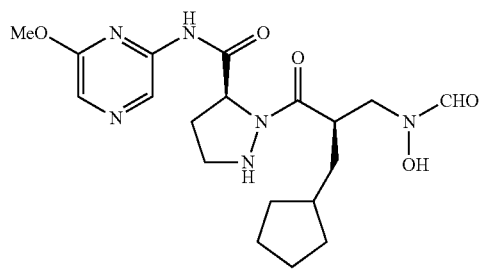 [SMILES: COc1cncc(NC(=O)[C@@H]2CCNN2C(=O)[C@H](CC2CCCC2)CN(O)C=O)n1]

Pre Step A 6-(Methyloxy)-2-pyrazinamine

A mixture of 6-chloro-2-pyrazinamine (200 mg, 1.544 mmol) and sodium methoxide (250 mg, 4.63 mmol) in methanol (3.9 ml) was heated to 130° C. via a microwave reactor for 60 min. The crude product mixture was purified by RP-HPLC to give 6-(methyloxy)-2-pyrazinamine (154 mg, 1.231 mmol, 80% yield). MS (ES+) m/z 125.8 (MH+).

A procedure similar to Example 59 (Method B), Parts A and B was used, except that 6-(methyloxy)-2-pyrazinamine (52.4 mg, 0.419 mmol) was used instead of 4-pyrimidinamine to add to the reaction mixture in Part A, to provide the Title compound. MS (ES+) m/z 420.9 (MH+). ¹H NMR (400 MHz, METHANOL-$d_4$) δ ppm 1.07-1.24 (m, 2H) 1.34-1.45 (m, 1H) 1.47-1.68 (m, 4H) 1.70-1.97 (m, 4H) 2.14-2.29 (m, 1H) 2.46-2.61 (m, 1H) 2.84-2.99 (m, 1H) 3.19-3.29 (m, 1H) 3.50 (dd, J=14.02, 4.42 Hz, 1H) 3.61-3.81 (m, 1H) 3.86-4.01 (m, 4H) 4.72 (q, J=7.49 Hz, 1H) 7.86 (s, 0.7H) 7.88-7.94 (m, 1H) 8.26 (s, 0.3H) 8.89 (s, 1H)

Example 75

(3S)-2-((2R)-3-Cyclopentyl-2-{[formyl(hydroxy)amino]methyl}propanoyl)-N-[3-(methyloxy)-2-pyrazinyl]-3-pyrazolidinecarboxamide

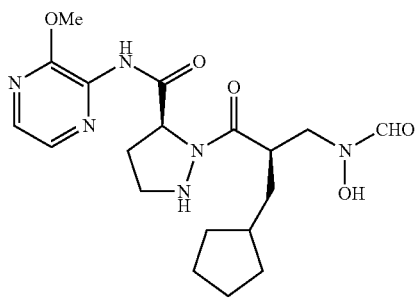 [SMILES: COc1nccnc1NC(=O)[C@@H]1CCNN1C(=O)[C@H](CC1CCCC1)CN(O)C=O]

Pre Step A 3-(Methyloxy)-2-pyrazinamine

A mixture of 3-chloro-2-pyrazinamine (200 mg, 1.544 mmol) and sodium methoxide (250 mg, 4.63 mmol) in methanol (3.9 ml) was heated to 130° C. via a microwave reactor for 60 min. The crude product mixture was purified by RP-HPLC to give 3-(methyloxy)-2-pyrazinamine (113 mg, 0.903 mmol, 59% yield). MS (ES+) m/z 125.8 (MH+).

A procedure similar to Example 59 (Method B), Parts A and B was used, except that 3-(methyloxy)-2-pyrazinamine (52.4 mg, 0.419 mmol) was used instead of 4-pyrimidinamine to add to the reaction mixture in Part A, to provide the Title compound. MS (ES+) m/z 420.8 (MH+). ¹H NMR (400 MHz, METHANOL-$d_4$) δ ppm 1.04-1.21 (m, 2H) 1.36-1.63 (m, 5H) 1.70-1.91 (m, 4H) 2.30-2.44 (m, 1H) 2.44-2.55 (m, 1H) 2.82-2.98 (m, 1H) 3.20-3.29 (m, 1H) 3.51 (dd, J=14.02, 4.42 Hz, 1H) 3.59-3.86 (m, 1H) 3.96 (td, J=9.47, 4.80 Hz, 1H) 4.03 (s, 3H) 4.79-4.87 (m, 1H) 7.79-7.94 (m, 2.7H) 8.26 (s, 0.3H)

Example 76

(3S)-2-((2R)-3-Cyclopentyl-2-{[formyl(hydroxy)amino]methyl}propanoyl)-N-(2-fluoro-4-pyrimidinyl)-3-pyrazolidinecarboxamide

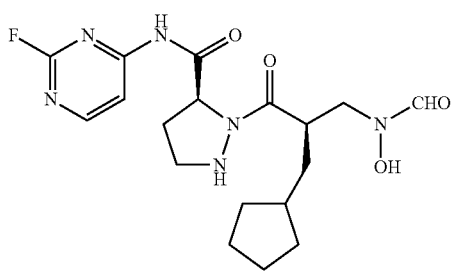 [SMILES: O=CN(O)C[C@@H](CC1CCCC1)C(=O)N1NCC[C@H]1C(=O)Nc1ccnc(F)n1]

Pre Step A

2-Fluoro-4-pyrimidinamine

A mixture of 2,4-difluoropyrimidine (200 mg, 1.723 mmol) and ammonia (1600 μl, 22.18 mmol) in 1,4-dioxane (2 ml) was stirred at −21° C. (Salt-Ice bath) for 5 min. The MeOH (1 mL) was added to the reaction mixture, and then the crude product was purified by RP-HPLC to give 2-fluoro-4-pyrimidinamine (94 mg, 0.831 mmol, 48% yield) as a white solid. MS (ES+) m/z 114.1 (MH+).

A procedure similar to Example 59 (Method B), Parts A and B was used, except that 2-fluoro-4-pyrimidinamine (44.2 mg, 0.391 mmol) was used instead of 4-pyrimidinamine to add to the reaction mixture in Part A, to provide the Title compound. MS (ES+) m/z 409.1 (MH+).

Example 77

(3S)-2-((2R)-3-Cyclopentyl-2-{[formyl(hydroxy)amino]methyl}propanoyl)-N-[2-(4-methyl-1-piperazinyl)-4-pyrimidinyl]-3-pyrazolidinecarboxamide

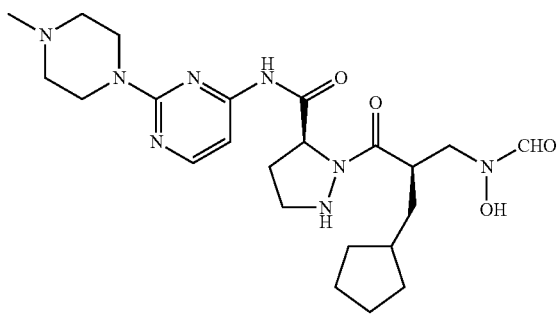 [SMILES: CN1CCN(c2nccc(NC(=O)[C@@H]3CCNN3C(=O)[C@H](CC3CCCC3)CN(O)C=O)n2)CC1]

Pre Step A

2-(4-Methyl-1-piperazinyl)-4-pyrimidinamine

A mixture of 2-chloro-4-pyrimidinamine (300 mg, 2.316 mmol) and 1-methylpiperazine (771 μl, 6.95 mmol) in N,N-dimethylformamide (DMF) (3 ml) was heated to 220° C. via a microwave reactor for 60 min. The reaction was purified by RP-HPLC to yield 2-(4-methyl-1-piperazinyl)-4-pyrimidinamine (300 mg, 1.552 mmol, 67% yield). MS (ES+) m/z 194.2 (MH+).

A procedure similar to Example 59 (Method B), Parts A and B was used, except that 2-(4-methyl-1-piperazinyl)-4-pyrimidinamine (81 mg, 0.419 mmol) was used instead of 4-pyrimidinamine to add to the reaction mixture in Part A, to provide the Title compound. MS (ES+) m/z 489.2 (MH+). $^1$H NMR (400 MHz, METHANOL-d$_4$) δ ppm 1.15 (dd, J=11.24, 7.20 Hz, 2H) 1.33-1.44 (m, 1H) 1.46-1.68 (m, 4H) 1.69-1.97 (m, 4H) 2.14-2.28 (m, 1H) 2.33 (s, 3H) 2.48 (t, J=5.05 Hz, 5H) 2.79-2.98 (m, 1H) 3.18-3.29 (m, 1H) 3.49 (dd, J=13.89, 4.55 Hz, 1H) 3.70-3.86 (m, 5H) 3.93 (tt, J=9.54, 4.86 Hz, 1H) 4.60-4.75 (m, 1H) 7.32 (d, J=5.56 Hz, 1H) 7.85 (s, 0.7H) 8.19 (d, J=5.56 Hz, 1H) 8.25 (s, 0.3H)

Example 78

(3S)-2-((2R)-3-Cyclopentyl-2-{[formyl(hydroxy)amino]methyl}propanoyl)-N-[2-(dimethylamino)-4-pyrimidinyl]-3-pyrazolidinecarboxamide

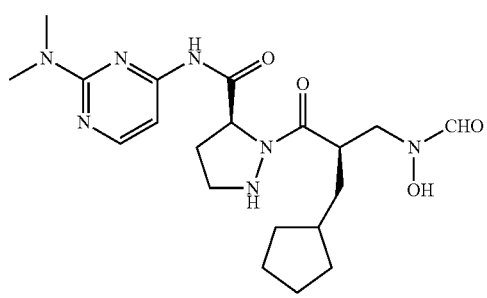 [SMILES: CN(C)c1nccc(NC(=O)[C@@H]2CCNN2C(=O)[C@H](CC2CCCC2)CN(O)C=O)n1]

Pre Step A

N$^2$,N$^2$-Dimethyl-2,4-pyrimidinediamine

40% Dimethylamine in water (1466 μl, 11.58 mmol) was added into the mixture of 2-chloro-4-pyrimidinamine (300 mg, 2.316 mmol) in N,N-dimethylformamide (DMF) (1.5 ml). The resulting reaction mixture was heated in a microwave reactor at 220° C. for 30 min. The reaction mixture was purified by RP-HPLC to yield N,N-dimethyl-2,4-pyrimidinediamine (290 mg, 2.099 mmol, 91% yield) as a white solid. MS (ES+) m/z 139.2 (MH+).

A procedure similar to Example 59 (Method B), Parts A and B was used, except that N,N-dimethyl-2,4-pyrimidinediamine (57.8 mg, 0.419 mmol) was used instead of 4-pyrimidinamine to add to the reaction mixture in Part A, to provide the Title compound. MS (ES+) m/z 434.1 (MH+). $^1$H NMR (400 MHz, METHANOL-d$_4$) δ ppm 1.05-1.23 (m, 2H) 1.34-1.44 (m, 1H) 1.44-1.68 (m, 4H) 1.69-1.96 (m, 4H) 2.13-2.27 (m, 1H) 2.43-2.57 (m, 1H) 2.81-2.97 (m, 1H) 3.13 (s, 6H) 3.19-3.29 (m, 1H) 3.49 (dd, J=14.15, 4.55 Hz, 1H) 3.59-3.84 (m, 1H) 3.94 (tt, J=9.51, 4.89 Hz, 1H) 4.68 (q, J=7.33 Hz, 1H) 7.28 (d, J=5.56 Hz, 1H) 7.85 (s, 0.7H) 8.15 (d, J=5.56 Hz, 1H) 8.25 (s, 0.3H)

Example 79

(3S)-2-((2R)-3-Cyclopentyl-2-{[formyl(hydroxy)amino]methyl}propanoyl)-N-(4-pyrimidinylmethyl)-3-pyrazolidinecarboxamide

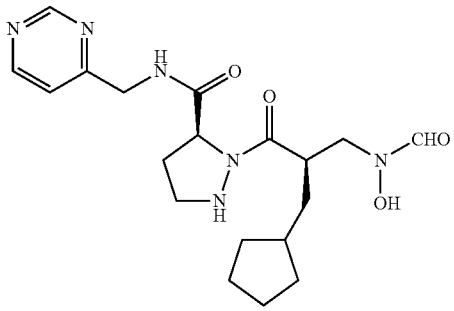 [SMILES: O=CN(O)C[C@@H](CC1CCCC1)C(=O)N1NCC[C@H]1C(=O)NCc1ccncn1]

(4-pyrimidinyl methyl)amine (65.0 mg, 0.446 mmol). MS (ES+) m/z 405.3 (MH+).

Example 80

(3S)-2-((2R)-3-Cyclopentyl-2-{[formyl(hydroxy)amino]methyl}propanoyl)-N-{2-[(2R)-2,4-dimethyl-1-piperazinyl]-4-pyrimidinyl}-3-pyrazolidinecarboxamide

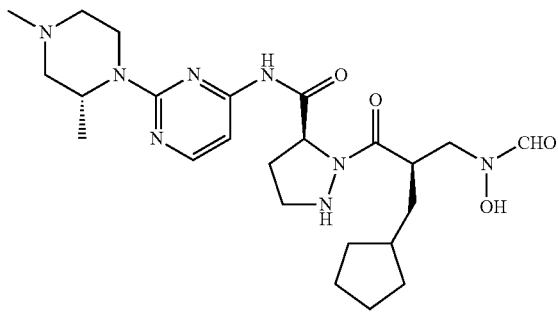 [SMILES: C[C@@H]1CN(C)CCN1c1nccc(NC(=O)[C@@H]2CCNN2C(=O)[C@H](CC2CCCC2)CN(O)C=O)n1]

Pre Step A

2-[(2R)-2,4-Dimethyl-1-piperazinyl]-4-pyrimidinamine

A mixture of 2-chloro-4-pyrimidinamine (300 mg, 2.316 mmol), Hunig's base (809 µl, 4.63 mmol) and (3R)-1,3-dimethylpiperazine (Ref.: WO2009061879 (A1)) (650 mg, 3.47 mmol) in N,N-dimethylformamide (DMF) (3 ml) was heated in a microwave reactor at 220° C. for 60 min. The reaction mixture was purified by RP-HPLC to yield 2-[(2R)-2,4-dimethyl-1-piperazinyl]-4-pyrimidinamine (88 mg, 0.425 mmol, 18% yield). MS (ES+) m/z 208.0 (MH+).

A procedure similar to Example 59 (Method B), Parts A and B was used, except that 2-[(2R)-2,4-dimethyl-1-piperazinyl]-4-pyrimidinamine (75 mg, 0.363 mmol) was used instead of 4-pyrimidinamine to add to the reaction mixture in Part A, to provide the Title compound. MS (ES+) m/z 503.0 (MH+). $^1$H NMR (400 MHz, METHANOL-$d_4$) δ ppm 1.06-1.22 (m, 2H) 1.26 (d, J=6.82 Hz, 3H) 1.34-1.45 (m, 1H) 1.45-1.68 (m, 4H) 1.68-1.95 (m, 4H) 2.00 (td, J=11.87, 3.54 Hz, 1H) 2.14-2.26 (m, 2H) 2.26-2.34 (m, 3H) 2.43-2.55 (m, 1H) 2.79 (d, J=11.37 Hz, 1H) 2.84-2.96 (m, 2H) 3.14 (td, J=12.88, 3.03 Hz, 1H) 3.19-3.29 (m, 1H) 3.49 (dd, J=14.02, 4.42 Hz, 1H) 3.57-3.85 (m, 1H) 3.94 (tt, J=9.57, 4.96 Hz, 1H) 4.45 (d, J=13.39 Hz, 1H) 4.68 (q, J=7.49 Hz, 1H) 4.78-4.87 (m, 1H) 7.31 (d, J=5.56 Hz, 1H) 7.84 (s, 0.7H) 8.19 (d, J=5.56 Hz, 1H) 8.25 (s, 0.3H).

Example 81

(3S)-2-((2R)-3-Cyclopentyl-2-{[formyl(hydroxy)amino]methyl}propanoyl)-N-(2-{[2-(dimethylamino)ethyl]oxy}-4-pyrimidinyl)-3-pyrazolidinecarboxamide

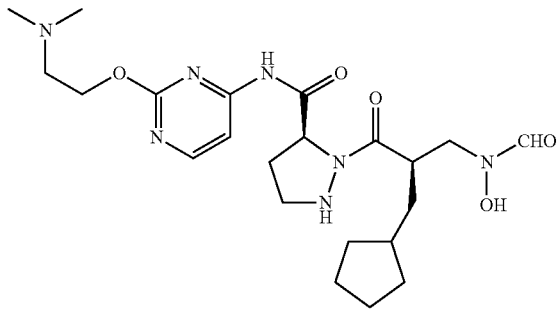 [SMILES: CN(C)CCOc1nccc(NC(=O)[C@@H]2CCNN2C(=O)[C@H](CC2CCCC2)CN(O)C=O)n1]

Pre Step A

2-{[2-(Dimethylamino)ethyl]oxy}-4-pyrimidinamine

A mixture of 2-chloro-4-pyrimidinamine (300 mg, 2.316 mmol), sodium ethoxide (189 mg, 2.78 mmol) and 2-(dimethylamino)ethanol (349 µl, 3.47 mmol) in N,N-dimethylformamide (DMF) (2.9 mL) was heated to 180° C. via a microwave reactor for min. The reaction was purified by RP-HPLC to yield 2-{[2-(dimethylamino)ethyl]oxy}-4-pyrimidinamine (111 mg, 0.609 mmol, 26% yield). MS (ES+) m/z 183.0 (MH+).

A procedure similar to Example 59 (Method B), Parts A and B was used, except that 2-{[2-(dimethylamino)ethyl]oxy}-4-pyrimidinamine (66.1 mg, 0.363 mmol) was used instead of 4-pyrimidinamine to add to the reaction mixture in Part A, to provide the Title compound. MS (ES+) m/z 478.0 (MH+).

Example 82

(3S)-2-((2R)-3-Cyclopentyl-2-{[formyl(hydroxy)amino]methyl}propanoyl)-N-(2-{[3-(dimethylamino)propyl]amino}-4-pyrimidinyl)-3-pyrazolidinecarboxamide

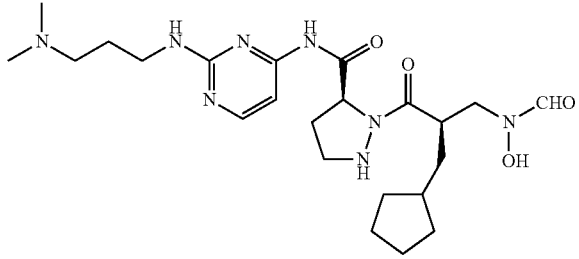 [SMILES: CN(C)CCCNc1nccc(NC(=O)[C@@H]2CCNN2C(=O)[C@H](CC2CCCC2)CN(O)C=O)n1]

Pre Step A

N2-[3-(Dimethylamino)propyl]-2,4-pyrimidinediamine

A mixture of 2-chloro-4-pyrimidinamine (300 mg, 2.316 mmol), DBU (419 µl, 2.78 mmol) and N,N-dimethyl-1,3-propanediamine (437 µl, 3.47 mmol) was heated to 220° C. via a microwave reactor for 30 min. The reaction mixture was purified by RP-HPLC to yield N2-[3-(dimethylamino)propyl]-2,4-pyrimidinediamine (256 mg, 1.311 mmol, 57% yield). MS (ES+) m/z 196.2 (MH+).

A procedure similar to Example 59 (Method B), Parts A and B was used, except that N2-[3-(dimethylamino) propyl]-2,4-pyrimidinediamine (72.6 mg, 0.372 mmol) was used instead of 4-pyrimidinamine to add to the reaction mixture in Part A, to provide the Title compound. MS (ES+) m/z 491.4 (MH+).

Example 83

(3S)-2-((2R)-3-Cyclopentyl-2-{[formyl(hydroxy)amino]methyl}propanoyl)-N-{2-[(3S)-3-(dimethylamino)-1-pyrrolidinyl]-4-pyrimidinyl}-3-pyrazolidine carboxamide

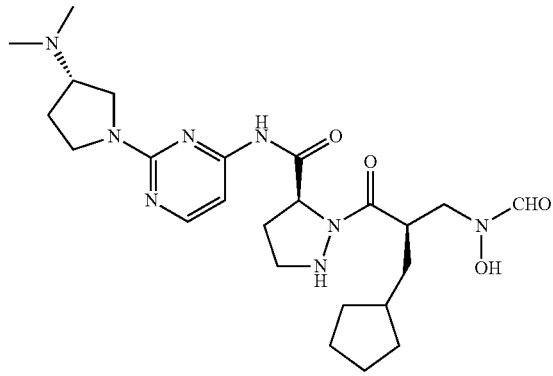 [SMILES: CN(C)[C@H]1CCN(c2nccc(NC(=O)[C@@H]3CCNN3C(=O)[C@H](CC3CCCC3)CN(O)C=O)n2)C1]

Part A

2-[(3S)-3-(Dimethylamino)-1-pyrrolidinyl]-4-pyrimidinamine

A mixture of 2-chloro-4-pyrimidinamine (200 mg, 1.544 mmol), Hunig's base (539 µl, 3.09 mmol) and (3S)—N,N-dimethyl-3-pyrrolidinamine (294 µl, 2.316 mmol) in N,N-dimethylformamide (DMF) (2 ml) was heated to 220° C. via a microwave reactor for 30 min. The reaction mixture was purified by RP-HPLC to yield 2-[(3S)-3-(dimethylamino)-1-pyrrolidinyl]-4-pyrimidinamine (205 mg, 0.989 mmol, 64% yield). MS (ES+) m/z 208.0 (MH+).

Part B (3S)-2-[(2R)-3-Cyclopentyl-2-({formyl[(phenylmethyl)oxy]amino}methyl)propanoyl]-1-{[(phenylmethyl)oxy]carbonyl}-3-pyrazolidinecarboxylic acid (2R)-3-Cyclopentyl-2-({formyl[(phenylmethyl)oxy]amino}methyl)propanoyl fluoride (11.37 g, 37 mmol) in 50 mL of DMF was added into the solution of 1-(benzyloxycarbonyl)pyrazolidine-3-carboxylic acid (12.04 g, 48.1 mmol) and Hunig's base (25.8 ml, 148 mmol) in 70 ml of DMF. The reaction was stirred at 25° C. for 5 hrs. The reaction was diluted with ethyl acetate, and the resulting solution was washed with aqueous NH4Cl (2×200 ml). The aqueous solution was extracted with ethyl acetate (5×100 ml). The combined organic layers were dried over anhydrous Na2SO4, filtered and concentrated to give a residue. The residue was purified by silica Gel chromatography and then recrystallization from ethyl acetate and hexane to yield (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (2.834 g, 5.27 mmol, 14% yield). MS (ES+) m/z 538.1 (MH+).

Part C

Phenylmethyl (3S)-2-[(2R)-3-cyclopentyl-2-({formyl[(phenylmethyl)oxy]amino}methyl)propanoyl]-3-[({2-[(3S)-3-(dimethylamino)-1-pyrrolidinyl]-4-pyrimidinyl}amino)carbonyl]-1-pyrazolidinecarboxylate 4-Methylmorpholine (36.8 µl, 0.335 mmol) was added into the solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (150 mg, 0.279 mmol) and 4-[4,6-bis(methyloxy)-1,3,5-triazin-2-yl]-4-methylmorpholin-4-ium (110 mg, 0.335 mmol) in acetonitrile (4.7 ml). The resulting solution was cooled to 0° C., and it was stirred at 0° C. for 15 min. To the reaction mixture was added 2-[(3S)-3-(dimethylamino)-1-pyrrolidinyl]-4-pyrimidinamine (69.4 mg, 0.335 mmol). After stirring for 2 days at ambient temperature, the reaction mixture was concentrated to yield a residue. The residue was dissolved in DCM. The resulting solution was washed with aqueous saturated Na2SO4 and brine, respectively. The solvent was removed to yield a residue again. The residue was purified by RP-HPLC to yield phenylmethyl (3S)-2-[(2R)-3-cyclopentyl-2-({formyl[(phenylmethyl)oxy]amino}methyl)propanoyl]-3-[({2-[(3S)-3-(dimethylamino)-1-pyrrolidinyl]-4-pyrimidinyl}amino)carbonyl]-1-pyrazolidinecarboxylate (91 mg, 0.125 mmol, 45% yield). MS (ES+) m/z 727.2 (MH+).

Part D (3S)-2-((2R)-3-Cyclopentyl-2-{[formyl(hydroxy)amino]methyl}propanoyl)-N-{2-[(3S)-3-(dimethylamino)-1-pyrrolidinyl]-4-pyrimidinyl}-3-pyrazolidine carboxamide A mixture of phenylmethyl (3S)-2-[(2R)-3-cyclopentyl-2-({formyl[(phenylmethyl)oxy]amino}methyl)propanoyl]-3-[({2-[(3S)-3-(dimethylamino)-1-pyrrolidinyl]-4-pyrimidinyl}amino)carbonyl]-1-pyrazolidinecarboxylate (91 mg, 0.125 mmol) and Pearlman's catalyst (17.58 mg, 0.025 mmol) in methanol (7.4 ml) was degassed and placed under 1 atm of $H_2$ at ambient temperature. After 2 hrs, the reaction mixture was filtered and concentrated to give a residue which was purified by RP-HPLC to give (3S)-2-((2R)-3-cyclopentyl-2-{[formyl(hydroxy)amino]methyl}propanoyl)-N-{2-[(3S)-3-(dimethylamino)-1-pyrrolidinyl]-4-pyrimidinyl}-3-pyrazolidinecarboxamide (45 mg, 0.089 mmol, 71% yield). MS (ES+) m/z 503.1 (MH+). $^1$H NMR (400 MHz, METHANOL-$d_4$) δ ppm 1.05-1.23 (m, 2H) 1.33-1.45 (m, 1H) 1.45-1.68 (m, 4H) 1.69-1.96 (m, 5H) 2.12-2.31 (m, 2H) 2.34 (s, 6H) 2.42-2.57 (m, 1H) 2.83-2.96 (m, 2H) 3.18-3.30 (m, 2H) 3.40-3.53 (m, 2H) 3.65-3.83 (m, 2H) 3.84-3.99 (m, 2H) 4.68 (q, J=7.16 Hz, 1H) 7.34 (d, J=5.56 Hz, 1H) 7.85 (s, 0.7H) 8.16 (d, J=5.81 Hz, 1H) 8.25 (s, 0.3H)

Example 84

(3S)-2-((2R)-3-Cyclopentyl-2-{[formyl(hydroxy)amino]methyl}propanoyl)-N-2-pyrimidinyl-3-pyrazolidinecarboxamide

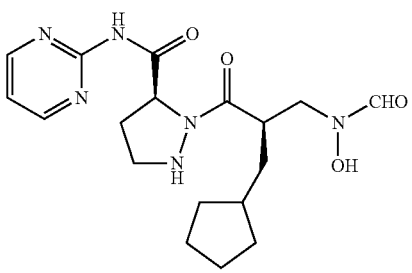

Part A 2,3-Bis(1,1-dimethylethyl) 1-(2-propen-1-yl) 1,2,3-pyrazolidinetricarboxylate Allyl chloroformate (0.488 ml, 4.59 mmol) was added dropwise to the solution of di-tert-butyl pyrazolidine-1,5-dicarboxylate (1 g, 3.67 mmol) and pyridine (0.371 ml, 4.59 mmol) in tetrahydrofuran (THF) (1.79 ml) at 0° C. The resulting solution was allowed to warm up to ambient temperature and stirred for 30 min. The reaction was filtered, and to the filtrate was added EtOAc. The solution was washed with brine. The organic layers were separated and dried over anhydrous $Na_2SO_4$. The crude product was purified by RP-HPLC to give 2,3-bis(1,1-dimethylethyl) 1-(2-propen-1-yl) 1,2,3-pyrazolidinetricarboxylate (749 mg, 2.101 mmol, 57% yield). MS (ES+) m/z 357.3 (MH+).

Part B

1-[(2-propen-1-yloxy)carbonyl]-3-pyrazolidinecarboxylic acid 2,3-Bis(1,1-dimethylethyl) 1-(2-propen-1-yl) 1,2,3-pyrazolidinetricarboxylate (1.2 g, 3.37 mmol) was dissolved in dichloromethane (DCM) (6.63 ml) under $N_2$ at ambient temperature. TFA (15.56 ml, 202 mmol) and water (1.820 ml, 101 mmol) were added in one portion. The reaction was stirred at ambient temperature for 3 days. The solvent was removed under reduced pressure to give crude 1-[(2-propen-1-yloxy)carbonyl]-3-pyrazolidinecarboxylic acid (0.674 g, 3.37 mmol, 100% crude yield). MS (ES+) m/z 201.0 (MH+).

Part C 2-((2R)-3-Cyclopentyl-2-{[formyl(tetrahydro-2H-pyran-2-yloxy)amino]methyl}propanoyl)-1-[(2-propen-1-yloxy)carbonyl]-3-pyrazolidinecarboxylic acid (2R)-3-Cyclopentyl-2-{[formyl(tetrahydro-2H-pyran-2-yloxy)amino]methyl}propanoyl fluoride (784 mg, 2.6 mmol) was added into the solution of 1-[(2-propen-1-yloxy)carbonyl]-3-pyrazolidine carboxylic acid (677 mg, 3.38 mmol) and Hunig's base (1811 µl, 10.40 mmol) in N,N-dimethylformamide (DMF) (11.1 ml). The reaction was stirred for 5 hrs at ambient temperature. The reaction was purified by RP-HPLC to give 2-((2R)-3-Cyclopentyl-2-{[formyl(tetrahydro-2H-pyran-2-yloxy)amino]methyl}propanoyl)-1-[(2-propen-1-yloxy)carbonyl]-3-pyrazolidinecarboxylic acid (428 mg, 0.889 mmol, 34% yield). MS (ES+) m/z 482.0 (MH+).

Part D

2-Propen-1-yl (3S)-2-((2R)-3-cyclopentyl-2-{[formyl(tetrahydro-2H-pyran-2-yloxy)amino]methyl}propanoyl)-3-[(2-pyrimidinylamino)carbonyl]-1-pyrazolidinecarboxylate 1-Methylimidazole (38.1 µl, 0.478 mmol) was added into the solution of 2-((2R)-3-cyclopentyl-2-{[formyl(tetrahydro-2H-pyran-2-yloxy)amino]methyl}propanoyl)-1-[(2-propen-1-yloxy)carbonyl]-3-pyrazolidinecarboxylic acid (115 mg, 0.239 mmol) in N,N-dimethylformamide (DMF) (1.6 ml). The resulting solution was cooled to 0° C., and then mesyl chloride (19.41 µl, 0.251 mmol) was added dropwise at 0° C. To the reaction mixture was added 2-pyrimidinamine (34.1 mg, 0.358 mmol). After stirring for 3.5 hrs at ambient temperature, the reaction solution was purified by RP-HPLC to yield 2-propen-1-yl (3S)-2-((2R)-3-cyclopentyl-2-[formyl(tetrahydro-2H-pyran-2-yloxy)amino]methyl}propanoyl)-3-[(2-pyrimidinylamino)carbonyl]-1-pyrazolidinecarboxylate (32 mg, 0.057 mmol, 24% yield). MS (ES+) m/z 559.0 (MH+).

Part E (3S)-2-((2R)-3-cyclopentyl-2-{[formyl(tetrahydro-2H-pyran-2-yloxy)amino]methyl}propanoyl)-N-2-pyrimidinyl-3-pyrazolidinecarboxamide $Pd(Ph_3P)_4$ (4.63 mg, 4.01 µmol) was added to a solution of 2-propen-1-yl 2-((2R)-3-cyclopentyl-2-{[formyl(tetrahydro-2H-pyran-2-yloxy)amino]methyl}propanoyl)-3-[(2-pyrimidinylamino)carbonyl]-1-pyrazolidinecarboxylate (32 mg, 0.057 mmol) and morpholine (15.87 µl, 0.182 mmol) in dichloromethane (DCM) (0.8 ml). The mixture was stirred at ambient temperature for 15 min. The solvent was removed to give a residue which was purified by RP-HPLC to give (3S)-2-((2R)-3-cyclopentyl-2-{[formyl(tetrahydro-2H-pyran-2-yloxy)amino]methyl}propanoyl)-N-2-pyrimidinyl-3-pyrazolidinecarboxamide (13 mg, 0.027 mmol, 60% yield). MS (ES+) m/z 475.1 (MH+).

Part F (3S)-2-((2R)-3-Cyclopentyl-2-{[formyl(hydroxy)amino]methyl}propanoyl)-N-2-pyrimidinyl-3-pyrazolidinecarboxamide A mixture of (3S)-2-((2R)-3-cyclopentyl-2-{[formyl(tetrahydro-2H-pyran-2-yloxy)amino]methyl}propanoyl)-N-2-pyrimidinyl-3-pyrazolidinecarboxamide (20 mg, 0.042 mmol) in the solution of Acetic Acid (2 ml) and Water (0.500 ml) was stirred at 25° C. for overnight. The solvent was removed to give a residue. The residue was purified by RP-HPLC to give (3S)-2-((2R)-3-cyclopentyl-2-{[formyl(hydroxy)amino]methyl}propanoyl)-N-2-pyrimidinyl-3-pyrazolidine carboxamide (9 mg, 0.023 mmol, 54% yield). MS (ES+) m/z 391.3 (MH+).

Example 85

(3S)-2-((2R)-3-Cyclopentyl-2-{[formyl(hydroxy)amino]methyl}propanoyl)-N-{6-[(2R)-2,4-dimethyl-1-piperazinyl]-4-pyrimidinyl}-3-pyrazolidinecarboxamide

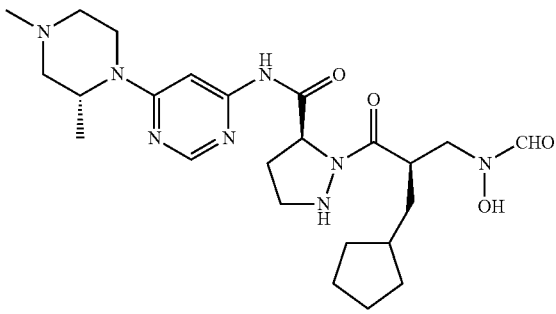 [SMILES: C[C@@H]1CN(C)CCN1c1cc(NC(=O)[C@@H]2CCNN2C(=O)[C@H](CC2CCCC2)CN(O)C=O)ncn1]

Part A

6-[(2R)-2,4-Dimethyl-1-piperazinyl]-4-pyrimidinamine

A mixture of 6-chloro-4-pyrimidinamine (200 mg, 1.544 mmol), Hunig's base (1.2 ml, 6.95 mmol) and (3R)-1,3-dimethylpiperazine (Ref.: WO2009061879 (A1)) (433 mg, 2.316 mmol) in N,N-dimethylformamide (DMF) (2 ml) was heated to 220° C. via a microwave reactor for 15 min. The reaction mixture was purified by RP-HPLC to yield 6-[(2R)-2,4-dimethyl-1-piperazinyl]-4-pyrimidinamine (76 mg, 0.367 mmol, 24% yield). MS (ES+) m/z 208.0 (MH+).

Part B

Phenyl methyl (3S)-2-[(2R)-3-cyclopentyl-2-({formyl[(phenylmethyl)oxy]amino}methyl)propanoyl]-3-[({6-[(2R)-2,4-dimethyl-1-piperazinyl]-4-pyrimidinyl}amino)carbonyl]-1-pyrazolidinecarboxylate 4-Methylmorpholine (73.6 µl, 0.670 mmol) was added into the solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (300 mg, 0.558 mmol) and 4-[4,6-bis(methyloxy)-1,3,5-triazin-2-yl]-4-methylmorpholin-4-ium (220 mg, 0.670 mmol) in acetonitrile (9.3 ml). The resulting solution was cooled to 0° C., and it was stirred at 0° C. for 15 min. To the reaction mixture was added 6-[(2R)-2,4-dimethyl-1-piperazinyl]-4-pyrimidinamine (139 mg, 0.670 mmol). After stirring for 2 days at ambient temperature, the reaction mixture was concentrated to yield a residue. The residue was dissolved in DCM, and the resulting solution was washed with Na$_2$SO$_4$ (sat.) and brine. The solvent was removed to give a residue again. The residue was purified by RP-HPLC to give an impure product. The impure product was purified by using Silica Gel chromatography (DCM/MeOH/NH$_4$OH=9/1/0.002) to yield phenylmethyl (3S)-2-[(2R)-3-cyclopentyl-2-({formyl[(phenylmethyl)oxy]amino}methyl)propanoyl]-3-[({6-[(2R)-2,4-dimethyl-1-piperazinyl]-4-pyrimidinyl}amino) carbonyl]-1-pyrazolidinecarboxylate (71 mg, 0.098 mmol, 18% yield). MS (ES+) m/z 727.1 (MH+).

Part C (3S)-2-((2R)-3-Cyclopentyl-2-{[formyl(hydroxy)amino]methyl}propanoyl)-N-{6-[(2R)-2,4-dimethyl-1-piperazinyl]-4-pyrimidinyl}-3-pyrazolidinecarboxamide A mixture of phenylmethyl (3S)-2-[(2R)-3-cyclopentyl-2-({formyl[(phenylmethyl)oxy]amino}methyl)propanoyl]-3-[({6-[(2R)-2,4-dimethyl-1-piperazinyl]-4-pyrimidinyl}amino)carbonyl]-1-pyrazolidinecarboxylate (71 mg, 0.098 mmol) and Perrlman's catalyst (13.72 mg, 0.020 mmol) in methanol (5.4 ml) was degassed and placed under 1 atm of H$_2$ at ambient temperature. After 2 hrs, the reaction mixture was filtered and concentrated to give a residue which was purified by RP-HPLC to give (3S)-2-((2R)-3-cyclopentyl-2-{[formyl(hydroxy)amino]methyl}propanoyl)-N-{6-[(2R)-2,4-dimethyl-1-piperazinyl]-4-pyrimidinyl}-3-pyrazolidinecarboxamide (42 mg, 0.083 mmol, 85% yield). MS (ES+) m/z 503.2 (MH+). $^1$H NMR (400 MHz, METHANOL-d$_4$) δ ppm 1.05-1.22 (m, 2H) 1.27 (d, J=6.82 Hz, 3H) 1.36-1.45 (m, 1H) 1.46-1.67 (m, 4H) 1.69-1.95 (m, 4H) 2.03 (td, J=11.94, 3.41 Hz, 1H) 2.22 (dd, J=11.62, 4.04 Hz, 2H) 2.26-2.34 (m, 3H) 2.41-2.56 (m, 1H) 2.81 (d, J=11.62 Hz, 1H) 2.85-2.98 (m, 2H) 3.10-3.27 (m, 2H) 3.49 (dd, J=14.02, 4.42 Hz, 1H) 3.59-3.84 (m, 1H) 3.84-3.99 (m, 1H) 4.17 (d, J=13.14 Hz, 1H) 4.53 (br. s., 1H) 4.61-4.72 (m, 1H) 7.41 (s, 1H) 7.86 (s, 0.7H) 8.24 (s, 1.3H).

Example 86

(3S)-2-((2R)-3-Cyclopentyl-2-{[formyl(hydroxy)amino]methyl}propanoyl)-N-[2-(4-methyl-4,7-diazaspiro[2.5]oct-7-yl)-4-pyrimidinyl]-3-pyrazolidinecarboxamide

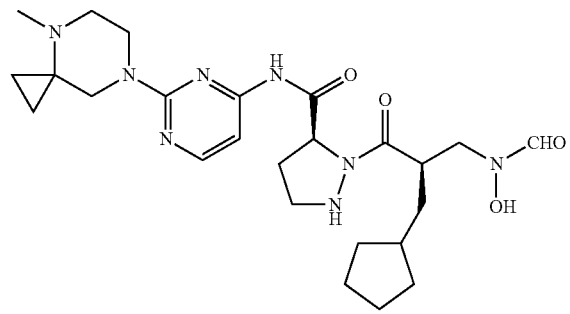 [SMILES: CN1CCN(c2nccc(NC(=O)[C@@H]3CCNN3C(=O)[C@H](CC3CCCC3)CN(O)C=O)n2)CC12CC2]

Part A 2-(4-Methyl-4,7-diazaspiro[2.5]oct-7-yl)-4-pyrimidinamine

A mixture of 2-chloro-4-pyrimidinamine (200 mg, 1.544 mmol), Hunig's base (1348 µl, 7.72 mmol) and 4-methyl-4,7-diazaspiro[2.5]octane (Ref.: WO2009061879 (A1)) (338 mg, 1.698 mmol) in N,N-dimethylformamide (DMF) (1.7 ml) was heated to 120° C. via a microwave reactor for 15 min. The reaction mixture was purified by RP-HPLC to yield 2-(4-methyl-4,7-diazaspiro[2.5]oct-7-yl)-4-pyrimidinamine (113 mg, 0.515 mmol, 33% yield). MS (ES+) m/z 220.1 (MH+).

2-(4-methyl-4,7-diazaspiro[2.5]oct-7-yl)-4-pyrimidinamine (98 mg, 0.446 mmol) was utilized instead of 6-[(2R)-2,4-dimethyl-1-piperazinyl]-4-pyrimidinamine in a similar method to Example 85 Parts B and C to give the Title Compound. MS (ES+) m/z 515.4 (MH+).

Example 87

(3S)-2-((2R)-3-Cyclopentyl-2-{[formyl(hydroxy)amino]methyl}propanoyl)-N-{2-[(2S)-2,4-dimethyl-1-piperazinyl]-4-pyrimidinyl}-3-pyrazolidinecarboxamide

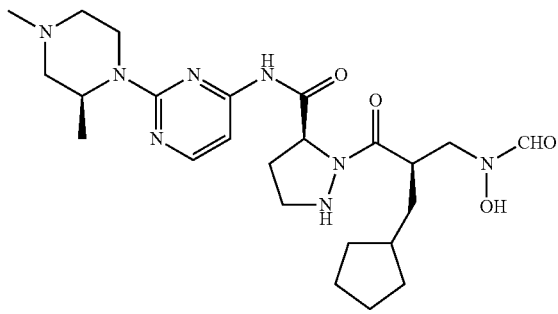 [SMILES: C[C@H]1CN(C)CCN1c1nccc(NC(=O)[C@@H]2CCNN2C(=O)[C@H](CC2CCCC2)CN(O)C=O)n1]

Part A

2-[(2S)-2,4-Dimethyl-1-piperazinyl]-4-pyrimidinamine

A mixture of 2-chloro-4-pyrimidinamine (200 mg, 1.544 mmol), Hunig's base (1348 µl, 7.72 mmol) and (3S)-1,3-dimethylpiperazine (Ref.: WO2009061879 (A1)) (318 mg, 1.698 mmol) in N,N-dimethylformamide (DMF) (1.7 ml) was heated to 220° C. via a microwave reactor for 15 min. The reaction mixture was purified by RP-HPLC to yield 2-[(2S)-2,4-dimethyl-1-piperazinyl]-4-pyrimidinamine (88 mg, 0.425 mmol, 28% yield). MS (ES+) m/z 208.0 (MH+).

Part B (3S)-2-[(2R)-3-Cyclopentyl-2-({formyl[(phenylmethyl)oxy]amino}methyl)propanoyl]-1-{[(phenylmethyl)oxy]carbonyl}-3-pyrazolidinecarboxylic acid (2R)-3-Cyclopentyl-2-({formyl[(phenylmethyl)oxy]amino}methyl)propanoyl fluoride (4 g, 13.01 mmol) was added into the solution of (3S)-1-{[(phenylmethyl)oxy]carbonyl}-3-pyrazolidine carboxylic acid (3.58 g, 14.32 mmol) in dichloromethane (DCM) (52.9 ml), and followed by adding Hunig's base (6.80 ml, 39.0 mmol). The reaction mixture was stirred for 2.5 hrs at ambient temperature. The reaction was diluted with DCM (200 ml), and then acetic acid (9 ml) was added. The resulting solution was washed with aqueous NH$_4$Cl (200 ml). The aqueous solution was extracted with DCM (2×50 ml). The combined organic layers were dried over anhydrous Na$_2$SO$_4$, filtered and concentrated to give a residue. The desired product was precipitated while ethyl acetate (a few ml) was added. The desired product was filtered and washed with ethyl acetate. 3.49 g of desired product as a white solid was collected. The filtrate was purified by silica Gel chromatography (0-100% Ethyl acetate in Hexane). The solvent was removed under reduced pressure to give a solid. The solid was added about 10 ml of MeCN. The desired product (870 mg) as a white solid was collected via filtration. All desired products were combined to yield the final batch of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (4.36 g, 8.11 mmol, 62% yield). MS (ES+) m/z 538.1 (MH+).

Part C

Phenyl methyl (3S)-2-[(2R)-3-cyclopentyl-2-({formyl[(phenylmethyl)oxy]amino}methyl)propanoyl]-3-[({2-[(2S)-2,4-dimethyl-1-piperazinyl]-4-pyrimidinyl}amino)carbonyl]-1-pyrazolidinecarboxylate 1-Methylimidazole (133 µl, 1.674 mmol) was added into the solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (300 mg, 0.558 mmol) in dichloromethane (DCM) (4 ml). The resulting solution was cooled to 0° C., and then mesyl chloride (45.4 µl, 0.586 mmol) was added dropwise at 0° C. To the reaction mixture was added 2-[(2S)-2,4-dimethyl-1-piperazinyl]-4-pyrimidinamine (127 mg, 0.614 mmol). After stirring for 1 h 40 min at ambient temperature, the reaction solution was purified by RP-HPLC to yield phenylmethyl (3S)-2-[(2R)-3-cyclopentyl-2-({formyl[(phenylmethyl)oxy]amino}methyl)propanoyl]-3-[({2-[(2S)-2,4-dimethyl-1-piperazinyl]-4-pyrimidinyl}amino)carbonyl]-1-pyrazolidinecarboxylate (236 mg, 0.325 mmol, 58% yield). MS (ES+) m/z 515.4 (MH+). MS (ES+) m/z 727.3 (MH+).

Part D (3S)-2-((2R)-3-Cyclopentyl-2-{[formyl(hydroxy)amino]methyl}propanoyl)-N-{2-[(2S)-2,4-dimethyl-1-piperazinyl]-4-pyrimidinyl}-3-pyrazolidinecarboxamide A mixture of phenylmethyl (3S)-2-[(2R)-3-cyclopentyl-2-({formyl[(phenylmethyl)oxy]amino}methyl)propanoyl]-3-[({2-[(2S)-2,4-dimethyl-1-piperazinyl]-4-pyrimidinyl}amino) carbonyl]-1-pyrazolidinecarboxylate (236 mg, 0.325 mmol) and Pearlman's catalyst (45.6 mg, 0.065 mmol) in methanol (1.81 ml) was degassed and placed under 1 atm of H$_2$ at ambient temperature. After 2 hrs, the reaction mixture was filtered and concentrated to give a residue which was purified by RP-HPLC to give (3S)-2-((2R)-3-cyclopentyl-2-{[formyl(hydroxy)amino]methyl}propanoyl)-N-{2-[(2S)-2,4-dimethyl-1-piperazinyl]-4-pyrimidinyl}-3-pyrazolidine carboxamide (125 mg, 0.244 mmol, 75% yield). MS (ES+) m/z 503.1 (MH+).

$^1$H NMR (400 MHz, METHANOL-d$_4$) δ ppm 1.05-1.21 (m, 2H) 1.25 (d, J=6.82 Hz, 3H) 1.35-1.67 (m, 5H) 1.67-1.94 (m, 4H) 1.99 (td, J=11.87, 3.28 Hz, 1H) 2.15-2.25 (m, 2H) 2.28 (s, 3H) 2.43-2.57 (m, 1H) 2.79 (d, J=11.37 Hz, 1H) 2.83-2.96 (m, 2H) 3.13 (td, J=12.95, 2.91 Hz, 1H) 3.19-3.28 (m, 1H) 3.49-3.93 (m, 3H) 4.45 (d, J=13.64 Hz, 1H) 4.63-4.74 (m, 1H) 4.77-4.87 (m, 1H) 7.31 (d, J=5.56 Hz, 1H) 7.86 (s, 0.7H) 8.18 (d, J=5.56 Hz, 1H) 8.25 (s, 0.3H)

Example 88

(3S)-2-((2R)-3-Cyclopentyl-2-{[formyl(hydroxy)amino]methyl}propanoyl)-N-[5-(methyloxy)-2-pyrimidinyl]-3-pyrazolidinecarboxamide

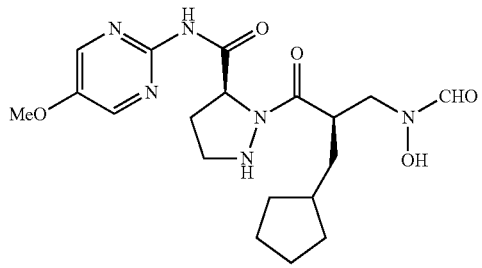 [SMILES: COc1cnc(NC(=O)[C@@H]2CCNN2C(=O)[C@H](CC2CCCC2)CN(O)C=O)nc1]

Part A

2-Propen-1-yl (3S)-2-((2R)-3-cyclopentyl-2-{[formyl(tetrahydro-2H-pyran-2-yloxy)amino]methyl}propanoyl)-3-({[5-(methyloxy)-2-pyrimidinyl]amino}carbonyl)-1-pyrazolidinecarboxylate 1-Methylimidazole (158 µl, 1.987 mmol) was added into the solution of 2-((2R)-3-cyclopentyl-2-{[formyl(tetrahydro-2H-pyran-2-yloxy)amino]methyl}propanoyl)-1-[(2-propen-1-yloxy)carbonyl]-3-pyrazolidinecarboxylic acid (319 mg, 0.662 mmol) in dichloromethane (DCM) (4.5 ml). The resulting solution was cooled to 0° C., and then mesyl chloride (53.8 µl, 0.696 mmol) was added dropwise at 0° C. To the reaction mixture was added 5-(methyloxy)-2-pyrimidinamine (87 mg, 0.696 mmol). After stirring for 30 min at ambient temperature, the solvent was removed under reduced pressure to give a residue which was purified by RP-HPLC to yield 2-propen-1-yl (3S)-2-((2R)-3-cyclopentyl-2-{[formyl(tetrahydro-2H-pyran-2-yloxy)amino]methyl}propanoyl)-3-({[5-(methyloxy)-2-pyrimidinyl]amino}carbonyl)-1-pyrazolidinecarboxylate (173 mg, 0.294 mmol, 44% yield). MS (ES+) m/z 589.1 (MH+).

Part B (3S)-2-((2R)-3-Cyclopentyl-2-{[formyl(tetrahydro-2H-pyran-2-yloxy)amino]methyl}propanoyl)-N-[5-(methyloxy)-2-pyrimidinyl]-3-pyrazolidinecarboxamide Pd(Ph3P)4 (23.77 mg, 0.021 mmol) was added to a solution of 2-propen-1-yl 2-((2R)-3-cyclopentyl-2-{[formyl(tetrahydro-2H-pyran-2-yloxy)amino]methyl}propanoyl)-3-({[5-(methyloxy)-2-pyrimidinyl]amino}carbonyl)-1-pyrazolidinecarboxylate (173 mg, 0.294 mmol) and morpholine (81 µl, 0.935 mmol) in dichloromethane (DCM) (4.1 ml). The mixture was stirred at ambient temperature for 30 min. The solvent was removed under reduced pressure to give a crude product which was purified by RP-HPLC to give (3S)-2-((2R)-3-cyclopentyl-2-{[formyl(tetrahydro-2H-pyran-2-yloxy)amino]methyl}propanoyl)-N-[5-(methyloxy)-2-pyrimidinyl]-3-pyrazolidine carboxamide (67 mg, 0.133 mmol, 45% yield). MS (ES+) m/z 505.2 (MH+).

Part C (3S)-2-((2R)-3-Cyclopentyl-2-{[formyl(hydroxy)amino]methyl}propanoyl)-N-[5-(methyloxy)-2-pyrimidinyl]-3-pyrazolidinecarboxamide A mixture of (3S)-2-((2R)-3-cyclopentyl-2-{[formyl(tetrahydro-2H-pyran-2-yloxy)amino]methyl}propanoyl)-N-[5-(methyloxy)-2-pyrimidinyl]-3-pyrazolidinecarboxamide (67 mg, 0.133 mmol) in acetic acid (7 ml)/water (1.8 ml) was stirred at ambient temperature for overnight. The solvent was removed to give a residue which was purified by RP-HPLC to give (3S)-2-((2R)-3-cyclopentyl-2-{[formyl(hydroxy)amino]methyl}propanoyl)-N-[5-(methyloxy)-2-pyrimidinyl]-3-pyrazolidinecarboxamide (27 mg, 0.061 mmol, 46% yield). MS (ES+) m/z 421.1 (MH+).

The following Examples 89 to 90 were prepared according to a method similar to that disclosed in Example 88 except that to the reaction mixture in Part A was added the indicated compound instead of 5-(methyloxy)-2-pyrimidinamine.

Example 89

(3S)-2-((2R)-3-Cyclopentyl-2-{[formyl(hydroxy)amino]methyl}propanoyl)-N-[4-(methyloxy)-2-pyrimidinyl]-3-pyrazolidinecarboxamide

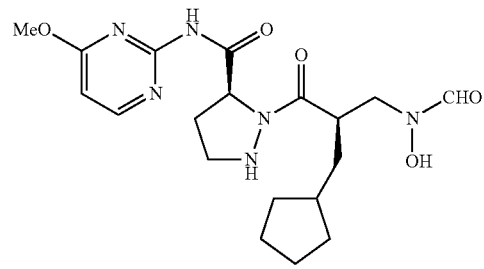

4-(methyloxy)-2-pyrimidinamine (96 mg, 0.768 mmol). MS (ES+) m/z 421.1 (MH+).

Example 90

(3S)-2-((2R)-3-Cyclopentyl-2-{[formyl(hydroxy)amino]methyl}propanoyl)-N-(5-fluoro-2-pyrimidinyl)-3-pyrazolidinecarboxamide

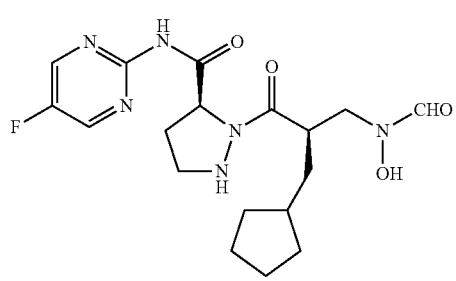 [SMILES: O=CN(O)C[C@@H](CC1CCCC1)C(=O)N1NCC[C@H]1C(=O)Nc1ncc(F)cn1]

Pre Step A

5-Fluoro-2-pyrimidinamine

A mixture of 2-chloro-5-fluoropyrimidine (280 µl, 2.264 mmol) and ammonia (5 ml, 68 mmol) in methanol (860 µl)

was heated to 110° C. via a microwave reactor for 30 min. The reaction was filtered, and the solid was washed with MeOH. The solid was dried to give 5-fluoro-2-pyrimidinamine (247 mg, 2.184 mmol, 96% yield) as a white crystal solid. MS (ES+) m/z 114.0 (MH+).

5-fluoro-2-pyrimidinamine (83 mg, 0.738 mmol). MS (ES+) m/z 409.4 (MH+). $^1$H NMR (400 MHz, METHANOL-$d_4$) δ ppm 1.06-1.23 (m, 2H) 1.32-1.43 (m, 1H) 1.51-1.66 (m, 4H) 1.73-1.94 (m, 4H) 2.15-2.29 (m, 1H) 2.48-2.63 (m, 1H) 2.85-2.99 (m, 1H) 3.20-3.29 (m, 1H) 3.49 (dd, J=14.02, 4.42 Hz, 1H) 3.69-3.84 (m, 1H) 3.94 (tt, J=9.57, 4.83 Hz, 1H) 4.76 (dd, J=6.82, 2.53 Hz, 1H) 7.85 (s, 0.7H) 8.25 (s, 0.3H) 8.58 (s, 2H)

Example 91

(3S)-2-((2R)-3-Cyclopentyl-2-{[formyl(hydroxy) amino]methyl}propanoyl)-N-{2-[(dimethylamino) methyl]-4-pyrimidinyl}-3-pyrazolidinecarboxamide

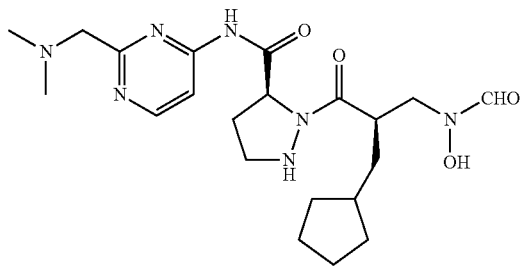 [SMILES: CN(C)Cc1nccc(NC(=O)[C@@H]2CCNN2C(=O)[C@H](CC2CCCC2)CN(O)C=O)n1]

Part A 2-(Dimethylamino)ethanimidamide

To a round bottom flask equipped with a stirring bar was added ammonium chloride (1.272 g, 23.78 mmol) in toluene (6.78 ml). The slurry was cooled to 0° C. under $N_2$. To this slurry was added trimethylaluminum (11.89 ml, 23.78 mmol) via a syringe over 5 min. Once addition was completed, the reaction was warmed to ambient temperature and stirred for 1 hr until all $NH_4Cl$ had reacted. To this mixture was added (dimethylamino)acetonitrile (1.15 ml, 11.89 mmol). The reaction mixture was heated to 110° C. for 3 hrs. The reaction was cooled to ambient temperature and poured slowly into a vigorously stirred slurry of $SiO_2$ in $CHCl_3$ that was cooled in an ice bath. After quenching was completed, the slurry was poured onto a glass filtration funnel and washed with $CHCl_3$ (30 mL). The solid was washed with the solvent mixture ($CHCl_3$/MeOH/$NH_4OH$=80:20:2). The collected solution was dried to yield 2-(dimethylamino) ethanimidamide (1.909 g, 8.32 mmol, 70% crude yield) as a brown oily residue, which was used to next step without purification.

Part B

2-[(Dimethylamino)methyl]-4-pyrimidinamine

To a solution of 2-chloro-2-propenenitrile (437 mg, 4.99 mmol) and 2-(dimethylamino)ethanimide amide (1168 mg, 8.49 mmol) in ethanol (5 mL) was added dropwise triethylamine (TEA) (12.53 mL, 90 mmol) at 0° C. The reaction mixture was stirred for 3 hrs at ambient temperature, and then another portion of 2-chloro-2-propenenitrile (218 mg, 2.50 mmol) was added to the reaction. The reaction mixture was stirred for 3 days at ambient temperature. The solvent was removed under reduced pressure to give a brown residue which was purified by silica gel chromatography (DCM/MeOH in 0.1% $NH_4OH$) twice to give 2-[(dimethylamino) methyl]-4-pyrimidinamine (279 mg, 1.833 mmol, 37% yield) as a brown oil. MS (ES+) m/z 153.0 (MH+).

Part C (3S)-2-[(2R)-3-Cyclopentyl-2-({formyl[(phenylmethyl)oxy]amino}methyl)propanoyl]-1-{[(phenylmethyl)oxy]carbonyl}-3-pyrazolidinecarboxylic acid (2R)-3-Cyclopentyl-2-({formyl[(phenylmethyl)oxy] amino}methyl)propanoyl fluoride (4 g, 13.01 mmol) was added into the solution of (3S)-1-{[(phenylmethyl)oxy]carbonyl}-3-pyrazolidine carboxylic acid (3.91 g, 15.62 mmol) in dichloromethane (DCM) (46.1 ml), followed by adding Hunig's base (6.80 ml, 39.0 mmol). The reaction mixture was stirred at ambient temperature for 5 hrs. The reaction was diluted with DCM, and acetic acid (10 ml) was added. The resulting solution was washed with aqueous $NH_4Cl$ (200 ml). The aqueous solution was extracted with DCM (2×50 ml). The combined organic layers were dried over anhydrous $Na_2SO_4$, filtered and concentrated to give a residue. Ethyl acetate (a few ml) was added. The desired product was filtered and washed with ethyl acetate. 3.21 g of desired product was collected as a white solid. The filtrate was purified by silica gel chromatography (0-100% ethyl acetate in hexane) to give a solid. The solid was added to 10 ml of MeCN. Another batch of the desired product (1.081 g) as a white solid was collected via filtration. These two batches of desired products were combined to yield (3S)-2-[(2R)-3-cyclopentyl-2-({formyl [(phenylmethyl)oxy]amino}methyl)propanoyl]-1-{[(phenylmethyl)oxy]carbonyl}-3-pyrazolidinecarboxylic acid (4.291 g, 7.98 mmol, 61% yield). MS (ES+) m/z 538.0 (MH+).

Part D

Phenylmethyl (3S)-2-[(2R)-3-cyclopentyl-2-({formyl[(phenylmethyl)oxy]amino}methyl)propanoyl]-3-[({2-[(dimethylamino) methyl]-4-pyrimidinyl}amino)carbonyl]-1-pyrazolidinecarboxylate 1-Methylimidazole (178 μl, 2.232 mmol) was added into the solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (400 mg, 0.744 mmol) in DCM (4.08 ml). The resulting solution was cooled to 0° C., and then mesyl chloride (60.5 μl, 0.781 mmol) was added dropwise at 0° C. To the reaction mixture was added 2-[(dimethylamino)methyl]-4-pyrimidinamine (147 mg, 0.967 mmol) in 1 ml of DCM. After stirring for 1.5 hrs at ambient temperature, the solvent was removed under reduced pressure to give a residue which was purified by RP-HPLC to yield phenylmethyl (3S)-2-[(2R)-3-cyclopentyl-2-({formyl[(phenylmethyl)oxy]amino}methyl)propanoyl]-3-[({2-[(dimethylamino) methyl]-4-pyrimidinyl}amino)carbonyl]-1-pyrazolidine carboxylate (104 mg, 0.147 mmol, 20% yield). MS (ES+) m/z 672.2 (MH+).

Part E (3S)-2-((2R)-3-Cyclopentyl-2-{[formyl(hydroxy)amino]methyl}propanoyl)-N-{2-[(dimethylamino)methyl]-4-pyrimidinyl}-3-pyrazolidinecarboxamide A mixture of phenylmethyl (3S)-2-[(2R)-3-cyclopentyl-2-({formyl[(phenylmethyl)oxy]amino}methyl)propanoyl]-3-[({2-[(dimethylamino)methyl]-4-pyrimidinyl}amino)carbonyl]-1-pyrazolidine carboxylate (104 mg, 0.155 mmol) and Pearlman's catalyst (21.74 mg, 0.031 mmol) in methanol (8.6 ml) was degassed and placed under 1 atm of $H_2$ at ambient temperature. After 2 hrs, the reaction mixture was filtered and concentrated to give a residue which was purified by RP-HPLC to give (3S)-2-((2R)-3-cyclopentyl-2-{[formyl(hydroxy)amino]methyl}propanoyl)-N-{2-[(dimethyl amino)methyl]-4-pyrimidinyl}-3-pyrazolidine carboxamide (41 mg, 0.090 mmol, 58% yield). MS (ES+) m/z 448.2 (MH+).

Example 92

(5S)-1-((2R)-3-Cyclopentyl-2-{[formyl(hydroxy)amino]methyl}propanoyl)-N-4-pyrimidinyl-4,5-dihydro-1H-pyrazole-5-carboxamide

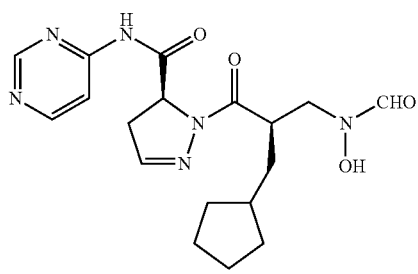

Part A 4,5-Dihydro-1H-pyrazole-5-carboxylic acid

TFA (19.01 ml, 247 mmol) was added into the solution of 1,1-dimethylethyl 4,5-dihydro-1H-pyrazole-5-carboxylate (1.4 g, 8.23 mmol) in dichloromethane (DCM) (22.85 ml). The resulting solution was stirred at ambient temperature for overnight. The solvent was removed under reduced pressure to give a crude 4,5-dihydro-1H-pyrazole-5-carboxylic acid (939 mg, 8.23 mmol, 100% crude yield). MS (ES+) m/z 115.1 (MH+).

Part B (5S)-1-[(2R)-3-Cyclopentyl-2-({formyl[(phenylmethyl)oxy]amino}methyl)propanoyl]-4,5-dihydro-1H-pyrazole-5-carboxylic acid 4,5-Dihydro-1H-pyrazole-5-carboxylic acid (939 mg, 8.23 mmol) in 20 ml of DCM was added into a solution of (2R)-3-cyclopentyl-2-({formyl[(phenylmethyl)oxy]amino}methyl)propanoyl fluoride (3035 mg, 9.88 mmol) in 21.8 ml of DCM, and followed by Hunig's base (4.3 ml, 24.69 mmol). The resulting solution was stirred at ambient temperature for 1 hr. HOAc (8 ml) was added to neutralize the solution, and then it was purified by RP-HPLC to give (5S)-1-[(2R)-3-cyclopentyl-2-({formyl[(phenylmethyl)oxy]amino}methyl)propanoyl]-4,5-dihydro-1H-pyrazole-5-carboxylic acid (660 mg, 1.644 mmol, 40% yield). MS (ES+) m/z 401.9 (MH+).

Part C (5S)-1-[(2R)-3-Cyclopentyl-2-({formyl[(phenylmethyl)oxy]amino}methyl)propanoyl]-N-4-pyrimidinyl-4,5-dihydro-1H-pyrazole-5-carboxamide 1-Methylimidazole (39.7 μl, 0.498 mmol) was added into the solution of (5S)-1-[(2R)-3-cyclopentyl-2-({formyl[(phenylmethyl)oxy]amino}methyl)propanoyl]-4,5-dihydro-1H-pyrazole-5-carboxylic acid (100 mg, 0.249 mmol) in N,N-dimethylformamide (DMF) (1.8 ml). The resulting solution was cooled to 0° C., and then mesyl chloride (20.24 μl, 0.262 mmol) was added dropwise at 0° C. To the reaction mixture was added 4-pyrimidinamine (26.1 mg, 0.274 mmol). After stirring for 2 h 10 min at ambient temperature, the reaction solution was purified by RP-HPLC to yield (5S)-1-[(2R)-3-cyclopentyl-2-({formyl[(phenylmethyl)oxy]amino}methyl)propanoyl]-N-4-pyrimidinyl-4,5-dihydro-1H-pyrazole-5-carboxamide (76 mg, 0.159 mmol, 64% yield). MS (ES+) m/z 478.8 (MH+).

Part D (5S)-1-((2R)-3-Cyclopentyl-2-{[formyl(hydroxy)amino]methyl}propanoyl)-N-4-pyrimidinyl-4,5-dihydro-1H-pyrazole-5-carboxamide A mixture of (5S)-1-[(2R)-3-cyclopentyl-2-({formyl[(phenylmethyl)oxy]amino}methyl)propanoyl]-N-4-pyrimidinyl-4,5-dihydro-1H-pyrazole-5-carboxamide (76 mg, 0.159 mmol) and Pearlman's catalyst (22.30 mg, 0.032 mmol) in methanol (8.8 ml) was degassed and placed under 1 atm of $H_2$ at ambient temperature. After 1 h 50 min, the reaction mixture was filtered and concentrated to give a residue which was purified by RP-HPLC to give (5S)-1-((2R)-3-cyclopentyl-2-{[formyl(hydroxy)amino]methyl}propanoyl)-N-4-pyrimidinyl-4,5-dihydro-1H-pyrazole-5-carboxamide (58 mg, 0.148 mmol, 93% yield). MS (ES+) m/z 389.2 (MH+). $^1$H NMR (400 MHz, METHANOL-$d_4$) δ ppm 1.04-1.21 (m, 2H) 1.37-1.67 (m, 5H) 1.70-1.99 (m, 4H) 3.05-3.20 (m, 1H) 3.35 (d, J=11.87 Hz, 1H) 3.55 (dd, J=14.02, 4.67 Hz, 1H) 3.75-3.90 (m, 1H) 3.90-4.02 (m, 1H) 4.99 (dd, J=11.87, 5.81 Hz, 1H) 7.11 (s, 1H) 7.89 (s, 0.7H) 8.14 (d, J=5.31 Hz, 1H) 8.22 (s, 0.3H) 8.60 (d, J=5.81 Hz, 1H) 8.83 (s, 1H)

Example 93

(5S)-1-((2R)-3-Cyclopentyl-2-{[formyl(hydroxy)amino]methyl}propanoyl)-N-(5-fluoro-2-pyridinyl)-4,5-dihydro-1H-pyrazole-5-carboxamide

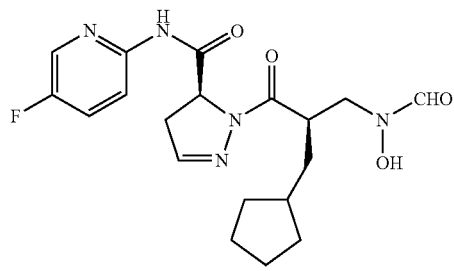 [SMILES: O=CN(O)C[C@@H](CC1CCCC1)C(=O)N1N=CC[C@H]1C(=O)Nc1ccc(F)cn1]

Part A (5S)-1-[(2R)-3-Cyclopentyl-2-({formyl[(phenylmethyl)oxy]amino}methyl)propanoyl]-N-(5-fluoro-2-pyridinyl)-4,5-dihydro-1H-pyrazole-5-carboxamide 1-Methylimidazole (59.6 µl, 0.747 mmol) was added into the solution of (5S)-1-[(2R)-3-cyclopentyl-2-({formyl[(phenylmethyl)oxy]amino}methyl)propanoyl]-4,5-dihydro-1H-pyrazole-5-carboxylic acid (150 mg, 0.374 mmol) in N,N-dimethylformamide (DMF) (2.7 ml). The resulting solution was cooled to 0° C., and then mesyl chloride (30.4 µl, 0.392 mmol) was added dropwise at 0° C. To the reaction mixture was added 5-fluoro-2-pyridinamine (46.1 mg, 0.411 mmol). After stirring for 2 h 10 min at ambient temperature, the reaction solution was purified by RP-HPLC to yield (5S)-1-[(2R)-3-cyclopentyl-2-({formyl[(phenylmethyl)oxy]amino}methyl)propanoyl]-N-(5-fluoro-2-pyridinyl)-4,5-dihydro-1H-pyrazole-5-carboxamide (104 mg, 0.210 mmol, 56% yield). MS (ES+) m/z 496.0 (MH+).

Part B (5S)-1-((2R)-3-Cyclopentyl-2-{[formyl(hydroxy)amino]methyl}propanoyl)-N-(5-fluoro-2-pyridinyl)-4,5-dihydro-1H-pyrazole-5-carboxamide A mixture of (5S)-1-[(2R)-3-cyclopentyl-2-({formyl[(phenylmethyl)oxy]amino}methyl)propanoyl]-N-(5-fluoro-2-pyridinyl)-4,5-dihydro-1H-pyrazole-5-carboxamide (104 mg, 0.210 mmol) and Pearlman's catalyst (29.5 mg, 0.042 mmol) in methanol (12.3 ml) was degassed and placed under 1 atm of $H_2$ at ambient temperature. After 2 hrs, the reaction mixture was filtered and concentrated to give a residue which was purified by RP-HPLC to give (5S)-1-((2R)-3-cyclopentyl-2-{[formyl(hydroxy)amino]methyl}propanoyl)-N-(5-fluoro-2-pyridinyl)-4,5-dihydro-1H-pyrazole-5-carboxamide (71 mg, 0.173 mmol, 83% yield). MS (ES+) m/z 406.1 (MH+) $^1$H NMR (400 MHz, METHANOL-$d_4$) δ ppm 1.12 (dq, J=11.78, 8.12 Hz, 2H) 1.37-1.67 (m, 5H) 1.70-1.99 (m, 4H) 3.05-3.19 (m, 1H) 3.27 (s, 1H) 3.54 (dd, J=14.15, 4.55 Hz, 1H) 3.75-3.89 (m, 1H) 3.89-4.03 (m, 1H) 4.97 (dd, J=11.87, 5.81 Hz, 1H) 7.11 (s, 1H) 7.50-7.62 (m, 1H) 7.89 (s, 0.7H) 8.12 (dd, J=9.09, 4.04 Hz, 1H) 8.18 (d, J=3.03 Hz, 1H) 8.22 (s, 0.3H)

The following Examples 94 to 99 were prepared according to a method similar to that disclosed in Example 93 except that to the reaction mixture in Part A was added the indicated compound instead of 5-fluoro-2-pyridinamine.

Example 94

(5S)-1-((2R)-3-Cyclopentyl-2-{[formyl(hydroxy)amino]methyl}propanoyl)-N-(5-fluoro-4-pyrimidinyl)-4,5-dihydro-1H-pyrazole-5-carboxamide

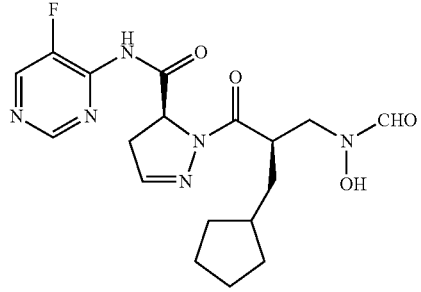

Pre Step A

5-Fluoro-4-pyrimidinamine

A mixture of 4-chloro-5-fluoropyrimidine (200 mg, 1.509 mmol) and ammonia (3.27 ml, 45.3 mmol) in methanol (580 µl) was heated to 110° C. via a microwave reactor for 30 min. The reaction was filtered to provide a solid. The solid was dried to give 5-fluoro-4-pyrimidinamine (100 mg, 0.875 mmol, 58% yield) as a white solid. MS (ES+) m/z 114.1 (MH+).

5-fluoro-4-pyrimidinamine (42.3 mg, 0.374 mmol). MS (ES+) m/z 407.3 (MH+). $^1$H NMR (400 MHz, METHANOL-$d_4$) δ ppm 1.02-1.22 (m, 2H) 1.36-1.66 (m, 5H) 1.70-1.99 (m, 4H) 3.09-3.22 (m, 1H) 3.33-3.45 (m, 1H) 3.55 (dd, J=14.15, 4.55 Hz, 1H) 3.74-4.04 (m, 2H) 5.16 (dd, J=11.62, 5.31 Hz, 1H) 7.12 (s, 1H) 7.89 (s, 0.7H) 8.21 (s, 0.3H) 8.64 (d, J=3.03 Hz, 1H) 8.71 (d, J=2.02 Hz, 1H)

Example 95

(5S)-1-((2R)-3-Cyclopentyl-2-{[formyl(hydroxy)amino]methyl}propanoyl)-N-2-pyrazinyl-4,5-dihydro-1H-pyrazole-5-carboxamide

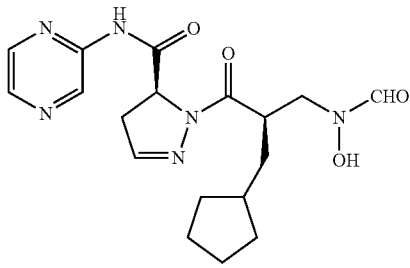 [SMILES: O=CN(O)C[C@@H](CC1CCCC1)C(=O)N1N=CC[C@H]1C(=O)Nc1cnccn1]

Pre Step A 4,5-Di hydro-1H-pyrazole-5-carboxylic acid

TFA (25.8 ml, 335 mmol) was added into a solution of 1,1-dimethylethyl 4,5-dihydro-1H-pyrazole-5-carboxylate (1.9 g, 11.16 mmol) in dichloromethane (DCM) (31.0 ml). The resulting solution was stirred at ambient temperature for overnight. The solvent was removed under reduced pressure to give crude 4,5-dihydro-1H-pyrazole-5-carboxylic acid (1.274 g, 11.17 mmol, 100% crude yield). MS (ES+) m/z 115.1 (MH+).

Pre Step B (5S)-1-[(2R)-3-Cyclopentyl-2-({formyl[(phenylmethyl)oxy]amino}methyl)propanoyl]-4,5-dihydro-1H-pyrazole-5-carboxylic acid 4,5-Dihydro-1H-pyrazole-5-carboxylic acid (1.273 g, 11.16 mmol) in 26.6 mL of DCM was added into a solution of (2R)-3-cyclopentyl-2-({formyl[(phenylmethyl)oxy]amino}methyl)propanoyl fluoride (4.12 g, 13.39 mmol) in 30 mL of DCM, and followed by Hunig's base (5.83 ml, 33.5 mmol). The resulting solution was stirred at ambient temperature for 2 hrs. HOAc (10 ml) was added to neutralize the solution, and then the solvent was removed to give a crude product which was purified by RP-HPLC to give (5S)-1-[(2R)-3-cyclopentyl-2-({formyl[(phenylmethyl)oxy]amino}methyl)propanoyl]-4,5-dihydro-1H-pyrazole-5-carboxylic acid (1.03 g, 2.57 mmol, 46% yield). MS (ES+) m/z 401.9 (MH+).

(5S)-1-[(2R)-3-cyclopentyl-2-({formyl[(phenylmethyl) oxy]amino}methyl)propanoyl]-4,5-dihydro-1H-pyrazole-5-carboxylic acid (100 mg, 0.249 mmol) and 2-pyrazinamine (35.5 mg, 0.374 mmol) were utilized using a similar method to Example 93 Parts A and B to give the Title Compound. MS (ES+) m/z 389.3 (MH+). $^1$H NMR (400 MHz, METHANOL-$d_4$) δ ppm 1.03-1.22 (m, 2H) 1.38-1.68 (m, 5H) 1.71-2.00 (m, 4H) 3.09-3.21 (m, 1H) 3.32-3.41 (m, 1H) 3.55 (dd, J=14.02, 4.67 Hz, 1H) 3.76-3.91 (m, 1H) 3.91-4.03 (m, 1H) 4.99 (dd, J=12.00, 5.94 Hz, 1H) 7.12 (s, 1H) 7.88 (s, 0.7H) 8.21 (s, 0.3H) 8.31 (d, J=2.53 Hz, 1H) 8.35-8.42 (m, 1H) 9.34 (s, 1H)

Example 96

(5S)-1-((2R)-3-Cyclopentyl-2-{[formyl(hydroxy) amino]methyl}propanoyl)-N-(2-fluoro-4-pyrimidinyl)-4,5-dihydro-1H-pyrazole-5-carboxamide

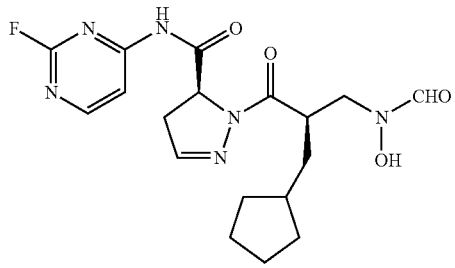

2-fluoro-4-pyrimidinamine (39.4 mg, 0.349 mmol). MS (ES+) m/z 407.1 (MH+).

Example 97

(5S)-1-((2R)-3-Cyclopentyl-2-{[formyl(hydroxy) amino]methyl}propanoyl)-N-(5-methyl-2-pyrazinyl)-4,5-dihydro-1H-pyrazole-5-carboxamide

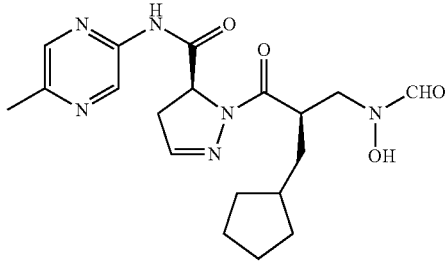 [SMILES: Cc1cnc(NC(=O)[C@@H]2CC=NN2C(=O)[C@H](CC2CCCC2)CN(O)C=O)cn1]

5-methyl-2-pyrazinamine (40.8 mg, 0.374 mmol). MS (ES+) m/z 403.0 (MH+).

Example 98

(5S)-1-((2R)-3-Cyclopentyl-2-{[formyl(hydroxy) amino]methyl}propanoyl)-N-(6-fluoro-2-pyridinyl)-4,5-dihydro-1H-pyrazole-5-carboxamide

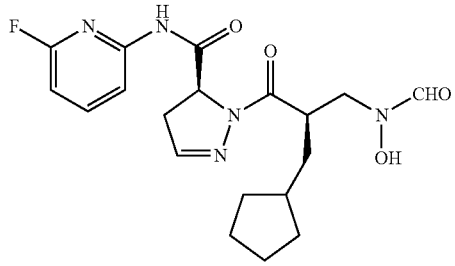

6-fluoro-2-pyridinamine (62.8 mg, 0.560 mmol). MS (ES+) m/z 406.1 (MH+). $^1$H NMR (400 MHz, METHANOL-$d_4$) δ ppm 1.02-1.23 (m, 2H) 1.37-1.67 (m, 5H) 1.70-2.00 (m, 4H) 3.02-3.19 (m, 1H) 3.27-3.35 (m, 1H) 3.54 (dd, J=13.89, 4.55 Hz, 1H) 3.75-4.04 (m, 2H) 4.95 (dd, J=11.75, 5.68 Hz, 1H) 6.73 (dd, J=8.08, 2.27 Hz, 1H) 7.10 (s, 1H) 7.80-7.93 (m, 1.7H) 7.98 (d, J=7.33 Hz, 1H) 8.21 (s, 0.3H)

Example 99

(5S)-1-((2R)-3-Cyclopentyl-2-{[formyl(hydroxy) amino]methyl}propanoyl)-N-[2-(methyloxy)-4-pyrimidinyl]-4,5-dihydro-1H-pyrazole-5-carboxamide

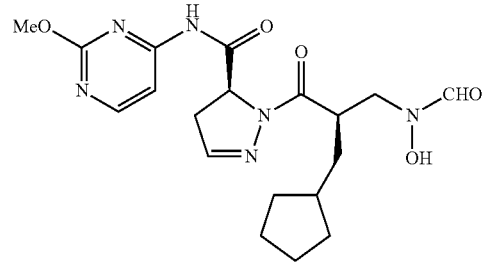 [SMILES: COc1nccc(NC(=O)[C@@H]2CC=NN2C(=O)[C@H](CC2CCCC2)CN(O)C=O)n1]

Pre Step A 2-(Methyloxy)-4-pyrimidinamine

A mixture of 2-chloro-4-pyrimidinamine (150 mg, 1.158 mmol) and sodium methoxide (188 mg, 3.47 mmol) in methanol (2.9 ml) was heated to 100° C. via a microwave reactor for 40 min. The crude product mixture was purified by RP-HPLC to give 2-(methyloxy)-4-pyrimidinamine (73 mg, 0.583 mmol, 50% yield). MS (ES+) m/z 126.0 (MH+).

2-(methyloxy)-4-pyrimidinamine (56.1 mg, 0.448 mmol). MS (ES+) m/z 419.0 (MH+). $^1$H NMR (400 MHz, METHANOL-$d_4$) δ ppm 1.03-1.21 (m, 2H) 1.37-1.67 (m, 5H) 1.71-2.00 (m, 4H) 3.04-3.18 (m, 1H) 3.27-3.39 (m, 1H) 3.55 (dd, J=14.15, 4.55 Hz, 1H) 3.74-3.87 (m, 1H) 3.90-4.05 (m, 4H) 4.98 (dd, J=12.13, 5.81 Hz, 1H) 7.10 (s, 1H) 7.74 (d, J=5.56 Hz, 1H) 7.89 (s, 0.7H) 8.21 (s, 0.3H) 8.38 (d, J=5.56 Hz, 1H)

Example 100

(3S)—N-(5-Fluoro-2-pyridinyl)-2-((2R)-2-{[formyl (hydroxy)amino]methyl}heptanoyl)-3-pyrazolidinecarboxamide

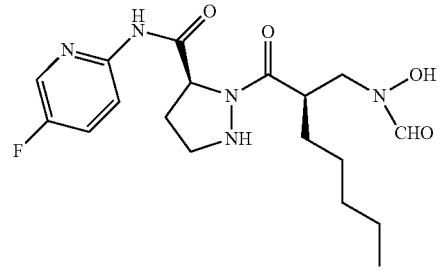 [SMILES: CCCCC[C@H](CN(O)C=O)C(=O)N1NCC[C@H]1C(=O)Nc1ccc(F)cn1]

Part A

(2R)-2-({Formyl[(phenylmethyl)oxy]amino}methyl)heptanoyl fluoride

To a 250 mL round-bottomed flask was added (2R)-2-({formyl[(phenylmethyl)oxy]amino}methyl)heptanoic acid (WO 2003101442, also named (2R)-[(benzyloxyformylamino)methyl]heptanoic acid) (4.40 g, 15 mmol) in dichloromethane (60 mL), followed by pyridine (1.453 mL, 18.00 mmol) and 2,4,6-trifluoro-1,3,5-triazine (cyanuric fluoride) (2.168 g, 16.05 mmol). The reaction mixture was stirred at room temperature for 2 h, then was diluted with DCM, and washed with 5% Citric acid (150 mL) and sat. NaHCO$_3$ (150 mL). The organic layer was dried over MgSO$_4$, filtered and concentrated. The residue was purified by flash chromatography to provide (2R)-2-({formyl[(phenylmethyl)oxy]amino}methyl)heptanoyl fluoride as a colorless oil (1.88 g, 42%). LCMS: (M+H)$^+$: 296.0.

Part B

(3S)-2-[(2R)-2-({Formyl[(phenylmethyl)oxy]amino}methyl)heptanoyl]-1-{[(phenylmethyl)oxy]carbonyl}-3-pyrazolidinecarboxylic acid To a 50 mL round-bottomed flask was added 1-{[(phenylmethyl)oxy]carbonyl}-3-pyrazolidinecarboxylic acid (3.00 g, 8.23 mmol) and Hunig's base (DIPEA) (4.41 mL, 25.3 mmol) in DMF (15 mL). To this mixture was added (2R)-2-({formyl[(phenylmethyl)oxy]amino}methyl)heptanoyl fluoride (1.87 g, 6.33 mmol) in DMF (5 mL) dropwise. The reaction mixture was stirred at room temperature overnight, then was stored in refrigerator for two days. HOAc (3 ml) was added to neutralize the excess Hunig's base. The resulting solution was purified by RP-HPLC to provide (3S)-2-[(2R)-2-({formyl[(phenylmethyl)oxy]amino}methyl)heptanoyl]-1-{[(phenylmethyl)oxy]carbonyl}-3-pyrazolidinecarboxylic acid as a white solid (1.153 g, 35%). LCMS: (M+H)$^+$: 526.0.

Part C

Phenylmethyl (3S)-3-{[(5-fluoro-2-pyridinyl)amino]carbonyl}-2-[(2R)-2-({formyl[(phenylmethyl)oxy]amino}methyl)heptanoyl]-1-pyrazolidine carboxylate To a solution of (3S)-2-[(2R)-2-({formyl[(phenylmethyl)oxy]amino}methyl)heptanoyl]-1-{[(phenylmethyl)oxy]carbonyl}-3-pyrazolidinecarboxylic acid (1.015 g, 1.931 mmol) in acetonitrile (30 mL) at 0° C. was added 4-methylmorpholine (0.467 mL, 4.25 mmol), followed by 4-[4,6-bis(methyloxy)-1,3,5-triazin-2-yl]-4-methylmorpholin-4-ium tetrafluoroborate (DMTMM) (0.559 g, 2.317 mmol). The solution was stirred for 15 min, then 5-fluoro-2-pyridinamine (0.260 g, 2.317 mmol) was added. The reaction mixture was warmed up to room temperature and stirred overnight. The solvent was evaporated, and the residue was dissolved in DCM. The solution was washed with 5% aq. NaHSO$_4$ followed by water, and the organic phase was dried over anhydrous Na$_2$SO$_4$, filtered, and concentrated in vacuo to afford a crude oil which was purified by RP-HPLC to yield phenylmethyl (3S)-3-{[(5-fluoro-2-pyridinyl)amino]carbonyl}-2-[(2R)-2-({formyl[(phenylmethyl)oxy]amino}methyl)heptanoyl]-1-pyrazolidinecarboxylate as a colorless gum (830 mg, 69%). LCMS: (M+H)$^+$: 620.2.

Part D

(3S)—N-(5-Fluoro-2-pyridinyl)-2-((2R)-2-{[formyl(hydroxy)amino]methyl}heptanoyl)-3-pyrazolidinecarboxamide To a 100 mL round-bottomed flask was added phenylmethyl (3S)-3-{[(5-fluoro-2-pyridinyl)amino]carbonyl}-2-[(2R)-2-({formyl[(phenylmethyl)oxy]amino}methyl)heptanoyl]-1-pyrazolidinecarboxylate (696 mg, 1.123 mmol) in methanol (15 ml), followed by Pearlman's catalyst (120 mg). The mixture was stirred under a balloon of H$_2$ for 80 min. The catalyst was filtered off, and the filtrate was concentrated to dryness to provide (3S)—N-(5-fluoro-2-pyridinyl)-2-((2R)-2-{[formyl(hydroxy)amino]methyl}heptanoyl)-3-pyrazolidinecarboxamide as a colorless oil. (420 mg, 94%). LCMS: (M+H)$^+$: 396.0. $^1$H NMR (400 MHz, METHANOL-d$_4$) δ ppm 0.75-1.00 (m, 3H) 1.16-1.39 (m, 6H) 1.47 (dd, J=8.59, 5.56 Hz, 1H) 1.52-1.68 (m, 1H) 2.02-2.31 (m, 1H) 2.49 (ddd, J=12.06, 6.25, 2.65 Hz, 1H) 2.86 (td, J=10.48, 6.06 Hz, 1H) 3.36 (br. s., 1H) 3.39-3.55 (m, 1H) 3.59-3.89 (m, 2H) 4.54-4.72 (m, 1H) 7.53 (ddd, J=9.16, 7.89, 3.16 Hz, 1H) 7.83 (s, 1H) 8.03-8.20 (m, 2H).

The following Examples 101 to 103 prepared according to a method similar to that disclosed in Example 100 except that to the reaction mixture in Part C was added the indicated compound instead of 5-fluoro-2-pyridinamine.

Example 101

(3S)-2-((2R)-2-{[Formyl(hydroxy)amino]methyl}heptanoyl)-N-4-pyrimidinyl-3-pyrazolidinecarboxamide

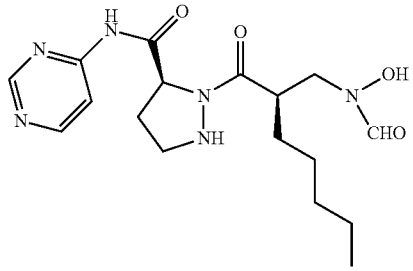 [SMILES: CCCCC[C@H](CN(O)C=O)C(=O)N1NCC[C@H]1C(=O)Nc1ccncn1]

4-pyrimidinamine. LCMS: (M+H)$^+$: 379.0. $^1$H NMR (400 MHz, METHANOL-d$_4$) δ ppm 0.82-1.00 (m, 3H) 1.31-1.43 (m, 5H) 1.43-1.69 (m, 3H) 2.10-2.38 (m, 1H) 2.43-2.68 (m, 1H) 2.83-3.06 (m, 1H) 3.41-3.57 (m, 1H) 3.68-3.90 (m, 2H) 4.69 (dd, J=8.46, 3.92 Hz, 2H) 7.87 (s, 1H) 8.18 (dd, J=5.81, 1.26 Hz, 1H) 8.60 (d, J=5.81 Hz, 1H) 8.83 (s, 1H).

Example 102

(3S)-2-((2R)-2-{[Formyl(hydroxy)amino]methyl}heptanoyl)-N-2-pyridinyl-3-pyrazolidinecarboxamide

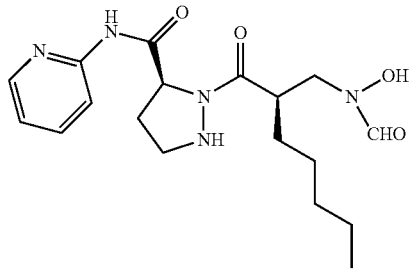 [SMILES: CCCCC[C@H](CN(O)C=O)C(=O)N1NCC[C@H]1C(=O)Nc1ccccn1]

2-pyridinamine. LCMS: (M+H)$^+$: 378.2.

Example 103

(3S)-2-((2R)-2-{[Formyl(hydroxy)amino]methyl}heptanoyl)-N-(1-oxido-2-pyridinyl)-3-pyrazolidinecarboxamide

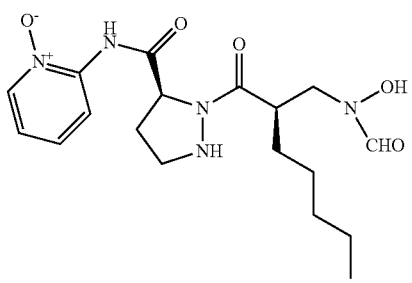 [SMILES: CCCCC[C@H](CN(O)C=O)C(=O)N1NCC[C@H]1C(=O)Nc1cccc[n+]1[O-]]

2-pyridinamine 1-oxide. LCMS: (M+H)$^+$: 394.0 $^1$H NMR (400 MHz, METHANOL-d$_4$) δ ppm 0.80-0.93 (m, 3H) 1.29-1.47 (m, 6H) 1.49-1.61 (m, 1H) 1.61-1.81 (m, 1H) 2.38 (m, J=9.85, 5.05, 5.05, 2.27 Hz, 1H) 2.53 (ddd, J=9.16, 6.13, 3.16 Hz, 1H) 2.92 (td, J=10.61, 6.57 Hz, 1H) 3.20-3.30 (m, 1H) 3.52 (dd, J=13.89, 4.29 Hz, 1H) 3.60-3.75 (m, 1H) 3.75-3.98 (m, 1H) 4.64 (br. s., 1H) 7.14-7.28 (m, 1H) 7.52-7.66 (m, 1H) 7.90 (s, 1H) 8.34 (d, J=6.57 Hz, 1H) 8.49 (dd, J=8.59, 1.52 Hz, 1H)

Example 104

(3S)—N-(5-Fluoro-1-oxido-2-pyridinyl)-2-((2R)-2-{[formyl(hydroxy)amino]methyl}heptanoyl)-3-pyrazolidinecarboxamide

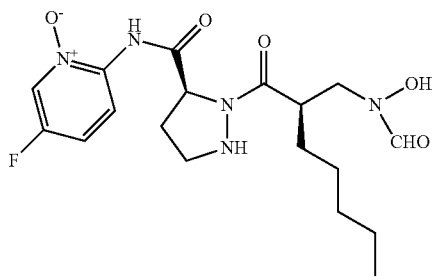 [SMILES: CCCCC[C@H](CN(O)C=O)C(=O)N1NCC[C@H]1C(=O)Nc1ccc(F)c[n+]1[O-]]

Part A

Phenylmethyl (3S)-3-{[(5-fluoro-1-oxido-2-pyridinyl)amino]carbonyl}-2-[(2R)-2-({formyl[(phenylmethyl)oxy]amino}methyl)heptanoyl]-1-pyrazolidine carboxylate To a solution of phenylmethyl (3S)-3-{[(5-fluoro-2-pyridinyl)amino]carbonyl}-2-[(2R)-2-({formyl[(phenylmethyl)oxy]amino}methyl)heptanoyl]-1-pyrazolidinecarboxylate (130 mg, 0.210 mmol) in dichloromethane (DCM) (4 mL) under nitrogen at 0° C. was added 3-chlorobenzenecarboperoxoic acid (141 mg, 0.629 mmol) in one portion. The reaction mixture was stirred at 0° C. for 10 min, then warmed up to room temperature and stirred overnight. The reaction was quenched by addition of sat. aq. NaHCO$_3$ and extracted with DCM twice. The combined organic extracts were dried over Na$_2$SO$_4$, filtered and concentrated to afford the crude product as a white semi-solid. The crude product was purified by RP-HPLC to provide phenylmethyl (3S)-3-{[(5-fluoro-1-oxido-2-pyridinyl)amino]carbonyl}-2-[(2R)-2-({formyl[(phenylmethyl)oxy]amino}methyl)heptanoyl]-1-pyrazolidinecarboxylate (103 mg, 77%). LCMS: (M+H)$^+$: 636.0.

Part B (3S)—N-(5-Fluoro-1-oxido-2-pyridinyl)-2-((2R)-2-{[formyl(hydroxy)amino]methyl}heptanoyl)-3-pyrazolidinecarboxamide To a 50 mL round-bottomed flask was added (3S)-3-{[(5-fluoro-1-oxido-2-pyridinyl)amino]carbonyl}-2-[(2R)-2-({formyl[(phenylmethyl)oxy]amino}methyl)heptanoyl]-1-pyrazolidinecarboxylate (103 mg, 0.162 mmol) in methanol (3 ml), followed by Pearlman's catalyst (10 mg). The mixture was stirred under a balloon of H$_2$ for 37 min, and the catalyst was filtered off. The filtrate was concentrated and the residue was purified by RP-HPLC to provide (3S)—N-(5-fluoro-1-oxido-2-pyridinyl)-2-((2R)-2-{[formyl(hydroxy)amino]methyl}heptanoyl)-3-pyrazolidinecarboxamide (49 mg, 73%). LCMS: (M+H)$^+$: 412.0. $^1$H NMR (400 MHz, METHANOL-d$_4$) δ ppm 0.76-0.98 (m, 3H) 1.26-1.46 (m, 6H) 1.48-1.57 (m, 1H) 1.63-1.77 (m, 1H) 2.30-2.44 (m, 1H) 2.46-2.59 (m, 1H) 2.91 (td, J=10.67, 6.44 Hz, 1H) 3.20-3.29 (m, 1H) 3.52 (dd, J=13.77, 4.42 Hz, 1H) 3.77-3.96 (m, 2H) 4.81-4.88 (m, 1H) 7.47 (ddd, J=9.66, 7.14, 2.65 Hz, 1H) 7.90 (s, 1H) 8.40-8.61 (m, 2H)

Example 105

(5S)-1-((2R)-3-Cyclopentyl-2-{[formyl(hydroxy)amino]methyl}propanoyl)-N-(1-oxido-2-pyridinyl)-4,5-dihydro-1H-pyrazole-5-carboxamide

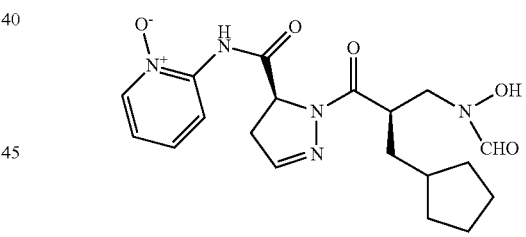

Part A (5S)-1-[(2R)-3-Cyclopentyl-2-({formyl [(phenylmethyl)oxy]amino}methyl)propanoyl]-N-(1-oxido-2-pyridinyl)-4,5-dihydro-1H-pyrazole-5-carboxamide To a solution of (5S)-1-[(2R)-3-cyclopentyl-2-({formyl [(phenylmethyl)oxy]amino}methyl)propanoyl]-4,5-dihydro-1H-pyrazole-5-carboxylic acid (88 mg, 0.219 mmol) in acetonitrile (4 mL) at 0° C. was added 4-methylmorpholine (0.053 mL, 0.482 mmol), followed by 4-[4,6-bis(methyloxy)-1,3,5-triazin-2-yl]-4-methylmorpholin-4-ium (DMTMM) (86 mg, 0.263 mmol). The solution was stirred for 15 min, and then 2-pyridinamine 1-oxide (31.4 mg, 0.285 mmol) was added. The reaction mixture was warmed up to room temperature and stirred overnight. The solvent was evaporated away, and residue was dissolved in DCM. The solution was washed with 5% aq. NaHSO₄ followed by water. The organic phase was dried over anhydrous Na₂SO₄, filtered, and concentrated in vacuo to afford a crude oil, which was purified by RP-HPLC to provide (5S)-1-[(2R)-3-cyclopentyl-2-({formyl[(phenylmethyl)oxy]amino}methyl)propanoyl]-N-(1-oxido-2-pyridinyl)-4,5-dihydro-1H-pyrazole-5-carboxamide as a colorless gum (67 mg, 62%). LCMS: (M+H)⁺: 494.0.

Part B (5S)-1-((2R)-3-Cyclopentyl-2-{[formyl(hydroxy)amino]methyl}propanoyl)-N-(1-oxido-2-pyridinyl)-4,5-dihydro-1H-pyrazole-5-carboxamide In a 50 mL round-bottomed flask was added (5S)-1-[(2R)-3-cyclopentyl-2-({formyl[(phenylmethyl)oxy]amino}methyl)propanoyl]-N-(1-oxido-2-pyridinyl)-4,5-dihydro-1H-pyrazole-5-carboxamide (67 mg, 0.136 mmol) in methanol (3 ml), followed by Pearlman's catalyst (7 mg). The mixture was stirred under a balloon of H₂ for 35 min, then catalyst was filtered off. Removal of the solvent provided (5S)-1-((2R)-3-cyclopentyl-2-{[formyl(hydroxy)amino]methyl}propanoyl)-N-(1-oxido-2-pyridinyl)-4,5-dihydro-1H-pyrazole-5-carboxamide as a colorless oil. (27 mg, 48%). LCMS: (M+H)⁺: 404.3. ¹H NMR (400 MHz, METHANOL-d₄) δ ppm 1.04-1.26 (m, 2H) 1.40-1.70 (m, 5H) 1.70-2.00 (m, 4H) 3.35-3.45 (m, 1H) 3.50-3.75 (m, 2H) 3.76-4.04 (m, 2H) 5.10-5.37 (m, 1H) 7.09-7.34 (m, 2H) 7.49-7.67 (m, 1H) 7.91 (s, 1H) 8.35 (d, J=6.57 Hz, 1H) 8.46 (dd, J=8.46, 1.64 Hz, 1H)

Example 106

(3S)-2-((2R)-3-Cyclopentyl-2-{[formyl(hydroxy)amino]methyl}propanoyl)-N-1H-imidazol-2-yl-3-pyrazolidinecarboxamide

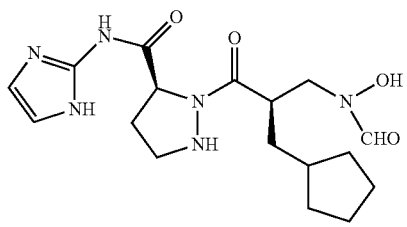 [SMILES: O=CN(O)C[C@@H](CC1CCCC1)C(=O)N1NCC[C@H]1C(=O)Nc1ncc[nH]1]

Part A

Phenylmethyl (3S)-2-[(2R)-3-cyclopentyl-2-({formyl[(phenylmethyl)oxy]amino}methyl)propanoyl]-3-[(1H-imidazol-2-ylamino)carbonyl]-1-pyrazolidine carboxylate To a solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (121 mg, 0.225 mmol) in acetonitrile (4 mL) at 0° C. was added 4-methylmorpholine (0.087 mL, 0.788 mmol), followed by 4-[4,6-bis(methyloxy)-1,3,5-triazin-2-yl]-4-methylmorpholin-4-ium (DMTMM) (89 mg, 0.270 mmol). The solution was stirred for 15 min, and then 1H-imidazol-2-amine sulfate (38.7 mg, 0.293 mmol) was added. The reaction mixture was warmed up to room temperature and stirred overnight. The solvent was evaporated and the residue was purified by RP-HPLC to provide phenylmethyl (3S)-2-[(2R)-3-cyclopentyl-2-({formyl[(phenylmethyl)oxy]amino}methyl)propanoyl]-3-[(1H-imidazol-2-ylamino)carbonyl]-1-pyrazolidinecarboxylate as a colorless gum (39 mg, 29%)

LCMS: (M+H)⁺: 603.3.

Part B (3S)-2-((2R)-3-Cyclopentyl-2-{[formyl(hydroxy)amino]methyl}propanoyl)-N-1H-imidazol-2-yl-3-pyrazolidinecarboxamide To a 50 mL round-bottomed flask was added phenylmethyl (3S)-2-[(2R)-3-cyclopentyl-2-({formyl[(phenylmethyl)oxy]amino}methyl)propanoyl]-3-[(1H-imidazol-2-ylamino)carbonyl]-1-pyrazolidinecarboxylate (39 mg, 0.065 mmol) in methanol (3 ml), followed by Pearlman's catalyst (9 mg). The mixture was stirred under a balloon of H₂ for 40 min, the catalyst was filtered off. Removal of the solvent provided (3S)-2-((2R)-3-cyclopentyl-2-{[formyl(hydroxy)amino]methyl}propanoyl)-N-1H-imidazol-2-yl-3-pyrazolidinecarboxamide as a off-white solid (23 mg, 92%). LCMS: (M+H)⁺: 379.4.

The following Example 107 was prepared according to a method similar to that disclosed in Example 106 except that to the reaction mixture in Part A was added the indicated compound instead of 1H-imidazol-2-amine sulfate.

Example 107

(3S)—N-1H-Benzimidazol-2-yl-2-((2R)-3-cyclopentyl-2-{[formyl(hydroxy)amino]methyl}propanoyl)-3-pyrazolidinecarboxamide

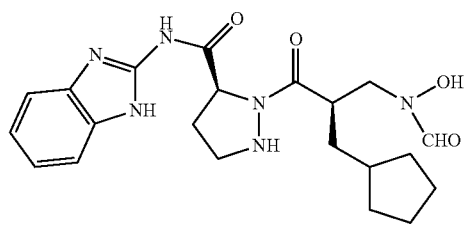 [SMILES: O=CN(O)C[C@@H](CC1CCCC1)C(=O)N1NCC[C@H]1C(=O)Nc1nc2ccccc2[nH]1]

1H-benzimidazol-2-amine. LCMS: (M+H)⁺: 429.0.

Example 108

(5S)—N-(5-Fluoro-2-pyridinyl)-1-((2R)-2-{[formyl(hydroxy)amino]methyl}heptanoyl)-4,5-dihydro-1H-pyrazole-5-carboxamide

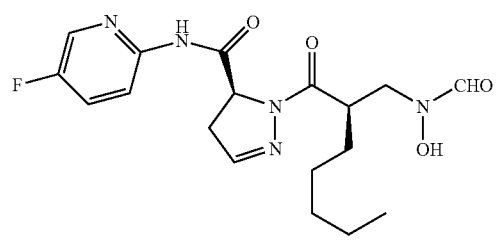 [SMILES: CCCCC[C@H](CN(O)C=O)C(=O)N1N=CC[C@H]1C(=O)Nc1ccc(F)cn1]

Part A (5S)—N-(5-Fluoro-2-pyridinyl)-1-[(2R)-2-({formyl[(phenylmethyl)oxy]amino}methyl)heptanoyl]-4,5-dihydro-1H-pyrazole-5-carboxamide To a solution of (5S)-1-[(2R)-2-({formyl[(phenylmethyl)oxy]amino}methyl)heptanoyl]-4,5-dihydro-1H-pyrazole-5-carboxylic acid (100 mg, 0.26 mmol) and 5-fluoro-2-pyridinamine (37 mg, 0.33 mmol) in acetonitrile (10 mL) was added 4-methylmorpholine (39 mg, 0.39 mmol) and 2-chloro-4,6-bis(methyloxy)-1,3,5-triazine (49.5 mg, 0.28 mmol). The mixture was stirred at rt overnight. LCMS showed that the reaction was complete. The solvent was removed under vacuum and ethyl acetate was added. The mixture was washed with 10% $KHSO_4$, sat. $NaHCO_3$, brine, dried and concentrated. The residue was purified by flash column chromatography eluting with petroleum ether/ethyl acetate (3:1 to 1:1) to provide the titled compound (108 mg, 85%) as a yellow oil.

Part B (5S)—N-(5-Fluoro-2-pyridinyl)-1-((2R)-2-{[formyl(hydroxy)amino]methyl}heptanoyl)-4,5-dihydro-1H-pyrazole-5-carboxamide To a solution of (5S)—N-(5-fluoro-2-pyridinyl)-1-[(2R)-2-({formyl[(phenylmethyl)oxy]amino}methyl)heptanoyl]-4,5-dihydro-1H-pyrazole-5-carboxamide (180 mg, 0.37 mmol) in methanol (15 mL) was added $Pd(OH)_2$/C (105 mg, 20%, 44% wt). The mixture was stirred under a $H_2$ atmosphere for 30 min and the catalyst was filtered off. The filtrate was concentrated and the residue was purified by HPLC to provide the titled compound (70 mg, 48%) as a white solid. LCMS: $(M+H)^+$: 394.2.

The following Examples 109 to 110 were prepared according to a method similar to that disclosed in Example 108 except that to the solution in Part A was added the indicated compound instead of 5-fluoro-2-pyridinamine.

Example 109

(5S)-1-((2R)-2-{[Formyl(hydroxy)amino]methyl}heptanoyl)-N-2-pyridinyl-4,5-dihydro-1H-pyrazole-5-carboxamide

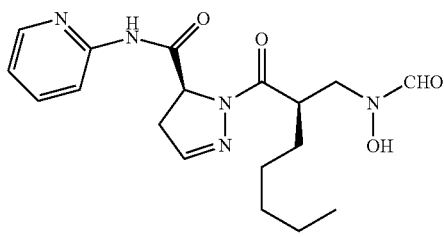 [SMILES: CCCCC[C@H](CN(O)C=O)C(=O)N1N=CC[C@H]1C(=O)Nc1ccccn1]

2-pyridinamine. LCMS: $(M+H)^+$: 376.2. 1H NMR (300 MHz, METHANOL) δ ppm 0.83-0.95 (m, 3H), 1.15-1.87 (m, 8H), 3.14-3.99 (m, 5H), 5.00-5.05 (m, 1H), 7.13-7.17 (m, 2H), 7.74-7.88 (m, 1H), 7.94 (s, 0.6H), 8.12 (d, J=8.2 Hz, 1H), 8.26 (s, 0.4H), 8.30-8.36 (m, 1H).

Example 110

(5S)-1-((2R)-2-{[Formyl(hydroxy)amino]methyl}heptanoyl)-N-4-pyrimidinyl-4,5-dihydro-1H-pyrazole-5-carboxamide

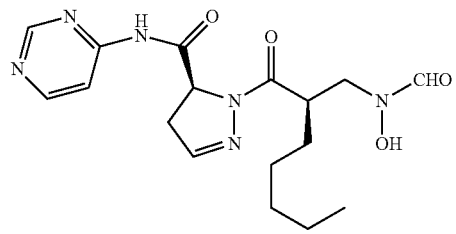 [SMILES: CCCCC[C@H](CN(O)C=O)C(=O)N1N=CC[C@H]1C(=O)Nc1ccncn1]

4-pyrimidinamine. LCMS: $(M+H)^+$: 377.2.

Example 111

(3S)-2-((2R)-2-{[Formyl(hydroxy)amino]methyl}heptanoyl)-N-3-pyridazinyl-3-pyrazolidinecarboxamide

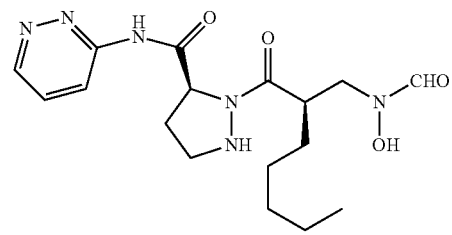 [SMILES: CCCCC[C@H](CN(O)C=O)C(=O)N1NCC[C@H]1C(=O)Nc1cccnn1]

Part A

Phenylmethyl (3S)-2-[(2R)-2-({formyl[(phenylmethyl)oxy]amino}methyl)heptanoyl]-3-[(3-pyridazinylamino)carbonyl]-1-pyrazolidinecarboxylate To a solution of (3S)-2-[(2R)-2-({formyl[(phenylmethyl)oxy]amino}methyl)heptanoyl]-1-{[(phenylmethyl)oxy]carbonyl}-3-pyrazolidinecarboxylic acid (590 mg, 0.95 mmol), 3-pyridazinamine (100 mg, 1.05 mmol) and 2-chloro-4,6-bis(methyloxy)-1,3,5-triazine (183 mg, 1.05 mmol) in acetonitrile (30 mL) under $N_2$ was added 4-methylmorpholine (212 mg, 2.1 mmol) dropwise. The mixture was stirred at rt overnight. TLC showed that the reaction was complete. The mixture was diluted with ethyl acetate and washed with 5% citric acid, followed by brine. The organic phase was dried over $Na_2SO_4$, filtered and concentrated. The residue was purified by flash column chromatography eluting with petroleum ether/ethyl acetate (2:1) to provide the titled compound (460 mg, 79%)

Part B (3S)-2-((2R)-2-{[Formyl(hydroxy)amino]methyl}heptanoyl)-N-3-pyridazinyl-3-pyrazolidinecarboxamide To a solution of phenylmethyl (3S)-2-[(2R)-2-({formyl[(phenylmethyl)oxy]amino}methyl)heptanoyl]-3-[(3-pyridazinylamino) carbonyl]-1-pyrazolidinecarboxylate (460 mg, 0.764 mmol) in methanol (15 mL) was added Pd(OH)$_2$/C (300 mg). The mixture was stirred under an H2 atmosphere for 2 h and the catalyst was filtered off. The filtrate was concentrated and the residue was purified by pre-HPLC to provide the titled compound (100 mg, 30%) as a yellowish solid. LCMS: (M+H)$^+$: 379.2.

$^1$H NMR (300 MHz, DMSO-d6) δ ppm 0.73-0.85 (m, 3H), 1.10-1.48 (m, 8H), 2.00-2.09 (m, 1H), 2.38-2.46 (m, 1H), 2.70-2.80 (m, 1H), 3.10-3.18 (m, 1H), 3.41-3.87 (m, 3H), 4.63 (t, J=8.1 Hz, 1H), 5.28-5.65 (m, 1H), 7.68 (dd, J=9.0, 4.7 Hz, 1H), 7.82 (s, 0.6H), 8.17-8.29 (m, 1.4H), 8.97 (dd, J=4.7, 1.4 Hz, 1H), 11.12 (d, J=8.4 Hz, 1H).

Example 112

(3S)-2-((2R)-3-Cyclopentyl-2-{[formyl(hydroxy)amino]methyl}propanoyl)-N-[2-(4-morpholinyl)-5-pyrimidinyl]-3-pyrazolidinecarboxamide

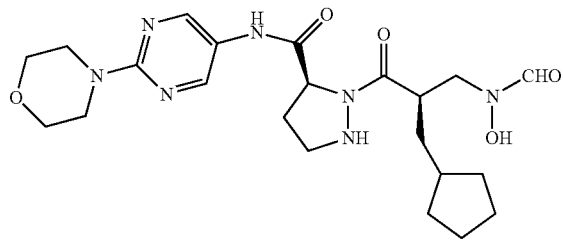 [SMILES: O=CN(O)C[C@@H](CC1CCCC1)C(=O)N1NCC[C@H]1C(=O)Nc1cnc(N2CCOCC2)nc1]

(3S)-2-((2R)-3-Cyclopentyl-2-{[formyl(hydroxy)amino]methyl}propanoyl)-N-[2-(4-morpholinyl)-5-pyrimidinyl]-3-pyrazolidinecarboxamide was prepared according to Example 111, utilizing (3S)-2-[(2R)-3-cyclopentyl-2-({formyl[(phenylmethyl)oxy]amino}methyl)propanoyl]-1-{[(phenylmethyl)oxy]carbonyl}-3-pyrazolidine carboxylic acid in place of (3S)-2-[(2R)-2-({formyl[(phenylmethyl)oxy]amino}methyl)heptanoyl]-1-{[(phenylmethyl)oxy]carbonyl}-3-pyrazolidinecarboxylic acid, and 2-(4-morpholinyl)-5-pyrimidinamine in place of 3-pyridazinamine in part A. LCMS: (M+H)$^+$: 476.0.

Example 113

(3S)-2-((2R)-2-{[Formyl(hydroxy)amino]methyl}hexanoyl)-N-(1-oxido-2-pyridinyl)-3-pyrazolidinecarboxamide

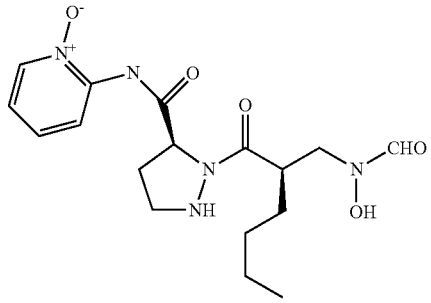 [SMILES: CCCC[C@H](CN(O)C=O)C(=O)N1NCC[C@H]1C(=O)Nc1cccc[n+]1[O-]]

Part A

Phenylmethyl (3S)-2-[(2R)-2-({formyl[(phenylmethyl)oxy]amino}methyl)hexanoyl]-3-[(2-pyridinylamino)carbonyl]-1-pyrazolidinecarboxylate To a solution of (3S)-2-[(2R)-2-({formyl[(phenylmethyl)oxy]amino}methyl)hexanoyl]-1-{[(phenylmethyl)oxy]carbonyl}-3-pyrazolidinecarboxylic acid (Intermediate 4) (150 mg, 0.3 mmol), 2-pyridinamine (32 mg, 0.33 mmol) and 2-chloro-4,6-bis(methyloxy)-1,3,5-triazine (58 mg, 0.33 mmol) in acetonitrile (4 mL) under N$_2$ was added 4-methylmorpholine (65 mg, 0.66 mmol) dropwise. The mixture was stirred at rt overnight. TLC showed that the reaction was complete. The mixture was diluted with ethyl acetate and washed with 5% citric acid, followed by brine. The organic phase was dried over Na$_2$SO$_4$, filtered and concentrated. The residue was purified by flash column chromatography to provide the titled compound (110 mg, 70%).

Part B

Phenylmethyl (3S)-2-[(2R)-2-({formyl[(phenylmethyl)oxy]amino}methyl)hexanoyl]-3-{[(1-oxido-2-pyridinyl)amino]carbonyl}-1-pyrazolidinecarboxylate To a solution of phenylmethyl (3S)-2-[(2R)-2-({formyl[(phenylmethyl)oxy]amino}methyl)hexanoyl]-3-[(2-pyridinylamino)carbonyl]-1-pyrazolidinecarboxylate (70 mg, 0.12 mmol) in EtOAc (6 mL) was added per carbamide (45 mg, 0.48 mmol) and 2-benzofuran-1,3-dione (71 mg, 0.48 mmol). The mixture was stirred overnight until TLC showed the completion of the reaction. The mixture was washed with aq. Na$_2$CO$_3$ and brine, dried over Na$_2$SO$_4$, filtered and concentrated. The residue was purified by flash column chromatography to provide the titled compound (86 mg, 85%)

Part C (3S)-2-((2R)-2-{[Formyl(hydroxy)amino]methyl}hexanoyl)-N-(1-oxido-2-pyridinyl)-3-pyrazolidinecarboxamide To a solution of phenylmethyl (3S)-2-[(2R)-2-({formyl[(phenylmethyl)oxy]amino}methyl)hexanoyl]-3-{[(1-oxido-2-pyridinyl)amino]carbonyl}-1-pyrazolidinecarboxylate (85 mg, 0.14 mmol) in EtOH (15 mL) was added Pd (OH)$_2$/C (30 mg). The mixture was degassed and placed under H$_2$ atmosphere for 1 h at rt. The catalyst was filtered off and the filtrate was concentrated. The residue was purified by pre-HPLC to provide the titled compound (22 mg, 40%). LCMS: (M+H)$^+$: 380.2.

Example 114

(3S)—N-(5-Fluoro-1-oxido-2-pyridinyl)-2-((2R)-2-{[formyl(hydroxy)amino]methyl}hexanoyl)-3-pyrazolidinecarboxamide

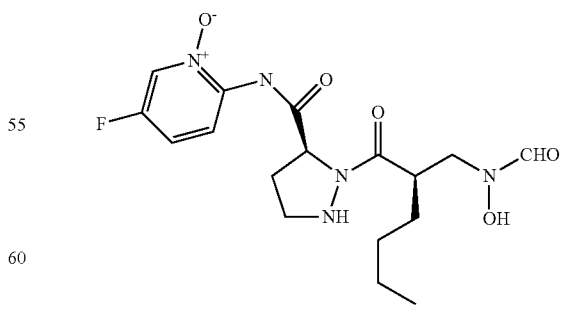

(3S)—N-(5-Fluoro-1-oxido-2-pyridinyl)-2-((2R)-2-{[formyl(hydroxy)amino]methyl}hexanoyl)-3-pyrazolidinecarboxamide was prepared according to Example 113, utilizing 5-fluoro-2-pyridinamine in place of 2-pyridinamine in part A. LCMS: (M+H)$^+$: 398.0.

Example 115

(3S)-2-((2R)-2-{[Formyl(hydroxy)amino]methyl}hexanoyl)-N-4-pyrimidinyl-3-pyrazolidinecarboxamide

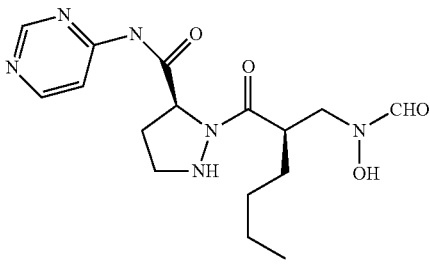 [SMILES: CCCC[C@H](CN(O)C=O)C(=O)N1NCC[C@H]1C(=O)Nc1ccncn1]

Part A

Phenyl methyl (3S)-2-[(2R)-2-({formyl[(phenylmethyl)oxy]amino}methyl)hexanoyl]-3-[(4-pyrimidinylamino)carbonyl]-1-pyrazolidinecarboxylate To a solution of (3S)-2-[(2R)-2-({formyl[(phenylmethyl)oxy]amino}methyl)hexanoyl]-1-{[(phenylmethyl)oxy]carbonyl}-3-pyrazolidinecarboxylic acid (80 mg, 0.156 mmol) in acetonitrile (3 mL) under $N_2$ was added 4-[4,6-bis(methyloxy)-1,3,5-triazin-2-yl]-4-methylmorpholin-4-ium tetrafluoroborate (103 mg, 0.313 mmol) and 4-methylmorpholine (47 mg, 0.468 mmol), followed by 4-pyrimidinamine (18 mg, 0.187 mmol). The mixture was stirred at 0° C. for 2 h and then warmed up to 35° C. overnight. The mixture was concentrated. The residue was purified by flash column chromatography eluting with petroleum ether/ethyl acetate (10:1 to 2:1) to provide the title compound (80 mg, 80%)

Part B (3S)-2-((2R)-2-{[Formyl(hydroxy)amino]methyl}hexanoyl)-N-4-pyrimidinyl-3-pyrazolidinecarboxamide To a solution of phenylmethyl (3S)-2-[(2R)-2-({formyl[(phenylmethyl)oxy]amino}methyl)hexanoyl]-3-[(4-pyrimidinylamino)carbonyl]-1-pyrazolidinecarboxylate (80 mg, 0.136 mmol) in ethanol (30 mL) was added $Pd(OH)_2/C$ (40 mg). The mixture was stirred under an H2 atmosphere for 1 h and the catalyst was filtered off. The filtrate was concentrated and the residue was purified by pre-HPLC to provide the title compound (40 mg, 70%). LCMS: $(M+H)^+$: 365.2.

Example 116

4-({[(3S)-2-((2R)-3-Cyclopentyl-2-{[formyl(hydroxy)amino]methyl}propanoyl)-3-pyrazolidinyl]carbonyl}amino)benzoic acid

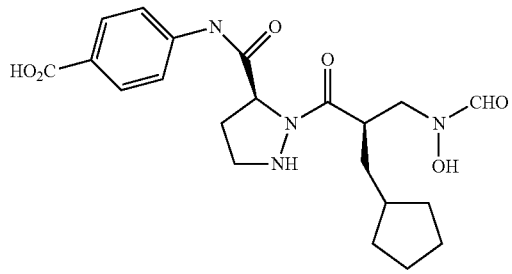 [SMILES: O=CN(O)C[C@@H](CC1CCCC1)C(=O)N1NCC[C@H]1C(=O)Nc1ccc(C(=O)O)cc1]

Part A

Phenylmethyl (3S)-2-[(2R)-3-cyclopentyl-2-({formyl[(phenylmethyl)oxy]amino}methyl)propanoyl]-3-{[(4-{[(phenylmethyl)oxy]carbonyl}phenyl)amino]carbonyl}-1-pyrazolidinecarboxylate To a solution of (3S)-2-[(2R)-3-cyclopentyl-2-({formyl[(phenylmethyl)oxy]amino}methyl)propanoyl]-1-{[(phenylmethyl)oxy]carbonyl}-3-pyrazolidinecarboxylic acid (300 mg, 0.558 mmol) in acetonitrile (10 mL) under $N_2$ at 0° C. was added 4-methylmorpholine (123 mg, 2.2 mmol), followed by 4-[4,6-bis(methyloxy)-1,3,5-triazin-2-yl]-4-methylmorpholin-4-ium tetrafluoroborate (366 mg, 1.116 mmol). The mixture was stirred for 1 h and to this mixture was added phenylmethyl 4-aminobenzoate (191 mg, 0.837 mmol). The mixture was stirred at rt overnight. The mixture was concentrated, and the residue was purified by flash column chromatography eluting with petroleum ether/ethyl acetate (5:1 to 3:1) to provide the title compound (330 mg).

Part B 4-({[(3S)-2-((2R)-3-Cyclopentyl-2-{[formyl(hydroxy)amino]methyl}propanoyl)-3-pyrazolidinyl]carbonyl}amino)benzoic acid To a solution of phenylmethyl (3S)-2-[(2R)-3-cyclopentyl-2-({formyl[(phenylmethyl)oxy]amino}methyl)propanoyl]-3-{[(4-{[(phenylmethyl)oxy]carbonyl}phenyl)amino]carbonyl}-1-pyrazolidinecarboxylate (330 mg, 0.442 mmol) in methanol (20 mL) was added $Pd(OH)_2/C$ (330 mg). The mixture was stirred at rt under H2 atmosphere for 2 h. The catalyst was filtered off, the filtrate was concentrated under vacuum, and the residue was purified by preparative HPLC to provide the title compound (100 mg). LCMS: $(M+H)^+$: 482.2.

The following Examples 117 to 124 were prepared according to a method similar to that disclosed in Example 116 except that to the mixture in Part A was added the indicated compound instead of phenylmethyl 4-aminobenzoate.

Example 117

(3S)-2-((2R)-3-Cyclopentyl-2-{[formyl(hydroxy)amino]methyl}propanoyl)-N-(5-hydroxy-2-pyridinyl)-3-pyrazolidinecarboxamide

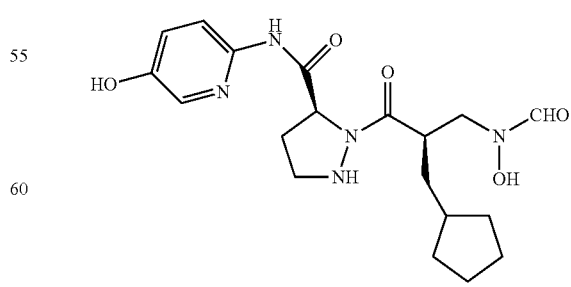

{4-[(phenylmethyl)oxy]phenyl}amine. LCMS: $(M+H)^+$: 406.2.

Example 118

6-({[(3S)-2-((2R)-3-Cyclopentyl-2-{[formyl(hydroxy)amino]methyl}propanoyl)-3-pyrazolidinyl]carbonyl}amino)-3-pyridinecarboxylic acid

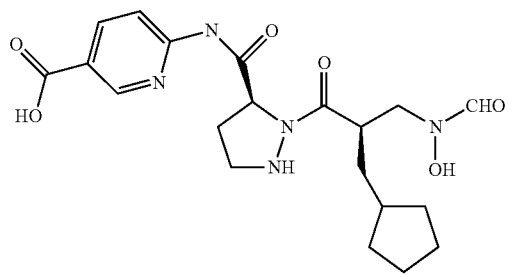 [SMILES: O=CN(O)C[C@@H](CC1CCCC1)C(=O)N1NCC[C@H]1C(=O)Nc1ccc(C(=O)O)cn1]

phenylmethyl 6-amino-3-pyridinecarboxylate. LCMS: (M+H)⁺: 434.2.

Example 119

2-({[(3S)-2-((2R)-3-Cyclopentyl-2-{[formyl(hydroxy)amino]methyl}propanoyl)-3-pyrazolidinyl]carbonyl}amino)-4-pyridinecarboxylic acid

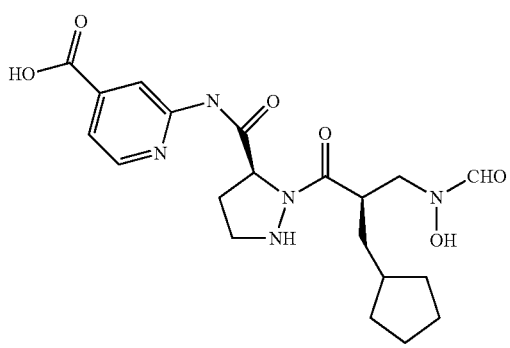 [SMILES: O=CN(O)C[C@@H](CC1CCCC1)C(=O)N1NCC[C@H]1C(=O)Nc1cccc(C(=O)O)c1]

phenylmethyl 2-amino-4-pyridinecarboxylate. LCMS: (M+H)⁺: 434.2.

Example 120

3-({[(3S)-2-((2R)-3-Cyclopentyl-2-{[formyl(hydroxy)amino]methyl}propanoyl)-3-pyrazolidinyl]carbonyl}amino)benzoic acid

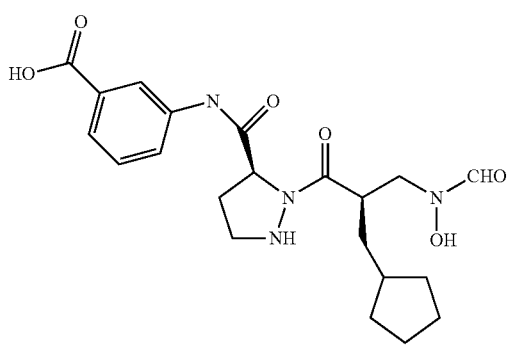

phenylmethyl 3-aminobenzoate. LCMS: (M+H)⁺: 433.1.

Example 121

(3S)-2-((2R)-3-Cyclopentyl-2-{[formyl(hydroxy)amino]methyl}propanoyl)-N-(4-hydroxy-2-pyridinyl)-3-pyrazolidinecarboxamide

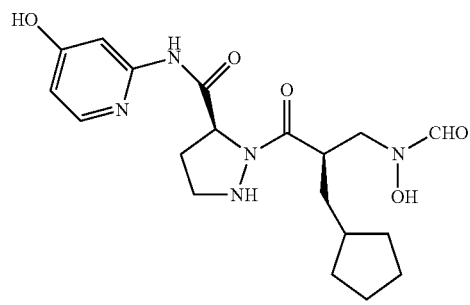 [SMILES: O=CN(O)C[C@@H](CC1CCCC1)C(=O)N1NCC[C@H]1C(=O)Nc1cc(O)ccn1]

4-[(phenylmethyl)oxy]-2-pyridinamine. LCMS: (M+H)⁺: 406.2.

Example 122

(3S)-2-((2R)-3-Cyclopentyl-2-{[formyl(hydroxy)amino]methyl}propanoyl)-N-(3-hydroxyphenyl)-3-pyrazolidinecarboxamide

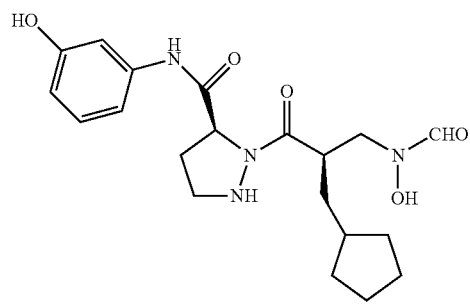 [SMILES: O=CN(O)C[C@@H](CC1CCCC1)C(=O)N1NCC[C@H]1C(=O)Nc1cccc(O)c1]

3-aminophenol. LCMS: (M+H)⁺: 405.1.

Example 123

(3S)-2-((2R)-3-Cyclopentyl-2-{[formyl(hydroxy)amino]methyl}propanoyl)-N-(4-hydroxyphenyl)-3-pyrazolidinecarboxamide

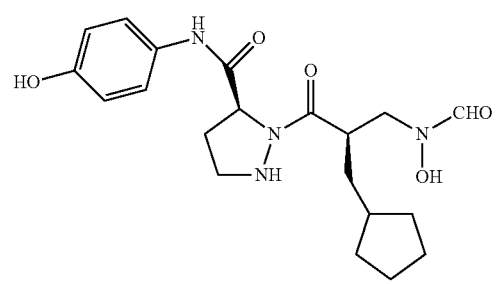 [SMILES: O=CN(O)C[C@@H](CC1CCCC1)C(=O)N1NCC[C@H]1C(=O)Nc1ccc(O)cc1]

4-aminophenol. LCMS: (M+H)⁺: 405.1.

Example 124

(3S)-2-((2R)-3-Cyclopentyl-2-{[formyl(hydroxy)amino]methyl}propanoyl)-N-[2-(2-pyridinyl)-5-pyrimidinyl]-3-pyrazolidinecarboxamide

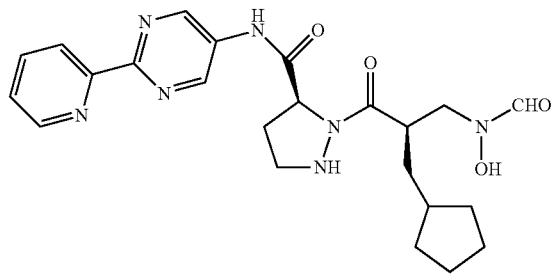 [SMILES: O=CN(O)C[C@@H](CC1CCCC1)C(=O)N1NCC[C@H]1C(=O)Nc1cnc(-c2ccccn2)nc1]

2-(2-pyridinyl)-5-pyrimidinamine. LCMS: (M+H)+: 468.0.

Example 125

(3S)—N-(5-Fluoro-2-pyridinyl)-2-((2R)-2-{[formyl(hydroxy)amino]methyl}hexanoyl)-3-pyrazolidinecarboxamide

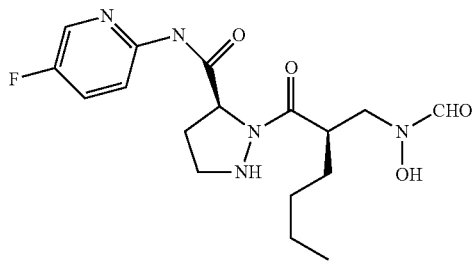 [SMILES: CCCC[C@H](CN(O)C=O)C(=O)N1NCC[C@H]1C(=O)Nc1ccc(F)cn1]

Part A

Phenylmethyl (3S)-3-{[(5-fluoro-2-pyridinyl)amino]carbonyl}-2-[(2R)-2-({formyl[(phenylmethyl)oxy]amino}methyl)hexanoyl]-1-pyrazolidinecarboxylate To a solution of (3S)-2-[(2R)-2-({formyl[(phenylmethyl)oxy]amino}methyl)hexanoyl]-1-{[(phenylmethyl)oxy]carbonyl}-3-pyrazolidinecarboxylic acid (1 g, 1.95 mmol) in THF (15 mL) under N$_2$ was added 2,4,6-trichlorobenzoyl chloride (0.572 g, 2.34 mmol) and DIPEA (1.68 mL, 9.75 mmol). The mixture was stirred at rt for 2 h. THF was removed under vacuum and toluene (15 mL) was added. To this mixture was added 5-fluoro-2-pyridinamine (0.262 g, 2.34 mmol) and DMAP (47.5 mg, 0.39 mmol). After being stirred at rt overnight, the mixture was diluted with EtOAc (50 mL) and washed with citric acid and brine. The organic solution was dried and concentrated. The residue was purified by flash column chromatography eluting with EA/PE (1:5) to provide the title compound (0.23 g, 19%) as colorless oil.

Part B (3S)—N-(5-fluoro-2-pyridinyl)-2-((2R)-2-{[formyl(hydroxy)amino]methyl}hexanoyl)-3-pyrazolidinecarboxamide To a solution of phenylmethyl (3S)-3-{[(5-fluoro-2-pyridinyl)amino]carbonyl}-2-[(2R)-2-({formyl[(phenylmethyl)oxy]amino}methyl)hexanoyl]-1-pyrazolidinecarboxylate (230 mg, 0.38 mmol) in methanol (30 mL) was added Pd(OH)$_2$/C (230 mg). The mixture was degassed and then stirred under an H2 atmosphere for 3 h at rt. The catalyst was filtered off. The filtrate was concentrated and the residue was purified by pre-HPLC to provide the title compound (67 mg, 48%). LCMS: (M+H)+: 382.2.

The following Examples 126 to 127 were prepared according to a method similar to that disclosed in Example 125 except that to the mixture in Part A was added the indicated compound instead of 5-fluoro-2-pyridinamine.

Example 126

(3S)-2-((2R)-2-{[Formyl(hydroxy)amino]methyl}hexanoyl)-N-3-pyridazinyl-3-pyrazolidinecarboxamide

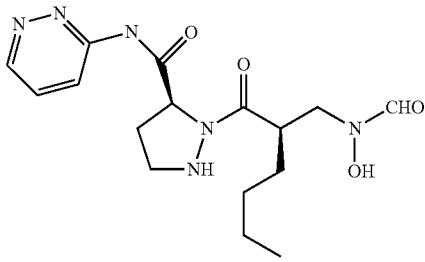 [SMILES: CCCC[C@H](CN(O)C=O)C(=O)N1NCC[C@H]1C(=O)Nc1cccnn1]

3-pyridazinamine. LCMS: (M+H)+: 365.2.

Example 127

(3S)-2-((2R)-2-{[Formyl(hydroxy)amino]methyl}hexanoyl)-N-2-pyridinyl-3-pyrazolidinecarboxamide

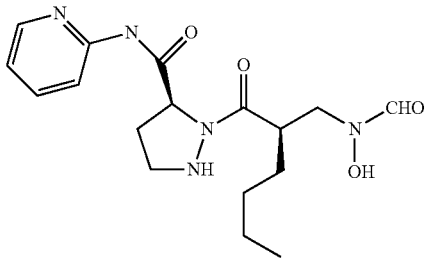 [SMILES: CCCC[C@H](CN(O)C=O)C(=O)N1NCC[C@H]1C(=O)Nc1ccccn1]

2-pyridinamine. LCMS: (M+H)+: 364.2.

Example 128

(3S)-2-((2R)-3-Cyclopentyl-2-{[formyl(hydroxy)amino]methyl}propanoyl)-N-[4-(2-pyridinyl)-2-pyrimidinyl]-3-pyrazolidinecarboxamide

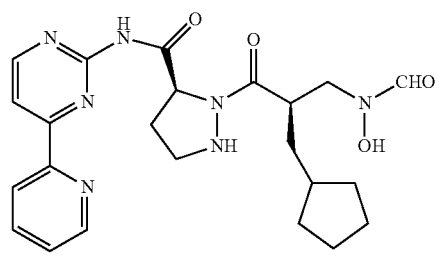 [SMILES: O=CN(O)C[C@@H](CC1CCCC1)C(=O)N1NCC[C@H]1C(=O)Nc1nccc(-c2ccccn2)n1]

Part A

Phenylmethyl (3S)-2-((2R)-3-cyclopentyl-2-{[formyl(tetrahydro-2H-pyran-2-yloxy)amino]methyl}propanoyl)-3-({[4-(2-pyridinyl)-2-pyrimidinyl]amino}carbonyl)-1-pyrazolidinecarboxylate To a solution of (3S)-2-((2R)-3-cyclopentyl-2-{[formyl(tetrahydro-2H-pyran-2-yloxy)amino]methyl}propanoyl)-1-

{[(phenylmethyl)oxy]carbonyl}-3-pyrazolidinecarboxylic acid (800 mg, 1.5 mmol) in THF (10 mL) under $N_2$ was added 2,4,6-trichlorobenzoyl chloride (477 mg, 2 mmol) and DIPEA (1.3 mL, 7.5 mmol). The mixture was stirred at rt for 2 h. THF was removed under vacuum and toluene (10 mL) was added. To this mixture was added 4-(2-pyridinyl)-2-pyrimidinamine (337 mg, 2 mmol) and DMAP (37 mg, 0.3 mmol). After being stirred at rt overnight, the mixture was diluted with EtOAc (50 mL) and washed with 5% citric acid and sat. $NaHCO_3$. The organic solution was dried ($Na_2SO_4$) and concentrated. The residue was purified by flash column chromatography to provide the title compound (400 mg, 39%).

Part B

Phenylmethyl (3S)-2-((2R)-3-cyclopentyl-2-{[formyl(hydroxy)amino]methyl}propanoyl)-3-({[4-(2-pyridinyl)-2-pyrimidinyl]amino}carbonyl)-1-pyrazolidinecarboxylate A solution of phenylmethyl (3S)-2-((2R)-3-cyclopentyl-2-{[formyl(tetrahydro-2H-pyran-2-yloxy)amino] methyl}propanoyl)-3-({[4-(2-pyridinyl)-2-pyrimidinyl] amino}carbonyl)-1-pyrazolidinecarboxylate in AcOH/water (5 mL, 4:1) was stirred at rt for 48 h. The solvents were removed under vacuum and the residue was purified by RP-HPLC to provide the title compound (32 mg, 9.1%) as light-yellow gum.

Part C (3S)-2-((2R)-3-Cyclopentyl-2-{[formyl(hydroxy) amino]methyl}propanoyl)-N-[4-(2-pyridinyl)-2-pyrimidinyl]-3-pyrazolidinecarboxamide To a solution of phenylmethyl (3S)-2-((2R)-3-cyclopentyl-2-{[formyl(hydroxy)amino]methyl}propanoyl)-3-({[4-(2-pyridinyl)-2-pyrimidinyl]amino}carbonyl)-1-pyrazolidinecarboxylate (32 mg, 0.053 mmol) in methanol (3 mL) was added $Pd(OH)_2$/C (7 mg). The mixture was degassed and then stirred under an H2 atmosphere for 2 h at rt. The catalyst was filtered off. The filtrate was concentrated and the residue was purified by pre-HPLC to provide the title compound (14 mg, 56%). LCMS: $(M+H)^+$: 468.2.

Example 129

(5S)-1-[(2R)-2-(Cyclopentyl methyl)-4-(hydroxyamino)-4-oxobutanoyl]-N-2-pyrimidinyl-4,5-dihydro-1H-pyrazole-5-carboxamide

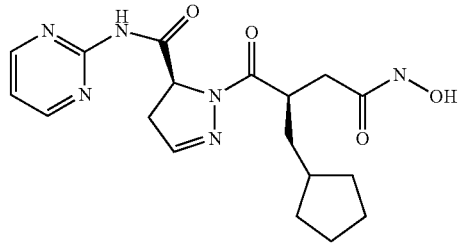

Part A 1,1-Dimethylethyl (3R)-3-(cyclopentyl methyl)-4-oxo-4-{5-[(2-pyrimidinylamino)carbonyl]-4,5-dihydro-1H-pyrazol-1-yl}butanoate 1-Methyl-1H-imidazole (0.24 mL, 3.0 mmol) was added into a solution of 1-{(2R)-2-(cyclopentylmethyl)-4-[(1,1-dimethylethyl)oxy]-4-oxobutanoyl}-4,5-dihydro-1H-pyrazole-5-carboxylic acid (352 mg, 1.0 mmol) in dichloromethane (DCM) (5.0 mL). The resulting solution was cooled to 0° C., and then methanesulfonyl chloride (0.08 mL, 1.05 mmol) was added dropwise at 0° C. To the reaction mixture was then added 2-pyrimidinamine (105 mg, 1.1 mmol), and stirring continued for 30 min at room temperature. After this time, the solvent was removed under reduced pressure to provide a residue which was purified by Combi-flash automated silica gel chromatography (80-100% EtOAc in Hex) to afford 1,1-dimethylethyl (3R)-3-(cyclopentylmethyl)-4-oxo-4-{5-[(2-pyrimidinylamino)carbonyl]-4,5-dihydro-1H-pyrazol-1-yl}butanoate (270 mg, 0.63 mmol, 63% yield). MS: 430 ([M+H]+).

Part B (3R)-3-(Cyclopentylmethyl)-4-oxo-4-{5-[(2-pyrimidinylamino)carbonyl]-4,5-dihydro-1H-pyrazol-1-yl}butanoic acid To a solution of 1,1-dimethylethyl (3R)-3-(cyclopentylmethyl)-4-oxo-4-{5-[(2-pyrimidinylamino)carbonyl]-4,5-dihydro-1H-pyrazol-1-yl}butanoate (0.21 g, 0.49 mmol) in 1,4-dioxane (10.0 mL) was added 4.0 M hydrochloric acid in 1,4-dioxane (6.11 mL, 24.4 mmol) at room temperature. The reaction mixture was stirred overnight. The solvent was then removed by reduced pressure to afford the crude product (~100% yield), which was used directly in the next step. MS: 374 ([M+H]$^+$).

Part C (5S)-1-{(2R)-2-(Cyclopentylmethyl)-4-oxo-4-[(tetrahydro-2H-pyran-2-yloxy)amino]butanoyl}-N-2-pyrimidinyl-4,5-dihydro-1H-pyrazole-5-carboxamide To a solution of (3R)-3-(cyclopentylmethyl)-4-oxo-4-{5-[(2-pyrimidinylamino)carbonyl]-4,5-dihydro-1H-pyrazol-1-yl}butanoic acid (183 mg, 0.49 mmol) in dichloromethane (DCM) (10 mL) was added N-methylmorpholine (0.14 mL, 1.27 mmol), O-(tetrahydro-2H-pyran-2-yl)hydroxylamine (69 mg, 0.59 mmol), EDC (112 mg, 0.59 mmol) and 3H-[1,2,3]triazolo[4,5-b]pyridin-3-ol (67 mg, 0.49 mmol) at 0° C. The reaction mixture was allowed to warm to room temperature and was stirred for 2 hours. The reaction mixture was then washed with water (5 mL) and $NaHCO_3$ solution (5 mL×3), and concentrated to provide the crude product as a mixture of diastereomers. This mixture was purified by Gilson HPLC (Sunfire Column 19×50 mm, flowrate 25 mL/min, 10 min, 5-70% MeCN:H2O) to afford (5S)-1-{(2R)-2-(cyclopentylmethyl)-4-oxo-4-[(tetrahydro-2H-pyran-2-yloxy)

amino]butanoyl}-N-2-pyrimidinyl-4,5-dihydro-1H-pyrazole-5-carboxamide (80 mg, 34% yield). MS: 473 ([M+H]+).

Part D (5S)-1-[(2R)-2-(Cyclopentylmethyl)-4-(hydroxyamino)-4-oxobutanoyl]-N-2-pyrimidinyl-4,5-dihydro-1H-pyrazole-5-carboxamide A mixture of (5S)-1-{(2R)-2-(cyclopentylmethyl)-4-oxo-4-[(tetrahydro-2H-pyran-2-yloxy)amino]butanoyl}-N-2-pyrimidinyl-4,5-dihydro-1H-pyrazole-5-carboxamide (80 mg, 0.17 mmol) in acetic acid (8 mL) and water (2 mL) was stirred at room temperature for 3 days. The solvent was then removed to provide a residue which was purified by Gilson HPLC (Sunfire Column 19×50 mm, flowrate 25 mL/min, 10 min, 5-70% MeCN:H2O) to afford (5S)-1-[(2R)-2-(cyclopentylmethyl)-4-(hydroxyamino)-4-oxobutanoyl]-N-2-pyrimidinyl-4,5-dihydro-1H-pyrazole-5-carboxamide (24 mg, 35% yield). 1H NMR (400 MHz, CHLOROFORM-d) δ ppm 1.15 (br. s., 2H) 1.37-1.94 (m, 9H) 2.41 (br. s., 1H) 2.64 (br. s., 1H) 3.24 (br. s., 2H) 3.52 (br. s., 1H) 3.83 (br. s., 1H) 5.11 (br. s., 1H) 6.99-7.07 (m, 2H) 8.64 (d, J=4.80 Hz, 2H) 9.21 (br. s., 1H) 10.33 (s, 1H).

Example 130

(5S)-1-[(2R)-2-(Cyclopentylmethyl)-4-(hydroxyamino)-4-oxobutanoyl]-N-(6-ethyl-2-pyridinyl)-4,5-dihydro-1H-pyrazole-5-carboxamide

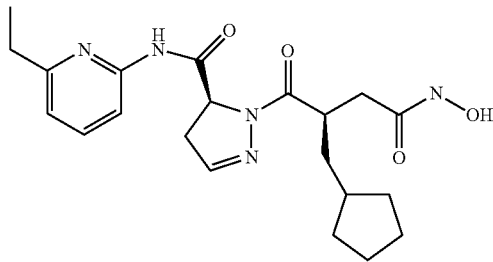 [SMILES: CCc1cccc(NC(=O)[C@@H]2CC=NN2C(=O)[C@@H](CC(=O)NO)CC2CCCC2)n1]

Part A 1,1-Dimethylethyl (3R)-3-(cyclopentylmethyl)-4-(5-{[(6-ethyl-2-pyridinyl)amino]carbonyl}-4,5-dihydro-1H-pyrazol-1-yl)-4-oxobutanoate To a solution of 1-{(2R)-2-(cyclopentylmethyl)-4-[(1,1-dimethylethyl)oxy]-4-oxobutanoyl}-4,5-dihydro-1H-pyrazole-5-carboxylic acid (352 mg, 1.0 mmol) in acetonitrile (10 mL) at 0° C. was added 4-[4,6-bis(methyloxy)-1,3,5-triazin-2-yl]-4-methylmorpholin-4-ium (656 mg, 2.0 mmol) and N-methylmorpholine (0.28 mL, 2.5 mmol). The reaction mixture was stirred for 2 hours. After this time, 6-ethyl-2-pyridinamine (159 mg, 1.3 mmol) was added to the mixture, which was then allowed to warm to room temperature and stirred for 3 hours. The solvent was removed under reduced pressure, and water (5 mL) and DCM (15 mL) were added to the resulting residue. The phases were separated. The aqueous phase was extracted twice with DCM (15 mL), and the combined organic phases were dried over sodium sulfate and concentrated. The crude product residue was purified by Combiflash silica gel chromatography (0-100% EtOAc in hex) to provide 1,1-dimethylethyl (3R)-3-(cyclopentylmethyl)-4-(5-{[(6-ethyl-2-pyridinyl)amino]carbonyl}-4,5-dihydro-1H-pyrazol-1-yl)-4-oxobutanoate (359 mg, 0.79 mmol, 79% yield) as a clear oil. MS: 457 ([M+H]+).

Part B (3R)-3-(Cyclopentylmethyl)-4-(5-{[(6-ethyl-2-pyridinyl)amino]carbonyl}-4,5-dihydro-1H-pyrazol-1-yl)-4-oxobutanoic acid To a solution of 1,1-dimethylethyl (3R)-3-(cyclopentylmethyl)-4-(5-{[(6-ethyl-2-pyridinyl)amino]carbonyl}-4,5-dihydro-1H-pyrazol-1-yl)-4-oxobutanoate (359 mg, 0.79 mmol) in 1,4-dioxane (10.0 mL) was added 4.0 M hydrochloric acid in 1,4-dioxane (9.8 mL, 39 mmol) at room temperature. The reaction mixture was stirred for 5 hours. The solvent was then removed by reduced pressure to afford the crude product (3R)-3-(cyclopentyl methyl)-4-(5-{[(6-ethyl-2-pyridinyl)amino]carbonyl}-4,5-dihydro-1H-pyrazol-1-yl)-4-oxobutanoic acid (314 mg, 100%), which was used directly in the next step. MS: 401 ([M+H]+).

Part C (5S)-1-((2R)-2-(Cyclopentylmethyl)-4-oxo-4-{[(phenylmethyl)oxy]amino}butanoyl)-N-(6-ethyl-2-pyridinyl)-4,5-dihydro-1H-pyrazole-5-carboxamide To a solution of (3R)-3-(cyclopentylmethyl)-4-(5-{[(6-ethyl-2-pyridinyl)amino]carbonyl}-4,5-dihydro-1H-pyrazol-1-yl)-4-oxobutanoic acid (314 mg, 0.79 mmol) in dichloromethane (DCM) (10 mL) was added N-methylmorpholine (0.22 mL, 2.04 mmol), O-(phenylmethyl)hydroxylamine hydrochloride (188 mg, 1.18 mmol), EDC (181 mg, 0.94 mmol) and 3H-[1,2,3]triazolo[4,5-b]pyridin-3-ol (107 mg, 0.79 mmol) at 0° C. The reaction mixture was allowed to warm to room temperature and was stirred overnight. The reaction mixture was then washed with water (5 mL) and NaHCO3 solution (5 mL×3), and concentrated to provide the crude product as a mixture of diastereomers. This mixture was purified by Gilson HPLC (Sunfire Column 19×50 mm, flowrate 25 mL/min, 10 min, 5-65% MeCN:H2O) to afford (5S)-1-((2R)-2-(cyclopentylmethyl)-4-oxo-4-{[(phenylmethyl)oxy]amino}butanoyl)-N-(6-ethyl-2-pyridinyl)-4,5-dihydro-1H-pyrazole-5-carboxamide (157 mg, 39% yield). MS: 506 ([M+H]+).

Part D (5S)-1-[(2R)-2-(Cyclopentyl methyl)-4-(hydroxyamino)-4-oxobutanoyl]-N-(6-ethyl-2-pyridinyl)-4,5-dihydro-1H-pyrazole-5-carboxamide (5S)-1-((2R)-2-(Cyclopentylmethyl)-4-oxo-4-{[(phenylmethyl)oxy]amino}butanoyl)-N-(6-ethyl-2-pyridinyl)-4,5-dihydro-1H-pyrazole-5-carboxamide (157 mg, 0.31 mmol) was dissolved in methanol (8 mL), and Pearlman's catalyst (43 mg, 0.06 mmol) was added to the solution. The mixture was stirred under 1 atm of H2 for 4 hours. After 4 hours, the reaction mixture was filtered, and the filtrate was concentrated and purified by Gilson HPLC (Sunfire Column 19×50 mm Flowrate 25 mL/min, 10 min, 5-65% MeCN:H2O) to afford (5S)-1-[(2R)-2-(cyclopentylmethyl)-4-(hydroxyamino)-4-oxobutanoyl]-N-(6-ethyl-2-pyridinyl)-4,5-dihydro-1H-pyrazole-5-carboxamide (62 mg, 0.14 mmol, 45% yield) as a white solid. 1H NMR (400 MHz, METHA- NOL-d4) δ ppm 1.14 (m, J=5.81 Hz, 1H) 1.29 (t, J=7.58 Hz, 3H) 1.39-1.68 (m, 5H) 1.70-1.97 (m, 4H) 2.27 (dd, J=14.53, 6.19 Hz, 1H) 2.47 (dd, J=14.40, 9.09 Hz, 1H) 2.76 (q, J=7.66 Hz, 2H) 3.17 (m, J=5.68, 1.89 Hz, 1H) 3.87 (tt, J=8.62, 6.03 Hz, 1H) 5.00 (dd, J=11.12, 5.05 Hz, 1H) 7.04 (d, J=7.58 Hz, 1H) 7.12 (s, 1H) 7.72 (t, J=7.83 Hz, 1H) 7.87 (d, J=8.59 Hz, 1H). MS: 417 ([M+H]+).

Example 131

(5S)-1-[(2R)-2-(Cyclopentylmethyl)-4-(hydroxyamino)-4-oxobutanoyl]-N-(5-fluoro-1-oxido-2-pyridinyl)-4,5-dihydro-1H-pyrazole-5-carboxamide

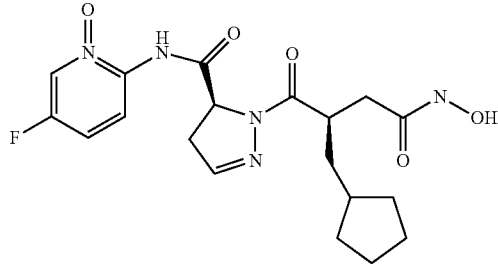 [SMILES: O=C(C[C@@H](CC1CCCC1)C(=O)N1N=CC[C@H]1C(=O)Nc1ccc(F)c[n+]1[O-])NO]

Part A 1,1-Dimethylethyl (3R)-3-(cyclopentylmethyl)-4-(5-{[(5-fluoro-2-pyridinyl)amino]carbonyl}-4,5-dihydro-1H-pyrazol-1-yl)-4-oxobutanoate To a solution of 1-{(2R)-2-(cyclopentylmethyl)-4-[(1,1-dimethylethyl)oxy]-4-oxobutanoyl}-4,5-dihydro-1H-pyrazole-5-carboxylic acid (352 mg, 1.0 mmol) in acetonitrile (10 mL) at 0° C. was added 4-[4,6-bis(methyloxy)-1,3,5-triazin-2-yl]-4-methylmorpholin-4-ium (656 mg, 2.0 mmol) and N-methylmorpholine (0.28 mL, 2.5 mmol). The reaction mixture was stirred for 2 hours at 0° C. After this time, 5-fluoro-2-pyridinamine (146 mg, 1.3 mmol) was added to the mixture, which was then allowed to warm to room temperature and stirred for 3 hours. The solvent was removed under reduced pressure, and water (5 mL) and DCM (15 mL) were added to the remaining residue. The phases were separated. The aqueous phase was extracted twice with DCM (15 mL), and the combined organic phases were dried over sodium sulfate and concentrated. The remaining residue was purified by Combiflash silica gel chromatography (0-100% EtOAc in hex) to give 1,1-dimethylethyl (3R)-3-(cyclopentylmethyl)-4-(5-{[(5-fluoro-2-pyridinyl)amino]carbonyl}-4,5-dihydro-1H-pyrazol-1-yl)-4-oxobutanoate (350 mg, 0.78 mmol, 78% yield) as a yellow oil. MS: 447 ([M+H]+).

Part B (3R)-3-(Cyclopentylmethyl)-4-(5-{[(5-fluoro-2-pyridinyl)amino]carbonyl}-4,5-dihydro-1H-pyrazol-1-yl)-4-oxobutanoic acid To a solution of 1,1-dimethylethyl (3R)-3-(cyclopentylmethyl)-4-(5-{[(5-fluoro-2-pyridinyl)amino]carbonyl}-4,5-dihydro-1H-pyrazol-1-yl)-4-oxobutanoate (323 mg, 0.72 mmol) in 1,4-dioxane (5.0 mL) was added 4.0 M hydrochloric acid in 1,4-dioxane (9.0 mL, 36 mmol) at room temperature. The reaction mixture was stirred for 4 hours. After this time, the solvent was removed by reduced pressure to afford the crude product, (3R)-3-(cyclopentylmethyl)-4-(5-{[(5-fluoro-2-pyridinyl)amino]carbonyl}-4,5-dihydro-1H-pyrazol-1-yl)-4-oxobutanoic acid (283 mg, 100%), which was used directly in the next step. MS: 491 ([M+H]+).

Part C (5S)-1-((2R)-2-(Cyclopentylmethyl)-4-oxo-4-{[(phenylmethyl)oxy]amino}butanoyl)-N-(5-fluoro-2-pyridinyl)-4,5-dihydro-1H-pyrazole-5-carboxamide To a solution of (3R)-3-(cyclopentylmethyl)-4-(5-{[(5-fluoro-2-pyridinyl)amino]carbonyl}-4,5-dihydro-1H-pyrazol-1-yl)-4-oxobutanoic acid (283 mg, 0.72 mmol) in dichloromethane (DCM) (10 mL) was added N-methylmorpholine (0.20 mL, 1.88 mmol), O-(phenylmethyl)hydroxylamine hydrochloride (173 mg, 1.08 mmol), EDC (167 mg, 0.87 mmol) and 3H-[1,2,3]triazolo[4,5-b]pyridin-3-ol (99 mg, 0.72 mmol) at 0° C. The reaction mixture was allowed to warm to room temperature and was stirred for 4 hours. The reaction mixture was then washed with water (5 mL) and NaHCO₃ solution (5 mL×3), and concentrated to provide the crude product as a mixture of diastereomers. This mixture was purified by Gilson HPLC (Sunfire Column 19×50 mm, flowrate 25 mL/min, 10 min, 5-65% MeCN:H2O) to afford (5S)-1-((2R)-2-(cyclopentylmethyl)-4-oxo-4-{[(phenylmethyl)oxy]amino}butanoyl)-N-(5-fluoro-2-pyridinyl)-4,5-dihydro-1H-pyrazole-5-carboxamide (140 mg, 39% yield).

Part D (5S)-1-((2R)-2-(Cyclopentylmethyl)-4-oxo-4-{[(phenylmethyl)oxy]amino}butanoyl)-N-(5-fluoro-1-oxido-2-pyridinyl)-4,5-dihydro-1H-pyrazole-5-carboxamide To a stirring solution of (5S)-1-((2R)-2-(cyclopentylmethyl)-4-oxo-4-{[(phenylmethyl)oxy]amino}butanoyl)-N-(5-fluoro-2-pyridinyl)-4,5-dihydro-1H-pyrazole-5-carboxamide (140 mg, 0.28 mmol) in dichloromethane (DCM) (5 mL) under nitrogen at 0° C. was added 3-chlorobenzenecarboperoxoic acid (147 mg, 0.85 mmol) in one portion. The reaction mixture was stirred at 0° C. for 10 min, then warmed to room temperature and stirred overnight. The reaction mixture was quenched with sat. aq. NaHCO₃ and then extracted with DCM. The organics were dried over Na₂SO₄, filtered, and concentrated to provide the crude product which was purified by Gilson HPLC (Sunfire Column 19×50 mm, flowrate 25 mL/min, 10 min, 5-65% MeCN:H2O) to afford (5S)-1-((2R)-2-(cyclopentylmethyl)-4-oxo-4-{[(phenylmethyl)oxy]amino}butanoyl)-N-(5-fluoro-1-oxido-2-pyridinyl)-4,5-dihydro-1H-pyrazole-5-carboxamide (90 mg, 0.18 mmol, 62% yield) as a white solid. MS: 512 ([M]+).

Part E (5S)-1-[(2R)-2-(Cyclopentylmethyl)-4-(hydroxyamino)-4-oxobutanoyl]-N-(5-fluoro-1-oxido-2-pyridinyl)-4,5-dihydro-1H-pyrazole-5-carboxamide (5S)-1-((2R)-2-(Cyclopentylmethyl)-4-oxo-4-{[(phenylmethyl)oxy]amino}butanoyl)-N-(5-fluoro-1-oxido-2-pyridinyl)-4,5-dihydro-1H-pyrazole-5-carboxamide (90 mg, 0.18 mmol) was dissolved in methanol (8 mL), and Pearlman's catalyst (24 mg, 0.03 mmol) was added to the solution. The mixture was stirred under 1 atm of H₂ (balloon) for 1 hour. After 1 hour, the reaction mixture was filtered, concentrated, and purified by Gilson HPLC (Sunfire Column 19×50 mm, flowrate 25 mL/min, 10 min, 5-65% MeCN:H2O) to afford (5S)-1-[(2R)-2-(cyclopentylmethyl)-4-(hydroxyamino)-4-oxobutanoyl]-N-(5-fluoro-1-oxido-2-pyridinyl)-4,5-dihydro-1H-pyrazole-5-carboxamide (38 mg, 0.09 mmol, 50% yield) as a white solid. 1H NMR (400 MHz, CHLOROFORM-d) δ ppm 0.79-0.94 (m, 1H) 1.04-1.24 (m, 3H) 1.41-1.68 (m, 7H) 1.72-2.32 (m, 18H) 2.39-2.52 (m, 2H) 2.58-2.74 (m, 2H) 3.21-3.31 (m, 1H) 3.39-3.50 (m, 1H) 3.69-3.81 (m, 1H) 5.08-5.22 (m, 1H) 7.03-7.07 (m, 1H) 7.17-7.24 (m, 2H) 8.23-8.29 (m, 1H) 8.42-8.49 (m, 1H) 10.92-11.05 (m, 1H). MS: 422 ([M+H]+).

Example 132

(5S)-1-[(2R)-2-(Cyclopentyl methyl)-4-(hydroxyamino)-4-oxobutanoyl]-N,N-di methyl-4,5-dihydro-1H-pyrazole-5-carboxamide

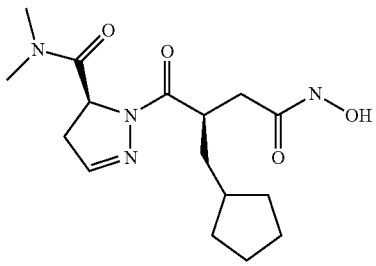 [SMILES: CN(C)C(=O)[C@@H]1CC=NN1C(=O)[C@@H](CC(=O)NO)CC1CCCC1]

Part A 1,1-Dimethylethyl (3R)-3-(cyclopentylmethyl)-4-{5-[(dimethylamino)carbonyl]-4,5-dihydro-1H-pyrazol-1-yl}-4-oxobutanoate To a solution of 1-{(2R)-2-(cyclopentylmethyl)-4-[(1,1-dimethylethyl)oxy]-4-oxobutanoyl}-4,5-dihydro-1H-pyrazole-5-carboxylic acid (353 mg, 1.0 mmol), Hunig's base (0.35 ml, 2.0 mmol), EDC (231 mg, 1.2 mmol) and aza-HOBt (136 mg, 1.0 mmol) in dichloromethane (DCM) (10 ml) was added N-methylmethanamine (1.0 ml, 2.0 mmol), which was in THF. The reaction mixture was stirred at room temperature overnight. The mixture was then washed with water (5 mL), NaHCO3 solution (5 mL×3), and concentrated to provide the crude product which was purified by Combiflash automated silica gel chromatography (0-50% EtOAc in hex) to afford 1,1-dimethylethyl (3R)-3-(cyclopentyl methyl)-4-{5-[(dimethylamino)carbonyl]-4,5-dihydro-1H-pyrazol-1-yl}-4-oxobutanoate (315 mg, 0.83 mmol, 83% yield) as a yellow solid. MS: 380 ([M+H]+).

Part B (3R)-3-(Cyclopentylmethyl)-4-{5-[(dimethylamino)carbonyl]-4,5-dihydro-1H-pyrazol-1-yl}-4-oxobutanoic acid To a solution of 1,1-dimethylethyl (3R)-3-(cyclopentylmethyl)-4-{5-[(dimethylamino)carbonyl]-4,5-dihydro-1H-pyrazol-1-yl}-4-oxobutanoate (315 mg, 0.83 mmol) in 1,4-dioxane (5.0 mL) was added 4.0 M hydrochloric acid in 1,4-dioxane (10.4 mL, 42 mmol) at room temperature. The reaction mixture was stirred for 4 hours. The solvent was then removed by reduced pressure to afford the crude product, (3R)-3-(cyclopentylmethyl)-4-{5-[(dimethylamino)carbonyl]-4,5-dihydro-1H-pyrazol-1-yl}-4-oxobutanoic acid (269 mg, 100% yield), which was used directly in the next step. MS: 324 ([M+H]+).

Part C (5S)-1-((2R)-2-(Cyclopentylmethyl)-4-oxo-4-{[(phenylmethyl)oxy]amino}butanoyl)-N,N-dimethyl-4,5-dihydro-1H-pyrazole-5-carboxamide To a solution of (3R)-3-(cyclopentylmethyl)-4-{5-[(dimethylamino)carbonyl]-4,5-dihydro-1H-pyrazol-1-yl}-4-oxobutanoic acid (269 mg, 0.83 mmol) in dichloromethane (DCM) (10 ml) was added O-(phenylmethyl)hydroxylamine (133 mg, 1.08 mmol), EDC (191 mg, 1.0 mmol), 4-methylmorpholine (0.24 ml, 2.16 mmol), 3H-[1,2,3]triazolo[4,5-b]pyridin-3-ol (113 mg, 0.83 mmol) at 0° C. The reaction mixture was allowed to warm to room temperature and was stirred for 5 hours. The reaction mixture was then washed with water (15 mL) and NaHCO3 solution (15 mL×3), and concentrated to provide the crude product as a mixture of diastereomers. This mixture was purified by Gilson HPLC (Sunfire Column 19×50 mm, flowrate 25 mL/min, 10 min, 5-65% MeCN:H2O) to afford (5S)-1-((2R)-2-(cyclopentylmethyl)-4-oxo-4-{[(phenylmethyl)oxy]amino}butanoyl)-N,N-dimethyl-4,5-dihydro-1H-pyrazole-5-carboxamide (120 mg, 33% yield). MS: 429 ([M+H]+).

Part D (5S)-1-[(2R)-2-(Cyclopentylmethyl)-4-(hydroxyamino)-4-oxobutanoyl]-N,N-dimethyl-4,5-dihydro-1H-pyrazole-5-carboxamide To a solution of (5S)-1-((2R)-2-(cyclopentylmethyl)-4-oxo-4-{[(phenylmethyl)oxy]amino}butanoyl)-N,N-dimethyl-4,5-dihydro-1H-pyrazole-5-carboxamide (120 mg, 0.28 mmol) in methanol (10 mL) was added Pearlman's catalyst (39 mg, 0.056 mmol). The resulting mixture was stirred under 1 atm of H2 for 1 hour. After 1 hour, the mixture was filtered, concentrated, and purified by Gilson HPLC (Sunfire Column 19×50 mm, flowrate 25 mL/min, 10 min, 5-65% MeCN:H2O) to afford (5S)-1-[(2R)-2-(cyclopentylmethyl)-4-(hydroxyamino)-4-oxobutanoyl]-N,N-dimethyl-4,5-dihydro-1H-pyrazole-5-carboxamide (78 mg, 0.23 mmol, 82% yield) as a yellow solid. MS: 389 ([M+H]+). 1H NMR (400 MHz, CHLOROFORM-d) δ ppm 1.09-1.26 (m, 2H) 1.59 (br. s., 35H) 1.78-1.97 (m, 5H) 2.43-2.52 (m, 1H) 2.62-2.73 (m, 1H) 2.85-2.95 (m, 1H) 3.01 (s, 3H) 3.19 (s, 4H) 3.58-3.67 (m, 1H) 5.08-5.18 (m, 1H) 6.88-6.97 (m, 1H).

Example 133

(3R)-3-(Cyclopentyl methyl)-N-hydroxy-4-[(5S)-5-(4-morpholinylcarbonyl)-4,5-dihydro-1H-pyrazol-1-yl]-4-oxobutanamide

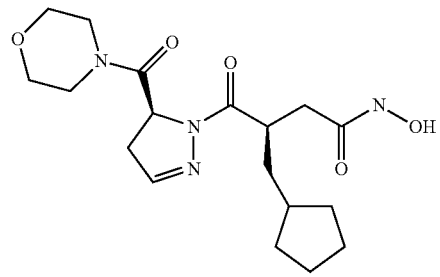 [SMILES: O=C(C[C@@H](CC1CCCC1)C(=O)N1N=CC[C@H]1C(=O)N1CCOCC1)NO]

Part A

1,1-Dimethylethyl (3R)-3-(cyclopentylmethyl)-4-[5-(4-morpholinylcarbonyl)-4,5-dihydro-1H-pyrazol-1-yl]-4-oxobutanoate To a solution of 1-{(2R)-2-(cyclopentylmethyl)-4-[(1,1-dimethylethyl)oxy]-4-oxobutanoyl}-4,5-dihydro-1H-pyrazole-5-carboxylic acid (353 mg, 1.0 mmol), Hunig's base (0.35 ml, 2.0 mmol), EDC (231 mg, 1.2 mmol) and aza-HOBt (136 mg, 1.0 mmol) in dichloromethane (DCM) (10 ml) was added morpholine (0.131 ml, 1.5 mmol). The reaction mixture was stirred at room temperature overnight. After this time, the mixture was washed with water (5 mL) and NaHCO$_3$ solution (5 mL×3), and concentrated to provide the crude product which was purified by Combiflash automated silica gel chromatography (0-100% EtOAc in hex) to afford 1,1-dimethylethyl (3R)-3-(cyclopentylmethyl)-4-[5-(4-morpholinylcarbonyl)-4,5-dihydro-1H-pyrazol-1-yl]-4-oxobutanoate (244 mg, 0.58 mmol, 58% yield) as a white solid. MS: 422 ([M+H]+).

Part B

(3R)-3-(Cyclopentyl methyl)-4-[5-(4-morpholinylcarbonyl)-4,5-dihydro-1H-pyrazol-1-yl]-4-oxobutanoic acid To 1,1-dimethylethyl (3R)-3-(cyclopentylmethyl)-4-[5-(4-morpholinylcarbonyl)-4,5-dihydro-1H-pyrazol-1-yl]-4-oxobutanoate (244 mg, 0.58 mmol) in 1,4-dioxane (5.0 mL) was added 4.0 M hydrochloric acid in 1,4-dioxane (7.25 mL, 29.0 mmol) at room temperature. The resulting reaction mixture was stirred for 4 hours. The solvent was then removed by reduced pressure to afford the crude product (3R)-3-(cyclopentylmethyl)-4-[5-(4-morpholinylcarbonyl)-4,5-dihydro-1H-pyrazol-1-yl]-4-oxobutanoic acid (212 mg, 0.58 mmol, 100% yield), which was used directly in the next step. MS: 366 ([M+H]+).

Part C

(3R)-3-(Cyclopentylmethyl)-4-[(5S)-5-(4-morpholinylcarbonyl)-4,5-dihydro-1H-pyrazol-1-yl]-4-oxo-N-[(phenylmethyl)oxy]butanamide To a solution of (3R)-3-(cyclopentylmethyl)-4-[5-(4-morpholinylcarbonyl)-4,5-dihydro-1H-pyrazol-1-yl]-4-oxobutanoic acid (212 mg, 0.58 mmol) in dichloromethane (DCM) (10 ml) was added O-(phenylmethyl)hydroxylamine (93 mg, 0.75 mmol), 4-methylmorpholine (0.17 ml, 1.5 mmol), 3H-[1,2,3]triazolo[4,5-b]pyridin-3-ol (79 mg, 0.58 mmol), and N-[3-(dimethylamino)propyl]-N'-ethylcarbodiimide hydrochloride (133 mg, 0.70 mmol) at 0° C. The reaction mixture was allowed to warm to room temperature and was stirred for 5 hours. The reaction mixture was then washed with water (15 mL) and NaHCO$_3$ solution (15 mL×3), and concentrated to provide the crude product as a mixture of diastereomers. This mixture was purified by Gilson HPLC (Sunfire Column 19×50 mm, flowrate 25 mL/min, 10 min, 5-65% MeCN:H2O) to afford (3R)-3-(cyclopentyl methyl)-4-[(5S)-5-(4-morpholinylcarbonyl)-4,5-dihydro-1H-pyrazol-1-yl]-4-oxo-N-[(phenylmethyl)oxy]butanamide (57 mg, 21% yield). MS: 472 ([M+H]+).

Part D

(3R)-3-(Cyclopentyl methyl)-N-hydroxy-4-[(5S)-5-(4-morpholinylcarbonyl)-4,5-dihydro-1H-pyrazol-1-yl]-4-oxobutanamide To a solution of (3R)-3-(cyclopentylmethyl)-4-[(5S)-5-(4-morpholinylcarbonyl)-4,5-dihydro-1H-pyrazol-1-yl]-4-oxo-N-[(phenylmethyl)oxy]butanamide (57 mg, 0.12 mmol) in methanol (5 mL) was added Pearlman's catalyst (17 mg, 0.024 mmol). The mixture then was stirred under 1 atm of H$_2$ for 1 hour. After 1 hour, the mixture was filtered, concentrated, and purified by Gilson HPLC (Sunfire Column 19×50 mm, flowrate 25 mL/min, 10 min, 5-65% MeCN:H2O) to afford (3R)-3-(cyclopentylmethyl)-N-hydroxy-4-[(5S)-5-(4-morpholinylcarbonyl)-4,5-dihydro-1H-pyrazol-1-yl]-4-oxobutanamide (19 mg, 0.047 mmol, 39% yield) as a white solid. MS: 381 ([M+H]+). 1H NMR (400 MHz, METHANOL-d4) δ ppm 1.07-1.29 (m, 2H) 1.36-1.48 (m, 1H) 1.50-1.69 (m, 4H) 1.72-2.03 (m, 5H) 2.19-2.30 (m, 1H) 2.36-2.53 (m, 1H) 2.77-3.01 (m, 2H) 3.46-3.98 (m, 10H) 5.15-5.29 (m, 1H) 7.03-7.07 (m, 1H).

Example 134

(5S)-1-[(2R)-2-(Cyclopentyl methyl)-4-(hydroxyamino)-4-oxobutanoyl]-N-phenyl-4,5-dihydro-1H-pyrazole-5-carboxamide

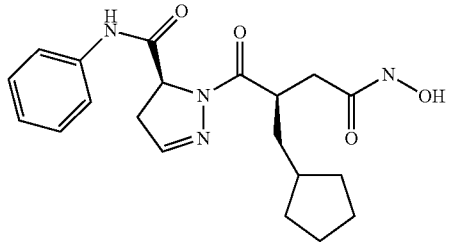 [SMILES: O=C(C[C@@H](CC1CCCC1)C(=O)N1N=CC[C@H]1C(=O)Nc1ccccc1)NO]

Part A

1,1-Dimethylethyl (3R)-3-(cyclopentylmethyl)-4-oxo-4-{5-[(phenylamino)carbonyl]-4,5-dihydro-1H-pyrazol-1-yl}butanoate To a solution of 1-{(2R)-2-(cyclopentylmethyl)-4-[(1,1-dimethylethyl)oxy]-4-oxobutanoyl}-4,5-dihydro-1H-pyrazole-5-carboxylic acid (352 mg, 1.0 mmol) in acetonitrile (10 mL) at 0° C. was added 4-[4,6-bis(methyloxy)-1,3,5-triazin-2-yl]-4-methylmorpholin-4-ium (656 mg, 2.0 mmol) and N-methylmorpholine (0.29 mL, 2.6 mmol). The reaction was stirred for 2 hours at 0° C. Aniline (93 mg, 1.0 mmol) was added to the reaction, which was allowed to warm to room temperature and stirred for 3 hours. The solvent was then removed under reduced pressure, and water (5 mL) and DCM (15 mL) were added to the residue. The phases were separated. The aqueous phase was extracted twice with DCM (15 mL), and the combined organics were dried over sodium sulfate and concentrated. The resulting residue was purified by Combiflash silica gel chromatography (0-60% EtOAc in hex) to give 1,1-dimethylethyl (3R)-3-(cyclopentylmethyl)-

4-oxo-4-{5-[(phenylamino)carbonyl]-4,5-dihydro-1H-pyrazol-1-yl}butanoate (386 mg, 0.90 mmol, 90% yield) as a yellow oil. MS: 428 ([M+H]).

Part B (3R)-3-(Cyclopentylmethyl)-4-oxo-4-{5-[(phenylamino)carbonyl]-4,5-dihydro-1H-pyrazol-1-yl}butanoic acid To a solution of 1,1-dimethylethyl (3R)-3-(cyclopentylmethyl)-4-oxo-4-{5-[(phenylamino)carbonyl]-4,5-dihydro-1H-pyrazol-1-yl}butanoate (386 mg, 0.90 mmol) in 1,4-dioxane (5.0 mL) was added 4.0 M hydrochloric acid in 1,4-dioxane (11.3 mL, 45.2 mmol) at room temperature. The reaction mixture was stirred for 4 hours. LCMS showed the reaction was complete. The solvent was removed by reduced pressure to afford (3R)-3-(cyclopentylmethyl)-4-oxo-4-{5-[(phenylamino)carbonyl]-4,5-dihydro-1H-pyrazol-1-yl}butanoic acid (336 mg, 100%), which was used directly in the next step.

Part C (5S)-1-((2R)-2-(Cyclopentylmethyl)-4-oxo-4-{[(phenylmethyl)oxy]amino}butanoyl)-N-phenyl-4,5-dihydro-1H-pyrazole-5-carboxamide To a solution of (3R)-3-(cyclopentylmethyl)-4-oxo-4-{5-[(phenylamino)carbonyl]-4,5-dihydro-1H-pyrazol-1-yl}butanoic acid (336 mg, 0.90 mmol) in dichloromethane (DCM) (10 ml) was added O-(phenylmethyl)hydroxylamine (167 mg, 1.36 mmol), 4-methylmorpholine (0.26 ml, 2.35 mmol), 3H-[1,2,3]triazolo[4,5-b]pyridin-3-ol (123 mg, 0.90 mmol), and EDC (208 mg, 1.09 mmol) at 0° C. The reaction was left to warm to room temperature and stirred overnight. The reaction was washed with water (15 mL) and NaHCO3 solution (15 mL×3), and then concentrated to give the crude product as a mixture of diastereomers, which was purified by Gilson HPLC (Sunfire Column 19×50 mm, flowrate 25 mL/min, 10 min, 5-65% MeCN:H2) to afford (5S)-1-((2R)-2-(cyclopentylmethyl)-4-oxo-4-{[(phenylmethyl)oxy]amino}butanoyl)-N-phenyl-4,5-dihydro-1H-pyrazole-5-carboxamide (110 mg, 25% yield). MS: 477 ([M+H]).

Part D (5S)-1-[(2R)-2-(Cyclopentylmethyl)-4-(hydroxyamino)-4-oxobutanoyl]-N-phenyl-4,5-dihydro-1H-pyrazole-5-carboxamide (5S)-1-((2R)-2-(Cyclopentylmethyl)-4-oxo-4-{[(phenylmethyl)oxy]amino}butanoyl)-N-phenyl-4,5-dihydro-1H-pyrazole-5-carboxamide (110 mg, 0.23 mmol) was dissolved in methanol (8 mL), and Pearlman's catalyst (37 mg, 0.05 mmol) was added. The resulting mixture was stirred under 1 atm of $H_2$ for 30 min. After 30 min, the mixture was filtered, concentrated, and purified by Gilson HPLC (Sunfire Column 19×50 mm, flowrate 25 mL/min, 10 min, 5-65% MeCN:H2O) to afford (5S)-1-[(2R)-2-(cyclopentylmethyl)-4-(hydroxyamino)-4-oxobutanoyl]-N-phenyl-4,5-dihydro-1H-pyrazole-5-carboxamide (60 mg, 0.15 mmol, 66% yield) as a white solid. MS: 387 ([M+H]+). 1H NMR (400 MHz, METHANOL-d4) δ ppm 1.13 (none, 2H) 1.37-1.68 (m, 5H) 1.72-2.02 (m, 4H) 2.20-2.33 (m, 1H) 2.38-2.50 (m, 1H) 3.05-3.21 (m, 1H) 3.79-3.92 (m, 1H) 7.08-7.15 (m, 2H) 7.28-7.36 (m, 2H) 7.54-7.59 (m, 1H).

Example 135

(5S)-1-[(2R)-2-(Cyclopentyl methyl)-4-(hydroxyamino)-4-oxobutanoyl]-N-(6-ethyl-1-oxido-2-pyridinyl)-4,5-dihydro-1H-pyrazole-5-carboxamide

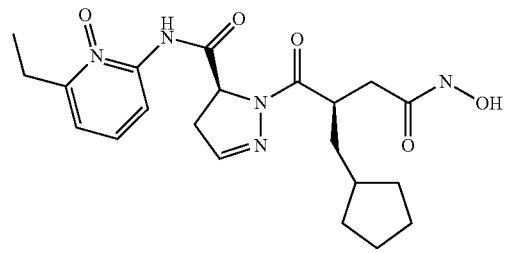 [SMILES: CCc1cccc(NC(=O)[C@@H]2CC=NN2C(=O)[C@@H](CC(=O)NO)CC2CCCC2)[n+]1[O-]]

Part A 1,1-Dimethylethyl (3R)-3-(cyclopentylmethyl)-4-(5-{[(6-ethyl-2-pyridinyl)amino]carbonyl}-4,5-dihydro-1H-pyrazol-1-yl)-4-oxobutanoate To a solution of 1-{(2R)-2-(cyclopentylmethyl)-4-[(1,1-dimethylethyl)oxy]-4-oxobutanoyl}-4,5-dihydro-1H-pyrazole-5-carboxylic acid (352 mg, 1.0 mmol) in acetonitrile (10 mL) at 0° C. was added 4-[4,6-bis(methyloxy)-1,3,5-triazin-2-yl]-4-methylmorpholin-4-ium (656 mg, 2.0 mmol) and N-methylmorpholine (0.29 mL, 2.6 mmol). The reaction was stirred for 2 hours at 0° C., and then 6-(1-methylethyl)-2-pyridinamine (177 mg, 1.30 mmol) was added to the reaction. The mixture was allowed to warm to room temperature and was stirred for 3 hours. The solvent was removed under reduced pressure, and then water (5 mL) and DCM (15 mL) were added. The phases were separated. The aqueous phase was extracted twice with DCM (15 mL), and the combined organics were dried over sodium sulfate and concentrated. The resulting residue was purified by Combiflash silica gel chromatography (0-100% EtOAc in hex) to give 1,1-dimethylethyl (3R)-3-(cyclopentylmethyl)-4-(5-{[(6-ethyl-2-pyridinyl)amino]carbonyl}-4,5-dihydro-1H-pyrazol-1-yl)-4-oxobutanoate (368 mg, 0.81 mmol, 81% yield) as a yellow oil. MS: 457 ([M+H]+).

Part B (3R)-3-(Cyclopentylmethyl)-4-(5-{[(6-ethyl-2-pyridinyl)amino]carbonyl}-4,5-dihydro-1H-pyrazol-1-yl)-4-oxobutanoic acid To a solution of 1,1-dimethylethyl (3R)-3-(cyclopentylmethyl)-4-(5-{[(6-ethyl-2-pyridinyl)amino]carbonyl}-4,5-dihydro-1H-pyrazol-1-yl)-4-oxobutanoate (368 mg, 0.81 mmol) in 1,4-dioxane (5.0 mL) was added 4.0 M hydrochloric acid in 1,4-dioxane (10.1 mL, 40 mmol) at room temperature. The reaction mixture was stirred for 4 hours. LCMS showed the reaction was complete. The solvent was then removed by reduced pressure to afford (3R)-3-(cyclopentylmethyl)-4-(5-{[(6-ethyl-2-pyridinyl)amino]carbonyl}-4,5- dihydro-1H-pyrazol-1-yl)-4-oxobutanoic acid (323 mg, 100% yield), which was used directly in the next step. MS: 401 ([M+H]+).

Part C (5S)-1-((2R)-2-(Cyclopentylmethyl)-4-oxo-4-{[(phenylmethyl)oxy]amino}butanoyl)-N-(6-ethyl-2-pyridinyl)-4,5-dihydro-1H-pyrazole-5-carboxamide To a solution of (3R)-3-(cyclopentylmethyl)-4-(5-{[(6-ethyl-2-pyridinyl)amino]carbonyl}-4,5-dihydro-1H-pyrazol-1-yl)-4-oxobutanoic acid (323 mg, 0.81 mmol) in dichloromethane (DCM) (10 ml) was added O-(phenylmethyl) hydroxylamine (129 mg, 1.05 mmol), 4-methylmorpholine (0.23 ml, 2.1 mmol), 3H-[1,2,3]triazolo[4,5-b]pyridin-3-ol (110 mg, 0.81 mmol), and EDC (186 mg, 0.97 mmol) at 0° C. The reaction was left to warm to room temperature and stirred overnight. The reaction was then washed with water (15 mL) and NaHCO$_3$ solution (15 mL×3), then concentrated to provide the crude product as a mixture of diastereomers, which was purified by Gilson HPLC (Sunfire Column 19×50 mm, flowrate 25 mL/min, 10 min, 5-65% MeCN: H2O) to afford (5S)-1-((2R)-2-(cyclopentylmethyl)-4-oxo-4-{[(phenylmethyl)oxy]amino}butanoyl)-N-(6-ethyl-2-pyridinyl)-4,5-dihydro-1H-pyrazole-5-carboxamide (119 mg, 29% yield). MS: 506 ([M+H]+).

Part D (5S)-1-((2R)-2-(Cyclopentylmethyl)-4-oxo-4-{[(phenylmethyl)oxy]amino}butanoyl)-N-(6-ethyl-1-oxido-2-pyridinyl)-4,5-dihydro-1H-pyrazole-5-carboxamide To a solution of (5S)-1-((2R)-2-(cyclopentylmethyl)-4-oxo-4-{[(phenylmethyl)oxy]amino}butanoyl)-N-(6-ethyl-2-pyridinyl)-4,5-dihydro-1H-pyrazole-5-carboxamide (119 mg, 0.24 mmol) in dichloromethane (DCM) (5 mL) stirred under nitrogen at 0° C. was added 3-chlorobenzenecarboperoxoic acid (122 mg, 0.71 mmol) in one portion. The reaction mixture was stirred at 0° C. for 10 min, then warmed to room temperature and stirred overnight. The reaction mixture was then quenched with sat. aq. NaHCO$_3$ and extracted with DCM. The organic phase was dried over Na$_2$SO$_4$, filtered, and concentrated to provide the crude product, which was purified by Gilson HPLC (Sunfire Column 19×50 mm, flowrate 25 mL/min, 10 min, 5-65% MeCN:H2O) to afford (5S)-1-((2R)-2-(cyclopentylmethyl)-4-oxo-4-{[(phenylmethyl)oxy]amino}butanoyl)-N-(6-ethyl-1-oxido-2-pyridinyl)-4,5-dihydro-1H-pyrazole-5-carboxamide (61 mg, 0.12 mmol, 50% yield) as a white solid. MS: 522 ([M+H]+).

Part E (5S)-1-[(2R)-2-(Cyclopentyl methyl)-4-(hydroxyamino)-4-oxobutanoyl]-N-(6-ethyl-1-oxido-2-pyridinyl)-4,5-dihydro-1H-pyrazole-5-carboxamide (5S)-1-((2R)-2-(Cyclopentylmethyl)-4-oxo-4-{[(phenylmethyl)oxy]amino}butanoyl)-N-(6-ethyl-1-oxido-2-pyridinyl)-4,5-dihydro-1H-pyrazole-5-carboxamide (61 mg, 0.12 mmol) was dissolved in methanol (8 mL), and Pearlman's catalyst (16 mg, 0.02 mmol) was added. The resulting mixture was stirred under 1 atm of H$_2$ for 30 min. After 30 min, the mixture was filtered, concentrated, and purified by Gilson HPLC (Sunfire Column 19×50 mm, flowrate 25 mL/min, 10 min, 5-65% MeCN:H2O) to afford (5S)-1-[(2R)-2-(cyclopentylmethyl)-4-(hydroxyamino)-4-oxobutanoyl]-N-(6-ethyl-1-oxido-2-pyridinyl)-4,5-dihydro-1H-pyrazole-5-carboxamide (35 mg, 0.08 mmol, 68% yield) as a white solid. 1H NMR (400 MHz, METHANOL-d4) δ ppm 1.01-1.23 (m, 2H) 1.34 (s, 3H) 1.43-1.65 (m, 5H) 1.70-1.77 (m, 1H) 1.79-1.92 (m, 3H) 2.21-2.37 (m, 1H) 2.42-2.57 (m, 1H) 2.87-3.04 (m, 2H) 3.81-3.96 (m, 1H) 5.11-5.20 (m, 1H) 7.10-7.24 (m, 2H) 7.45-7.56 (m, 1H) 8.30-8.40 (m, 1H). MS: 432 ([M+H]+).

Example 136

(5S)-1-[(2R)-2-(Cyclopentylmethyl)-4-(hydroxyamino)-4-oxobutanoyl]-N-2-pyridinyl-4,5-dihydro-1H-pyrazole-5-carboxamide

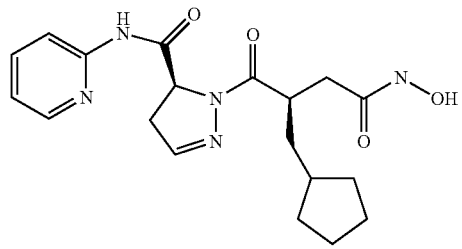 [SMILES: O=C(C[C@@H](CC1CCCC1)C(=O)N1N=CC[C@H]1C(=O)Nc1ccccn1)NO]

Part A (5S)-4,5-Dihydro-1H-pyrazole-5-carboxylic acid, hydrochloride

To a 2000 ml round bottom flask was added (5S)-1-{[(1,1-dimethylethyl)oxy]carbonyl}-4,5-dihydro-1H-pyrazole-5-carboxylic acid (34 g, 159 mmol) in tetrahydrofuran (THF) (600 mL), followed by HCl (397 mL, 1587 mmol) (4 M in dioxane). The mixture was stirred at room temperature for 18 hours, and then ether (600 mL) was added. After stirring for 5 min, the mixture was allowed to stand for 10 min and then the organic solvents were decanted. The solid was collected by filtration and dried under high vacuum to provide (5S)-4,5-dihydro-1H-pyrazole-5-carboxylic acid, hydrochloride (22.4 g, 149 mmol, 94% yield) as a pale yellow solid. $^1$H NMR (400 MHz, METHANOL-d4): δ ppm 3.40-3.66 (m, 2H) 4.75-4.84 (m, 1H) 8.05-8.13 (m, 1H).

Part B (5S)-1-{(2R)-2-(Cyclopentylmethyl)-4-[(1,1-dimethylethyl)oxy]-4-oxobutanoyl}-4,5-dihydro-1H-pyrazole-5-carboxylic acid To a 1000 ml round bottom flask under N$_2$ was added (2R)-2-(cyclopentylmethyl)-4-[(1,1-dimethylethyl)oxy]-4-oxobutanoic acid (Tetrahedron, 2001, 57(36), 7675-7683) (38.1 g, 149 mmol) in acetonitrile (650 mL) at 0° C., followed by N-methylmorpholine (82 mL, 744 mmol) and 4-[4,6-bis(methyloxy)-1,3,5-triazin-2-yl]-4-methylmorpholin-4-ium (53.7 g, 164 mmol). The solution was stirred at the same temperature for 2 hours and then (5S)-4,5-dihydro-1H-pyrazole-5-carboxylic acid, hydrochloride (22.4 g, 149 mmol) was added. The solution was allowed to warm up to room temperature and stirring continued overnight. LCMS showed that the reaction was complete. The acetonitrile was removed under reduced pressure, and the residue was taken up in DCM (500 mL) and neutralized by the addition of 2 N HCl. The organic phase was washed with brine, dried over $Na_2SO_4$, filtered and concentrated. The residue was purified by Combiflash automated silica gel chromatography (0-5% methanol containing 1% formic acid/DCM) to provide (5S)-1-{(2R)-2-(cyclopentylmethyl)-4-[(1,1-dimethylethyl)oxy]-4-oxobutanoyl}-4,5-dihydro-1H-pyrazole-5-carboxylic acid (27.7 g, 79 mmol, 53% yield) as a clear oil. LCMS: $[M+H]^+$: 353.4.

Part C 1,1-Dimethylethyl (3R)-3-(cyclopentyl methyl)-4-oxo-4-{(5S)-5-[(2-pyridinylamino)carbonyl]-4,5-dihydro-1H-pyrazol-1-yl}butanoate To a 1000 ml round bottom flask under $N_2$ was added (5S)-1-{(2R)-2-(cyclopentylmethyl)-4-[(1,1-dimethylethyl)oxy]-4-oxobutanoyl}-4,5-dihydro-1H-pyrazole-5-carboxylic acid (27.7 g, 79 mmol) in dichloromethane (DCM) (700 mL) at 0° C., followed by 2-pyridinamine (14.79 g, 157 mmol), DIPEA (68.6 mL, 393 mmol), 3H-[1,2,3]triazolo[4,5-b]pyridin-3-ol (21.40 g, 157 mmol) and EDC (30.1 g, 157 mmol). The mixture was allowed to warm up to room temperature and stirring continued overnight. LCMS showed that the desired product was ~56%. After another 24 h, LCMS indicated no starting material left. The organic solution was washed with water (300 mL), 10% citric acid (2×300 mL) and brine, dried ($Na_2SO_4$), filtered, and concentrated to afford 1,1-dimethylethyl (3R)-3-(cyclopentylmethyl)-4-oxo-4-{(5S)-5-[(2-pyridinylamino)carbonyl]-4,5-dihydro-1H-pyrazol-1-yl}butanoate (29.1 g, 58.4 mmol, 74% yield) as a brown gummy solid. LCMS: $[M+H]^+$: 429.2.

Part D (3R)-3-(Cyclopentyl methyl)-4-oxo-4-{(5S)-5-[(2-pyridinylamino)carbonyl]-4,5-dihydro-1H-pyrazol-1-yl}butanoic acid To a 500 ml round bottom flask was added 1,1-dimethylethyl (3R)-3-(cyclopentylmethyl)-4-oxo-4-{(5S)-5-[(2-pyridinylamino)carbonyl]-4,5-dihydro-1H-pyrazol-1-yl}butanoate (29.1 g, 58.4 mmol) and 4 M HCl in 1,4-dioxane (240 mL, 960 mmol). The mixture was stirred at room temperature and monitored by LCMS. After 90 min, no starting material remained. The mixture was concentrated to dryness and co-evaporated with dioxane (2×15 mL) to afford the crude (3R)-3-(cyclopentylmethyl)-4-oxo-4-{(5S)-5-[(2-pyridinylamino)carbonyl]-4,5-dihydro-1H-pyrazol-1-yl}butanoic acid, hydrochloride (34.0 g, 58.5 mmol, 100% yield) as a light brown foamy solid that was used directly for the next step. LCMS: $[M+H]^+$: 373.2.

Part E (5S)-1-((2R)-2-(Cyclopentylmethyl)-4-oxo-4-{[(phenylmethyl)oxy]amino}butanoyl)-N-2-pyridinyl-4,5-dihydro-1H-pyrazole-5-carboxamide To a 1000 ml round bottom flask under $N_2$ was added (3R)-3-(cyclopentylmethyl)-4-oxo-4-{(5S)-5-[(2-pyridinylamino)carbonyl]-4,5-dihydro-1H-pyrazol-1-yl}butanoic acid, hydrochloride (34 g, 58.4 mmol) in dichloromethane (DCM) (600 mL), followed by O-benzylhydroxylamine, hydrochloride (13.98 g, 88 mmol), N-methylmorpholine (32.1 mL, 292 mmol), 3H-[1,2,3]triazolo[4,5-b]pyridin-3-ol (11.92 g, 88 mmol) and EDC (16.79 g, 88 mmol). The mixture was stirred at room temperature overnight. The mixture was then washed with water (300 mL) and brine (300 mL), dried ($Na_2SO_4$), filtered, and concentrated to a volume of ~40 mL. The mixture was loaded onto a 220 g redi-sep gold column and purified by Combi-Flash automated flash chromatography eluting with 0-80% ethyl acetate/hexanes. The pure fractions were collected and concentrated to dryness to afford 6.1 g white foamy solid. Fractions contaminated with the by-product diastereomer were combined and concentrated to ~150 mL and the white precipitates were collected by filtration to afford another batch of pure product (8.8 g). The filtrate was concentrated and purified again by CombiFlash to provide 3.2 g of the desired product. Total amount of purified product: (5S)-1-((2R)-2-(cyclopentylmethyl)-4-oxo-4-{[(phenylmethyl)oxy]amino}butanoyl)-N-2-pyridinyl-4,5-dihydro-1H-pyrazole-5-carboxamide (18.1 g, 37.9 mmol, 65% yield). LCMS: $[M+H]^+$: 478.2.

Part F (5S)-1-[(2R)-2-(Cyclopentylmethyl)-4-(hydroxyamino)-4-oxobutanoyl]-N-2-pyridinyl-4,5-dihydro-1H-pyrazole-5-carboxamide To a 500 ml round bottom flask under $N_2$ was added (5S)-1-((2R)-2-(cyclopentylmethyl)-4-oxo-4-{[(phenylmethyl)oxy]amino}butanoyl)-N-2-pyridinyl-4,5-dihydro-1H-pyrazole-5-carboxamide (15.2 g, 31.8 mmol) in methanol (220 mL), followed by Pearlman's catalyst (3.17 g, 4.5 mmol). The mixture was degassed and hydrogenated using a $H_2$ balloon. After 4 hours, LCMS indicated completion of the reaction. The mixture was kept under $N_2$ in a refrigerator overnight. The clear solution on the top was decanted and filtered through 4 Acrodisc CR 25 mm Syringe Filters. The catalyst on the bottom was washed thoroughly with methanol (2×30 mL) and filtered. The combined filtrates were concentrated to dryness to provide (5S)-1-[(2R)-2-(cyclopentylmethyl)-4-(hydroxyamino)-4-oxobutanoyl]-N-2-pyridinyl-4,5-dihydro-1H-pyrazole-5-carboxamide (11.84 g, 30.6 mmol, 96% yield) as a white solid. $^1$H NMR (400 MHz, METHANOL-d4) δ ppm 1.05-1.23 (m, 2H) 1.37-1.68 (m, 5H) 1.70-2.00 (m, 4H) 2.20-2.33 (m, 1H) 2.44 (d, J=9.09 Hz, 1H) 3.11-3.24 (m, 1H) 3.29-3.37 (m, 1H) 3.81-3.93 (m, 1H) 4.96-5.08 (m, 1H) 7.11 (s, 2H) 7.73-7.83 (m, 1H) 8.08 (d, J=8.34 Hz, 1H) 8.25-8.35 (m, 1H) 8.30 (d, J=4.80 Hz, 1H). LCMS: $[M+H]^+$: 388.2.

What is claimed is:
1. A compound of Formula (I):

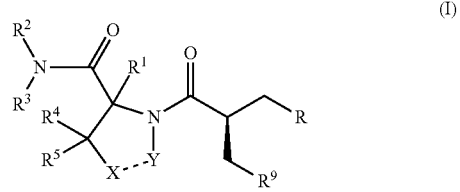

wherein:
X—Y is —C(H)$_2$—N(R$^a$)— or —C(H)=N—;
R is —C(O)N(H)OH or —N(OH)C(O)H;
R$^1$ is —H or —C$_1$-C$_6$ alkyl;
R$^2$ is aryl, —(CH$_2$)$_n$-aryl, heteroaryl or —(CH$_2$)heteroaryl;

$R^3$ is —H or —$C_1$-$C_6$ alkyl;
$R^4$ is —H, halo, —OH, $C_1$-$C_3$ alkoxy, —$NR^6R^7$ or $C_1$-$C_6$ alkyl;
$R^5$ is —H, halo, —OH, $C_1$-$C_3$ alkoxy, —$NR^6R^7$ or $C_1$-$C_6$ alkyl;
$R^9$ is —$C_3$-$C_6$ cycloalkyl or —$C_1$-$C_6$ alkyl;
wherein:
n is 0 or an integer from 1 to 5;
$R^a$ is —H or —$C_1$-$C_3$ alkyl;
each aryl or heteroaryl as defined in $R^2$ optionally is substituted with one, two, or three $R^8$ groups;
$R^6$ is —H or —$C_1$-$C_6$ alkyl;
$R^7$ is —H or —$C_1$-$C_6$ alkyl;
$R^8$ each independently is selected from —$C_1$-$C_6$ alkyl, —$C_1$-$C_6$ haloalkyl, heterocyclyl, aryl, heteroaryl, —$C(O)OR^{10}$, —$OR^{11}$, —$NR^{10}R^{11}$, —$O(CH_2)_2NR^{10}R^{11}$, —$(CH_2)NR^{10}R^{11}$ or —$N(H)(CH_2)_3$—$NR^{10}R^{11}$;
wherein:
$R^{10}$ or $R^{11}$ each independently is —H or —$C_1$-$C_6$ alkyl;
heterocyclyl, aryl or heteroaryl optionally is substituted with at least one $R^{12}$ group;
wherein:
$R^{12}$ is —$C_1$-$C_6$ alkyl, —$NR^{13}R^{14}$, $OR^{15}$ or halo;
wherein:
$R^{13}$, $R^{14}$ or $R^{15}$ each independently is —H or —$C_1$-$C_6$ alkyl; or
a pharmaceutically acceptable salt thereof.

2. A compound of Formula (II):

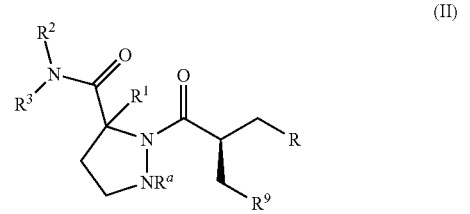

(II)

wherein:
$R^a$ is —H or —$C_1$-$C_3$ alkyl;
R is —C(O)N(H)OH or —N(OH)C(O)H;
$R^1$ is —H or —$C_1$-$C_6$ alkyl;
$R^2$ is aryl, —$(CH_2)_n$-aryl, heteroaryl or —$(CH_2)$heteroaryl
$R^3$ is —H or —$C_1$-$C_6$ alkyl;
$R^9$ is —$C_3$-$C_6$ cycloalkyl or —$C_1$-$C_6$ alkyl;
wherein:
n is 0 or an integer from 1 to 5;
each aryl or heteroaryl as defined in $R^2$ optionally is substituted with one, two, or three $R^8$ groups;
$R^8$ each independently is selected from —$C_1$-$C_6$ alkyl, —$C_1$-$C_6$ haloalkyl, heterocyclyl, aryl, heteroaryl, —$C(O)OR^{10}$, —$OR^{10}$, —$NR^{10}R^{11}$, —$O(CH_2)_2NR^{10}R^{11}$, —$(CH_2)NR^{10}R^{11}$ or —$N(H)(CH_2)_3$—$NR^{10}R^{11}$;
wherein:
$R^{10}$ or $R^{11}$ each independently is —H or —$C_1$-$C_6$ alkyl;
heterocyclyl, aryl or heteroaryl optionally is substituted with at least one $R^{12}$ group;
wherein:
$R^{12}$ is —$C_1$-$C_6$ alkyl, —$NR^{13}R^{14}$, $OR^{15}$ or halo;
wherein:
$R^{13}$, $R^{14}$ or $R^{15}$ each independently is —H or —$C_1$-$C_6$ alkyl; or
a pharmaceutically acceptable salt thereof.

3. A compound of Formula (III):

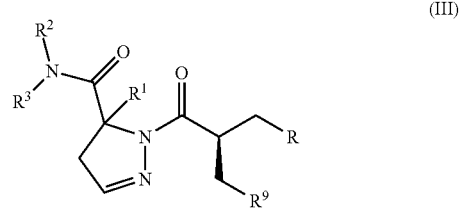

(III)

wherein:
R is —C(O)N(H)OH or —N(OH)C(O)H $R^1$ is —H or —$C_1$-$C_6$ alkyl;
$R^2$ is aryl, —$(CH_2)_n$-aryl, heteroaryl or —$(CH_2)$heteroaryl
$R^3$ is —H or —$C_1$-$C_6$ alkyl;
wherein:
n is 0 or an integer from 1 to 5;
each aryl or heteroaryl as defined in $R^2$ optionally is substituted with one, two, or three $R^8$ groups;
$R^8$ each independently is selected from —$C_1$-$C_6$ alkyl, —$C_1$-$C_6$ haloalkyl, heterocyclyl, aryl, heteroaryl, —$C(O)OR^{10}$, —$OR^{10}$, —$NR^{10}R^{11}$, —$O(CH_2)_2NR^{10}R^{11}$, —$(CH_2)NR^{10}R^{11}$ or —$N(H)(CH_2)_3$—$NR^{10}R^{11}$;
wherein:
$R^{10}$ or $R^{11}$ each independently is —H or —$C_1$-$C_6$ alkyl;
heterocyclyl, aryl or heteroaryl optionally is substituted with at least one $R^{12}$ group;
wherein:
$R^{12}$ is —$C_1$-$C_6$ alkyl, —$NR^{13}R^{14}$, $OR^{15}$ or halo;
wherein:
$R^{13}$, $R^{14}$ or $R^{15}$ each independently is —H or —$C_1$-$C_6$ alkyl; or
a pharmaceutically acceptable salt thereof.

4. A compound of Formula (IV)

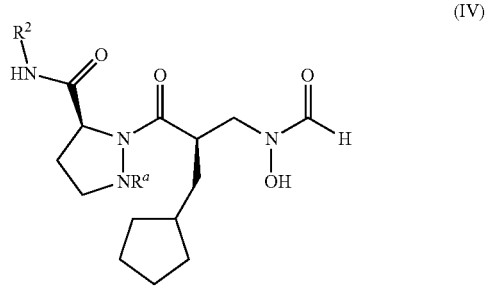

(IV)

wherein:
$R^a$ is —H or —$C_1$-$C_3$ alkyl;
$R^2$ is aryl, —$(CH_2)_n$-aryl, heteroaryl or —$(CH_2)$heteroaryl;
wherein:
n is 0 or an integer from 1 to 5;
each aryl or heteroaryl as defined in $R^2$ optionally is substituted with one, two, or three $R^8$ groups;
$R^8$ each independently is selected from —$C_1$-$C_6$ alkyl, —$C_1$-$C_6$ haloalkyl, heterocyclyl, aryl, heteroaryl, —$C(O)OR^{10}$, —$OR^{10}$, —$NR^{10}R^{11}$, —$O(CH_2)_2NR^{10}R^{11}$, —$(CH_2)NR^{10}R^{11}$ or —$N(H)(CH_2)_3$—$NR^{10}R^{11}$;

wherein:

R¹⁰ or R¹¹ each independently is —H or —C₁-C₆ alkyl;

heterocyclyl, aryl or heteroaryl optionally is substituted with at least one R¹² group;

wherein:

R¹² is —C₁-C₆ alkyl, —NR¹³R¹⁴, —OR¹⁵ or halo;

wherein:

R¹³, R¹⁴ or R¹⁵ each independently is —H or —C₁-C₆ alkyl; or a pharmaceutically acceptable salt thereof.

5. A compound which is (3S)-2-((2R)-3-Cyclopentyl-2-{[formyl(hydroxy)amino]methyl}propanoyl)-N-(3-methyl-2-pyridinyl)-3-pyrazolidinecarboxamide;

(3S)-2-((2R)-3-Cyclopentyl-2-{[formyl(hydroxy)amino]methyl}propanoyl)-N-(3,4-dimethyl-2-pyridinyl)-3-pyrazolidinecarboxamide;

(3S)-2-((2R)-3-Cyclopentyl-2-{[formyl(hydroxy)amino]methyl}propanoyl)-N-(6-ethyl-3-methyl-2-pyridinyl)-3-pyrazolidinecarboxamide;

(3S)-2-((2R)-3-Cyclopentyl-2-{[formyl(hydroxy)amino]methyl}propanoyl)-N-4-isoquinolinyl-3-pyrazolidinecarboxamide;

(3S)-2-((2R)-3-Cyclopentyl-2-{[formyl(hydroxy)amino]methyl}propanoyl)-N-(6-ethyl-2-pyridinyl)-3-pyrazolidinecarboxamide;

(3S)-2-((2R)-3-Cyclopentyl-2-{[formyl(hydroxy)amino]methyl}propanoyl)-N-(4-ethyl-2-pyridinyl)-3-pyrazolidinecarboxamide;

(3S)-2-((2R)-3-Cyclopentyl-2-{[formyl(hydroxy)amino]methyl}propanoyl)-N-1,3-thiazol-2-yl-3-pyrazolidinecarboxamide;

(3S)—N-(5-Chloro-2-pyridinyl)-2-((2R)-3-cyclopentyl-2-{[formyl(hydroxy)amino]methyl}propanoyl)-3-pyrazolidinecarboxamide;

(3S)-2-((2R)-3-Cyclopentyl-2-{[formyl(hydroxy)amino]methyl}propanoyl)-N-3-isoxazolyl-3-pyrazolidinecarboxamide;

(3S)-2-((2R)-3-Cyclopentyl-2-{[formyl(hydroxy)amino]methyl}propanoyl)-N-(5-phenyl-2-pyridinyl)-3-pyrazolidinecarboxamide;

(3S)-2-((2R)-3-Cyclopentyl-2-{[formyl(hydroxy)amino]methyl}propanoyl)-N-[3-(methyloxy)phenyl]-3-pyrazolidinecarboxamide;

(3S)-2-((2R)-3-Cyclopentyl-2-{[formyl(hydroxy)amino]methyl}propanoyl)-N-(4-fluorophenyl)-3-pyrazolidinecarboxamide;

(3S)-2-((2R)-3-Cyclopentyl-2-{[formyl(hydroxy)amino]methyl}propanoyl)-N-(3-fluorophenyl)-3-pyrazolidinecarboxamide;

(3S)-2-((2R)-3-Cyclopentyl-2-{[formyl(hydroxy)amino]methyl}propanoyl)-N-(4,5-dimethyl-1,3-thiazol-2-yl)-3-pyrazolidinecarboxamide;

(3S)-2-((2R)-3-Cyclopentyl-2-{[formyl(hydroxy)amino]methyl}propanoyl)-N-phenyl-3-pyrazolidinecarboxamide;

(3S)-2-((2R)-3-Cyclopentyl-2-{[formyl(hydroxy)amino]methyl}propanoyl)-N-(5-fluoro-2-pyridinyl)-3-pyrazolidinecarboxamide;

(3S)-2-((2R)-3-Cyclopentyl-2-{[formyl(hydroxy)amino]methyl}propanoyl)-N-2-pyridinyl-3-pyrazolidinecarboxamide;

(3S)-2-((2R)-3-Cyclopentyl-2-{[formyl(hydroxy)amino]methyl}propanoyl)-N-3-pyridinyl-3-pyrazolidinecarboxamide;

(3S)-2-((2R)-3-Cyclopentyl-2-{[formyl(hydroxy)amino]methyl}propanoyl)-N-3-pyridazinyl-3-pyrazolidinecarboxamide;

(3S)-2-((2R)-3-Cyclopentyl-2-{[formyl(hydroxy)amino]methyl}propanoyl)-N-[4-(trifluoromethyl)phenyl]-3-pyrazolidinecarboxamide;

(3S)-2-((2R)-3-Cyclopentyl-2-{[formyl(hydroxy)amino]methyl}propanoyl)-N-(2-fluorophenyl)-3-pyrazolidinecarboxamide;

(3S)-2-((2R)-3-Cyclopentyl-2-{[formyl(hydroxy)amino]methyl}propanoyl)-N-(6-fluoro-2-pyridinyl)-3-pyrazolidinecarboxamide;

(3S)-2-((2R)-3-Cyclopentyl-2-{[formyl(hydroxy)amino]methyl}propanoyl)-N-[4-(trifluoromethyl)-2-pyridinyl]-3-pyrazolidinecarboxamide;

(3S)-2-((2R)-3-Cyclopentyl-2-{[formyl(hydroxy)amino]methyl}propanoyl)-N-(2-pyridinylmethyl)-3-pyrazolidinecarboxamide;

(3S)-2-((2R)-3-Cyclopentyl-2-{[formyl(hydroxy)amino]methyl}propanoyl)-N-(6-methyl-2-pyridinyl)-3-pyrazolidinecarboxamide;

(3S)-2-((2R)-3-Cyclopentyl-2-{[formyl(hydroxy)amino]methyl}propanoyl)-N-[6-(trifluoromethyl)-2-pyridinyl]-3-pyrazolidinecarboxamide;

(3S)-2-((2R)-3-Cyclopentyl-2-{[formyl(hydroxy)amino]methyl}propanoyl)-N-(4,6-dimethyl-2-pyridinyl)-3-pyrazolidinecarboxamide;

Ethyl 5-({[(3S)-2-((2R)-3-cyclopentyl-2-{[formyl(hydroxy)amino]methyl}propanoyl)-3-pyrazolidinyl]carbonyl}amino)-1,3,4-oxadiazole-2-carboxylate;

(3S)—N-(6-Chloro-2-pyridinyl)-2-((2R)-3-cyclopentyl-2-{[formyl(hydroxy)amino]methyl}propanoyl)-3-pyrazolidinecarboxamide;

(3S)-2-((2R)-3-Cyclopentyl-2-{[formyl(hydroxy)amino]methyl}propanoyl)-N-[6-(4-morpholinyl)-3-pyridinyl]-3-pyrazolidinecarboxamide;

(3S)-2-((2R)-3-Cyclopentyl-2-{[formyl(hydroxy)amino]methyl}propanoyl)-N-5-isoquinolinyl-3-pyrazolidinecarboxamide;

(3S)-2-((2R)-3-Cyclopentyl-2-{[formyl(hydroxy)amino]methyl}propanoyl)-N-1-isoquinolinyl-3-pyrazolidinecarboxamide;

(3S)-2-((2R)-3-Cyclopentyl-2-{[formyl(hydroxy)amino]methyl}propanoyl)-N-2-quinolinyl-3-pyrazolidinecarboxamide;

(3S)-2-((2R)-3-Cyclopentyl-2-{[formyl(hydroxy)amino]methyl}propanoyl)-N-3-quinolinyl-3-pyrazolidinecarboxamide;

(3S)-2-((2R)-3-Cyclopentyl-2-{[formyl(hydroxy)amino]methyl}propanoyl)-N-{5-[4-(methyloxy)phenyl]-2-pyridinyl}-3-pyrazolidinecarboxamide;

(3S)-2-((2R)-3-Cyclopentyl-2-{[formyl(hydroxy)amino]methyl}propanoyl)-N-{5-[3-(methyloxy)phenyl]-2-pyridinyl}-3-pyrazolidinecarboxamide;

(3S)-2-((2R)-3-Cyclopentyl-2-{[formyl(hydroxy)amino]methyl}propanoyl)-N-5-quinolinyl-3-pyrazolidinecarboxamide;

(3S)-2-((2R)-3-Cyclopentyl-2-{[formyl(hydroxy)amino]methyl}propanoyl)-N-[6-(4-morpholinyl)-2-pyridinyl]-3-pyrazolidinecarboxamide;

(3S)-2-((2R)-3-Cyclopentyl-2-{[formyl(hydroxy)amino]methyl}propanoyl)-N-(1,2,3,4-tetrahydro-5-quinolinyl)-3-pyrazolidinecarboxamide;

(3S)-2-((2R)-3-Cyclopentyl-2-{[formyl(hydroxy)amino]methyl}propanoyl)-N-8-quinolinyl-3-pyrazolidinecarboxamide;

(3S)-2-((2R)-3-Cyclopentyl-2-{[formyl(hydroxy)amino]methyl}propanoyl)-N-[5-(4-fluorophenyl)-2-pyridinyl]-3-pyrazolidinecarboxamide;

(3S)-2-((2R)-3-Cyclopentyl-2-{[formyl(hydroxy)amino]methyl}propanoyl)-N-[6-(methyloxy)-1,5-naphthyridin-3-yl]-3-pyrazolidinecarboxamide;

(3S)-2-((2R)-3-Cyclopentyl-2-{[formyl(hydroxy)amino]methyl}propanoyl)-N-(5-fluoro-1-oxido-2-pyridinyl)-3-pyrazolidinecarboxamide;

(3S)-2-((2R)-3-Cyclopentyl-2-{[formyl(hydroxy)amino]methyl}propanoyl)-N-(5-methyl-2-pyridinyl)-3-pyrazolidinecarboxamide;

(3S)-2-((2R)-3-Cyclopentyl-2-{[formyl(hydroxy)amino]methyl}propanoyl)-N-(1-oxido-2-pyridinyl)-3-pyrazolidinecarboxamide;

Methyl 6-({[(3S)-2-((2R)-3-cyclopentyl-2-{[formyl(hydroxy)amino]methyl}propanoyl)-3-pyrazolidinyl]carbonyl}amino)-2-pyridinecarboxylate;

(3S)-2-((2R)-3-Cyclopentyl-2-{[formyl(hydroxy)amino]methyl}propanoyl)-N-(5-methyl-3-isoxazolyl)-3-pyrazolidinecarboxamide;

(3S)-2-((2R)-3-Cyclopentyl-2-{[formyl(hydroxy)amino]methyl}propanoyl)-N-(2-fluoro-3-pyridinyl)-3-pyrazolidinecarboxamide;

(3S)-2-((2R)-3-Cyclopentyl-2-{[formyl(hydroxy)amino]methyl}propanoyl)-N-(1-oxido-4-pyrimidinyl)-3-pyrazolidinecarboxamide;

(3S)—N-1H-1,2,3-Benzotriazol-5-yl-2-((2R)-3-cyclopentyl-2-{[formyl(hydroxy)amino]methyl}propanoyl)-3-pyrazolidinecarboxamide;

(3S)-2-((2R)-3-Cyclopentyl-2-{[formyl(hydroxy)amino]methyl}propanoyl)-1-methyl-N-4-pyrimidinyl-3-pyrazolidinecarboxamide;

(3S)-2-((2R)-3-Cyclopentyl-2-{[formyl(hydroxy)amino]methyl}propanoyl)-N-(5-fluoro-2-pyridinyl)-1-methyl-3-pyrazolidinecarboxamide;

(3S)-2-((2R)-3-Cyclopentyl-2-{[formyl(hydroxy)amino]methyl}propanoyl)-1-methyl-N-2-pyrazinyl-3-pyrazolidinecarboxamide;

(3S)-2-((2R)-3-Cyclopentyl-2-{[formyl(hydroxy)amino]methyl}propanoyl)-1-methyl-N-[2-(methyloxy)-4-pyrimidinyl]-3-pyrazolidinecarboxamide;

(3S)-2-((2R)-3-Cyclopentyl-2-{[formyl(hydroxy)amino]methyl}propanoyl)-1-methyl-N-[6-(methyloxy)-2-pyrazinyl]-3-pyrazolidinecarboxamide;

(3S)-2-((2R)-3-Cyclopentyl-2-{[formyl(hydroxy)amino]methyl}propanoyl)-N-(6-fluoro-2-pyridinyl)-1-methyl-3-pyrazolidinecarboxamide;

(3S)-2-((2R)-3-Cyclopentyl-2-{[formyl(hydroxy)amino]methyl}propanoyl)-N-(3-fluoro-4-pyridinyl)-1-methyl-3-pyrazolidinecarboxamide;

(3S)-2-((2R)-3-Cyclopentyl-2-{[formyl(hydroxy)amino]methyl}propanoyl)-1-methyl-N-[3-(methyloxy)-2-pyrazinyl]-3-pyrazolidinecarboxamide;

(3S)-2-((2R)-3-Cyclopentyl-2-{[formyl(hydroxy)amino]methyl}propanoyl)-N-4-pyrimidinyl-3-pyrazolidinecarboxamide;

(3S)-2-((2R)-3-Cyclopentyl-2-{[formyl(hydroxy)amino]methyl}propanoyl)-N-2-pyrazinyl-3-pyrazolidinecarboxamide;

(3S)-2-((2R)-3-Cyclopentyl-2-{[formyl(hydroxy)amino]methyl}propanoyl)-N-4-pyridinyl-3-pyrazolidinecarboxamide;

(3S)-2-((2R)-3-Cyclopentyl-2-{[formyl(hydroxy)amino]methyl}propanoyl)-N-[6-(1H-imidazol-1-yl)-2-pyridinyl]-3-pyrazolidinecarboxamide;

(3S)-2-((2R)-3-Cyclopentyl-2-{[formyl(hydroxy)amino]methyl}propanoyl)-N-[5-(1H-imidazol-1-yl)-2-pyridinyl]-3-pyrazolidinecarboxamide;

(3S)-2-((2R)-3-Cyclopentyl-2-{[formyl(hydroxy)amino]methyl}propanoyl)-N-(3-fluoro-4-pyridinyl)-3-pyrazolidinecarboxamide;

(3S)-2-((2R)-3-Cyclopentyl-2-{[formyl(hydroxy)amino]methyl}propanoyl)-N-(2-quinolinylmethyl)-3-pyrazolidinecarboxamide;

(3S)-2-((2R)-3-Cyclopentyl-2-{[formyl(hydroxy)amino]methyl}propanoyl)-N-5-pyrimidinyl-3-pyrazolidinecarboxamide;

(3S)-2-((2R)-3-Cyclopentyl-2-{[formyl(hydroxy)amino]methyl}propanoyl)-N-[6-(methyloxy)-4-pyrimidinyl]-3-pyrazolidinecarboxamide;

(3S)-2-((2R)-3-Cyclopentyl-2-{[formyl(hydroxy)amino]methyl}propanoyl)-N-(4-methyl-2-pyridinyl)-3-pyrazolidinecarboxamide;

(3S)-2-((2R)-3-Cyclopentyl-2-{[formyl(hydroxy)amino]methyl}propanoyl)-N-(7-methyl-7H-purin-6-yl)-3-pyrazolidinecarboxamide;

(3S)-2-((2R)-3-Cyclopentyl-2-{[formyl(hydroxy)amino]methyl}propanoyl)-N-[2-(methyloxy)-4-pyrimidinyl]-3-pyrazolidinecarboxamide;

(3S)-2-((2R)-3-Cyclopentyl-2-{[formyl(hydroxy)amino]methyl}propanoyl)-N-(5-fluoro-4-pyrimidinyl)-3-pyrazolidinecarboxamide;

(3S)-2-((2R)-3-Cyclopentyl-2-{[formyl(hydroxy)amino]methyl}propanoyl)-N-(3-quinolinylmethyl)-3-pyrazolidinecarboxamide;

(3S)-2-((2R)-3-Cyclopentyl-2-{[formyl(hydroxy)amino]methyl}propanoyl)-N-(5-methyl-2-pyrazinyl)-3-pyrazolidinecarboxamide;

(3S)-2-((2R)-3-Cyclopentyl-2-{[formyl(hydroxy)amino]methyl}propanoyl)-N-[6-(methyloxy)-2-pyrazinyl]-3-pyrazolidinecarboxamide;

(3S)-2-((2R)-3-Cyclopentyl-2-{[formyl(hydroxy)amino]methyl}propanoyl)-N-[3-(methyloxy)-2-pyrazinyl]-3-pyrazolidinecarboxamide;

(3S)-2-((2R)-3-Cyclopentyl-2-{[formyl(hydroxy)amino]methyl}propanoyl)-N-(2-fluoro-4-pyrimidinyl)-3-pyrazolidinecarboxamide;

(3S)-2-((2R)-3-Cyclopentyl-2-{[formyl(hydroxy)amino]methyl}propanoyl)-N-[2-(4-methyl-1-piperazinyl)-4-pyrimidinyl]-3-pyrazolidinecarboxamide;

(3S)-2-((2R)-3-Cyclopentyl-2-{[formyl(hydroxy)amino]methyl}propanoyl)-N-[2-(dimethylamino)-4-pyrimidinyl]-3-pyrazolidinecarboxamide;

(3S)-2-((2R)-3-Cyclopentyl-2-{[formyl(hydroxy)amino]methyl}propanoyl)-N-(4-pyrimidinylmethyl)-3-pyrazolidinecarboxamide;

(3S)-2-((2R)-3-Cyclopentyl-2-{[formyl(hydroxy)amino]methyl}propanoyl)-N-{2-[(2R)-2,4-dimethyl-1-piperazinyl]-4-pyrimidinyl}-3-pyrazolidinecarboxamide;

(3S)-2-((2R)-3-Cyclopentyl-2-{[formyl(hydroxy)amino]methyl}propanoyl)-N-(2-{[2-(dimethylamino)ethyl]oxy}-4-pyrimidinyl)-3-pyrazolidinecarboxamide;

(3S)-2-((2R)-3-Cyclopentyl-2-{[formyl(hydroxy)amino]methyl}propanoyl)-N-(2-{[3-(dimethylamino)propyl]amino}-4-pyrimidinyl)-3-pyrazolidinecarboxamide;

(3S)-2-((2R)-3-Cyclopentyl-2-{[formyl(hydroxy)amino]methyl}propanoyl)-N-{2-[(3S)-3-(dimethylamino)-1-pyrrolidinyl]-4-pyrimidinyl}-3-pyrazolidine carboxamide;

(3S)-2-((2R)-3-Cyclopentyl-2-{[formyl(hydroxy)amino]methyl}propanoyl)-N-2-pyrimidinyl-3-pyrazolidinecarboxamide;

(3S)-2-((2R)-3-Cyclopentyl-2-{[formyl(hydroxy)amino]methyl}propanoyl)-N-{6-[(2R)-2,4-dimethyl-1-piperazinyl]-4-pyrimidinyl}-3-pyrazolidinecarboxamide;

(3S)-2-((2R)-3-Cyclopentyl-2-{[formyl(hydroxy)amino]methyl}propanoyl)-N-[2-(4-methyl-4,7-diazaspiro[2.5]oct-7-yl)-4-pyrimidinyl]-3-pyrazolidinecarboxamide;

(3S)-2-((2R)-3-Cyclopentyl-2-{[formyl(hydroxy)amino]methyl}propanoyl)-N-{2-[(2S)-2,4-dimethyl-1-piperazinyl]-4-pyrimidinyl}-3-pyrazolidinecarboxamide;

(3S)-2-((2R)-3-Cyclopentyl-2-{[formyl(hydroxy)amino]methyl}propanoyl)-N-[5-(methyloxy)-2-pyrimidinyl]-3-pyrazolidinecarboxamide;

(3S)-2-((2R)-3-Cyclopentyl-2-{[formyl(hydroxy)amino]methyl}propanoyl)-N-[4-(methyloxy)-2-pyrimidinyl]-3-pyrazolidinecarboxamide;

(3S)-2-((2R)-3-Cyclopentyl-2-{[formyl(hydroxy)amino]methyl}propanoyl)-N-(5-fluoro-2-pyrimidinyl)-3-pyrazolidinecarboxamide;

(3S)-2-((2R)-3-Cyclopentyl-2-{[formyl(hydroxy)amino]methyl}propanoyl)-N-{2-[(dimethylamino)methyl]-4-pyrimidinyl}-3-pyrazolidinecarboxamide;

(5S)-1-((2R)-3-Cyclopentyl-2-{[formyl(hydroxy)amino]methyl}propanoyl)-N-4-pyrimidinyl-4,5-dihydro-1H-pyrazole-5-carboxamide;

(5S)-1-((2R)-3-Cyclopentyl-2-{[formyl(hydroxy)amino]methyl}propanoyl)-N-(5-fluoro-2-pyridinyl)-4,5-dihydro-1H-pyrazole-5-carboxamide;

(5S)-1-((2R)-3-Cyclopentyl-2-{[formyl(hydroxy)amino]methyl}propanoyl)-N-(5-fluoro-4-pyrimidinyl)-4,5-dihydro-1H-pyrazole-5-carboxamide;

(5S)-1-((2R)-3-Cyclopentyl-2-{[formyl(hydroxy)amino]methyl}propanoyl)-N-2-pyrazinyl-4,5-dihydro-1H-pyrazole-5-carboxamide;

(5S)-1-((2R)-3-Cyclopentyl-2-{[formyl(hydroxy)amino]methyl}propanoyl)-N-(2-fluoro-4-pyrimidinyl)-4,5-dihydro-1H-pyrazole-5-carboxamide;

(5S)-1-((2R)-3-Cyclopentyl-2-{[formyl(hydroxy)amino]methyl}propanoyl)-N-(5-methyl-2-pyrazinyl)-4,5-dihydro-1H-pyrazole-5-carboxamide;

(5S)-1-((2R)-3-Cyclopentyl-2-{[formyl(hydroxy)amino]methyl}propanoyl)-N-(6-fluoro-2-pyridinyl)-4,5-dihydro-1H-pyrazole-5-carboxamide;

(5S)-1-((2R)-3-Cyclopentyl-2-{[formyl(hydroxy)amino]methyl}propanoyl)-N-[2-(methyloxy)-4-pyrimidinyl]-4,5-dihydro-1H-pyrazole-5-carboxamide;

(3S)—N-(5-Fluoro-2-pyridinyl)-2-((2R)-2-{[formyl(hydroxy)amino]methyl}heptanoyl)-3-pyrazolidinecarboxamide;

(3S)-2-((2R)-2-{[Formyl(hydroxy)amino]methyl}heptanoyl)-N-4-pyrimidinyl-3-pyrazolidinecarboxamide;

(3S)-2-((2R)-2-{[Formyl(hydroxy)amino]methyl}heptanoyl)-N-2-pyridinyl-3-pyrazolidinecarboxamide;

(3S)-2-((2R)-2-{[Formyl(hydroxy)amino]methyl}heptanoyl)-N-(1-oxido-2-pyridinyl)-3-pyrazolidinecarboxamide;

(3S)—N-(5-Fluoro-1-oxido-2-pyridinyl)-2-((2R)-2-{[formyl(hydroxy)amino]methyl}heptanoyl)-3-pyrazolidinecarboxamide;

(5S)-1-((2R)-3-Cyclopentyl-2-{[formyl(hydroxy)amino]methyl}propanoyl)-N-(1-oxido-2-pyridinyl)-4,5-dihydro-1H-pyrazole-5-carboxamide;

(3S)-2-((2R)-3-Cyclopentyl-2-{[formyl(hydroxy)amino]methyl}propanoyl)-N-1H-imidazol-2-yl-3-pyrazolidinecarboxamide;

(3S)—N-1H-Benzimidazol-2-yl-2-((2R)-3-cyclopentyl-2-{[formyl(hydroxy)amino]methyl}propanoyl)-3-pyrazolidinecarboxamide;

(5S)—N-(5-Fluoro-2-pyridinyl)-1-((2R)-2-{[formyl(hydroxy)amino]methyl}heptanoyl)-4,5-dihydro-1H-pyrazole-5-carboxamide;

(5S)-1-((2R)-2-{[Formyl(hydroxy)amino]methyl}heptanoyl)-N-2-pyridinyl-4,5-dihydro-1H-pyrazole-5-carboxamide;

(5S)-1-((2R)-2-{[Formyl(hydroxy)amino]methyl}heptanoyl)-N-4-pyrimidinyl-4,5-dihydro-1H-pyrazole-5-carboxamide;

(3S)-2-((2R)-2-{[Formyl(hydroxy)amino]methyl}heptanoyl)-N-3-pyridazinyl-3-pyrazolidinecarboxamide;

(3S)-2-((2R)-3-Cyclopentyl-2-{[formyl(hydroxy)amino]methyl}propanoyl)-N-[2-(4-morpholinyl)-5-pyrimidinyl]-3-pyrazolidinecarboxamide;

(3S)-2-((2R)-2-{[Formyl(hydroxy)amino]methyl}hexanoyl)-N-(1-oxido-2-pyridinyl)-3-pyrazolidinecarboxamide;

(3S)—N-(5-Fluoro-1-oxido-2-pyridinyl)-2-((2R)-2-{[formyl(hydroxy)amino]methyl}hexanoyl)-3-pyrazolidinecarboxamide;

(3S)-2-((2R)-2-{[Formyl(hydroxy)amino]methyl}hexanoyl)-N-4-pyrimidinyl-3-pyrazolidinecarboxamide;

4-({[(3S)-2-((2R)-3-Cyclopentyl-2-{[formyl(hydroxy)amino]methyl}propanoyl)-3-pyrazolidinyl]carbonyl}amino)benzoic acid;

(3S)-2-((2R)-3-Cyclopentyl-2-{[formyl(hydroxy)amino]methyl}propanoyl)-N-(5-hydroxy-2-pyridinyl)-3-pyrazolidinecarboxamide;

6-({[(3S)-2-((2R)-3-Cyclopentyl-2-{[formyl(hydroxy)amino]methyl}propanoyl)-3-pyrazolidinyl]carbonyl}amino)-3-pyridinecarboxylic acid;

2-({[(3S)-2-((2R)-3-Cyclopentyl-2-{[formyl(hydroxy)amino]methyl}propanoyl)-3-pyrazolidinyl]carbonyl}amino)-4-pyridinecarboxylic acid;

3-({[(3S)-2-((2R)-3-Cyclopentyl-2-{[formyl(hydroxy)amino]methyl}propanoyl)-3-pyrazolidinyl]carbonyl}amino)benzoic acid;

(3S)-2-((2R)-3-Cyclopentyl-2-{[formyl(hydroxy)amino]methyl}propanoyl)-N-(4-hydroxy-2-pyridinyl)-3-pyrazolidinecarboxamide;

(3S)-2-((2R)-3-Cyclopentyl-2-{[formyl(hydroxy)amino]methyl}propanoyl)-N-(3-hydroxyphenyl)-3-pyrazolidinecarboxamide;

(3S)-2-((2R)-3-Cyclopentyl-2-{[formyl(hydroxy)amino]methyl}propanoyl)-N-(4-hydroxyphenyl)-3-pyrazolidinecarboxamide;

(3S)-2-((2R)-3-Cyclopentyl-2-{[formyl(hydroxy)amino]methyl}propanoyl)-N-[2-(2-pyridinyl)-5-pyrimidinyl]-3-pyrazolidinecarboxamide;

(3S)—N-(5-Fluoro-2-pyridinyl)-2-((2R)-2-{[formyl(hydroxy)amino]methyl}hexanoyl)-3-pyrazolidinecarboxamide;

(3S)-2-((2R)-2-{[Formyl(hydroxy)amino]methyl}hexanoyl)-N-3-pyridazinyl-3-pyrazolidinecarboxamide;

(3S)-2-((2R)-2-{[Formyl(hydroxy)amino]methyl}hexanoyl)-N-2-pyridinyl-3-pyrazolidinecarboxamide;

(3S)-2-((2R)-3-Cyclopentyl-2-{[formyl(hydroxy)amino]methyl}propanoyl)-N-[4-(2-pyridinyl)-2-pyrimidinyl]-3-pyrazolidinecarboxamide; or a pharmaceutically acceptable salt thereof.

6. A compound which is (3S)-2-((2R)-3-cyclopentyl-2-{[formyl(hydroxy)amino]methyl}propanoyl)-N-4-pyrimidinyl-3-pyrazolidinecarboxamide:

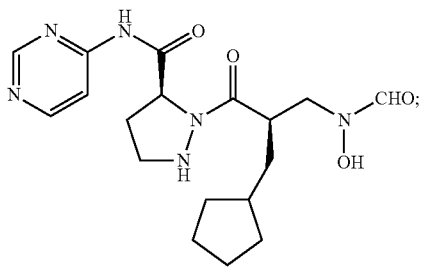 [SMILES: O=CN(O)C[C@@H](CC1CCCC1)C(=O)N1NCC[C@H]1C(=O)Nc1ccncn1]

or a pharmaceutically acceptable salt thereof.

7. A compound which is (3S)-2-((2R)-3-cyclopentyl-2-{[formyl(hydroxy)amino]methyl}propanoyl)-N-4-pyrimidinyl-3-pyrazolidinecarboxamide:

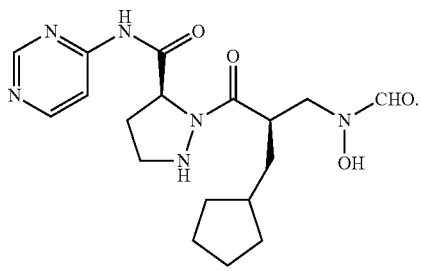 [SMILES: O=CN(O)C[C@@H](CC1CCCC1)C(=O)N1NCC[C@H]1C(=O)Nc1ccncn1]

8. A pharmaceutical composition comprising a compound of Formula (I) according to claim 1 or a pharmaceutically acceptable salt thereof and at least one pharmaceutically acceptable excipient.

9. A pharmaceutical composition comprising a compound according to claim 6 and a pharmaceutically acceptable excipient.

10. A pharmaceutical composition comprising a compound according to claim 7 and a pharmaceutically acceptable excipient.

11. A method for treatment of a bacterial infection comprising administering an effective amount of a compound of Formula (I) according to claim 1 or a pharmaceutically acceptable salt thereof to a human suffering from said bacterial infection.

12. The method according to claim 11, wherein the bacterial infection is caused by *Streptococcus, Staphylococcus, Moraxella, Haemophilus, Neisseria, Mycoplasma, Legionella, Chlamydia, Bacteroides, Clostridium, Fusobacterium, Propionibacterium,* or *Peptostreptococcus.*

13. The method according to claim 12, wherein the bacterial infection is caused by:
*Streptococcus* selected from *S. pneumoniae* or *S. pyogenes*;
*Staphylococcus* selected from *S. aureus, S. epidermidis,* or *S. saprophyticus*;
*Moraxella* selected from *M. catarrhalis*;
*Haemophilus* selected from *H. influenza* or *Neisseria*;
*Mycoplasma* selected from M pneumonia;
*Legionella* selected from *L. pneumophila*; or
*Chlamydia* selected from *C. pneumoniae, Bacteroides, Clostridium, Fusobacterium, Propionibacterium* or *Peptostreptococcus.*

14. A method for treatment of a bacterial infection comprising administering an effective amount of a compound according to claim 5 or a pharmaceutically acceptable salt thereof to a human suffering from said bacterial infection.

15. A method for treatment of a bacterial infection comprising administering an effective amount of a compound according to claim 6 or a pharmaceutically acceptable salt thereof to a human suffering from said bacterial infection.

16. A method for treatment of a bacterial infection comprising administering an effective amount of a compound according to claim 7 or a pharmaceutically acceptable salt thereof to a human suffering from said bacterial infection.

17. A method for treatment of a bacterial infection comprising administering an effective amount of a pharmaceutical composition according to claim 8 to a human suffering from said bacterial infection.

18. A method for treatment of a bacterial infection comprising administering an effective amount of a pharmaceutical composition according to claim 9 to a human suffering from said bacterial infection.

19. A method for treatment of a bacterial infection comprising administering an effective amount of a pharmaceutical composition according to claim 10 to a human suffering from said bacterial infection.

* * * * *